United States Patent
Romero et al.

(10) Patent No.: US 12,247,019 B2
(45) Date of Patent: *Mar. 11, 2025

(54) INHIBITORS OF DIHYDROCERAMIDE DESATURASE FOR TREATING DISEASE

(71) Applicant: Centaurus Therapeutics, Half Moon Bay, CA (US)

(72) Inventors: Donna L. Romero, San Francisco, CA (US); Jeremy Blitzer, San Francisco, CA (US)

(73) Assignee: Centaurus Therapeutics, Half Moon Bay, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/106,305

(22) Filed: Feb. 6, 2023

(65) Prior Publication Data

US 2023/0357187 A1 Nov. 9, 2023

Related U.S. Application Data

(63) Continuation of application No. 16/959,807, filed as application No. PCT/US2019/013193 on Jan. 11, 2019, now Pat. No. 11,597,715.

(60) Provisional application No. 62/616,253, filed on Jan. 11, 2018.

(51) Int. Cl.
| | | |
|---|---|---|
| C07D 401/12 | (2006.01) | |
| A61K 9/00 | (2006.01) | |
| A61K 45/06 | (2006.01) | |
| C07D 213/75 | (2006.01) | |
| C07D 213/76 | (2006.01) | |
| C07D 241/04 | (2006.01) | |
| C07D 401/04 | (2006.01) | |
| C07D 401/14 | (2006.01) | |
| C07D 405/12 | (2006.01) | |

(52) U.S. Cl.
CPC ......... *C07D 401/12* (2013.01); *C07D 213/75* (2013.01); *C07D 213/76* (2013.01); *C07D 241/04* (2013.01); *C07D 401/04* (2013.01); *C07D 401/14* (2013.01); *C07D 405/12* (2013.01); *A61K 9/0053* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,124,299 A | 9/2000 | Baindur et al. | |
| 6,375,957 B1 | 4/2002 | Kaiko et al. | |
| 6,395,740 B1 | 5/2002 | Baindur et al. | |
| 6,667,319 B2 | 12/2003 | Stamford et al. | |
| 6,894,063 B2 | 5/2005 | Greenlee et al. | |
| 7,129,235 B2 | 10/2006 | Zheng et al. | |
| 7,304,076 B2 | 12/2007 | Stamford | |
| 7,348,343 B2 | 3/2008 | Zhang et al. | |
| 7,491,720 B2 | 2/2009 | Ohkubo et al. | |
| 7,598,249 B2 | 10/2009 | Apodaca et al. | |
| 7,790,726 B2 | 9/2010 | Zhang et al. | |
| 7,834,018 B2 | 11/2010 | Ohkubo et al. | |
| 7,851,473 B2 | 12/2010 | Matsumoto et al. | |
| 8,143,257 B2 | 3/2012 | Choi et al. | |
| 8,530,476 B2 | 9/2013 | Apodaca et al. | |
| 8,846,600 B2 | 9/2014 | Darwish et al. | |
| 9,169,224 B2 | 10/2015 | Apodaca et al. | |
| 9,982,231 B2 | 5/2018 | Cao et al. | |
| 11,597,715 B2 * | 3/2023 | Romero | C07D 239/47 |
| 2010/0048714 A1 | 2/2010 | Summers | |
| 2011/0124730 A1 | 5/2011 | Atkinson et al. | |
| 2011/0172230 A1 | 7/2011 | Ishii et al. | |
| 2019/0328720 A1 * | 10/2019 | Romero | C07C 233/75 |

FOREIGN PATENT DOCUMENTS

| | | |
|---|---|---|
| CN | 103172635 | 4/2016 |
| EP | 1849773 A1 | 10/2007 |
| EP | 2937341 | 10/2015 |
| FR | 2939135 A1 | 3/2010 |
| JP | 862249945 A | 10/1987 |
| JP | 2006527211 A | 11/2006 |
| JP | 2006527212 A | 11/2006 |
| JP | 2007501805 A | 2/2007 |
| JP | 2010195688 A | 9/2010 |
| WO | 1999021585 | 5/1999 |
| WO | 2002050018 | 6/2002 |
| WO | 2010023512 | 3/2010 |
| WO | 2011078369 | 6/2011 |
| WO | 2018002220 | 1/2018 |
| WO | 2018112077 | 6/2018 |

OTHER PUBLICATIONS https://pubmed.ncbi.nlm.nih.gov/19852077/, downloaded on May 6, 2024 (Year: 2024).*
Grassmé et al. (2013) "Ceramide in Cystic Fibrosis" Handbook of Experimental Pharmacology 216: 265-274.
Guilbault et al. (2008) "Fenretinide Corrects Newly Found Ceramide Deficiency in Cystic Fibrosis" Am. J. Respir. Cell Mol. Biol. 38: 47-56.
Guilbault et al. (2009) "Cystic Fibrosis Fatty Acid Imbalance Is Linked to Ceramide Deficiency and Corrected by Fenretinide" Am. J. Respir. Cell Mol. Biol. 41: 100-106.
Pubmed Compound Summary for CID 74296, 'N-Phenylbenzenesulfonamide', U.S. National Library of Medicine, Mar. 26, 2005 (Mar. 26, 2005), p. 1-24; p. 3 (https://pubchem.ncbi.nlm.nih.gov/compound/74296).
Rosloniec et al. (1996) "Collagen-Induced Arthritis" Current Protocols in Immunology 20(1): 15.5.1-15.5.24.
Zheng (2006) "Fenretinide increases dihydroceramide and dihydrosphingolipids due to inhibition of dihydroceramide desaturase" Georgia Institute of Technology, pp. 1-44 (retrieved on Mar. 8, 2019 from https://smartech.gatech.edu/handle/1853/11621 ); p. 23.

(Continued)

*Primary Examiner* — Amy C Bonaparte
(74) *Attorney, Agent, or Firm* — Edward J. Baba; Bozicevic, Field & Francis LLP

(57) ABSTRACT

Disclosed herein are dihydroceramide desaturase 1 (Des1) inhibitor compounds and compositions, which are useful in the treatment of diseases, such as metabolic disorders, where inhibition of Des1 is expected to be therapeutic to a patient. Methods of inhibition of Des1 activity in a human or animal subject are also provided.

31 Claims, No Drawings

(56) References Cited

OTHER PUBLICATIONS

Ziobro et al. (2013) "E. Ceramide mediates lung fibrosis in cystic fibrosis" Biochemical Biophysical Research Communication 434:4 705-709.
Dahl et al.(2017) "In-loop" [11C]CO2-Fixation: Prototype and Proof-of-Concept, 252-262.
Falco et al., (1952) "Studies on Condensed Pyrimidine Systems, X. Some 1,3-Oxazolo (5,4-d)pyrimidines." J. Amer. Chem Soc., vol. 74, pp. 4897-4902.
Faler, et al., (2006) "Aminolysis of allyl esters with bislithium aryl amides." Tet. Lett., vol. 47, pp. 7229-7231.
Flouzat et al., (1992) "Synthesis and N-Sustitution of an Uncommon Heterocyclic System: Oxazolo[5,4-b]Pyridin-2(1H)-One." Tet. Lett., vol. 33, No. 32, pp. 4571-4574.
Glaros et al. (2008) "Myriocin slows the progression of established atherosclerotic lesions in apolipoprotein E gene knockout mice" J. Lipid Res. 49: 324-331.

* cited by examiner

INHIBITORS OF DIHYDROCERAMIDE DESATURASE FOR TREATING DISEASE

This application claims the benefit of priority of U.S. Provisional Application No. 62/616,253, filed Jan. 11, 2018, the disclosure of which is hereby incorporated by reference as if written herein in its entirety.

STATEMENT REGARDING FEDERALLY SPONSORED RESEARCH OR DEVELOPMENT

This invention was made with government support under grant number 2 R44 DK116450-02, awarded by the National Institutes of Health. The government has certain rights in the invention.

The present disclosure relates to new dihydroceramide desaturase (Des) inhibitor compounds and compositions, and their application as pharmaceuticals for the treatment of disease. Methods of inhibition of dihydroceramide desaturase 1 (Des1) and/or Des2 activity in a human or animal subject are also provided for the treatment of metabolic, cardiovascular, fibrotic, kidney, autoimmune/chronic inflammatory diseases, as well as cystic fibrosis, various cancers, lipid storage disorders, neurodegenerative disorders, and ischemia/reperfusion injury.

Dihydroceramide desaturases catalyze the formation of ceramide by introducing a 4, 5-trans double bond into the sphinogoid base backbone of dihydroceramide. Studies using cultured cells and isolated muscles revealed that endogenous ceramides and glucosylceramides antagonize insulin-stimulated glucose uptake and anabolism, and thus could mimic the effects of exogenous sphingolipid analogs. Additionally, studies in rodent models of obesity revealed that genetic or pharmacological inhibition of ceramide or glucosylceramide biosynthesis is insulin sensitizing. Therefore, the excessive production of ceramides is now appreciated as an important nutrient metabolite that accumulates in obesity, altering cellular metabolism and promoting apoptosis, and thus giving rise to many of the hallmark events associated with metabolic disease.

There are at least two isoforms of the human dihydroceramide desaturase proteins, Des1 and Des2. Des1 was identified first and is more broadly expressed; therefore most of the published research to date concerns this isoform. The published data suggest inhibitors of ceramide synthesis, i.e., inhibitors of dihydroceramide desaturases (e.g., Des1), may prove efficacious as therapeutics to treat insulin resistance and metabolic disease. Moreover, the published data suggest that inhibitors of dihydroceramide desaturases (e.g., Des1), may also prove efficacious as therapeutics to treat various cancers, cystic fibrosis, fibrotic diseases, cardiovascular disease, autoimmune/chronic inflammatory diseases, and ischemia reperfusion injury.

Novel compounds and pharmaceutical compositions, certain of which have been found to inhibit dihydroceramide desaturase have been discovered, together with methods of synthesizing and using the compounds including methods for the treatment of metabolic disorders in a patient by administering the compounds.

DETAILED DESCRIPTION

Provided herein is Embodiment 1: a compound having structural Formula (I):

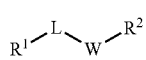

(I)

or a salt thereof, wherein:

L is chosen from —C(=O)—, —S(=O)$_2$—, —NR$_3$S(=O)$_2$—, —NR$_3$C(=O)—, and —OC(=O)—;

W is chosen from —NH— and —O—;

R$^1$ is chosen from alkyl, cycloalkyl, heterocycloalkyl, aryl, and heteroaryl, any of which is optionally substituted with 1, 2, or 3 R$^5$ groups;

R$^2$ is chosen from aryl and heteroaryl, and is optionally substituted with 1, 2, or 3 R$^4$ groups;

R$^3$ is H, or is chosen from alkyl, cycloalkyl, heterocycloalkyl, aryl, and heteroaryl, any of which is optionally substituted with 1, 2, or 3 R$^5$ groups, or R$^3$ combines with R$^1$ and the intervening N to form a heterocycloalkyl, which is optionally substituted with 1, 2, or 3 R$^5$ groups;

at least one R$^4$ is hydroxy, and the other(s) may be one or more other optional substituent(s);

each R$^5$ is independently chosen from alkyl, cycloalkyl, heterocycloalkyl, aryl, heteroaryl, (aryl)alkyl, (heteroaryl)alkyl, (aryl)aryl, (heteroaryl)aryl, (aryl)heteroaryl, and (heteroaryl)heteroaryl, and is optionally substituted with 1, 2, or 3 R$^6$ groups; and each R$^6$ is independently chosen from alkoxy, alkyl, amino, carboxy, cyano, halo, haloalkoxy, haloalkyl, and hydroxy.

Certain compounds disclosed herein may possess useful Des1 inhibiting activity, and may be used in the treatment or prophylaxis of a disease or condition in which Des1 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting Des1. Other embodiments provide methods for treating a Des1-mediated disorder in a patient in need of such treatment, comprising administering to the patient a therapeutically effective amount of a compound or composition according to the present invention. Also provided is the use of certain compounds disclosed herein for use in the manufacture of a medicament for the treatment of a disease or condition ameliorated by the inhibition of Des1.

In certain embodiments, L is —C(=O)—.

In certain embodiments, L is chosen from —S(=O)$_2$—, —NR$_3$S(=O)$_2$—.

In certain embodiments, L is —S(=O)$_2$—.

In certain embodiments, L is —NR$_3$S(=O)$_2$—.

In certain embodiments, L is chosen from —NR$_3$C(=O)—, and —OC(=O)—.

In certain embodiments, L is —NR$_3$C(=O)—.

In certain embodiments, L is —OC(=O)—.

In certain embodiments, W is —NH—.

In certain embodiments, W is —O—.

In certain embodiments, R$^2$ is chosen from phenyl, pyridinyl, pyridazinyl, pyrimidinyl, and pyrazinyl, and is optionally substituted with 1 or 2 R$^4$ groups.

In certain embodiments, R$^2$ is chosen from phenyl, pyridinyl, pyridazinyl, pyrimidinyl, and pyrazinyl, and is substituted with 1 or 2 R$^4$ groups.

In certain embodiments, R$^2$ is chosen from phenyl and pyridin-2-yl, and is substituted with 1 or 2 R$^4$ groups.

In certain embodiments, R$^2$ is chosen from phenyl and pyridin-2-yl, and is optionally substituted with 1 or 2 R$^4$ groups.

In certain embodiments, R$^3$ combines with R$^1$ and the intervening N to form a heterocycloalkyl, which is optionally substituted with 1, 2, or 3 R$^5$ groups.

In certain embodiments, $R^3$ combines with $R^1$ and the intervening N to form a 6-membered heterocycloalkyl, which is optionally substituted with 1 or 2 $R^5$ groups.

In certain embodiments, $R^3$ combines with $R^1$ and the intervening N to form a piperidine or piperazine ring substituted with an $R^5$ group.

In certain embodiments, $R^3$ combines with $R^1$ and the intervening N to form a 7-membered heterocycloalkyl, which is optionally substituted with 1 or 2 $R^5$ groups.

In certain embodiments, $R^3$ combines with $R^1$ and the intervening N to form a azepane or diazepane ring substituted with an $R^5$ group.

In certain embodiments, $R^5$ is chosen from alkyl and heteroalkyl, and is optionally substituted with 1 or 2 $R^6$ groups.

In certain embodiments, $R^5$ is chosen from phenyl, pyridinyl, pyridazinyl, pyrimidinyl, and pyrazinyl, and is optionally substituted with 1 or 2 $R^6$ groups.

In certain embodiments, $R^5$ is chosen from phenyl and pyridinyl, and is optionally substituted with 1 or 2 $R^6$ groups.

In certain embodiments, $R^5$ is phenyl optionally substituted with 1 or 2 $R^6$ groups.

In certain embodiments, $R^5$ is pyridinyl optionally substituted with 1 or 2 $R^6$ groups.

In certain embodiments, $R^5$ is chosen from (aryl)alkyl and (heteroaryl)alkyl, either of which is optionally substituted with 1 or 2 $R^6$ groups.

In certain embodiments, $R^5$ is chosen from (aryl)methyl and (heteroaryl)methyl, either of which is optionally substituted with 1 or 2 $R^6$ groups.

In certain embodiments, $R^5$ is (phenyl)methyl, and is optionally substituted with 1 or 2 $R^6$ groups.

In certain embodiments, $R^5$ is chosen from 2-fluorophenyl, 4-fluorophenyl, 2,4-difluorophenyl, 4-(trifluoromethyl)phenyl, 4-(trifluoromethyl)pyridin-2-yl, 5-(trifluoromethyl)pyridin-2-yl, 5-fluoropyridin-2-yl, and 3,5-difluoropyridin-2-yl.

In certain embodiments, $R^5$ is chosen from 2-fluorophenyl, 4-fluorophenyl, 2,4-difluorophenyl, and 4-(trifluoromethyl)phenyl.

In certain embodiments, $R^5$ is chosen from 4-(trifluoromethyl)pyridin-2-yl, 5-(trifluoromethyl)pyridin-2-yl, 5-fluoropyridin-2-yl, and 3,5-difluoropyridin-2-yl.

In certain embodiments, $R^5$ is chosen from 4-fluorophenyl, 4-chlorophenyl, 4-(trifluoromethyl)phenyl, 2,4-difluorophenyl, 2,4-dichlorophenyl, 5-fluoropyridin-2-yl, and 5-(trifluoro)pyridin-2-yl.

In certain embodiments, each $R^6$ is independently chosen from halo, haloalkyl, and cyano.

In certain embodiments, each $R^6$ is independently chosen from halo and haloalkyl.

In certain embodiments, each $R^6$ is independently chosen from fluoro, chloro, and trifluoromethyl.

In certain embodiments, each $R^6$ is independently chosen from fluoro and chloro.

In certain embodiments, each $R^6$ is independently chosen from fluoro and trifluoromethyl.

The disclosure provides the further embodiments:

Embodiment 2: The compound as recited in Embodiment 1, wherein:
each $R^4$ is independently chosen from alkyl, alkoxy, cyano, halo, and hydroxy, and
at least one $R^4$ is hydroxy.

Embodiment 3: The compound as recited in Embodiment 2, wherein:
each $R^4$ is independently chosen from cyano, halo, and hydroxy; and
at least one $R^4$ is hydroxy.

Embodiment 4: The compound as recited in Embodiment 3, wherein each $R^4$ is hydroxy.

Embodiment 5: The compound as recited in any one of Embodiments 1-4 wherein $R^2$ is chosen from phenyl, pyridinyl, pyridazinyl, pyrimidinyl, and pyrazinyl, and is optionally substituted with 1, 2, or 3 $R^4$ groups.

Embodiment 6: The compound as recited in Embodiment 5, wherein $R^2$ is chosen from phenyl, pyridin-2-yl, pyridazin-3-yl, pyrimidin-2-yl, and pyrazin-2-yl, and is optionally substituted with 1, 2, or 3 $R^4$ groups.

Embodiment 7: The compound as recited in Embodiment 5, wherein $R^2$ is chosen from phenyl, pyridin-2-yl, pyridazin-3-yl, and pyrimidin-2-yl, and is optionally substituted with 1, 2, or 3 $R^4$ groups.

Embodiment 8: The compound as recited in Embodiment 7, wherein $R^2$ is chosen from phenyl and pyridin-2-yl, and is optionally substituted with 1, 2, or 3 $R^4$ groups.

Embodiment 9: The compound as recited in Embodiment 8, wherein $R^2$ is pyridin-2-yl, and is substituted with 1, 2, or 3 $R^4$ groups.

Embodiment 10: The compound as recited in any one of Embodiments 1-9, wherein:
$R^2$ is substituted with 1, 2, or 3 $R^4$ groups, and
at least one $R^4$ is hydroxy.

Embodiment 11: The compound as recited in Embodiment 10, wherein:
$R^2$ is substituted with 1 or 2 $R^4$ groups, and
at least one $R^4$ is hydroxy.

Embodiment 12: The compound as recited in Embodiment 11, wherein $R^2$ is substituted with 1 hydroxy group.

Embodiment 13: The compound as recited in any one of Embodiments 10-12, wherein $R^2$ is substituted with an $R^4$ group in the position para to the point of attachment of W.

Embodiment 14: The compound as recited in Embodiment 13, wherein $R^2$ is substituted with a hydroxy in the position para to the point of attachment of W.

Embodiment 15: The compound as recited in Embodiment 1, wherein $R^2$ is 4-hydroxyphenyl.

Embodiment 16: The compound as recited in Embodiment 1, wherein $R^2$ is 5-hydroxypyridin-2-yl.

Embodiment 17: The compound as recited in Embodiment 1, wherein $R^2$ is 5-hydroxypyrimidin-2-yl.

Embodiment 18: The compound as recited in Embodiment 1, wherein $R^2$ is 5-hydroxypyrazin-2-yl.

Embodiment 19: The compound as recited in Embodiment 1, wherein $R^2$ is 6-hydroxypyridazin-3-yl.

Embodiment 20: The compound as recited in any one of Embodiments 1-19, wherein W is —NH—.

Embodiment 21: The compound as recited in any one of Embodiments 1-19, wherein W is —O—.

Embodiment 22: The compound as recited in either one of Embodiments 20 and 21, wherein L is chosen from —C(=O)—, —S(=O)$_2$—, and —OC(=O)—.

Embodiment 23: The compound as recited in Embodiment 22, wherein L is —C(=O)—.

Embodiment 24: The compound as recited in Embodiment 22, wherein L is —S(=O)$_2$—.

Embodiment 25: The compound as recited in Embodiment 22, wherein L is —OC(=O)—.

Embodiment 26: The compound as recited in either one of Embodiments 20 and 21, wherein L is chosen from —NR$^3$S(=O)$_2$— and —NR$^3$C(=O)—.

Embodiment 27: The compound as recited in Embodiment 26, wherein L is —NR$^3$S(=O)$_2$—.

Embodiment 28: The compound as recited in Embodiment 26, wherein L is —NR³C(=O)—.

Embodiment 29: The compound as recited in any one of Embodiments 1-19, wherein L-W is —NR³C(=O)NH—.

Embodiment 30: The compound as recited in any one of Embodiments 1-19, wherein L-W is —NR³C(=O)O—.

Embodiment 31: The compound as recited in any one of Embodiments 1-19, wherein L-W is —NR³S(=O)₂NH—.

Embodiment 32: The compound as recited in any one of Embodiments 1-19, wherein L-W is —OC(=O)NH—.

Embodiment 33: The compound as recited in any one of Embodiments 1-19, wherein L-W is —S(=O)₂NH—.

Also provided herein is Embodiment 34: the compound of Embodiment 1 having structural Formula II:

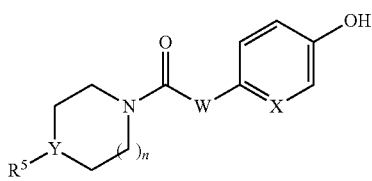

(II)

or a salt thereof, wherein:
W is chosen from —NH— and —O—;
X and Y are independently chosen from CH and N;
R⁵ is chosen from alkyl, cycloalkyl, heterocycloalkyl, aryl, heteroaryl, (aryl)alkyl, (heteroaryl)alkyl, (aryl)aryl, (heteroaryl)aryl, (aryl)heteroaryl, and (heteroaryl)heteroaryl, and is optionally substituted with 1, 2, or 3 R⁶ groups;
each R⁶ is independently chosen from alkoxy, alkyl, amino, carboxy, cyano, halo, haloalkoxy, haloalkyl, and hydroxy; and
n is chosen from 1 and 2.

In certain embodiments of the compound of Formula II, X is N.

In certain embodiments of the compound of Formula II, X is CH.

In certain embodiments of the compound of Formula II, n is 1.

In certain embodiments of the compound of Formula II, n is 2.

Also provided herein is Embodiment 35: the compound of Embodiment 1 having structural Formula III:

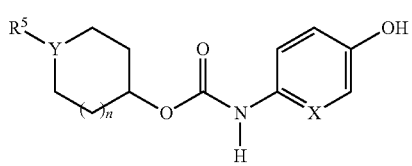

(III)

or a salt thereof, wherein:
X and Y are independently chosen from CH and N;
R⁵ is chosen from alkyl, cycloalkyl, heterocycloalkyl, aryl, heteroaryl, (aryl)alkyl, (heteroaryl)alkyl, (aryl)aryl, (heteroaryl)aryl, (aryl)heteroaryl, and (heteroaryl)heteroaryl, and is optionally substituted with 1, 2, or 3 R⁶ groups;
each R⁶ is independently chosen from alkoxy, alkyl, amino, carboxy, cyano, halo, haloalkoxy, haloalkyl, and hydroxy; and
n is chosen from 1 and 2.

Embodiment 36: The compound as recited in either one of Embodiments 34 and 35 wherein n is 1.

Embodiment 37: The compound as recited in either one of Embodiments 34 and 35 wherein n is 2.

Embodiment 38: The compound as recited in any one of Embodiments 34-37 wherein Y is CH.

Embodiment 39: The compound as recited in any one of Embodiments 34-37 wherein Y is N.

Also provided herein is Embodiment 40: the compound of Embodiment 1 having structural Formula IV:

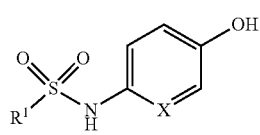

(IV)

X is chosen from CH and N;
R¹ is chosen from alkyl, cycloalkyl, heterocycloalkyl, aryl, and heteroaryl, any of which is optionally substituted with 1, 2, or 3 R⁵ groups, or
R³ is H, or is chosen from alkyl, cycloalkyl, heterocycloalkyl, aryl, and heteroaryl, any of which is optionally substituted with 1, 2, or 3 R⁵ groups, or R³ combines with R¹ and the intervening N to form a heterocycloalkyl, which is optionally substituted with 1, 2, or 3 R⁵ groups;
each R⁵ is independently chosen from alkyl, cycloalkyl, heterocycloalkyl, aryl, heteroaryl, (aryl)alkyl, and (heteroaryl)alkyl, and is optionally substituted with 1, 2, or 3 R⁶ groups; and
each R⁶ is independently chosen from alkoxy, alkyl, amino, carboxy, cyano, halo, haloalkoxy, haloalkyl, and hydroxy.

Also provided herein is Embodiment 41: the compound of Embodiment 1 having structural Formula V:

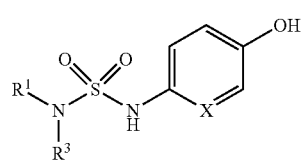

(V)

X is chosen from CH and N;
R³ is H, or is chosen from alkyl, cycloalkyl, heterocycloalkyl, aryl, and heteroaryl, any of which is optionally substituted with 1, 2, or 3 R⁵ groups, or R³ combines with R¹ and the intervening N to form a heterocycloalkyl, which is optionally substituted with 1, 2, or 3 R⁵ groups;
each R⁵ is independently chosen from alkyl, cycloalkyl, heterocycloalkyl, aryl, heteroaryl, (aryl)alkyl, and (heteroaryl)alkyl, and is optionally substituted with 1, 2, or 3 R⁶ groups; and
each R⁶ is independently chosen from alkoxy, alkyl, amino, carboxy, cyano, halo, haloalkoxy, haloalkyl, and hydroxy.

Embodiment 42: The compound as recited in any one of Embodiments 34-41 wherein X is CH.

Embodiment 43: The compound as recited in any one of Embodiments 34-41 wherein X is N.

Embodiment 44: The compound as recited in any one of Embodiments 26-31 and 41, wherein $R^3$ is H.

Embodiment 45: The compound as recited in any one of Embodiments 26-31 and 41, wherein $R^3$ is chosen from alkyl, cycloalkyl, heterocycloalkyl, aryl, and heteroaryl, any of which is optionally substituted with 1, 2, or 3 $R^5$ groups.

Embodiment 46: The compound as recited in any one of Embodiments 26-31 and 41, wherein $R^3$ combines with $R^1$ and the intervening N to form a heterocycloalkyl, which is optionally substituted with 1, 2, or 3 $R^5$ groups.

Embodiment 47: The compound as recited in Embodiment 46, wherein $R^3$ combines with $R^1$ and the intervening N to form a 6-membered heterocycloalkyl, which is optionally substituted with 1, 2, or 3 $R^5$ groups.

Embodiment 48: The compound as recited in Embodiment 47, wherein $R^3$ combines with $R^1$ and the intervening N to form a piperidine or piperazine ring, which is optionally substituted with 1, 2, or 3 $R^5$ groups.

Embodiment 49: The compound as recited in Embodiment 46, wherein $R^3$ combines with $R^1$ and the intervening N to form a 7-membered heterocycloalkyl, which is optionally substituted with 1, 2, or 3 $R^5$ groups.

Embodiment 50: The compound as recited in Embodiment 49, wherein $R^3$ combines with $R^1$ and the intervening N to form an azepane or diazepane ring, which is optionally substituted with 1, 2, or 3 $R^5$ groups.

Embodiment 51: The compound as recited in any one of Embodiments 46-50, wherein the heterocycloalkyl that is formed by the combination of $R^3$, $R^1$, and the intervening N is optionally substituted with 1 or 2 $R^5$ groups.

Embodiment 52: The compound as recited in Embodiment 51, wherein the heterocycloalkyl that is formed by the combination of $R^3$, $R^1$, and the intervening N is substituted with 1 or 2 $R^5$ groups.

Embodiment 53: The compound as recited in Embodiment 51, wherein the heterocycloalkyl that is formed by the combination of $R^3$, $R^1$, and the intervening N is optionally substituted with 1 $R^5$ group.

Embodiment 54: The compound as recited in Embodiment 53, wherein the heterocycloalkyl that is formed by the combination of $R^3$, $R^1$, and the intervening N is substituted with 1 $R^5$ group.

Embodiment 55: The compound as recited in Embodiment 53, wherein the heterocycloalkyl that is formed by the combination of $R^3$, $R^1$, and the intervening N is unsubstituted.

Embodiment 56: The compound as recited in any one of Embodiments 1-45, wherein $R^1$ is chosen from $C_{1-16}$alkyl, $C_{3-7}$cycloalkyl, 3-7 membered monocyclic heterocycloalkyl, $C_{6-10}$aryl, and 5-10 membered heteroaryl, any of which is optionally substituted with 1, 2, or 3 $R^5$ groups.

Embodiment 57: The compound as recited in Embodiment 56, wherein $R^1$ is chosen from cyclopentyl, cyclohexyl, cycloheptyl, tetrahydrofuryl, tetrahydropyranyl, oxepanyl, pyrrolidinyl, piperidinyl, and azepanyl, any of which is optionally substituted with 1, 2, or 3 $R^5$ groups.

Embodiment 58: The compound as recited in Embodiment 57, wherein $R^1$ is chosen from cyclopentyl, cyclohexyl, tetrahydrofuryl, tetrahydropyranyl, pyrrolidinyl, and piperidinyl, any of which is optionally substituted with 1, 2, or 3 $R^5$ groups.

Embodiment 59: The compound as recited in Embodiment 56, wherein $R^1$ is chosen from phenyl, naphthalenyl, quinolinyl, isoquinolinyl, pyridinyl, pyridazinyl, pyrimidinyl, and pyrazinyl, any of which is optionally substituted with 1, 2, or 3 $R^5$ groups.

Embodiment 60: The compound as recited in Embodiment 59, wherein $R^1$ is chosen from phenyl and pyridine, any of which is optionally substituted with 1, 2, or 3 $R^5$ groups.

Embodiment 61: The compound as recited in Embodiment 56, wherein $R^1$ is $C_{1-12}$alkyl, and is optionally substituted with 1, 2, or 3 $R^5$ groups.

Embodiment 62: The compound as recited in Embodiment 61, wherein $R^1$ is $C_{1-10}$alkyl, and is optionally substituted with 1, 2, or 3 $R^5$ groups.

Embodiment 63: The compound as recited in Embodiment 62, wherein $R^1$ is $C_{1-8}$alkyl, and is optionally substituted with 1, 2, or 3 $R^5$ groups.

Embodiment 64: The compound as recited in Embodiment 63, wherein $R^1$ is $C_{4-8}$alkyl, and is optionally substituted with 1, 2, or 3 $R^5$ groups.

Embodiment 65: The compound as recited in Embodiment 64, wherein $R^1$ is $C_{6-8}$alkyl, and is optionally substituted with 1, 2, or 3 $R^5$ groups.

Embodiment 66: The compound as recited in any one of Embodiments 1-45 and 56-65, wherein $R^1$ is optionally substituted with 1 or 2 $R^5$ groups.

Embodiment 67: The compound as recited in Embodiment 66, wherein $R^1$ is substituted with 1 or 2 $R^5$ groups.

Embodiment 68: The compound as recited in Embodiment 66, wherein $R^1$ is optionally substituted with 1 $R^5$ group.

Embodiment 69: The compound as recited in Embodiment 68, wherein $R^1$ is substituted with 1 $R^5$ group.

Embodiment 70: The compound as recited in Embodiment 66, wherein $R^1$ is unsubstituted.

Embodiment 71: The compound as recited in Embodiment 56, wherein:
$R^1$ is $(CH_2)_m CH_3$, and
m is an integer between 3 and 15, inclusive.

Embodiment 72: The compound as recited in Embodiment 71, wherein m is less than 14.

Embodiment 73: The compound as recited in Embodiment 72, wherein m is less than 12.

Embodiment 74: The compound as recited in Embodiment 73, wherein m is less than 10.

Embodiment 75: The compound as recited in Embodiment 74, wherein m is less than 8.

Embodiment 76: The compound as recited in Embodiment 75, wherein m is less than 6.

Embodiment 77: The compound as recited in any one of Embodiments 71-76, wherein m is greater than 4.

Embodiment 78: The compound as recited in any one of Embodiments 71-75, wherein m is greater than 6.

Embodiment 79: The compound as recited in any one of Embodiments 71-74, wherein m is greater than 8.

Embodiment 80: The compound as recited in any one of Embodiments 71-73, wherein m is greater than 10.

Embodiment 81: The compound as recited in Embodiment 56, wherein $R^1$ is chosen from

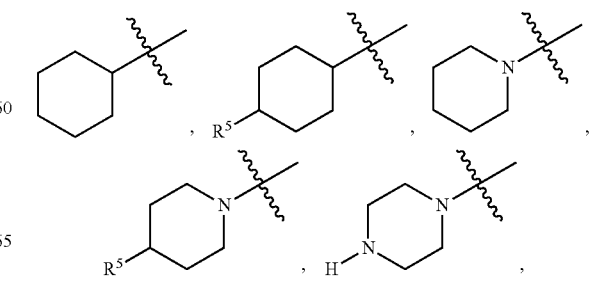

-continued

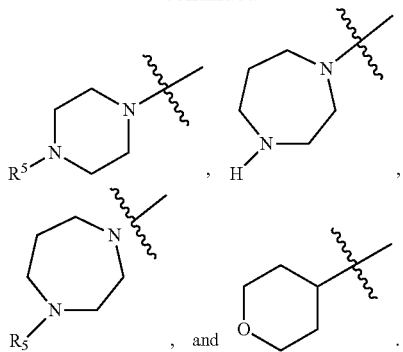

Embodiment 82: The compound as recited in Embodiment 56, wherein R¹ is chosen from

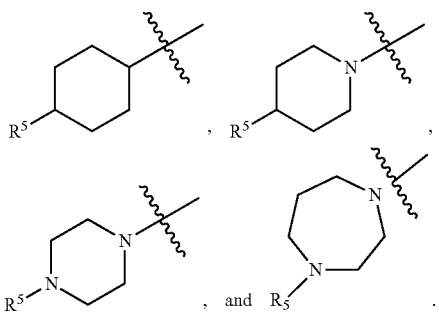

Embodiment 83: The compound as recited in either one of Embodiments 81 and 82, wherein L is —C(=O)—.

Embodiment 84: The compound as recited in Embodiment 83, wherein W is —NH—.

Embodiment 85: The compound as recited in any one of Embodiments 1-54, 56-69, and 81-84, wherein $R^5$ is chosen from alkyl, cycloalkyl, heterocycloalkyl, aryl, heteroaryl, (aryl)methyl, and (heteroaryl)methyl, and is optionally substituted with 1, 2, or 3 $R^6$ groups.

Embodiment 86: The compound as recited in Embodiment 85, wherein $R^5$ is chosen from phenyl, naphthyl, monocyclic heteroaryl, and bicyclic heteroaryl, and is optionally substituted with 1 or 2 $R^6$ groups.

Embodiment 87: The compound as recited in Embodiment 86, wherein $R^5$ is chosen from quinolinyl, isoquinolinyl, benzimidazolyl, indazolyl, pyrrolopyridinyl, and imidazopyridinyl, and is optionally substituted with 1 or 2 $R^6$ groups.

Embodiment 88: The compound as recited in Embodiment 87, wherein $R^5$ is indazolyl, and is optionally substituted with 1 or 2 $R^6$ groups.

Embodiment 89: The compound as recited in Embodiment 88, wherein $R^5$ is indazol-4-yl and indazol-6-yl, and is optionally substituted with 1 or 2 $R^6$ groups.

Embodiment 90: The compound as recited in Embodiment 86, wherein $R^5$ is chosen from pyrrolyl, imidazolyl, and pyrazolyl, and is optionally substituted with 1 or 2 $R^6$ groups.

Embodiment 91: The compound as recited in Embodiment 86, wherein $R^5$ is chosen from indolyl and indazolyl, and is optionally substituted with 1 or 2 $R^6$ groups.

Embodiment 92: The compound as recited in Embodiment 86, wherein $R^5$ is chosen from phenyl, pyridinyl, pyridazinyl, pyrimidinyl, and pyrazinyl, and is optionally substituted with 1 or 2 $R^6$ groups.

Embodiment 93: The compound as recited in Embodiment 86, wherein $R^5$ is chosen from phenyl, pyridinyl, and pyrimidinyl, and is optionally substituted with 1 or 2 $R^6$ groups.

Embodiment 94: The compound as recited in Embodiment 86, wherein $R^5$ is chosen from phenyl, pyridin-2-yl, and pyrimidin-2-yl, and is optionally substituted with 1 or 2 $R^6$ groups.

Embodiment 95: The compound as recited in Embodiment 85, wherein $R^5$ is chosen from (aryl)alkyl, (heteroaryl)alkyl, and is optionally substituted with 1 or 2 $R^6$ groups.

Embodiment 96: The compound as recited in Embodiment 95, wherein $R^5$ is chosen from (aryl)methyl, (heteroaryl)methyl, and is optionally substituted with 1 or 2 $R^6$ groups.

Embodiment 97: The compound as recited in Embodiment 96, wherein $R^5$ is (phenyl)methyl, and is optionally substituted with 1 or 2 $R^6$ groups.

Embodiment 98: The compound as recited in any one of Embodiments 1-54, 56-69, 81-84, and 85-97, wherein each $R^5$ is optionally substituted with 1 or 2 $R^6$ groups.

Embodiment 99: The compound as recited in Embodiment 98, wherein each $R^5$ is substituted with 1 or 2 $R^6$ groups.

Embodiment 100: The compound as recited in Embodiment 98, wherein each $R^5$ is optionally substituted with 1 $R^6$ group.

Embodiment 101: The compound as recited in Embodiment 100, wherein each $R^5$ is substituted with 1 $R^6$ group.

Embodiment 102: The compound as recited in Embodiment 100, wherein each $R^5$ is unsubstituted.

Embodiment 103: The compound as recited in any one of Embodiments 1-54, 56-69, 81-84, and 85-101, wherein each $R^6$ is independently chosen from alkoxy, alkyl, amino, cyano, halo, haloalkoxy, haloalkyl, and hydroxy.

Embodiment 104: The compound as recited in Embodiment 103, wherein each $R^6$ is independently chosen from cyano, halo, hydroxy, and haloalkyl.

Embodiment 105: The compound as recited in Embodiment 104, wherein each $R^6$ is independently chosen from halo and haloalkyl.

Embodiment 106: The compound as recited in Embodiment 105, wherein each $R^6$ is independently chosen from fluoro, chloro, and trifluoromethyl.

Embodiment 107: The compound as recited in Embodiment 106, wherein each $R^6$ is independently chosen from halo and trifluoromethyl.

Embodiment 108: The compound as recited in Embodiment 103, wherein each $R^6$ is independently chosen from fluoro, chloro, methoxy, methyl, cyano, trifluoromethyl, and trifluoromethoxy.

Also provided are the following embodiments:

Embodiment C-2: The compound of Embodiment 1, wherein L is chosen from —S(=O)₂—, —NR₃S(=O)₂—, —NR₃C(=O)—, and —OC(=O)—.

Embodiment C-3: The compound of Embodiment C-2, wherein each $R^4$ is independently chosen from cyano, halo, and hydroxy.

Embodiment C-4: The compound of Embodiment C-3, wherein $R^2$ is chosen from phenyl, pyridinyl, pyridazinyl, pyrimidinyl, and pyrazinyl, and is substituted with 1 or 2 $R^4$ groups.

Embodiment C-5: The compound of Embodiment C-4, wherein $R^2$ is substituted with an $R^4$ group in the position para to the point of attachment of W.

Embodiment C-6: The compound of Embodiment C-5, wherein:

R² is

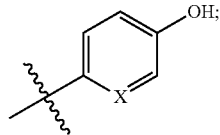

and

X is chosen from CH and N.

Embodiment C-7: The compound of Embodiment C-6, wherein L is —NR₃C(=O)—.

Embodiment C-8: The compound of Embodiment C-7, wherein L is —OC(=O)—.

Embodiment C-10: The compound of Embodiment 34, wherein X is N.

Embodiment C-11: The compound of Embodiment C-10, wherein $R^5$ is chosen from aryl and heteroaryl, and is optionally substituted with 1 or 2 $R^6$ groups.

Embodiment C-12: The compound of Embodiment C-11, wherein each $R^6$ is independently chosen from alkyl, halo, haloalkyl, and hydroxy.

Embodiment C-13: The compound of Embodiment C-12, wherein $R^5$ is chosen from phenyl, pyridinyl, pyridazinyl, pyrimidinyl, and pyrazinyl, and is optionally substituted with 1 or 2 $R^6$ groups.

Embodiment C-14: The compound of Embodiment C-13, wherein each $R^6$ is independently chosen from halo and trifluoromethyl.

Embodiment C-15: The compound of Embodiment C-14, wherein n is 1.

Embodiment C-16: The compound of Embodiment C-15, wherein W is NH.

Embodiment C-17: The compound of Embodiment C-16, wherein Y is N.

Embodiment C-18: The compound of Embodiment C-17, wherein $R^5$ is chosen from phenyl and pyridin-2-yl, and is optionally substituted with 1 or 2 $R^6$ groups.

Embodiment C-19: The compound of Embodiment C-18, wherein each $R^6$ is independently chosen from fluoro and trifluoromethyl.

Embodiment C-20: The compound of Embodiment C-19, wherein $R^5$ is chosen from 2-fluorophenyl, 4-fluorophenyl, 2,4-difluorophenyl, 4-(trifluoromethyl)phenyl, 4-(trifluoromethyl)pyridin-2-yl, 5-(trifluoromethyl)pyridin-2-yl, 5-fluoropyridin-2-yl, and 3,5-difluoropyridin-2-yl.

Embodiment C-21: The compound of Embodiment C-20, wherein $R^5$ is 2,4-difluorophenyl.

Embodiment C-23: The compound of Embodiment 35, wherein X is N.

Embodiment C-24: The compound of Embodiment C-23, wherein Y is N.

Embodiment C-25: The compound of Embodiment C-24, wherein each $R^6$ is independently chosen from halo and trifluoromethyl.

Embodiment C-26: The compound of Embodiment C-25, wherein $R^5$ is chosen from phenyl, pyridinyl, pyridazinyl, pyrimidinyl, and pyrazinyl, and is optionally substituted with 1 or 2 $R^6$ groups.

Embodiment C-27: The compound of Embodiment C-26, wherein $R^5$ is chosen from phenyl and pyridin-2-yl, and is optionally substituted with 1 or 2 $R^6$ groups.

Embodiment C-28: The compound of Embodiment C-27, wherein each $R^6$ is independently chosen from fluoro and chloro.

Embodiment C-29: The compound of Embodiment C-28, wherein $R^5$ is chosen from 4-fluorophenyl, 4-chlorophenyl, 4-(trifluoromethyl)phenyl, 2,4-difluorophenyl, 2,4-dichlorophenyl, 5-fluoropyridin-2-yl, and 5-(trifluoro)pyridin-2-yl.

Embodiment C-30: The compound of Embodiment 1, chosen from:

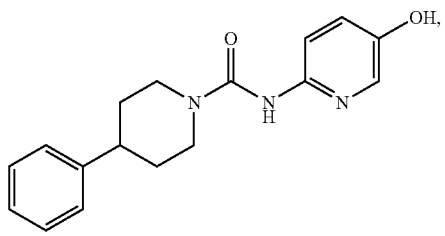

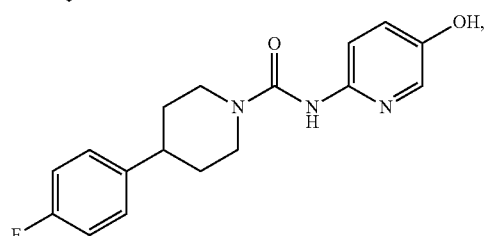

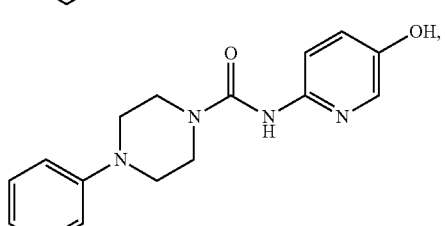

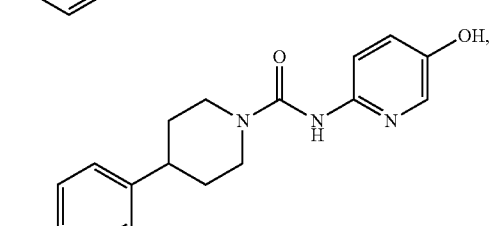

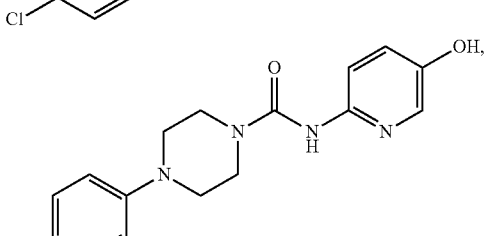

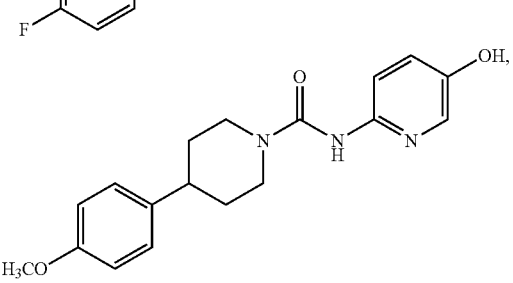

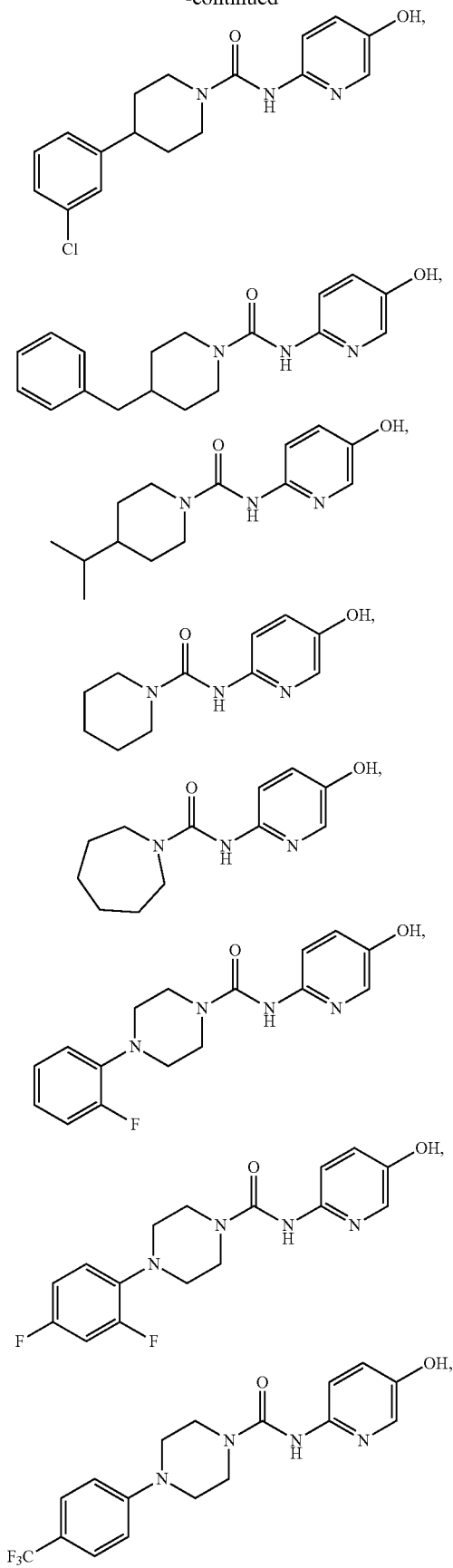
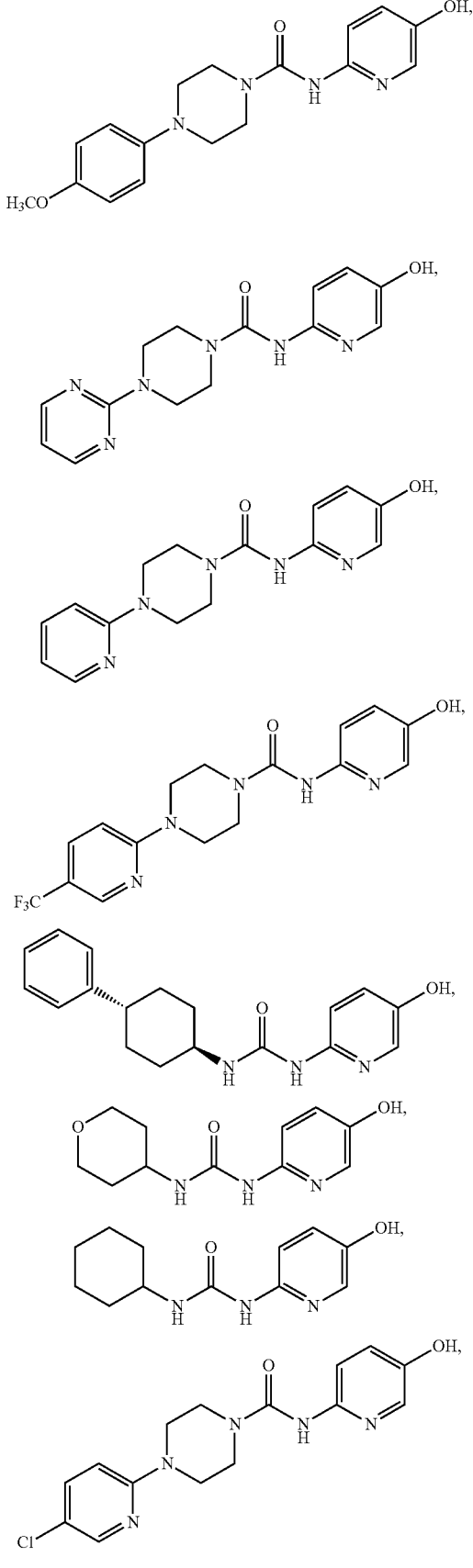

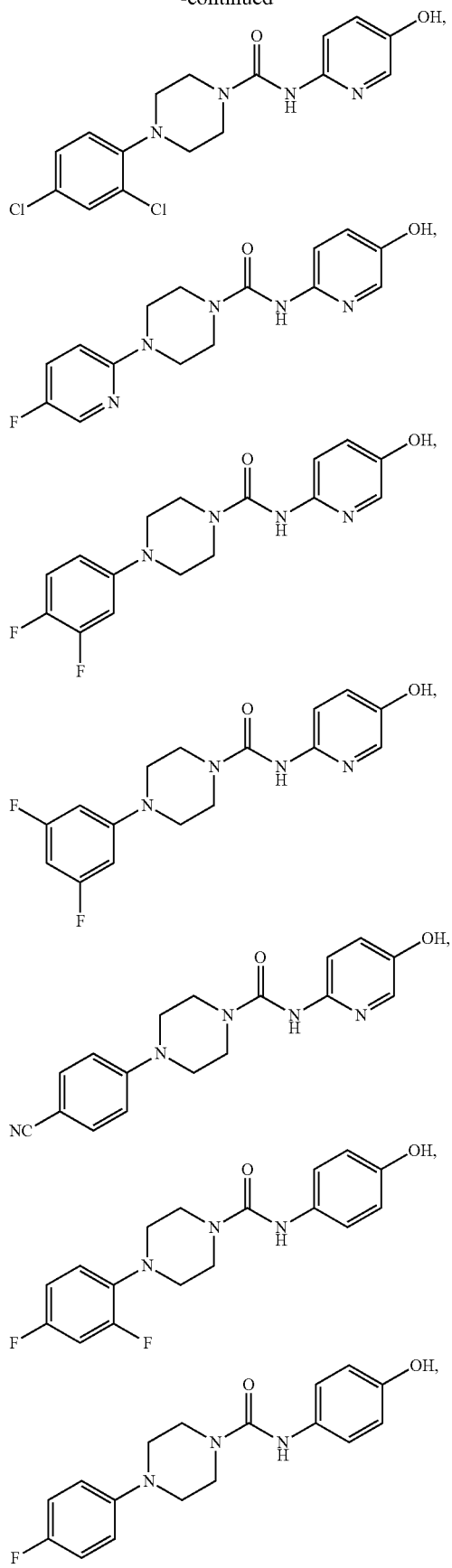
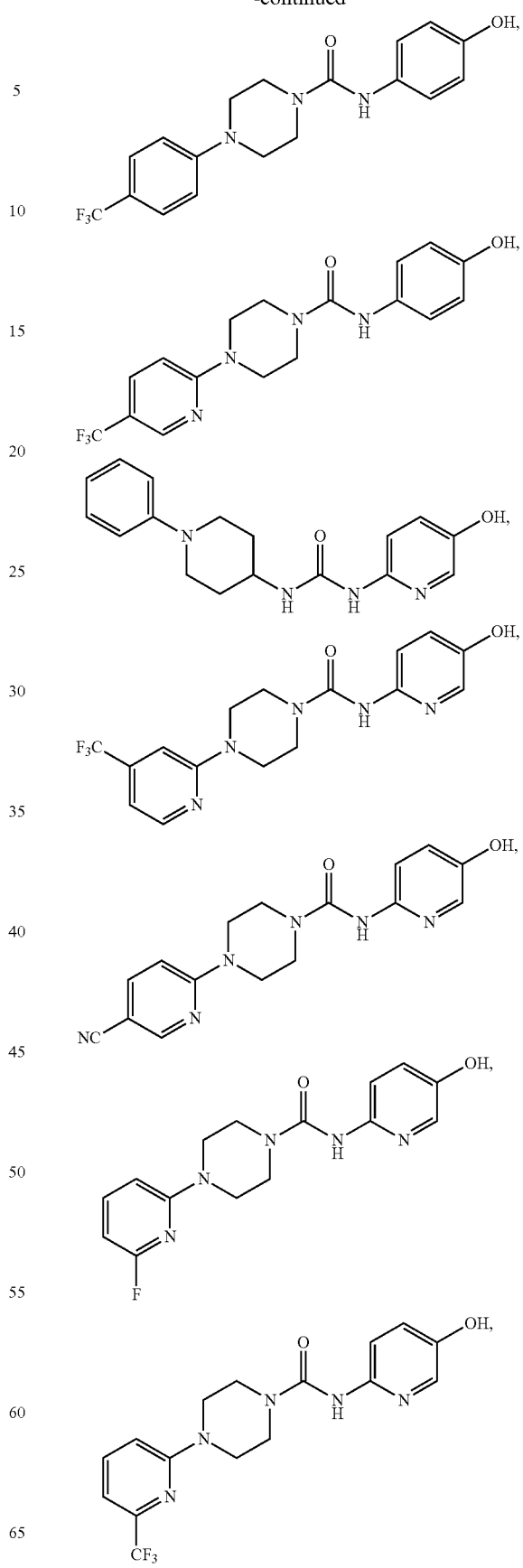

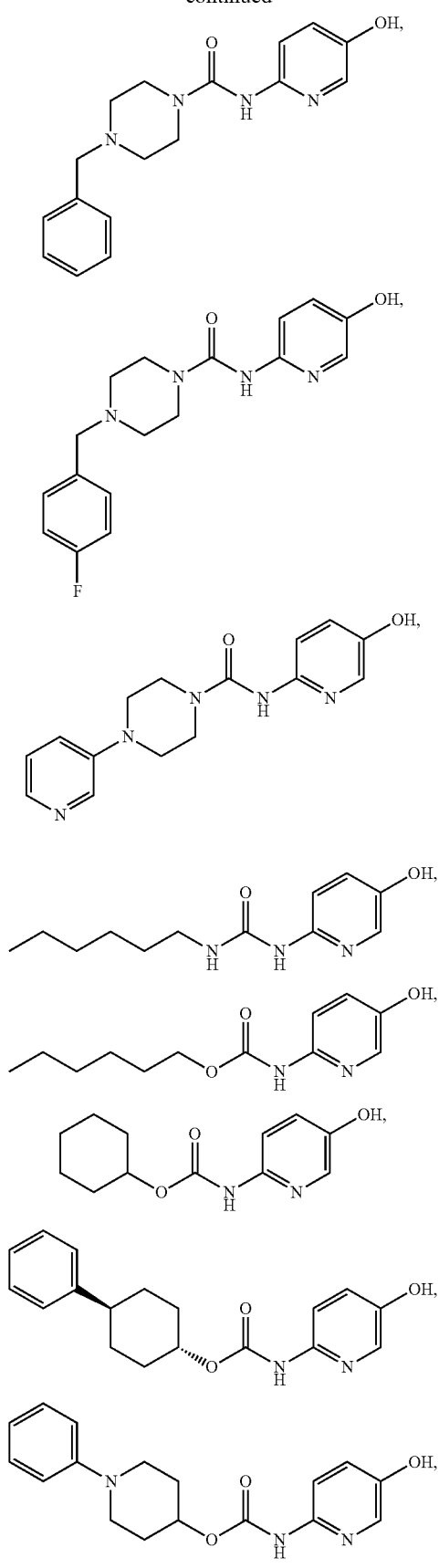
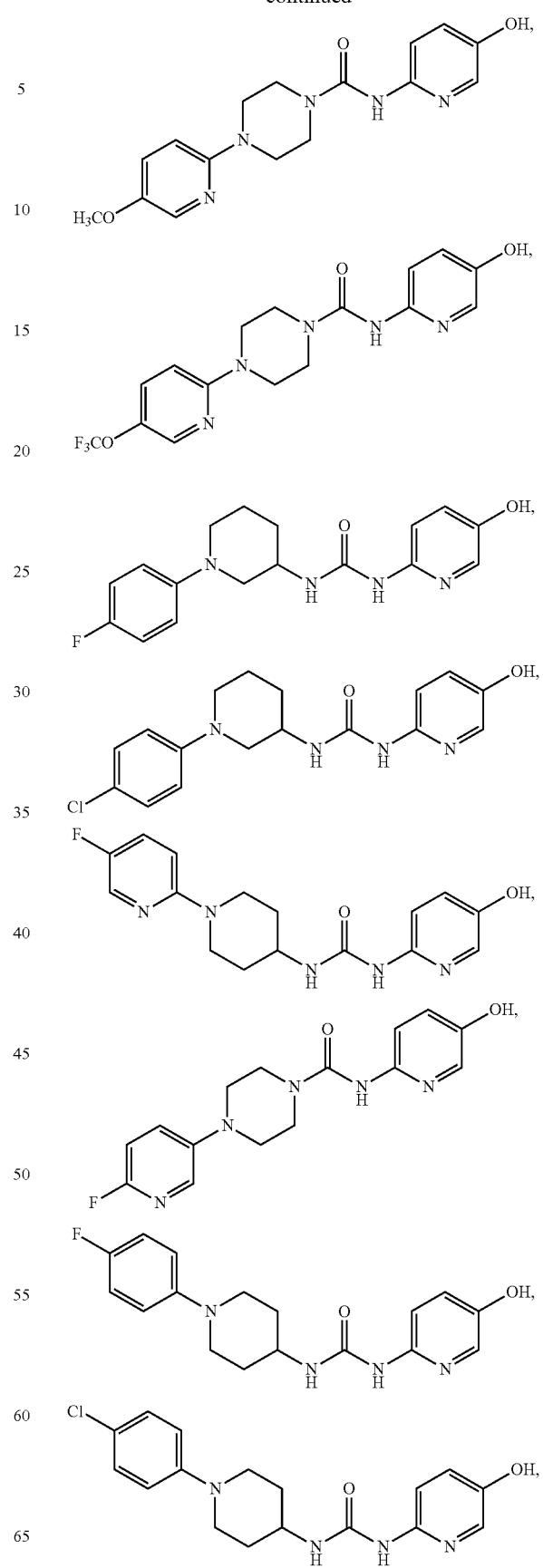

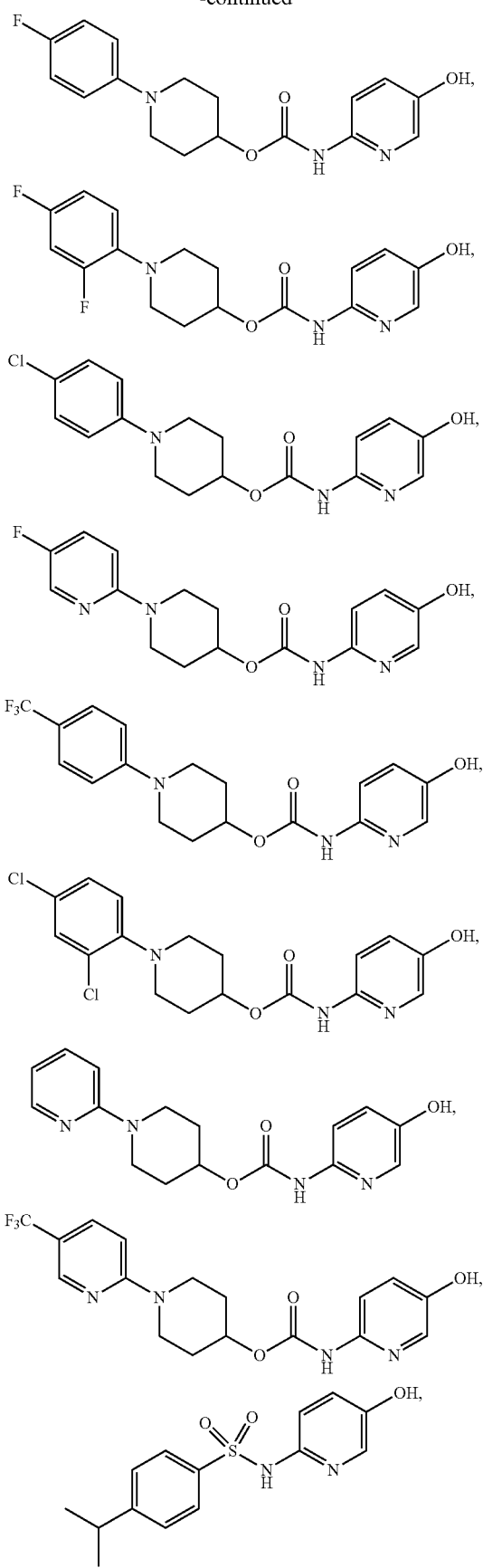
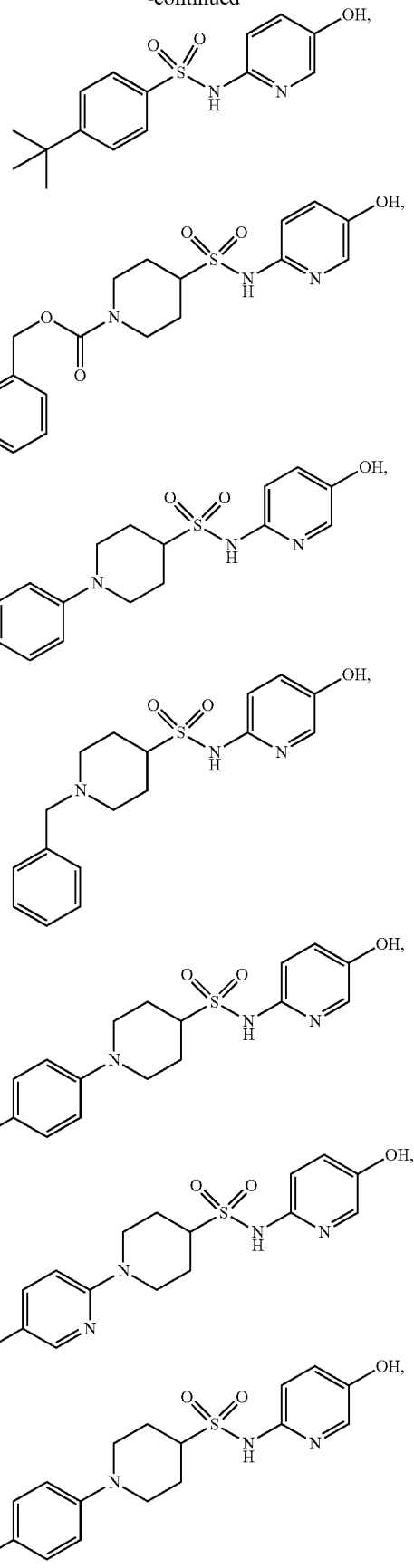

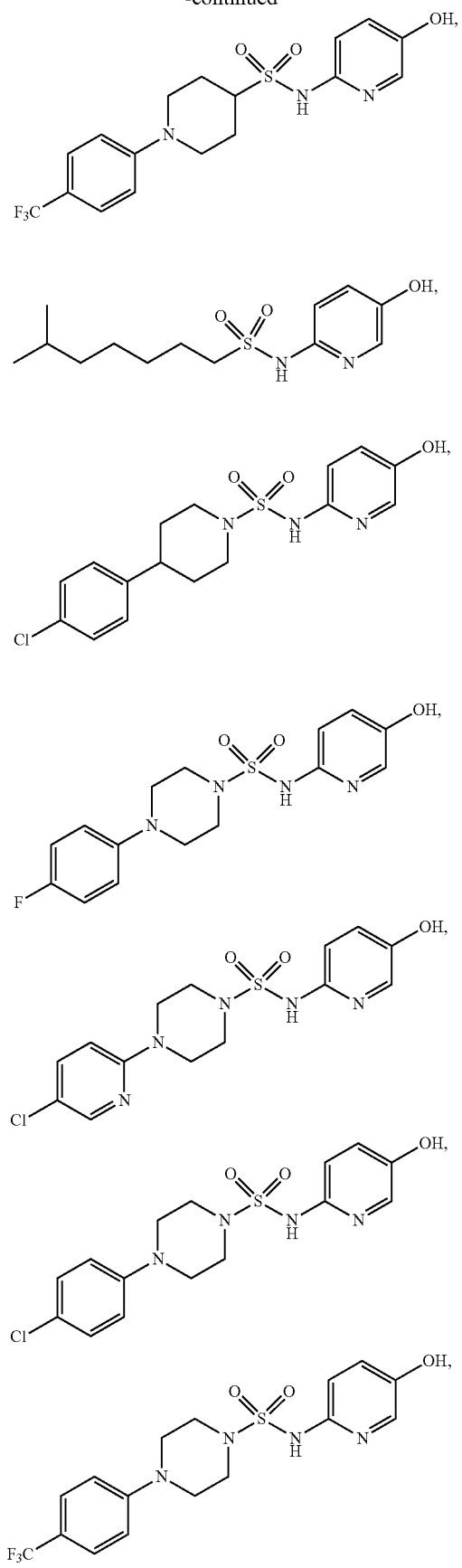
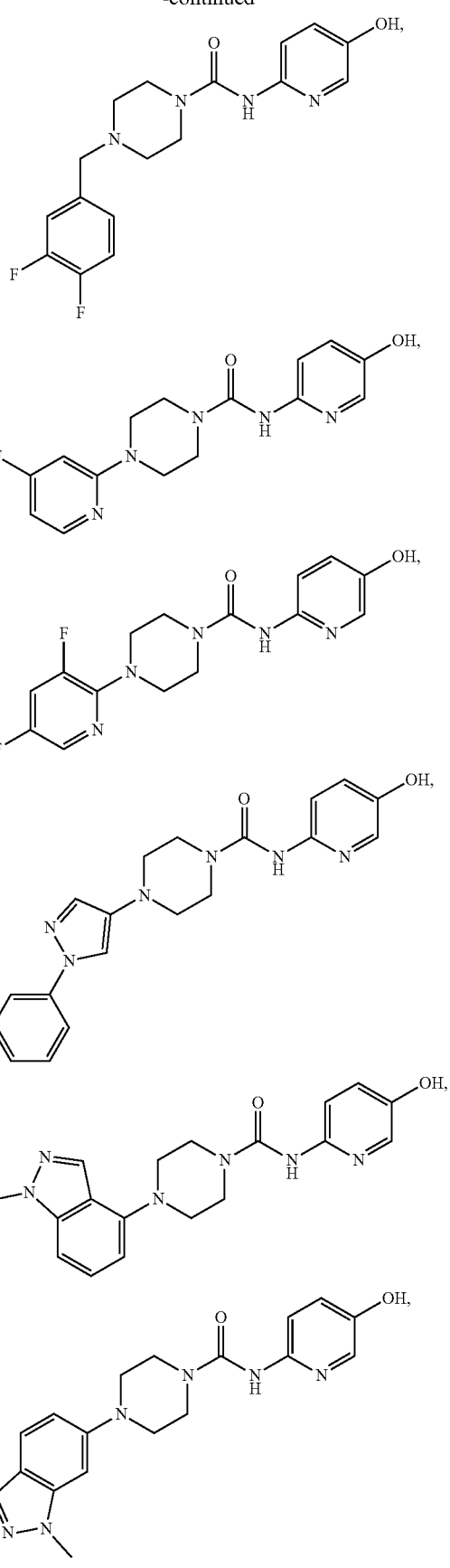

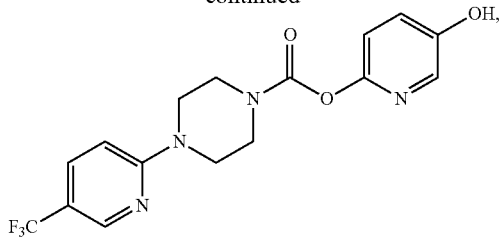
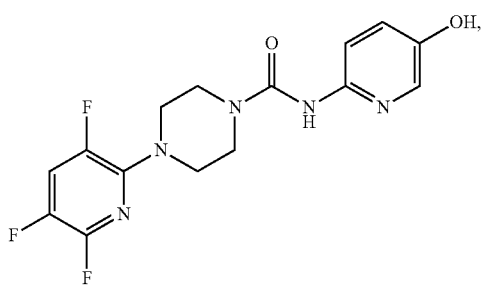
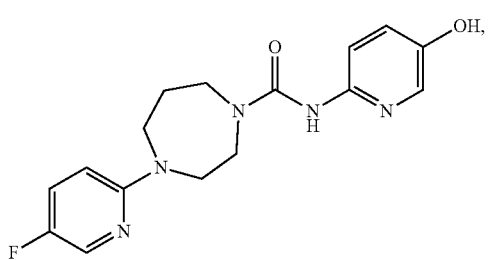
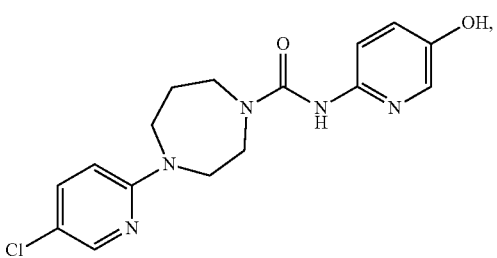
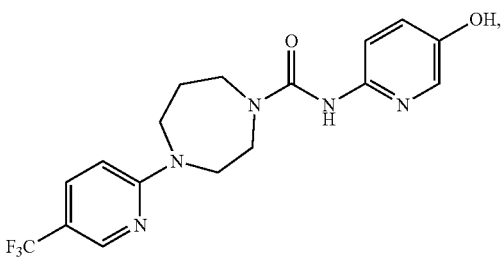
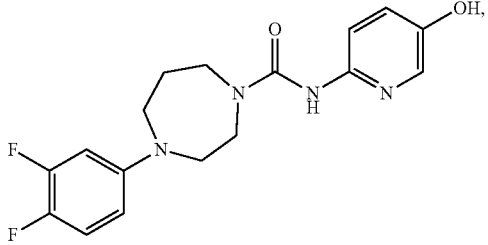
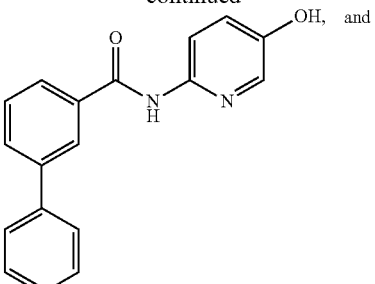
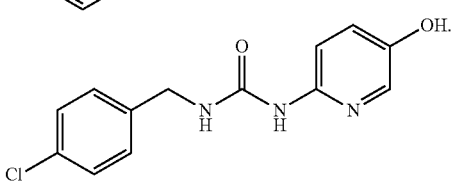

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present invention also relates to a method of inhibiting at least one Des1 function comprising the step of contacting Des1 with a compound as described herein. The cell phenotype, cell proliferation, activity of Des1, change in biochemical output produced by active Des1, expression of Des1, or binding of Des1 with a natural binding partner may be monitored. Such methods may be modes of treatment of disease, biological assays, cellular assays, biochemical assays, or the like.

Also provided herein is a method of treatment of a Des1-mediated disease comprising the administration of a therapeutically effective amount of a compound as disclosed herein, or a salt thereof, to a patient in need thereof.

Also provided herein is a compound as disclosed herein for use as a medicament.

Also provided herein is a compound as disclosed herein for use as a medicament for the treatment of a Des1-mediated disease.

Also provided is the use of a compound as disclosed herein as a medicament.

Also provided is the use of a compound as disclosed herein as a medicament for the treatment of a Des1-mediated disease.

Also provided is a compound as disclosed herein for use in the manufacture of a medicament for the treatment of a Des1-mediated disease.

Also provided is the use of a compound as disclosed herein for the treatment of a Des1-mediated disease.

Also provided herein is a method of inhibition of Des1 comprising contacting Des1 with a compound as disclosed herein, or a salt thereof.

In certain embodiments, the Des1-mediated disease is a metabolic disorder chosen from metabolic syndrome, diabetes, dyslipidemia, hypertriglyceridemia, hypercholesterolemia, fatty liver disease, alcoholic liver disease, nonalcoholic steatohepatitis, obesity, and insulin resistance.

In certain embodiments, the Des1-mediated disease is a lipid storage disorder chosen from Farber disease, Niemann-Pick disease, Fabry disease, Krabbe disease, Gaucher disease, Tay-Sachs disease, and Metachromatic leukodystrophy.

In certain embodiments, the Des1-mediated disease is an autoimmune disease.

In certain embodiments, the Des1-mediated disease is a chronic inflammatory disease.

In certain embodiments, the Des1-mediated disease is a cardiovascular disease.

In certain embodiments, the Des1-mediated disease is fibrosis or a related disease.

In certain embodiments, the Des1-mediated fibrosis is chosen from pulmonary fibrosis, cystic fibrosis, hepatic fibrosis, cirrhosis, atrial fibrosis, endomyocardial fibrosis, arthrofibrosis, myelofibrosis, glial scarring, Peyronie's disease, progressive massive fibrosis, pneumoconiosis, retroperitoneal fibrosis, scleroderma, systemic sclerosis, abdominal adhesions, and adhesive capsulitis.

In certain embodiments, the Des1-mediated fibrosis is cystic fibrosis.

In certain embodiments, the Des1-mediated disease is cancer.

In certain embodiments, the Des1-mediated cancer is chosen from a leukemia, a lymphoma, ovarian cancer, breast cancer, endometrial cancer, colon cancer (colorectal cancer), rectal cancer, bladder cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma, gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and a sarcoma.

Also provided is the use of a compound as disclosed herein for the treatment of an ischemia/reperfusion injury.

Also provided is the use of a compound as disclosed herein for the treatment of an ischemia/reperfusion injury that occurs in organ transplantation, acute kidney injury, cardiopulmonary bypass, pulmonary hypertension, sickle cell disease, myocardial infarction, stroke, surgical resections and reconstructive surgery, reattachment of an appendage or other body part, skin grafting, or trauma.

Also provided is a method of modulation of a Des1-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Abbreviations and Definitions

As used herein, the terms below have the meanings indicated.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "straight-chain alkyl" refers to an alkyl radical containing from 1 to 20 carbon atoms in a linear sequence without branches. Examples of straight-chain alkyl radicals include n-octyl (—CH$_2$CH$_2$CH$_2$CH$_2$CH$_2$CH$_2$CH$_2$CH$_2$—), n-butyl (—CH$_2$CH$_2$CH$_2$CH$_2$—), and ethyl (—CH$_2$CH$_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, the heteroaryl will comprise from 1 to 4 heteroatoms as ring members. In further embodiments, the heteroaryl will comprise from 1 to 2 heteroatoms as ring members. In certain embodiments, the heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each the heteroatom may be independently chosen from nitrogen, oxygen, and sulfur. In certain embodiments, the hetercycloalkyl will comprise from 1 to 4 heteroatoms as ring members. In further embodiments, the hetercycloalkyl will comprise from 1 to 2 heteroatoms as ring members. In certain embodiments, the hetercycloalkyl will comprise from 3 to 8 ring members in each ring. In further embodiments, the hetercycloalkyl will comprise from 3 to 7 ring members in each ring. In yet further embodiments, the hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS-group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Compounds containing hydroxypyridine groups may contain to varying degrees the pyridone tautomer. Both hydroxypyridine and pyridone tautomeric forms are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "Des" means dihydroceramide desaturase, and includes Des1 and Des2 isoforms. Where Des1 modulation by compounds is referenced, it should be understood that unless specifically stated to be selective for Des1, compounds may also modulate other isoforms.

The term Des inhibitor (including Des1 inhibitor) is used herein to refer to a compound that exhibits an $IC_{50}$ with respect to Des activity of no more than about 100 μM and more typically not more than about 50 μM, for example as measured in the Des1 cellular assay described generally herein below. $IC_{50}$ is that concentration of inhibitor that reduces the activity of an enzyme (e.g., Des) to half-maximal level. Certain compounds disclosed herein have been discovered to exhibit inhibition against Des. In certain embodiments, compounds will exhibit an $IC_{50}$ with respect to Des of no more than about 10 μM; in further embodiments, compounds will exhibit an $IC_{50}$ with respect to Des of no more than about 5 μM; in yet further embodiments, compounds will exhibit an $IC_{50}$ with respect to Des of not more than about 1 μM; in yet further embodiments, compounds will exhibit an $IC_{50}$ with respect to Des of not more than about 200 nM; in yet further embodiments, compounds will exhibit an $IC_{50}$ with respect to Des of not more than about 100 nM; in yet further embodiments, compounds will exhibit an $IC_{50}$ with respect to Des of not more than about 50 nM; in yet further embodiments, compounds will exhibit an $IC_{50}$ with respect to Des of not more than about 25 nM; in yet further embodiments, compounds will exhibit an $IC_{50}$ with respect to Des of not more than about 10 nM.

The term "fibrosis" describes the development of fibrous connective tissue as a reparative response to injury or damage. When referred to herein as a disease to be treated, fibrosis means the pathological formation/deposition of excess fibrous connective tissue in an organ or tissue, which interferes with normal organ or bodily function.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, "treating," "treatment," and the like means ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression, for example from prediabetes to diabetes. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

In the present disclosure, the term "radiation" means ionizing radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art. The amount of ionizing radiation needed in a given cell generally depends on the nature of that cell. Means for determining an effective amount of radiation are well known in the art. Used herein, the term "an effective dose" of ionizing radiation means a dose of ionizing radiation that produces an increase in cell damage or death.

The term "radiation therapy" refers to the use of electromagnetic or particulate radiation in the treatment of neoplasia and includes the use of ionizing and non-ionizing radiation.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein may be presented as discrete units such as capsules, tablets, cachets, packets, or ampules, each containing a predetermined amount of the active ingredient.

Compounds described herein can be administered as follows.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like.

Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Methods of Treatment

The present disclosure provides compounds and pharmaceutical compositions that inhibit Des activity and are thus useful in the treatment or prevention of disorders associated with Des. Compounds and pharmaceutical compositions of the present disclosure inhibit Des and are thus useful in the treatment or prevention of a range of disorders associated with Des1.

Metabolic Disorders

In some embodiments, the compounds and pharmaceutical compositions of the present disclosure are useful in the treatment or prevention of metabolic disorders.

In some embodiments, the metabolic disorder is chosen from metabolic syndrome, diabetes, dyslipidemia, hypertriglyceridemia, hypercholesterolemia, fatty liver disease, non-alcoholic steatohepatitis, obesity, and insulin resistance.

In some embodiments, the compounds and pharmaceutical compositions of the present disclosure are useful in the treatment or prevention of lipid storage disorders. In some embodiments, the lipid storage disorder is chosen from Farber's disease, Niemann-Pick disease, Fabry disease, Krabbe disease, Gaucher disease, Tay-Sachs disease, and Metachromatic leukodystrophy.

In some embodiments, the compounds and pharmaceutical compositions may demonstrate efficacy towards a condition chosen from dyslipidemia, type II diabetes, atherosclerosis, obesity, cardiovascular diseases, and liver disease.

In some embodiments, the compounds and pharmaceutical compositions may demonstrate efficacy towards a liver disease chosen from NASH and NAFLD.

In some embodiments, the compounds and pharmaceutical compositions may demonstrate efficacy towards insulin resistance.

In some embodiments, the compounds and pharmaceutical compositions may demonstrate efficacy towards hyperglycemia.

Cardiovascular Disorders

In some embodiments, the compounds and pharmaceutical compositions of the present disclosure may be useful in the treatment or prevention of atherosclerosis, including coronary artery disease and peripheral vascular disease, hypertension, and cardiomyopathy.

In some embodiments, the compounds and pharmaceutical compositions may be useful in the treatment of atherosclerosis.

Cystic Fibrosis

In some embodiments, the compounds and pharmaceutical compositions of the present disclosure may be useful in the treatment or prevention of cystic fibrosis. Various studies have demonstrated that sphingolipids, particularly ceramide, accumulate in the lungs of humans with cystic fibrosis, as well as the corresponding mouse models of cystic fibrosis, including the mice with genetic ablation of the cystic fibrosis transmembrane conductance regulator. This accumulation has been shown to cause inflammation, increased susceptibility to bacterial infections (Grassme et al. 2013 Ceramide in cystic fibrosis. Handb. Exp. Pharmacol. 216, 265-274), as well as lung fibrosis (Ziobro et al. 2013 Ceramide mediates lung fibrosis in cystic fibrosis. Biochem. Biophys. Res. Commun. 434, 705-709).

In some embodiments, the compounds and pharmaceutical compositions of the present disclosure are useful in the treatment or prevention of autoimmune diseases or disorders of inflammation, including acute and chronic inflammatory diseases.

Inflammatory conditions include, without limitation: arthritis, including sub-types and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritis and vitiligo. In addition, compounds of invention are also useful in organ transplant patients either alone or in combination with conventional immunomodulators. Autoimmune disorders are often classified as inflammatory disorders, as well.

Autoimmune disorders include Crohn's disease, ulcerative colitis, dermatitis, dermatomyositis, diabetes mellitus type 1, Goodpasture's syndrome, Graves' disease, Guillain-Barré syndrome (GBS), autoimmune encephalomyelitis (AE), Hashimoto's disease, idiopathic thrombocytopenic purpura, lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid ö arthritis (RA), Sjö gren's syndrome, scleroderma, temporal arteritis (also known as "giant cell arteritis"), vasculitis, and Wegener's granulomatosis.

In some embodiments, the autoimmune disease or chronic inflammatory disease is chosen from arthritis, multiple sclerosis, psoriasis, Crohn's disease, inflammatory bowel disease, lupus, Grave's disease and Hashimoto's thyroiditis, ankylosing spondylitis, and cystic fibrosis.

In certain embodiments, the compounds and pharmaceutical compositions of the present disclosure may have disease modifying anti-rheumatic drug (DMARD) activity. In certain embodiments, the compounds and pharmaceutical compositions of the present disclosure may be used for the treatment of rheumatoid arthritis. In certain further embodiments, treatment of rheumatoid arthritis with the compounds and pharmaceutical compositions of the present disclosure includes coadministration of another agent selected from an analgesic (including traditional NSAIDs and COX2-selective inhibitors), a steroid, methotrexate, a gold salt, hydroxychloroquine, a PAD4 inhibitor, sulfasalazine, leflunomide, anti-TNFα, an inhibitor of janus kinases, abatacept, rituximab, and anakinra.

In certain embodiments, the compounds and pharmaceutical compositions of the present disclosure may have synergistic activity against multiple sclerosis upon coadministration with a therapeutic chosen from fingolimod, a sphingosine-1-phosphate receptor modulator, teriflunomide, dimethyl fumarate, a PAD4 inhibitor, an anti-CD20 mAb, an anti-CD52 mAb, natalizumab, glatiramer acetate, and interferon-β.

In some embodiments, the autoimmune disease inflammatory disease is autoimmune arthritis.

In some embodiments, the autoimmune disease inflammatory disease is rheumatoid arthritis.

In certain embodiments, the compounds and pharmaceutical compositions of the present disclosure may have synergistic activity against arthritis upon coadministration with a therapeutic chosen from analgesics (including traditional NSAIDs and COX2-selective inhibitors), steroids, methotrexate, gold salts, hydroxychloroquine, PAD4 inhibitors, sulfasalazine, leflunomide, anti-TNFα, inhibitors of janus kinases, abatacept, rituximab, and anakinra.

In some embodiments, the compounds and pharmaceutical compositions of the present disclosure can be useful in the treatment or prevention of cardiovascular disease. In some embodiments, the cardiovascular disease is chosen from atherosclerosis, hypertension, and cardiomyopathy.

In some embodiments, the compounds and pharmaceutical compositions of the present disclosure can be useful in the treatment or prevention of ischemia/reperfusion injury. In some embodiments, ischemia/reperfusion injury occurs in organ transplantation, acute kidney injury, cardiopulmonary bypass, pulmonary hypertension, sickle cell disease, myocardial infarction, stroke, surgical resections and reconstructive surgery, reattachment of an appendage or other body part, skin grafting, or trauma.

Proliferative Disorders, e.g. Cancers

In some embodiments, the compounds and pharmaceutical compositions of the present disclosure can be useful in the treatment or prevention of cancer.

In some embodiments, the cancer is chosen from a leukemia, a lymphoma, ovarian cancer, breast cancer, endometrial cancer, colon cancer (colorectal cancer), rectal cancer, bladder cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma, gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and a sarcoma.

In certain embodiments, the compounds and pharmaceutical compositions of the present disclosure are effective against tumor growth, angiogenesis, and chemoresistance, and potentially can facilitate tumor killing either by direct cytotoxicity (including induction of apoptosis) or indirectly by enhancing the immune system's ability to kill the tumor.

In certain embodiments, the compounds and pharmaceutical compositions of the present disclosure may have synergistic activity against cancer upon coadministration with immune check-point inhibitors.

In certain embodiments, the compounds and pharmaceutical compositions of the present disclosure may have synergistic activity against cancer upon coadministration with monoclonal antibodies directed at a target chosen from PD1, PD-L1, CTLA-4, CD47, and OX40.

In certain embodiments, the compounds and pharmaceutical compositions of the present disclosure may have synergistic activity against cancer upon coadministration with small molecules directed at a target chosen from indoleamine-2,3-dioxygenase 1 and arginase-1.

In some embodiments, the compounds and pharmaceutical compositions of the present disclosure can be useful in the treatment or prevention of fibrosis and related diseases. Fibrosis is a pathologic condition involving excessive extracellular matrix production of connective tissue. Consequences can include tissue dysfunction and organ failure.

In some embodiments, the fibrosis affects a site chosen from lungs, kidney, liver, heart, skin, and connective tissues.

In some embodiments, the fibrosis can be: of the lungs, for example pulmonary fibrosis or cystic fibrosis; of the liver, for example cirrhosis; of the heart, for example atrial fibrosis, endomyocardial fibrosis, or fibrosis resulting from myocardial infarction; of the brain, for example a glial scar; kidney fibrosis, such as resulting from diabetic nephropathy; gall bladder fibrosis, skin or dermal fibrosis, such as scleroderma, hypertrophic scarring and keloids; bone marrow fibrosis such as in myelofibrosis; intestinal fibrosis, such as Crohn's disease; or from some other wound, in which case it may be referred to as scarring. The fibrosis may also be chosen from arthrofibrosis, Dupuytren's contracture, mediastinal fibrosis, myelofibrosis, Peyronie's disease, nephrogenic systemic fibrosis, progressive massive fibrosis, a complication of coal workers' pneumoconiosis, retroperitoneal fibrosis, scleroderma, systemic sclerosis, and adhesive capsulitis, and abdominal adhesions secondary to abdominal surgery.

In some embodiments, the compounds and pharmaceutical compositions of the present disclosure may be used to prevent, treat or ameliorate heart attack.

In some embodiments, the compounds and pharmaceutical compositions of the present disclosure may be used for the treatment of various types of congestive heart failure. In certain further embodiments, the congestive heart failure is secondary to ischemia. In certain further embodiments, the congestive heart failure is associated with a disorder selected from diabetes, obesity, and lipotoxicity. In certain further embodiments, treatment of congestive heart failure with the compounds and pharmaceutical compositions of the present disclosure includes coadministration of another agent selected from an angiotensin-converting enzyme (ACE) inhibitor, an angiotensin II receptor blocker (ARB), a β-adrenergic receptor blocker (including carvedilol), a diuretic (including furosemide), an aldosterone antagonist (including eplerenone), an inotrope (including milrinone), a guanylate cyclase inhibitor, and digoxin.

In some embodiments, the compounds and pharmaceutical compositions of the present disclosure may be used for the treatment of kidney disease. In certain further embodiments, the kidney disease is selected from diabetic kidney disease and nephropathy. In certain further embodiments, treatment of kidney disease with the compounds and pharmaceutical compositions of the present disclosure includes coadministration of a standard-of-care agent. In certain further embodiments, the standard-of-care agent is selected from an ACE inhibitor, an angiotensin receptor blocker (ARB), a cholesterol-lowering agent (including statins and/or PCSK9 inhibitors), and a medication that manages calcium phosphate levels for bone health (including sevelamer)

In some embodiments, the compounds and pharmaceutical compositions of the present disclosure may be used for the treatment of sarcopenia. In certain further embodiments, the etiology of the sarcopenia is selected from aging, chronic kidney disease, malignancy, and chemotherapy. In certain further embodiments, treatment of sarcopenia with the compounds and pharmaceutical compositions of the present disclosure includes coadministration of another agent selected from testosterone, a selective androgen receptor modulator, a ghrelin agonist, a myostatin antibody, an activin IIR antagonist, an ACE inhibitor, a beta antagonist, and a fast skeletal muscle troponin activator In some embodiments, the compounds and pharmaceutical compositions of the present disclosure may be used to prevent, treat or ameliorate a neurodegenerative disease. Elevated ceramide levels are often found associated with various neurodegenerative diseases.

In some embodiments, the neurodegenerative disease is chosen from Alzheimer's disease, vascular dementia, Parkinson's disease, Huntington's disease, amyotrophic lateral sclerosis, Lewy Body disease, spinal muscular atrophy, Friedrich's ataxia, and spinocerebellar ataxia.

In certain embodiments, the compounds and pharmaceutical compositions of the present disclosure may be used to treat Alzheimer's disease. In certain further embodiments, the compounds and pharmaceutical compositions of the present disclosure may have disease-modifying activity. In certain further embodiments, the compounds and pharmaceutical compositions of the present disclosure may provide symptomatic relief. In certain further embodiments, treatment of Alzheimer's disease with the compounds and pharmaceutical compositions of the present disclosure includes coadministration of another agent selected from a cholinesterase inhibitor and memantine.

In certain embodiments, the compounds and pharmaceutical compositions of the present disclosure may have synergistic activity against a neurodegenerative disease upon coadministration with a therapeutic agent chosen from cholinesterase inhibitors and memantine.

In certain embodiments, the compounds and pharmaceutical compositions of the present disclosure may have synergistic activity against ALS upon coadministration with a second therapeutic agent for ALS. In certain embodiments, the second therapeutic agent for ALS is chosen from riluzole and edavarone.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-metabolic disorder drugs, including metformin, inhibitors of HMG-CoA reductase, inhibitors of sodium/glucose co-transporters, fibrates, omega-3 fatty acids, glucagon-like peptide-1 analogs, and agonists of the glucagon-like peptide-1 receptor (e.g. PF-06882961), FXR agonists (e.g. obeticholic acid, INT-767, GS-9674, tropifexor, MET409, EDP-305), LXR ligands, PPAR agonists (e.g. elafibranor), vitamin E, FGF19 analogs (e.g. NGM-282), FGF21 analogs (e.g. BMS-986036), agonists of fibroblast growth factor receptor 1c-beta-klotho (e.g. NGM-313), inhibitors of acetyl CoA carboxylase (e.g. GS-0976, PF-05221304, MK4074), inhibitors of stearoyl CoA desaturase-1, CCR2/CCR5 antagonists (e.g. cenicriviroc), inhibitors of ketohexokinase (e.g. PF-06835919), inhibitors of diacylglycerol O-Acyltransferase 2 (e.g. PF-06865571), inhibitors of ASK1 (e.g. selonsertib, SRT-015), agonists of the thyroid hormone receptor-β (e.g. MGL-3196, MGL-3745, VK2809), inhibitors of dipeptidyl peptidase-4 (e.g. evogliptin), inhibitors of stearoyl-CoA desaturase-1 (e.g. aramchol), inhibitors of AOC3 (e.g. BI 1467335), inhibitors of caspase (e.g. emricasan), inhibitors of galectin-3 (e.g. GR-MD-02), inhibitors of ileal sodium bile acid transporter (e.g. volixibat), agonists of the P2Y13 receptor (e.g. CER209), DUR-928, DS102, and butanoic acid.

Additional non-limiting examples of possible combination therapies include use of a compound as disclosed herein, and at least one other agent selected from the group comprising: a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose co-transporter inhibitors such as empagliflozin, canagliflozin, dapagliflozin, T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as Januvia, Galvus, Onglyza, DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPAR delta agonist e.g. GI-262570; b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; PCSK9 antagonists, e.g. alirocumab and evolocumab; cholesterol absorption inhibitors, e.g. ezetimibe; bile resins, e.g. cholestyramine, colesevelam; fibrates; nicotinic acid and aspirin; c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists; d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin n antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; .quadrature.-adrenergic receptor blockers such as acebutolol, atenolol, betaxolol, bisoprolol, metoprolol, carvedilol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors; e) an HDL increasing compound; f) cholesterol absorption modulator such as ezetimibe and KT6-971; [0148] g) Apo-A1 analogues and mimetics; h) thrombin inhibitors such as Ximelagatran; aldosterone inhibitors such as anastrazole, fadrazole, and eplerenone; inhibitors of platelet aggregation such as aspirin, and clopidogrel bisulfate.

In another embodiment, the one or more additional pharmaceutically active compounds is selected from the group consisting of anti-cancer drugs, including chemotherapeutics: thiotepa and cyclophosphamide; alkyl sulfonates such as busulfan, improsulfan and piposulfan; aziridines such as benzodepa, carboquone, meturedopa, and uredopa; ethylenimines and methylamelamines including altretamine, triethylenemelamine, triethylenephosphoramide, triethylenethiophosphoramide and trimethylol melamine; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; desosamine; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; cytosine arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including both selective estrogen receptor modulators and selective estrogen receptor degraders), including for example tamoxifen, raloxifene, aromatase-inhibiting 4(5)-imidazoles, 4-hydroxytamoxifen, trioxifene, keoxifene, onapristone, toremifene, and fulvestrant; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Chemotherapeutic agents also include signal transduction inhibitors (STI). The term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol and palbociclib); (vi) phosphatidyl inositol kinase inhibitors; (vii) selective estrogen receptor modulators (e.g. tamoxifen); (viii) selective estrogen receptor degraders (e.g. fulvestrant); (ix) selective androgen receptor modulators (e.g. enzalutamide, apalutamide); (x) angiogenesis inhibitors (e.g. bevacizumab, Sutent).

Chemotherapeutic agents also include various immune-modulating agents, including checkpoint inhibitors (e.g. anti-PD1, anti-PDL1, anti-CTLA4 antibodies) and other immune-modulating agents including anti-GITR, anti-OX40, and anti-CD47 antibodies, IDO1 inhibitors, arginase-1 inhibitors, glucocorticoid receptor inhibitors, inhibitors of regulatory T cells, and inhibitors of myeloid-derived suppressor cells.

In another embodiment, the one or more additional pharmaceutically active compounds is selected from the group consisting of disease modifying anti-rheumatic drugs (DMARDs), including steroids, methotrexate, sulfasalazine, gold salts, as well as anti-TNF, anti-IL1, anti-IL6, and inhibitors of the NLRP3 inflammasome, and Janus kinase inhibitors.

In another embodiment, the one or more additional pharmaceutically active compounds is selected from the group consisting of multiple sclerosis drugs, including interferon-beta1a, interferon-beta1b, glatiramer acetate, mitoxantrone, fingolimod, teriflunomide, dimethyl fumarate, anti-alpha4 integrin monoclonal antibody, anti-CD52 monoclonal antibody, anti-CD25 monoclonal antibody, and anti-CD20 monoclonal antibody.

In another embodiment, the one or more additional pharmaceutically active compounds is selected from the group consisting enzyme replacement therapies. Enzyme replacement therapy may, for example, include recombinant human acid ceramidase.

In another embodiment, the one or more additional pharmaceutically active compounds is selected from the group consisting of pancreatic enzyme supplements, multivitamins, mucolytics, antibiotics, bronchodilators, anti-inflammatory agents, insulin, bisphosphonates, anti-fibrotic agents (e.g. pirfenidone, nintedanib), N-acetylcysteine, ivacaftor, and lumacaftor/ivacaftor.

In another embodiment, the one or more additional pharmaceutically active compounds is selected from the group consisting of donepezil, galantamine, rivastigmine, memantine, riluzole, levodopa/carbidopa, pramipexole, ropinirole, rotigotine, selegiline, apomorphine, selegiline, rasagiline, entacapone, tolcapone, benztropine, trihexyphenidyl, amantadine, tetrabenazine, haloperidol, risperidone, quetiapine, levetiracetam, clonazepam, edaravone.

Des inhibitor compounds and compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a Des1 inhibitor compound, as described herein, in combination with another therapeutic agent. By way of example only, the therapeutic effectiveness of a Des1 inhibitor is enhanced by administration of another therapeutic agent (which also includes a therapeutic regimen) that also has therapeutic benefit. Regardless of the disease, disorder or condition being treated, the overall benefit experienced by the patient may either simply be additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a Des inhibitor as described herein) may be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a Des inhibitor is optionally used in combination with procedures that provide additional benefit to the patient. A Des inhibitor and any additional therapies are optionally administered before, during or after the occurrence of a disease or condition, and the timing of administering the composition containing a Des inhibitor varies in some embodiments. Thus, for example, a Des inhibitor is used as a prophylactic and is administered continuously to subjects with a propensity to develop conditions or diseases in order to prevent the occurrence of the disease or condition. A Des inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

List of Abbreviations

Ac$_2$O=acetic anhydride; AcCl=acetyl chloride; AcOH=acetic acid; AIBN=azobisisobutyronitrile; aq.=aqueous; Bu$_3$SnH=tributyltin hydride; CD$_3$OD=deuterated methanol; CDCl$_3$=deuterated chloroform; CDI=1,1'-Carbonyldiimidazole; DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-d$_6$=deuterated dimethyl sulfoxide; DMSO=dimethyl sulfoxide; DPPA=diphenylphosphoryl azide; EDC·HCl=EDCI·HCl=1-ethyl-3-(3-dimethylaminopropyl)carbodiimide hydrochloride; Et$_2$O=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-PrOH=isopropanol; LAH=lithium aluminium hydride; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chlorosuccinimide; NMP=N-Methyl-2-pyrrolidone; Pd(Ph$_3$)$_4$=tetrakis(triphenylphosphine)palladium(0); Pd$_2$(dba)$_3$=tris(dibenzylideneacetone)dipalladium(0); PdCl$_2$(PPh$_3$)$_2$=bis(triphenylphosphine)palladium(II) dichloride; PG=protecting group; prep-HPLC=preparative high-performance liquid chromatography; PyBop=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TBS=TBDMS=tert-butyldimethylsilyl; TBSCl=TBDMSCl=tert-butyldimethylchlorosilane; TEA=Et$_3$N=triethylamine; TFA=trifluoroacetic acid; TFAA=trifluoroacetic anhydride; THF=tetrahydrofuran; Tol=toluene; TsCl=tosyl chloride; XPhos=2-dicyclohexylphosphino-2',4',6'-triisopropylbiphenyl.

General Synthetic Methods for Preparing Compounds

The following schemes can generally be used to practice the present invention.

Scheme I

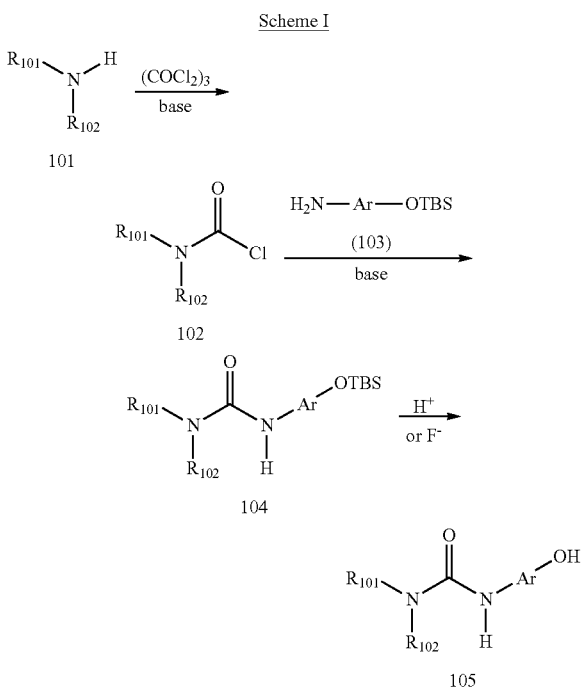

Example 1 can be synthesized using the following general synthetic procedure set forth in Scheme I. Amine 101 is converted to acid chloride 102 using triphosgene, here and elsewhere abbreviated as (COCl$_2$)$_3$, in the presence of base. The acid chloride is then reacted with an arylamine 103 in the presence of base to give urea 103. Here and elsewhere, the formula H$_2$N—Ar-OTBS for 103 represents an aryl compound substituted with both an NH$_2$ group and an OTBS group. Formula 103 includes, for example, 4-[(tert-butyldimethylsilyl)oxy]aniline and 5-[(tert-butyldimethylsilyl)oxy]pyridin-2-amine. In the final step, the TBS group is removed with either acid or fluoride to give 105.

Scheme II

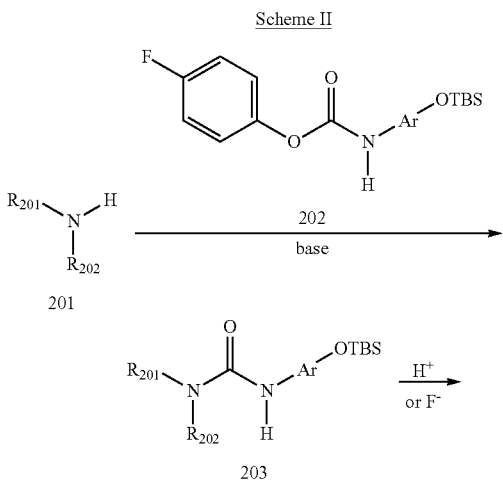

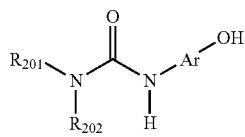

204

Examples 2-39 can be synthesized using the following general synthetic procedure set forth in Scheme II. In the first step, amine 201 is reacted directly with a 4-fluorophenyl carbamate having formula 202 in the presence of base to give urea 203. Here and elsewhere, the formula for carbamate 202 includes an arylamino moiety substituted with an OTBS group. Formula 202 includes, for example, 4-fluorophenyl N-[5-[(tert-butyldimethylsilyl)oxy]pyridin-2-yl]carbamate and 4-fluorophenyl N-[4-[(tert-butyldimethylsilyl)oxy]phenyl]carbamate. In the second step, the TBS group is removed with either acid or fluoride to give 204.

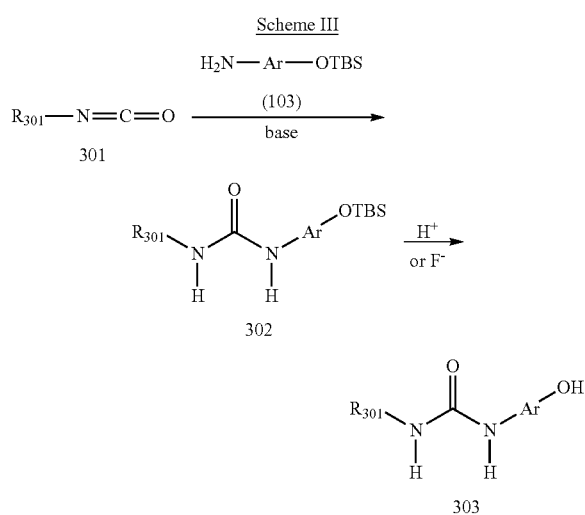

Example 40 can be synthesized using the following general synthetic procedure set forth in Scheme III. In the first step, alkyl isocyanate 301 is reacted with an arylamine 103, as defined in Scheme I, to give urea 302. The TBS group is removed by treatment with either acid of fluoride ion in the second step to give 303.

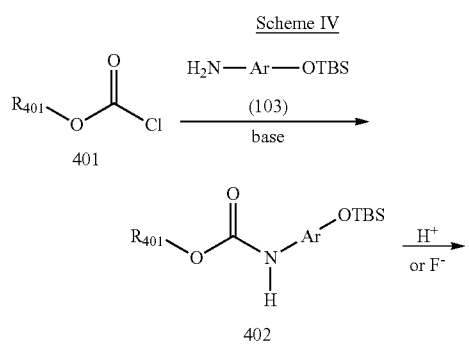

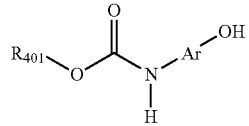

403

Examples 41-42 can be synthesized using the following general synthetic procedure set forth in Scheme IV. In the first step, acid chloride 401 is reacted with an arylamine 103, as defined in Scheme I, to give carbamate 402. The TBS group is removed by treatment with either acid of fluoride ion in the second step to give 403.

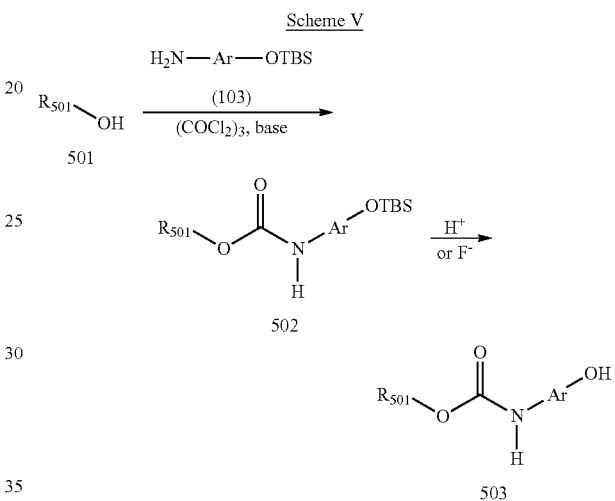

Examples 43-44 can be synthesized using the following general synthetic procedure set forth in Scheme V. Alcohol 501 is reacted with arylamine 103, as defined in Scheme I, in the presence of triphosgene and base to give carbamate 502. In the final step, the TBS group is removed with either acid or fluoride to give 503.

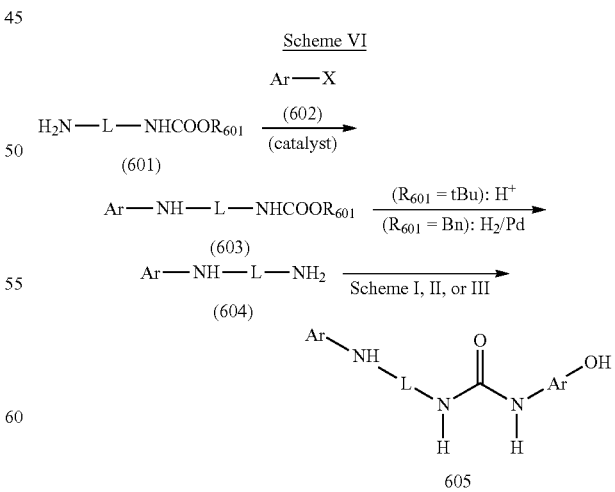

Examples 45-52 can be synthesized using the following general synthetic procedure set forth in Scheme VI. Synthesis begins with amine/carbamate 601, in which the "L"

moiety is a linking group. In some embodiments, 601 is 1-Boc-piperazine. In some embodiments, 601 is 1-Cbz-piperazine. In some embodiments, 601 is 3-(BocNH)-piperidine. In some embodiments, 601 is 4-(BocNH)-piperidine.

Amine/carbamate 601 is then reacted with arene 602 to give arylamine substitution product 603. In certain embodiments, arene 602 is substituted with an electron-withdrawing group that facilitates direct $S_NAr$ reaction. In certain embodiments, the substitution reaction is assisted by the presence of a metal catalyst.

In a final step, the carbamate protecting group of 603 is removed, using either acid for $R_{601}$=t-Bu (Boc protection), or hydrogenolysis for $R_{601}$=Bn (CBz protection). Other amine protecting groups known in the art may be used. Amine 604 is then converted to product 605 using any of Schemes I, II, or II, or other methods that may be available.

Scheme VII

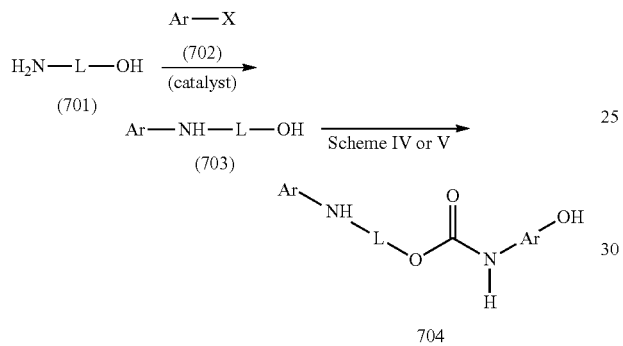

Examples 53-60 can be synthesized using the following general synthetic procedure set forth in Scheme VIII. Synthesis begins with amino alcohol 701, in which the "L" moiety is a linking group. In some embodiments, 701 is 4-hydroxypiperidine.

Amino alcohol 701 is then reacted with arene 702 to give arylamine substitution product 703. In certain embodiments, arene 702 is substituted with an electron-withdrawing group that facilitates direct $S_NAr$ reaction. In certain embodiments, the substitution reaction is assisted by the presence of a metal catalyst. Alcohol 703 is then converted to carbamate product 704 using either of Schemes IV or V, or other methods that may be available.

Scheme VIII

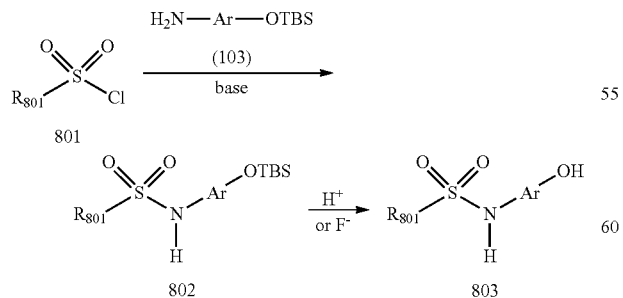

Examples 61-70 can be synthesized using the following general synthetic procedure set forth in Scheme VIII. In the first step, sulfonyl chloride 801 is reacted with an arylamine 103, as defined in Scheme I, to give sulfonamide 802. The TBS group is removed by treatment with either acid of fluoride ion in the second step to give 803.

Scheme IX

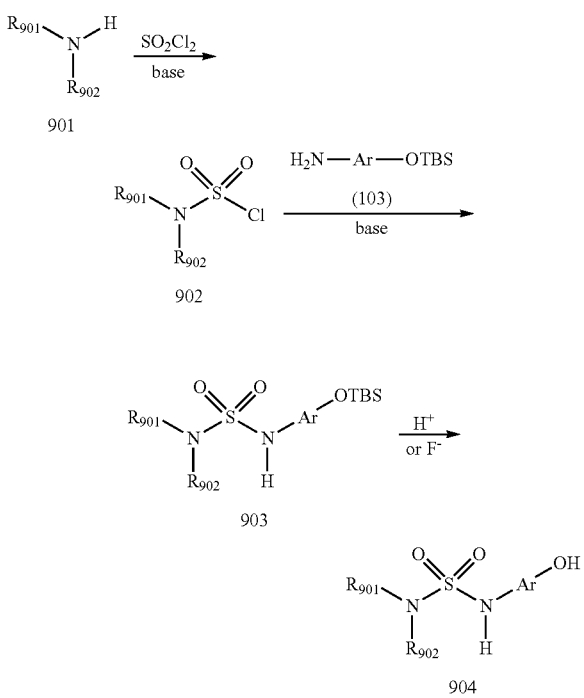

Example 71 can be synthesized using the following general synthetic procedure set forth in Scheme IX. In the first step, amine 901 is reacted with sulfuryl chloride to give acid chloride 902. In the next step, acid chloride 902 is reacted with an arylamine 103, as defined in to give sulfonamide 903. The TBS group is removed by treatment with either acid of fluoride ion in the second step to give 904.

Scheme X

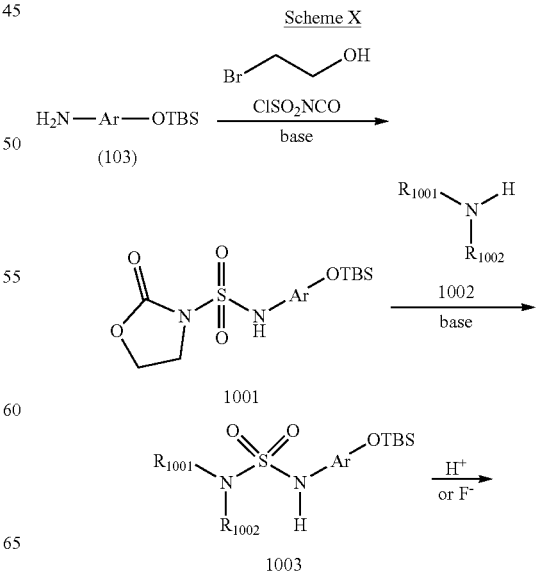

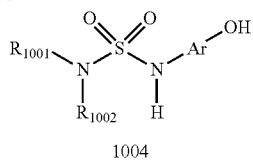

1004

Examples 72-75 can be synthesized using the following general synthetic procedure set forth in Scheme X. In the first step, arylamine 103, as defined in Scheme I is converted to oxazolidinone 1001 upon treatment with 2-bromoethanol and chlorosulfonyl isocyanate. In the next step, amine 1002 reacts with 1001 to form sulfonyl urea 1003. In the last step, the TBS group is removed by treatment with either acid of fluoride ion in the second step to give 1004.

Scheme XI

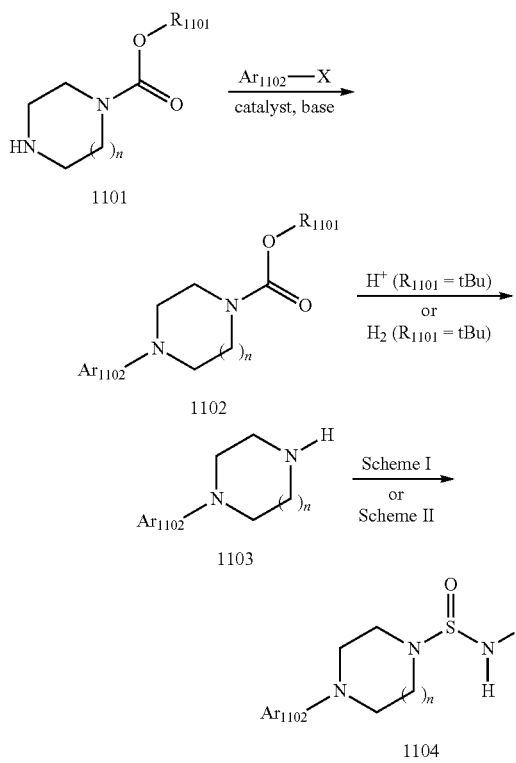

Examples 77-87 can be synthesized using the following general synthetic procedure set forth in Scheme XI. In the first step, carbamate protected cyclic amine 1101 (n=1, 2) is reacted with a suitable aryl halide to form coupled product 1102. In the next step, the carbamate protecting group is removed to give secondary amine 1103, which can then be treated with the steps of Scheme I or Scheme II to give 1104.

Scheme XII

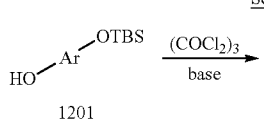

1201

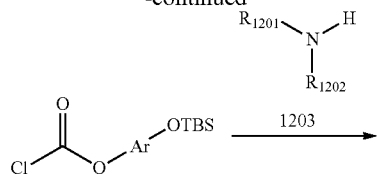

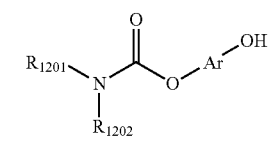

1205

Example 88 can be synthesized using the following general synthetic procedure set forth in Scheme I. Aryl or heteroaryl alcohol 1201 is converted to the chloroformate ester 1202 using $(COCl_2)_3$ in the presence of base. Here and elsewhere, the formula HO—Ar-OTBS for 1201 represents an aryl compound substituted with both an OH group and an OTBS group. Formula 1201 includes, for example, 4-[(tert-butyldimethylsilyl)oxy]phenol and 5-[(tert-butyldimethylsilyl)oxy]pyridin-2-ol. The chloroformate ester is then reacted with an amine 1203 in the presence of base to give carbamate 1204. In the final step, the TBS group is removed with either acid or fluoride to give 1205.

Scheme XIII

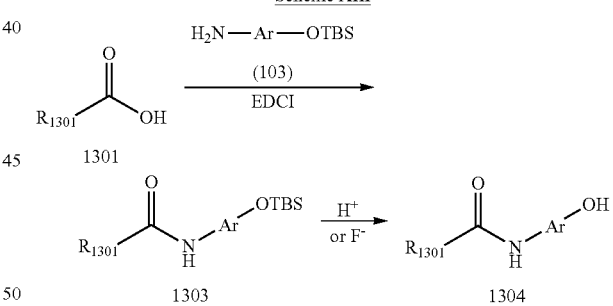

Example 89 can be synthesized using the following general synthetic procedure set forth in Scheme I. Carboxylic acid 1301 is coupled with arylamine 103, using a carbodiimide reagent such as EDCI (shown). In a second step, the TBS group is removed with either acid or fluoride to give 1303.

The invention is further illustrated by the following examples

Chromatographic Procedures
  Instrument "A": 2 #SHIMADZU.
  Instrument "B": 2 #-AnalyseHPLC-SHIMADZU.
  Column "A": XBridge OBD C18 Prep Column, 30×150 mm×5 μm.
  Column "B": XBridge OBD C18 Prep Column, 19×250 mm×5 μm.

Column "C": XSelect CSH C18 OBD Prep Column, 19×250 mm, 5 μm.
Column "D": Xselect CSH C18 OBD Column 30×150 mm 5 μm.
Column "E": SunFire C18 OBD Prep Column, 19 mm×250 mm, 5 μm.
Intermediates Intermediate "A"

4-Fluorophenyl N-[5-[(tert-butyldimethylsilyl)oxy]pyridin-2-yl]carbamate

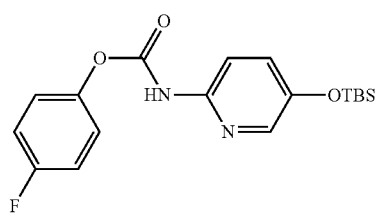 [SMILES: CC(C)(C)[Si](C)(C)Oc1ccc(NC(=O)Oc2ccc(F)cc2)nc1]

A solution of 5-[(tert-butyldimethylsilyl)oxy]pyridin-2-amine (3.7 g, 16.49 mmol, 1.00 eq), 4-fluorophenyl chloroformate (4.3 g, 24.63 mmol, 1.50 eq), and Et₃N (5 g, 49.41 mmol, 3.00 eq) in CH₂Cl₂ (40 mL) was stirred for 2 h at rt, then extracted with 3×80 mL of EtOAc. The combined organic layers were concentrated under vacuum and purified with silica gel chromatography using EtOAc/hexane (1:10) to afford 1.8 g (30%) of the title compound as a white solid.
LC-MS: (ES, m/z): 363
¹H NMR (300 MHz, DMSO-d₆) δ 10.58 (s, 1H), 7.93 (dd, J=3.0, 0.7 Hz, 1H), 7.69 (dd, J=8.9, 0.7 Hz, 1H), 7.35 (dd, J=9.0, 3.0 Hz, 1H), 7.25 (d, J=6.6 Hz, 4H), 0.95 (s, 9H), 0.19 (s, 6H).

Intermediate "B"

4-Fluorophenyl N-[4-[(tert-butyldimethylsilyl)oxy]phenyl]carbamate

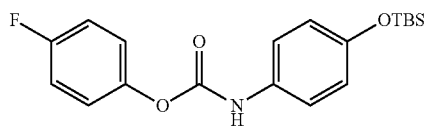 [SMILES: CC(C)(C)[Si](C)(C)Oc1ccc(NC(=O)Oc2ccc(F)cc2)cc1]

Step 1. Synthesis of 4-[(tert-butyldimethylsilyl)oxy]aniline

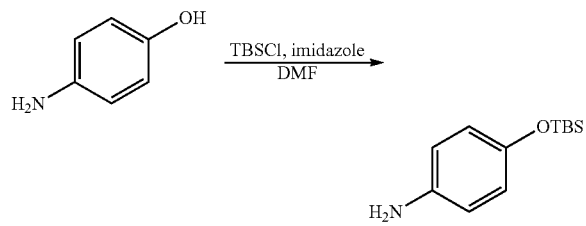

To a solution of 4-aminophenol (5 g, 45.82 mmol) in DMF (50 mL) was added imidazole (6.24 g), in portions, followed by the dropwise addition of TBSCl (8.26 g) with stirring at 0° C. over 5 min. The resulting solution was stirred for 2 h at rt, then quenched by the addition of 100 mL H₂O and extracted with 2×150 mL of EtOAc. The combined organic layers were concentrated under vacuum and purified with silica gel chromatography using EtOAc/hexane (1:5) to afford 4 g (39%) of the title compound as off-white oil.
LC-MS: (ES, m/z): 224
¹H NMR (400 MHz, DMSO-d₆) δ 6.57-6.48 (m, 2H), 6.49-6.40 (m, 2H), 4.60 (s, 2H), 0.92 (s, 9H), 0.11 (s, 6H).

Step 2. Synthesis of 4-fluorophenyl N-[4-[(tert-butyldimethylsilyl)oxy]phenyl]carbamate

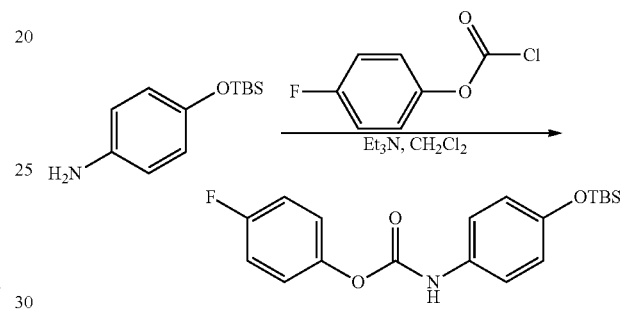

To a solution of the product from the previous step (2 g, 8.95 mmol) in CH₂Cl₂ (20 mL) was added in portions Et₃N (1.8 g, 17.79 mmol), followed by the addition of 4-fluorophenyl chloroformate (1.87 g, 10.71 mmol) dropwise with stirring at 0° C. over 2 min. The resulting solution was stirred for 2 h at 0° C., then quenched by the addition of 60 mL H₂O and extracted with 2×100 mL of EtOAc. The combined organic layers were concentrated under vacuum and purified with silica gel chromatography using EtOAc/hexane (1:5) to afford 1.5 g (46%) of the title compound as an off-white solid.
LC-MS: (ES, m/z): 362
¹H NMR (400 MHz, DMSO-d₆) δ 10.07 (s, 1H), 7.36 (d, J=8.5 Hz, 2H), 7.25 (d, J=6.5 Hz, 4H), 6.88-6.77 (m, 2H), 0.94 (s, 9H), 0.17 (s, 6H).

Scheme I

Example 1

N-(5-Hydroxypyridin-2-yl)-4-phenylpiperidine-1-carboxamide

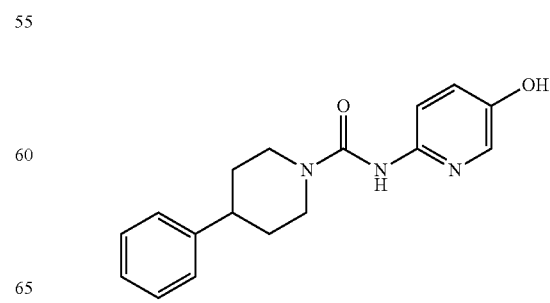

Step 1: Synthesis of 4-phenylpiperidine-1-carbonyl chloride

Step 3: Synthesis of N-(5-hydroxypyridin-2-yl)-4-phenylpiperidine-1-carboxamide

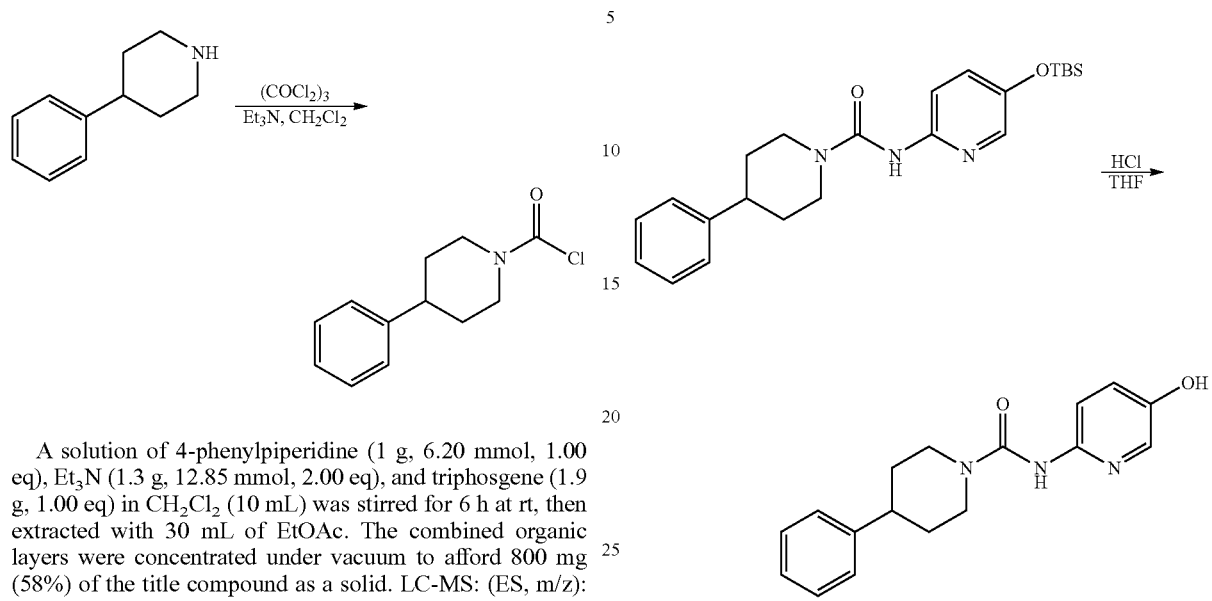

A solution of 4-phenylpiperidine (1 g, 6.20 mmol, 1.00 eq), Et₃N (1.3 g, 12.85 mmol, 2.00 eq), and triphosgene (1.9 g, 1.00 eq) in CH₂Cl₂ (10 mL) was stirred for 6 h at rt, then extracted with 30 mL of EtOAc. The combined organic layers were concentrated under vacuum to afford 800 mg (58%) of the title compound as a solid. LC-MS: (ES, m/z): 224

Step 2: Synthesis of N-[5-[(tert-butyldimethylsilyl)oxy]pyridin-2-yl]-4-phenylpiperidine-1-carboxamide

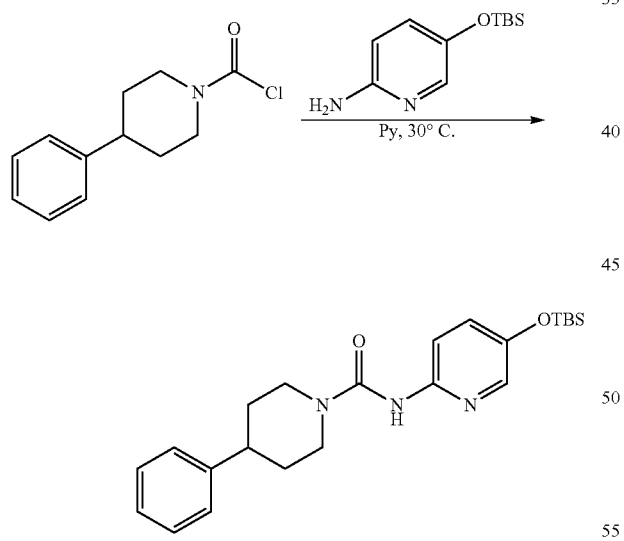

A solution of the product from the previous step (200 mg, 0.49 mmol, 1.00 eq) in aq HCl (1.5 mL) and THF (3 mL) was stirred for 2 h at rt, then concentrated under vacuum. The pH was adjusted to 7 with Et₃N. The crude product was purified by Prep-HPLC with the following conditions: Instrument "B"; Column "A"; mobile phase, water (0.1% FA) and ACN (18.0% ACN up to 48.0% in 7 min); Detector, UV 254/220 nm, to afford 48 mg (33%) of the title compound as a solid.

LC-MS: (ES, m/z): 298

¹H NMR (300 MHz, DMSO-d₆) δ 8.78 (s, 1H), 8.13 (s, 1H), 7.78 (d, J=2.9 Hz, 1H), 7.59 (d, J=8.9 Hz, 1H), 7.36-7.08 (m, 6H), 4.34-4.22 (m, 2H), 2.92-2.63 (m, 3H), 1.82-1.70 (m, 2H), 1.53 (qd, J=12.5, 4.0 Hz, 2H).

Scheme II

Example 2

N-[5-[Hydroxy]pyridin-2-yl]-4-(4-fluorophenyl)piperidine-1-carboxamide

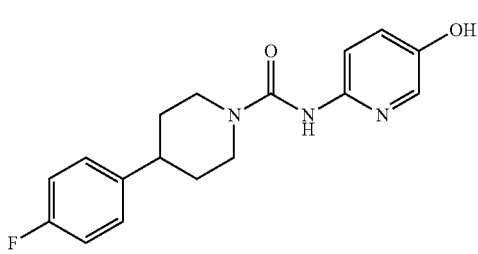 [SMILES: O=C(Nc1ccc(O)cn1)N1CCC(c2ccc(F)cc2)CC1]

A solution of the product from the previous step (500 mg, 2.24 mmol, 1.00 eq) and 5-[(tert-butyldimethylsilyl)oxy]pyridin-2-amine (502 mg, 2.24 mmol, 1.00 eq) in pyridine (5 mL) was stirred for 16 h at 30° C., then extracted with 20 mL of EtOAc. The combined organic layers were concentrated under vacuum and purified with prep-TLC (EtOAc/hexane 1:2) to afford 200 mg (22%) of the title compound as a solid. LC-MS: (ES, m/z): 412

Step 2: Synthesis of N-[5-[(tert-butyldimethylsilyl)oxy]pyridin-2-yl]-4-(4-fluorophenyl)piperidine-1-carboxamide

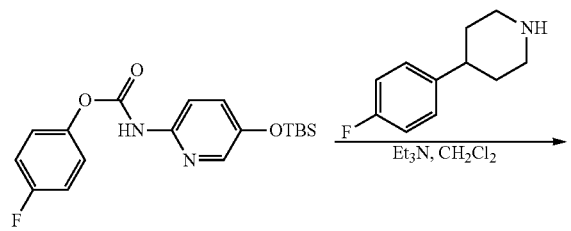

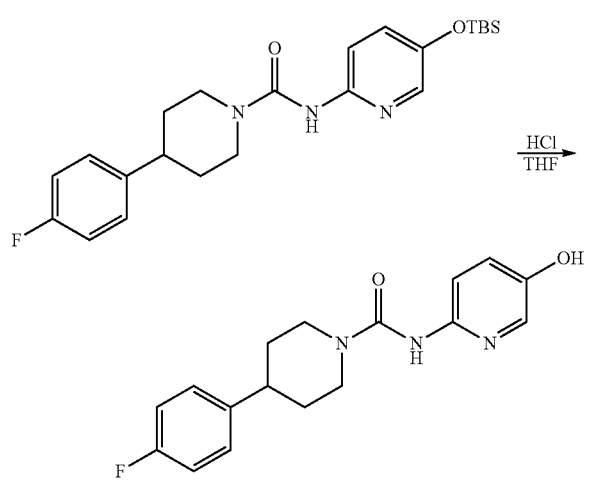

A solution of the product from the previous step (200 mg, 0.55 mmol, 1.00 eq), 4-(4-fluorophenyl)piperidine (300 mg, 1.67 mmol, 3.00 eq), and Et₃N (170 mg, 1.68 mmol, 3.00 eq) in CH₂Cl₂ (5 mL) was stirred for 2 h at rt, then extracted with 3×15 mL of EtOAc. The combined organic layers were concentrated under vacuum and purified with silica gel chromatography using EtOAc/hexane (1:2) to afford 150 mg (63%) of the title compound as a white solid.
LC-MS: (ES, m/z): 430

Step 3: Synthesis of N-[5-[(tert-butyldimethylsilyl)oxy]pyridin-2-yl]-4-(4-fluorophenyl)piperidine-1-carboxamide A solution of the product from the previous step (150 mg, 0.35 mmol, 1.00 eq) in 2 N aq HCl (1 mL) and THF (2 mL) was stirred for 2 h at rt. The resulting mixture was concentrated under vacuum and purified with Prep-HPLC using the following conditions: Instrument "B"; Column "B"; mobile phase, 10 mM aq NH₄HCO₃ and ACN (20.0% ACN up to 70.0% in 7 min); Detector, UV 254/220 nm, to afford 56.9 mg (52%) of the title compound as a white solid.
LC-MS: (ES, m/z): 316
¹H NMR (300 MHz, DMSO-d₆) δ 9.41 (s, 1H), 8.78 (s, 1H), 7.78 (d, J=2.9 Hz, 1H), 7.59 (d, J=8.9 Hz, 1H), 7.28 (dd, J=8.5, 5.6 Hz, 2H), 7.18-7.04 (m, 3H), 4.27 (d, J=13.1 Hz, 2H), 2.91-2.64 (m, 3H), 1.81-1.64 (m, 2H), 1.51 (qd, J=12.6, 4.0 Hz, 2H).

Example 3

N-(5-Hydroxypyridin-2-yl)-4-phenylpiperazine-1-carboxamide

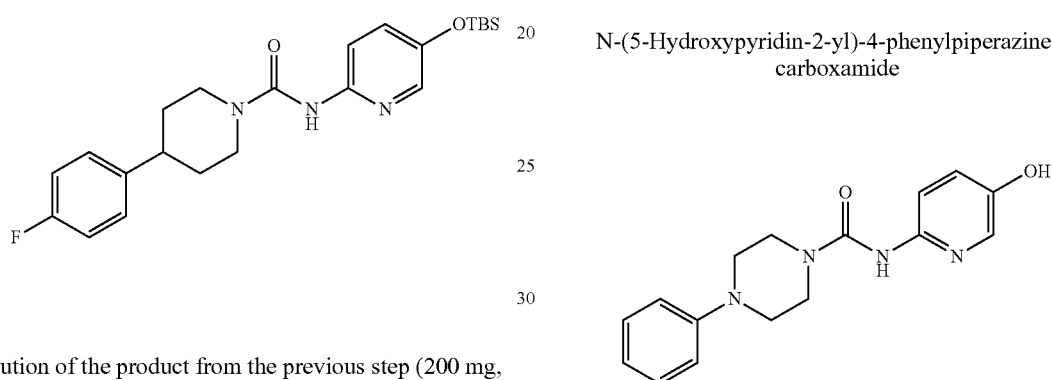

Step 1: Synthesis of N-[5-[(tert-butyldimethylsilyl)oxy]pyridin-2-yl]-4-phenylpiperazine-1-carboxamide

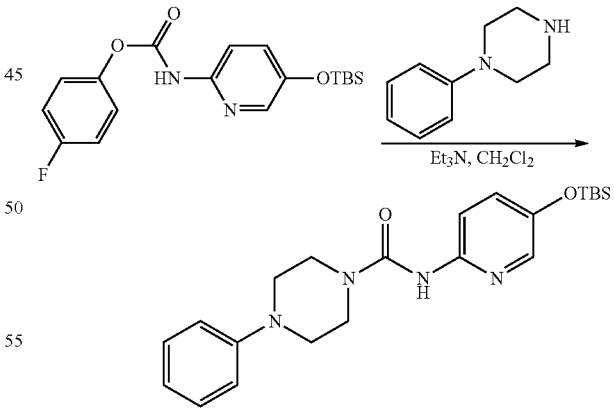

A solution of Intermediate "A" (200 mg, 0.55 mmol, 1.00 eq), 1-phenylpiperazine (270 mg, 1.66 mmol, 3.00 eq), and Et₃N (170 mg, 1.68 mmol, 3.00 eq) in CH₂Cl₂ (3 mL) was stirred for 2 h at rt, then extracted with 2×20 mL of EtOAc. The combined organic layers were concentrated under vacuum and purified with silica gel chromatography using EtOAc/hexane (1:2), to afford 200 mg (88%) of the title compound a white solid. LC-MS: (ES, m/z): 413

Step 2: Synthesis of N-(5-hydroxypyridin-2-yl)-4-phenylpiperazine-1-carboxamide

Step 1: Synthesis of N-[5-[(tert-butyldimethylsilyl)oxy]pyridin-2-yl]-4-(4-chlorophenyl)piperidine-1-carboxamide

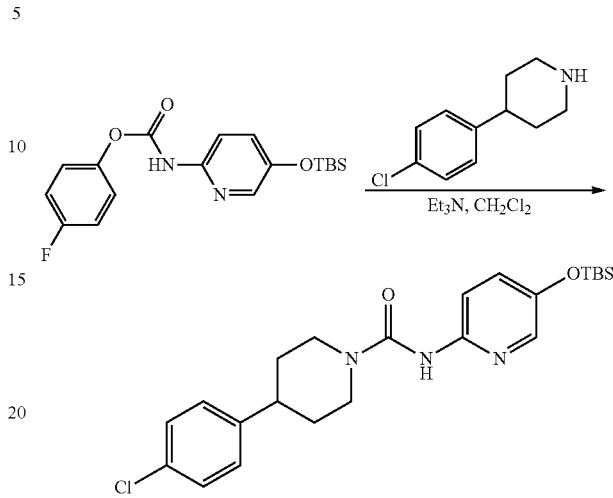

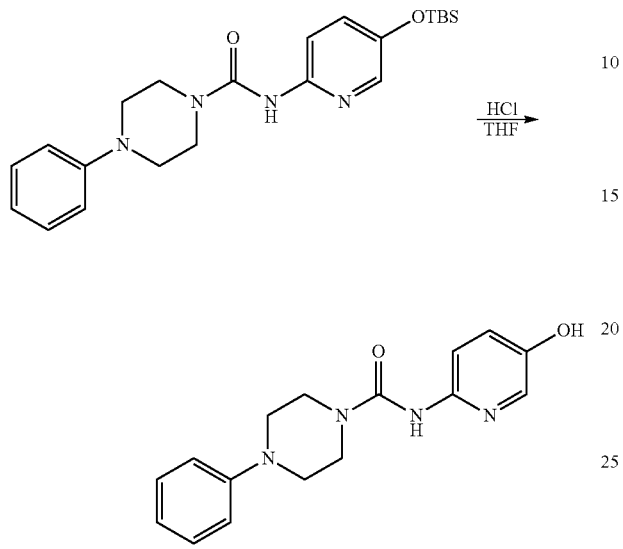

A solution of Intermediate "A" (200 mg, 0.55 mmol, 1.00 eq), 4-(4-chlorophenyl)piperidine (330 mg, 1.69 mmol, 3.00 eq), and Et$_3$N (170 mg, 1.68 mmol, 3.00 eq) in CH$_2$Cl$_2$ (3 mL) was stirred for 2 h at rt, then extracted with 2×20 mL of EtOAc. The combined organic layers were concentrated under vacuum and purified with silica gel chromatography using EtOAc/hexane (1:2) to afford 220 mg (89%) of the title compound as an off-white solid. LC-MS: (ES, m/z): 446.

Step 2: Synthesis of 4-(4-chlorophenyl)-N-(5-hydroxypyridin-2-yl)piperidine-1-carboxamide A solution of the product from the previous step (200 mg, 0.48 mmol, 1.00 eq) in 2 N aq HCl (1.5 mL) and THF (3 mL) was stirred for 2 h at rt. The resulting mixture was concentrated under vacuum. The crude product (200 mg) was purified by Prep-HPLC with the following conditions: Instrument "B"; Column "B"; mobile phase, 10 mM aq NH$_4$HCO$_3$ and ACN (5.0% ACN up to 75.0% in 7 min); Detector, UV 254/220 nm, to afford 54.7 mg (38%) of the title compound as a white solid.

LC-MS: (ES, m/z): 299

$^1$H NMR (300 MHz, DMSO-d$_6$) δ 9.49-9.39 (m, 1H), 8.90 (s, 1H), 7.79 (d, J=2.9 Hz, 1H), 7.59 (d, J=8.9 Hz, 1H), 7.28-7.08 (m, 3H), 6.96 (d, J=8.1 Hz, 2H), 6.80 (t, J=7.3 Hz, 1H), 3.59 (t, J=5.0 Hz, 4H), 3.12 (t, J=5.0 Hz, 4H).

Example 4

4-(4-Chlorophenyl)-N-(5-hydroxypyridin-2-yl)piperidine-1-carboxamide

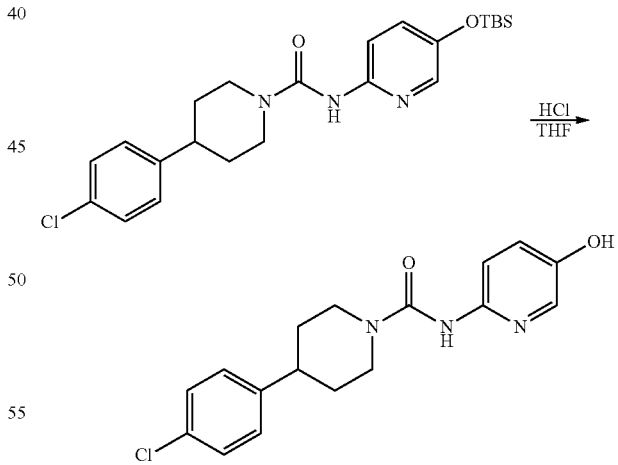

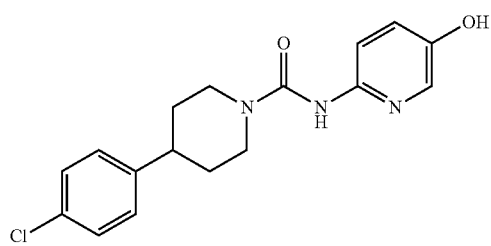 [SMILES: O=C(Nc1ccc(O)cn1)N1CCC(c2ccc(Cl)cc2)CC1]

A solution of the product from the previous step (220 mg, 0.49 mmol, 1.00 eq) in 2 N aq HCl (1 mL) and THF (2 mL) was stirred for 2 h at rt, then concentrated under vacuum. The crude product (220 mg) was purified by Prep-HPLC with the following conditions: Instrument "B"; Column "B"; mobile phase, 10 mM aq NH$_4$HCO$_3$ and ACN (25.0% ACN up to 80.0% in 7 min); Detector, UV 254/220 nm, to afford 102.8 mg (63%) of the title compound as a white solid.

LC-MS: (ES, m/z): 332

¹H NMR (300 MHz, DMSO-d₆) δ 9.48-9.27 (m, 1H), 8.78 (s, 1H), 7.78 (d, J=2.9 Hz, 1H), 7.59 (d, J=8.9 Hz, 1H), 7.39-7.22 (m, 4H), 7.13 (dd, J=9.0, 3.0 Hz, 1H), 4.27 (d, J=13.2 Hz, 2H), 2.91-2.64 (m, 2H), 1.80-1.68 (m, 2H), 1.51 (qd, J=12.7, 3.9 Hz, 2H).

Example 5

4-(4-Fluorophenyl)-N-(5-hydroxypyridin-2-yl)piperazine-1-carboxamide

Step 1: Synthesis of N-[5-[(tert-butyldimethylsilyl)oxy]pyridin-2-yl]-4-(4-fluorophenyl)piperazine-1-carboxamide

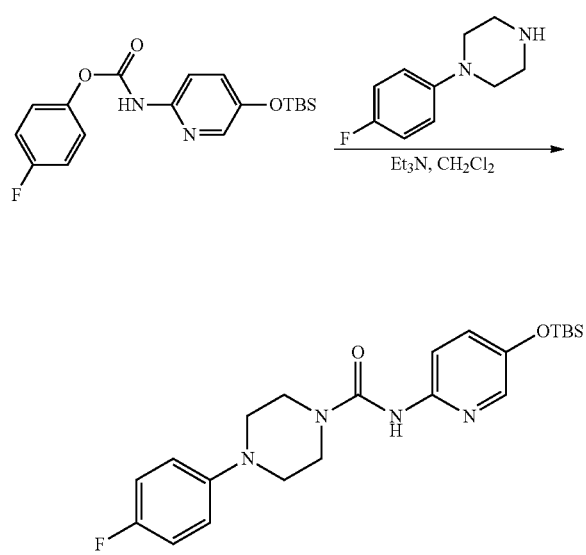 [SMILES: CC(C)(C)[Si](C)(C)Oc1ccc(NC(=O)Oc2ccc(F)cc2)nc1 ; Fc1ccc(N2CCNCC2)cc1 ; CC(C)(C)[Si](C)(C)Oc1ccc(NC(=O)N2CCN(c3ccc(F)cc3)CC2)nc1]

A solution of Intermediate "A" (200 mg, 0.55 mmol, 1.00 eq), 1-(4-fluorophenyl)piperazine (300 mg, 1.66 mmol, 3.00 eq), and Et₃N (170 mg, 1.68 mmol, 3.00 eq) in CH₂Cl₂ (3 mL) was stirred for 2 h at rt. The resulting solution was extracted with 3×20 mL of EtOAc, and the combined organic layers were concentrated under vacuum and purified with silica gel column chromatography using EtOAc/hexane (1:2) to afford 210 mg (88%) of the title compound as an off-white solid. LC-MS: (ES, m/z): 431

Step 2: Synthesis of 4-(4-fluorophenyl)-N-(5-hydroxypyridin-2-yl)piperazine-1-carboxamide

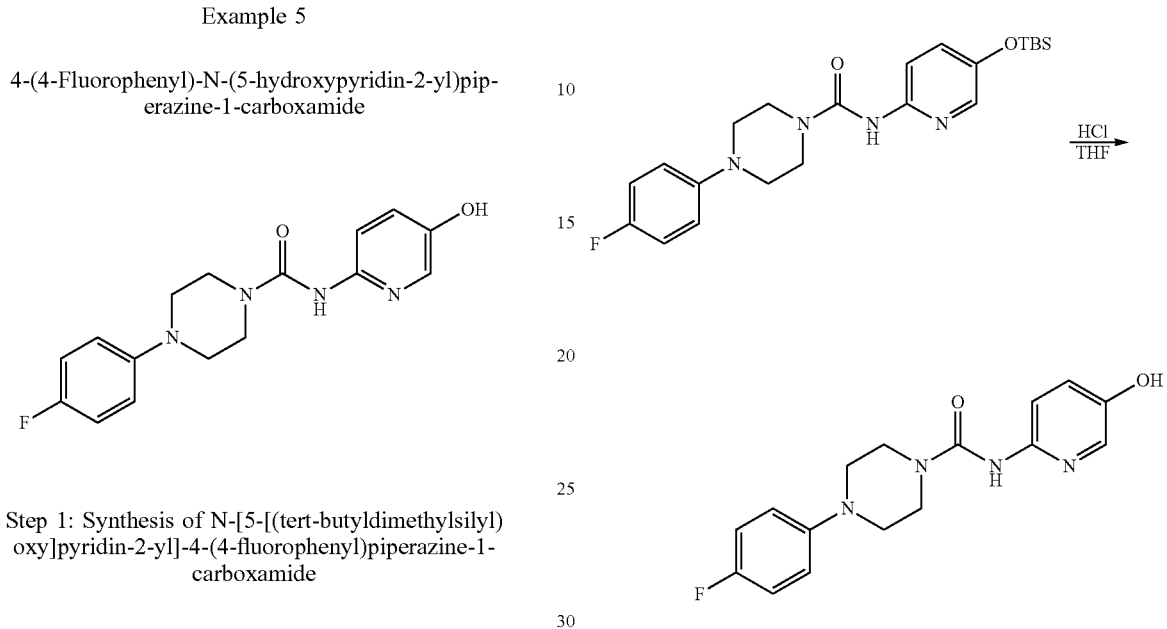

A solution of the product from the previous step (210 mg, 0.49 mmol, 1.00 eq) in 2 N aq. HCl (1 mL) and THF (2 mL) was stirred for 2 h at rt, then concentrated under vacuum. The crude product (210 mg) was purified by Prep-HPLC with the following conditions: Instrument "B"; Column "B"; mobile phase, 10 mM aq NH₄HCO₃ and ACN (20.0% ACN up to 65.0% in 7 min); Detector, UV 254/220 nm, to afford 68.2 mg (44%) of the title compound as an off-white solid.

LC-MS: (ES, m/z): 328

¹H NMR (300 MHz, DMSO-d₆) δ 9.52 (s, 1H), 8.91 (s, 1H), 7.79 (d, J=2.9 Hz, 1H), 7.59 (d, J=8.9 Hz, 1H), 7.19-6.92 (m, 5H), 3.58 (t, J=4.9 Hz, 4H), 3.06 (t, J=5.0 Hz, 4H).

Example 6

N-(5-Hydroxypyridin-2-yl)-4-(4-methoxyphenyl)piperidine-1-carboxamide

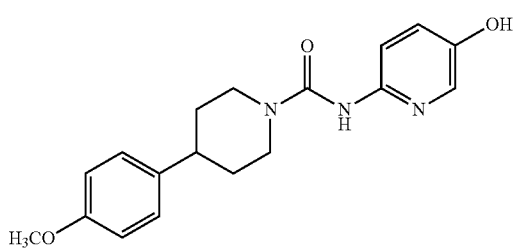 [SMILES: COc1ccc(C2CCN(C(=O)Nc3ccc(O)cn3)CC2)cc1]

Step 1: Synthesis of N-[5-[(tert-butyldimethylsilyl)oxy]pyridin-2-yl]-4-(4-methoxyphenyl)piperidine-1-carboxamide

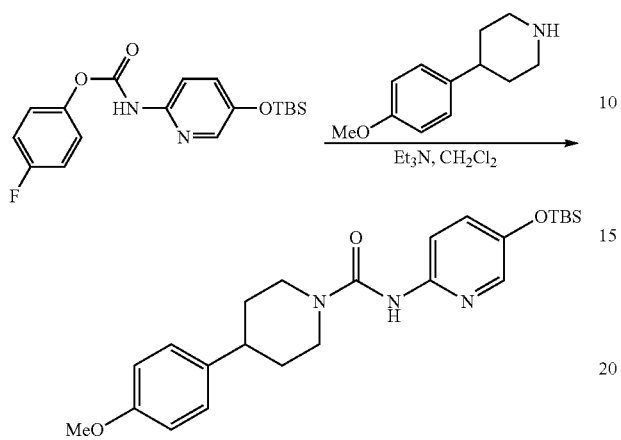

A solution of Intermediate "A" (200 mg, 0.55 mmol, 1.00 eq), 4-(4-methoxyphenyl)piperidine (320 mg, 1.67 mmol, 3.00 eq), and Et₃N (170 mg, 1.68 mmol, 3.00 eq) in CH₂Cl₂ (3 mL) was stirred for 16 h at rt. The resulting solution was extracted with 2×15 mL of EtOAc, and the combined organic layers were concentrated under vacuum and purified with silica gel chromatography using EtOAc/hexane (1:2) to afford 250 mg (103%) of the title compound as an off-white solid. LC-MS: (ES, m/z): 442

Step 2: Synthesis of N-(5-hydroxypyridin-2-yl)-4-(4-methoxyphenyl)piperidine-1-carboxamide

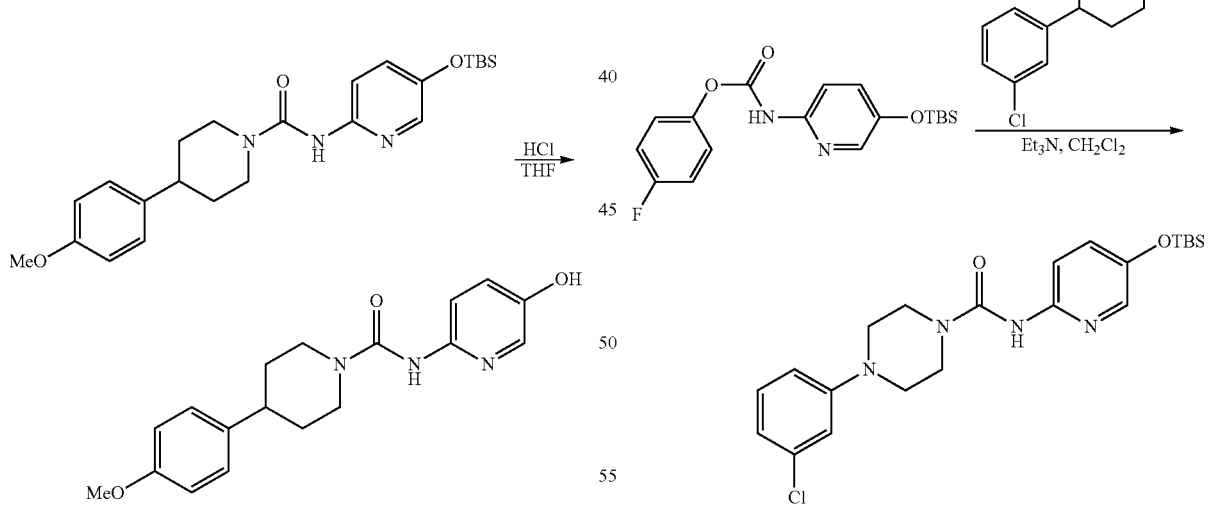

A solution of the product from the previous step (230 mg, 0.52 mmol, 1.00 eq) in 2 N aq. HCl (1 mL) and THF (2 mL) was stirred for 2 h at rt. The resulting mixture was concentrated under vacuum. The crude product (240 mg) was purified by Prep-HPLC with the following conditions: Instrument "A"; Column "A"; mobile phase, 10 mM aq NH₄HCO₃ and ACN (20.0% ACN up to 50.0% in 7 min); Detector, uv 254/220 nm, to afford 92.8 mg (55%) the title compound as an off-white solid.
LC-MS: (ES, m/z): 328

¹H NMR (300 MHz, DMSO-d₆) δ 9.32 (s, 1H), 8.76 (s, 1H), 7.78 (d, J=2.9 Hz, 1H), 7.60 (d, J=8.9 Hz, 1H), 7.13 (td, J=6.8, 3.3 Hz, 3H), 6.90-6.79 (m, 2H), 4.32-4.20 (m, 2H), 3.71 (s, 3H), 2.82 (td, J=12.9, 2.5 Hz, 2H), 2.50 (q, J=1.9 Hz, 1H), 1.79-1.67 (m, 2H), 1.49 (qd, J=12.6, 3.9 Hz, 2H).

Example 7

N-[5-Hydroxy]pyridin-2-yl]-4-(3-chlorophenyl)piperidine-1-carboxamide

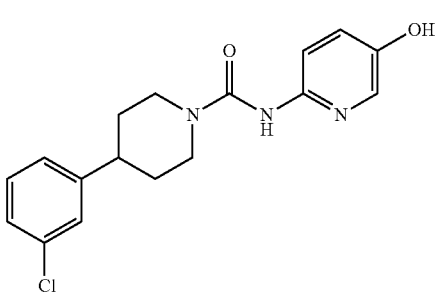 [SMILES: O=C(Nc1ccc(O)cn1)N1CCC(c2cccc(Cl)c2)CC1]

Step 1: Synthesis of N-[5-[(tert-butyldimethylsilyl)oxy]pyridin-2-yl]-4-(3-chlorophenyl)piperidine-1-carboxamide

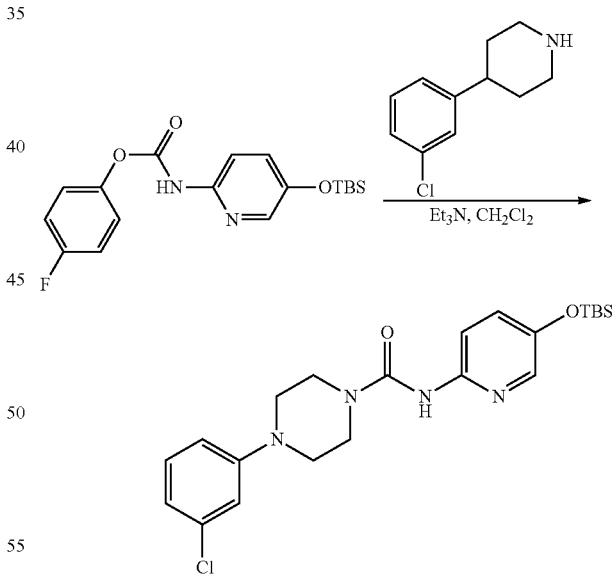

A solution of Intermediate "A" (200 mg, 0.55 mmol, 1.00 eq), 4-(3-chlorophenyl)piperidine (330 mg, 1.69 mmol, 3.00 eq), and Et₃N (170 mg, 1.68 mmol, 3.00 eq) in CH₂Cl₂ (3 mL) was stirred for 2 h at rt. The resulting solution was extracted with 2×20 mL of CH₂Cl₂ and the combined organic layers concentrated under vacuum and purified with silica gel chromatography using EtOAc/hexane (1:2) to afford 240 mg (98%) of the title compound as an off-white solid. LC-MS: (ES, m/z): 446

Step 2: Synthesis of N-[5-[(tert-butyldimethylsilyl)oxy]pyridin-2-yl]-4-(3-chlorophenyl)piperidine-1-carboxamide Step 1: Synthesis of 4-benzyl-N-[5-[(tert-butyldimethylsilyl)oxy]pyridin-2-yl]piperidine-1-carboxamide

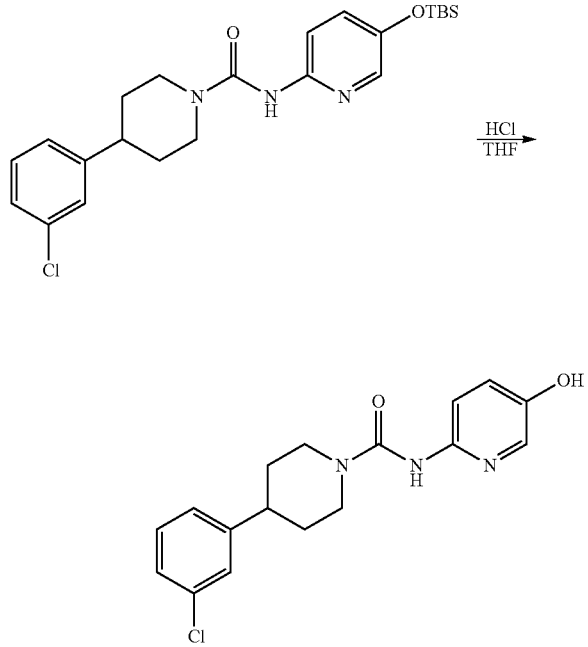

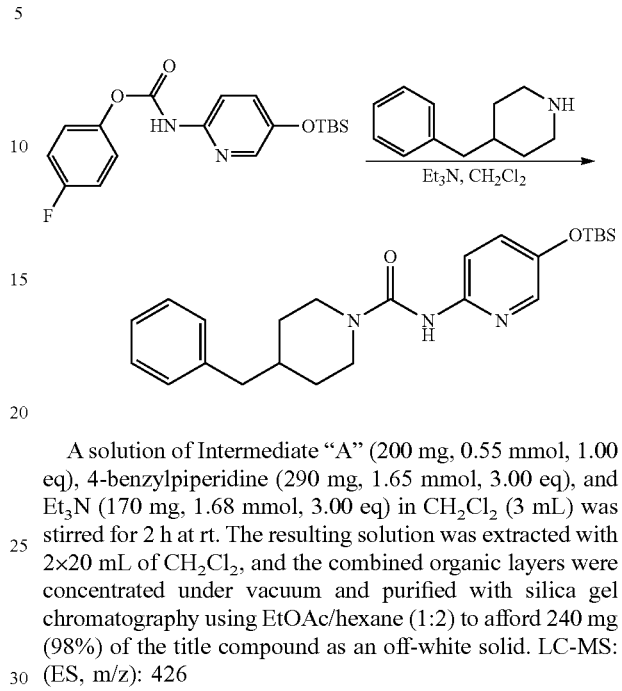

A solution of Intermediate "A" (200 mg, 0.55 mmol, 1.00 eq), 4-benzylpiperidine (290 mg, 1.65 mmol, 3.00 eq), and Et$_3$N (170 mg, 1.68 mmol, 3.00 eq) in CH$_2$Cl$_2$ (3 mL) was stirred for 2 h at rt. The resulting solution was extracted with 2×20 mL of CH$_2$Cl$_2$, and the combined organic layers were concentrated under vacuum and purified with silica gel chromatography using EtOAc/hexane (1:2) to afford 240 mg (98%) of the title compound as an off-white solid. LC-MS: (ES, m/z): 426

A solution of the product from the previous step 240 mg, 0.54 mmol, 1.00 eq) in 2 N aq. HCl (1 mL) and THF (2 mL) was stirred for 2 h at rt, then concentrated under vacuum. The crude product (240 mg) was purified by Prep-HPLC with the following conditions: Instrument "B"; Column "A"; mobile phase, 10 mM aq NH$_4$HCO$_3$ and ACN (25.0% ACN up to 60.0% in 7 min); Detector, uv 254/220 nm, to afford 107.2 mg (60%) of the title compound as an off-white solid.

LC-MS: (ES, m/z): 332

$^1$H NMR (300 MHz, DMSO-d$_6$) δ 9.38 (s, 1H), 8.78 (s, 1H), 7.78 (d, J=2.9 Hz, 1H), 7.59 (d, J=8.9 Hz, 1H), 7.36-7.29 (m, 2H), 7.25 (dt, J=7.5, 1.6 Hz, 2H), 7.13 (dd, J=8.9, 3.0 Hz, 1H), 4.27 (d, J=13.2 Hz, 2H), 2.79 (ddd, J=21.3, 12.5, 9.5 Hz, 3H), 1.82-1.69 (m, 2H), 1.53 (qd, J=12.7, 4.0 Hz, 2H).

Example 8

4-Benzyl-N-(5-hydroxypyridin-2-yl)piperidine-1-carboxamide

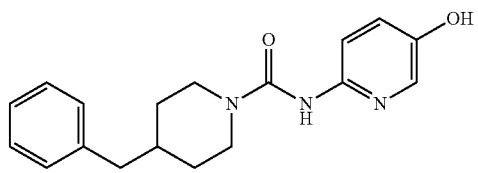 [SMILES: O=C(Nc1ccc(O)cn1)N1CCC(Cc2ccccc2)CC1]

Step 2: Synthesis of 4-benzyl-N-(5-hydroxypyridin-2-yl)piperidine-1-carboxamide

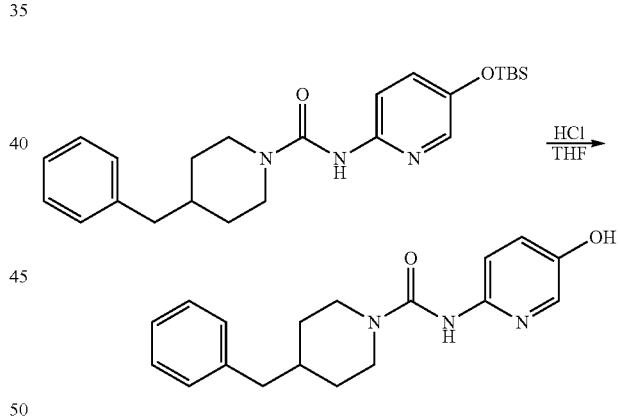

A solution of the product from the previous step (230 mg, 0.54 mmol, 1.00 eq) in 2 N aq. HCl (1 mL) and THF (2 mL) was stirred for 2 h at rt, then concentrated under vacuum. The crude product (230 mg) was purified by Prep-HPLC with the following conditions: Instrument "B"; Column "A"; mobile phase, 10 mM aq NH$_4$HCO$_3$ and ACN (25.0% ACN up to 60.0% in 7 min); Detector, uv 254/220 nm, to afford 96.7 mg (57%) of the title compound as an off-white solid.

LC-MS: (ES, m/z): 312

$^1$H NMR (300 MHz, Methanol-d$_4$) δ 7.80 (dd, J=3.0, 0.7 Hz, 1H), 7.50 (dd, J=8.9, 0.8 Hz, 1H), 7.34-7.11 (m, 6H), 4.13 (dq, J=13.7, 2.2 Hz, 2H), 2.85 (td, J=13.3, 2.6 Hz, 2H), 2.58 (d, J=7.1 Hz, 2H), 1.92-1.65 (m, 3H), 1.23 (qd, J=12.6, 4.2 Hz, 2H).

Example 9

N-(5-Hydroxypyridin-2-yl)-4-(propan-2-yl)piperidine-1-carboxamide

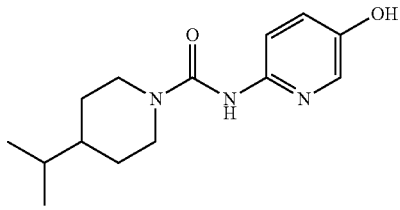 [SMILES: CC(C)C1CCN(C(=O)Nc2ccc(O)cn2)CC1]

Step 1: Synthesis of N-[5-[(tert-butyldimethylsilyl)oxy]pyridin-2-yl]-4-(propan-2-yl)piperidine-1-carboxamide

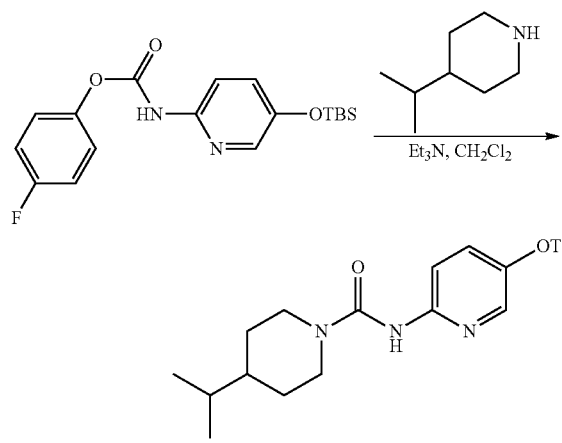

A solution of Intermediate "A" (200 mg, 0.55 mmol, 1.00 eq), 4-(propan-2-yl)piperidine (210 mg, 1.65 mmol, 3.00 eq), and Et$_3$N (170 mg, 3.00 eq) in CH$_2$Cl$_2$ (5 mL) was stirred for 2 h at rt. The resulting solution was extracted with 2×15 mL of CH$_2$Cl$_2$, and the combined organic layers were concentrated under vacuum, to afford 190 mg (91%) of the title compound as an off-white solid. LC-MS: (ES, m/z): 378

Step 2: Synthesis of N-(5-hydroxypyridin-2-yl)-4-(propan-2-yl)piperidine-1-carboxamide

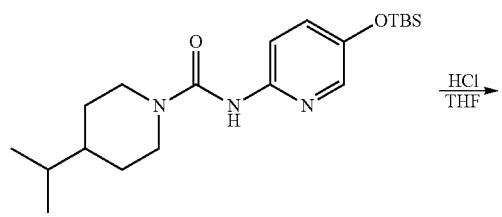

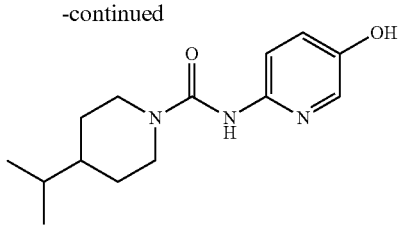

A solution of the product from the previous step (190 mg, 0.50 mmol, 1.00 eq) in 2 N aq. HCl (2 mL) and THF (4 mL) was stirred for 2 h at rt. The resulting mixture was concentrated under vacuum. The crude product was purified by Prep-HPLC with the following conditions: Instrument "B"; Column "C"; mobile phase, water (0.1% FA) and ACN (17.0% ACN up to 45.0% in 7 min); Detector, UV 254/220 nm, to afford 106 mg (80%) of the title compound as an off-white solid LC-MS: (ES, m/z): 264

$^1$H NMR (300 MHz, DMSO-d$_6$) δ 9.40 (s, 1H), 8.70 (s, 1H), 7.82-7.74 (m, 1H), 7.58 (d, J=8.9 Hz, 1H), 7.13 (d, J=8.9, 3.0 Hz, 1H), 4.19 (d, J=13.4, 3.5 Hz, 2H), 2.67 (td, J=12.4, 2.3 Hz, 2H), 1.68-1.56 (m, 2H), 1.43 (d, J=13.2, 6.7 Hz, 1H), 1.31-0.97 (m, 3H), 0.87 (d, J=6.7 Hz, 6H).

Example 10

N-(5-Hydroxypyridin-2-yl)piperidine-1-carboxamide

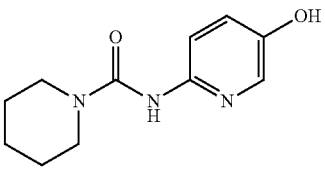 [SMILES: O=C(Nc1ccc(O)cn1)N1CCCCC1]

Step 1: Synthesis of N-[5-[(tert-butyldimethylsilyl)oxy]pyridin-2-yl]piperidine-1-carboxamide

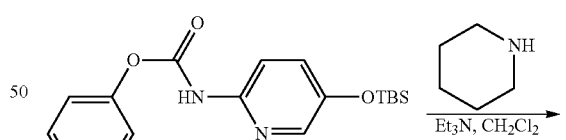

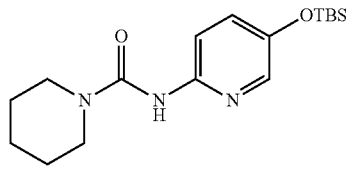

A solution of Intermediate "A" (200 mg, 0.55 mmol, 1.00 eq), piperidine (140 mg, 1.64 mmol, 3.00 eq), and Et$_3$N (170 mg, 3.00 eq) in CH$_2$Cl$_2$ (3 mL) was stirred for 2 h at rt. The resulting solution was extracted with 2×10 mL of CH$_2$Cl$_2$, and the combined organic layers were concentrated under vacuum to afford 170 mg (92%) of the title compound as a white solid. LC-MS: (ES, m/z): 336

Step 3: Synthesis of N-(5-hydroxypyridin-2-yl)piperidine-1-carboxamide

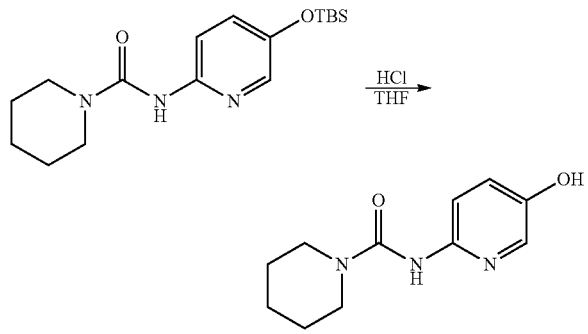

A solution of the product from the previous step (170 mg, 0.51 mmol, 1.00 eq) in 2 N aq. HCl (2 mL) and THF (4 mL) was stirred for 2 h at rt, then concentrated under vacuum. The crude product was purified by Prep-HPLC with the following conditions: Instrument "B"; Column "E"; mobile phase, water (0.1% FA) and ACN (5.0% ACN up to 50.0% in 7 min); Detector, UV 254/220 nm, to afford 71 mg (63%) of the title compound as a green solid.

LC-MS: (ES, m/z): 222
$^1$H-NMR (300 MHz, DMSO-$d_6$) δ 9.39 (s, 1H), 8.67 (s, 1H), 7.77 (d, J=2.9 Hz, 1H), 7.57 (d, J=8.9 Hz, 1H), 7.12 (d, J=8.9, 3.0 Hz, 1H), 3.45-3.37 (m, 4H), 1.51 (m, 6H).

Example 11

N-(5-hydroxypyridin-2-yl)azepane-1-carboxamide

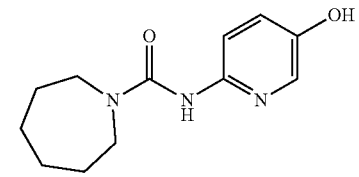 [SMILES: O=C(Nc1ccc(O)cn1)N1CCCCCC1]

Step 1: Synthesis of N-[5-[(tert-butyldimethylsilyl)oxy]pyridin-2-yl]azepane-1-carboxamide

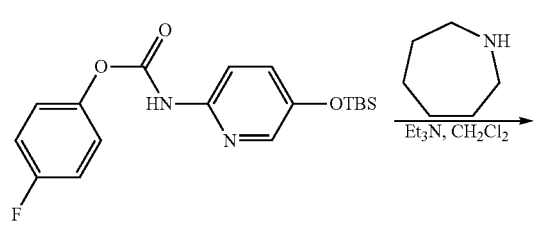

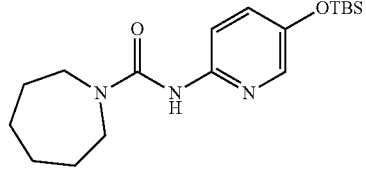

A solution of Intermediate "A" (200 mg, 0.55 mmol, 1.00 eq), azepane (160 mg, 1.61 mmol, 3.00 eq), and Et$_3$N (3 eq, 170 mg) in CH$_2$Cl$_2$ (5 mL) was stirred for 2 h at rt. The resulting solution was extracted with 2×15 mL of CH$_2$Cl$_2$, and the combined organic layers were concentrated under vacuum to afford 180 mg (93%) of the title compound as an off-white solid. LC-MS: (ES, m/z): 350

Step 2: Synthesis of N-(5-hydroxypyridin-2-yl)azepane-1-carboxamide

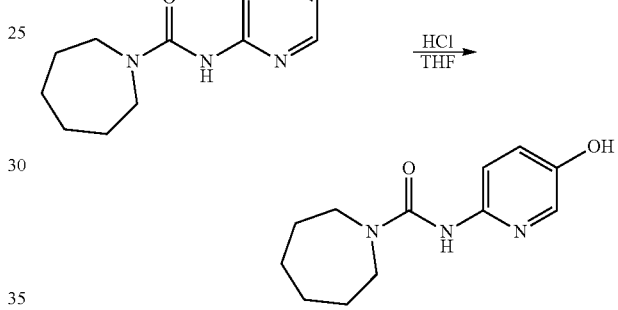

A solution of the product from the previous step (180 mg, 0.51 mmol, 1.00 eq) in 2 N aq. HCl (2 mL) and THF (4 mL) was stirred for 2 h at rt, then was extracted with EtOAc. The combined organic layers were purified by Prep-HPLC with the following conditions: Instrument "B"; Column "C"; mobile phase, water (0.1% FA) and ACN (12.0% ACN up to 31.0% in 7 min), to afford 66.2 mg (55%) of the title compound as an off-white solid.

LC-MS: (ES, m/z): 236
$^1$H NMR (300 MHz, DMSO-$d_6$) δ 10.85 (s, 1H), 10.23 (s, 1H), 7.94-7.76 (m, 3H), 3.55 (t, J=6.1 Hz, 4H), 1.71 (d, J=9.4, 4.7 Hz, 4H), 1.53 (t, J=4.9 Hz, 4H).

Example 12

4-(2-fluorophenyl)-N-(5-hydroxypyridin-2-yl)piperazine-1-carboxamide

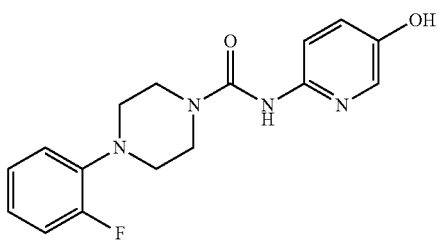 [SMILES: O=C(Nc1ccc(O)cn1)N1CCN(c2ccccc2F)CC1]

Step 1: Synthesis of N-[5-[(tert-butyldimethylsilyl)oxy]pyridin-2-yl]-4-(2-fluorophenyl)piperazine-1-carboxamide

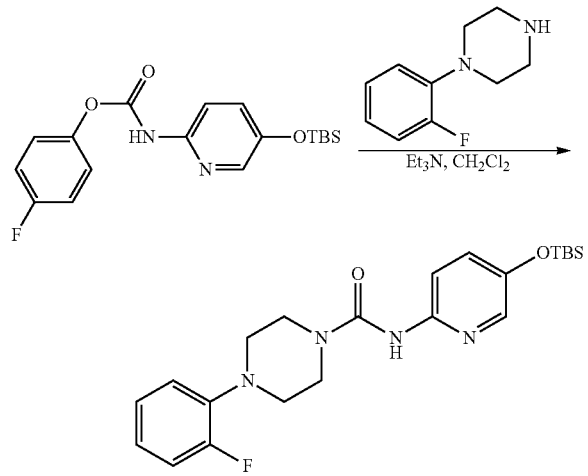

A solution of Intermediate "A" (200 mg, 0.55 mmol), 1-(2-fluorophenyl)-piperazine (298 mg, 1.65 mmol), and Et$_3$N (170 mg, 1.68 mmol) in CH$_2$Cl$_2$ (5 mL) was stirred for 16 h at rt. The resulting solution was extracted with 2×20 mL of CH$_2$Cl$_2$, and the combined organic layers were concentrated under vacuum and purified with silica gel column chromatography using EtOAc/hexane (1:2) to afford 230 mg (97%) of the title compound as an off-white solid. LC-MS: (ES, m/z): 431

Step 2: Synthesis of 4-(2-fluorophenyl)-N-(5-hydroxypyridin-2-yl)piperazine-1-carboxamide

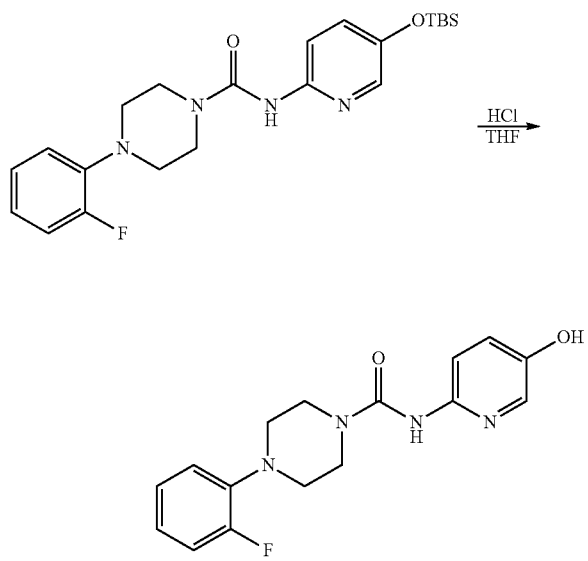

A solution of product from the previous step (230 mg, 0.53 mmol, 1.00 eq) in 2 N aq. HCl (1 mL) and THF (2 mL) was stirred for 2 h at rt, then concentrated under vacuum. The crude product (230 mg) was purified by Prep-HPLC with the following conditions: Instrument "B"; Column "B"; mobile phase, 10 mM aq NH$_4$HCO$_3$ and ACN (5.0% ACN up to 75.0% in 7 min); Detector, UV 254/220 nm, to afford 106.7 mg (63%) of the title compound as an off-white solid.

LC-MS: (ES, m/z): 317

$^1$H NMR (300 MHz, DMSO-d$_6$) δ 9.43 (s, 1H), 8.90 (s, 1H), 7.79 (d, J=2.9 Hz, 1H), 7.59 (d, J=8.9 Hz, 1H), 7.18-7.00 (m, 5H), 3.70-3.52 (m, 4H), 3.05-2.93 (m, 4H).

Example 13

4-(2,4-difluorophenyl)-N-(5-hydroxypyridin-2-yl)piperazine-1-carboxamide

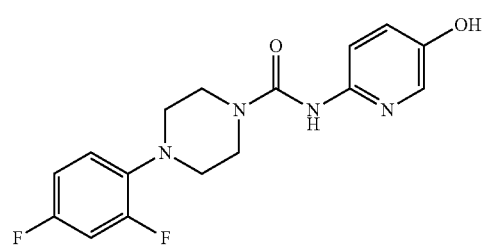 [SMILES: O=C(Nc1ccc(O)cn1)N1CCN(c2ccc(F)cc2F)CC1]

Step 1: Synthesis of N-[5-[(tert-butyldimethylsilyl)oxy]pyridin-2-yl]-4-(2,4-difluorophenyl)piperazine-1-carboxamide

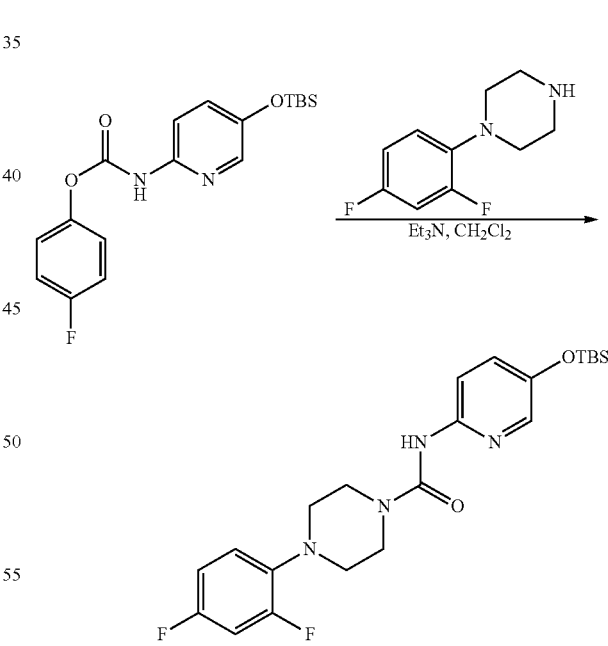

A solution of Intermediate "A" (200 mg, 0.55 mmol), 1-(2,4-difluorophenyl)-piperazine (328 mg, 1.65 mmol), and Et$_3$N (170 mg) in CH$_2$Cl$_2$ (5 g) was stirred for 16 h at rt, then extracted with 2×30 mL of CH$_2$Cl$_2$. The combined organic layers were concentrated under vacuum and purified with silica gel column chromatography using EtOAc/hexane (1:1) to afford 240 mg (97%) of the title compound as an off-white solid. LC-MS: (ES, m/z): 449.

Step 2: Synthesis of 4-(2,4-difluorophenyl)-N-(5-hydroxypyridin-2-yl)piperazine-1-carboxamide Step 1: Synthesis of N-[5-[(tert-butyldimethylsilyl)oxy]pyridin-2-yl]-4-[4-(trifluoromethyl)phenyl]piperazine-1-carboxamide

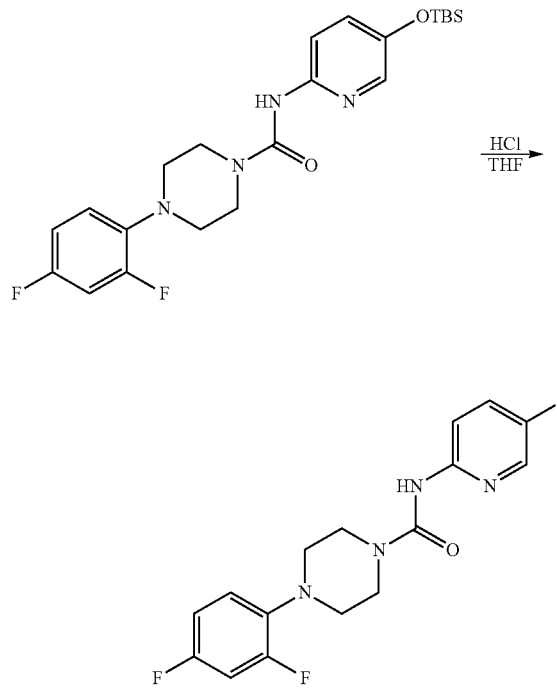

A solution of Intermediate "A" (200 mg, 0.55 mmol), 1-[4-(trifluoromethyl)-phenyl]piperazine (381 mg, 1.65 mmol), and Et₃N (170 mg, 1.68 mmol) in CH₂Cl₂ (5 mL) was stirred for 16 h at rt, then extracted with 2×20 mL of CH₂Cl₂. The combined organic layers were concentrated under vacuum and purified with silica gel column chromatography using EtOAc/hexane (1:2) to afford 260 mg (98%) of the title compound as an off-white solid. LC-MS: (ES, m/z): 481

Step 2: Synthesis of N-(5-hydroxypyridin-2-yl)-4-[4-(trifluoromethyl)phenyl]piperazine-1-carboxamide

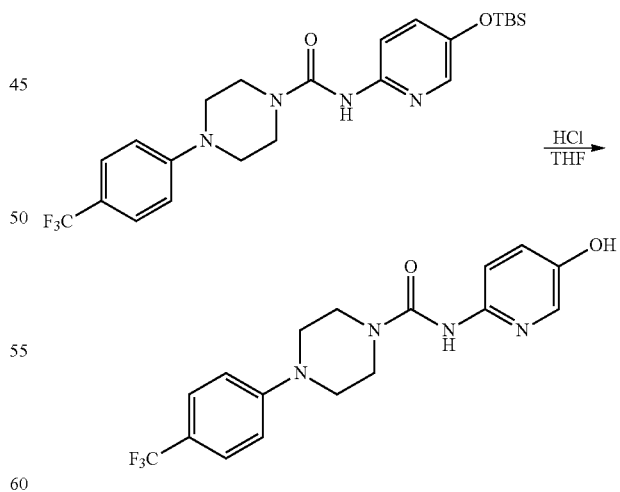

A solution of the product from the previous step (240 mg, 0.54 mmol) in 2N aq. HCl (1 mL) and THF (2 mL) was stirred for 2 h at rt, then concentrated under vacuum. The crude product (240 mg) was purified by Prep-HPLC under the following conditions: Instrument "B"; Column "B"; mobile phase, 10 mM aq NH₄HCO₃ and ACN (5.0% ACN up to 45.0% in 7 min), to afford 89.7 mg (50%) of the title compound as an off-white solid.

LC-MS: (ES, m/z): 335

¹H NMR (300 MHz, DMSO-d₆) δ 9.15 (s, 1H), 8.90 (s, 1H), 7.79 (d, J=2.9 Hz, 1H), 7.59 (d, J=8.9 Hz, 1H), 7.28-6.92 (m, 4H), 3.64-3.54 (m, 4H), 2.93 (t, J=4.9 Hz, 4H).

Example 14

N-(5-Hydroxypyridin-2-yl)-4-[4-(trifluoromethyl)phenyl]piperazine-1-carboxamide

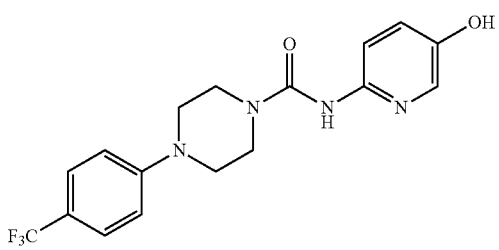 [SMILES: O=C(Nc1ccc(O)cn1)N1CCN(c2ccc(C(F)(F)F)cc2)CC1]

A solution of the product from the previous step (260 mg, 0.54 mmol) in 2N aq. HCl (1 mL) and THF (2 mL) was stirred for 2 h at rt, then concentrated under vacuum. The crude product (260 mg) was purified with Prep-HPLC using the following conditions: Instrument "B"; Column "B"; mobile phase, 10 mM aq NH₄HCO₃ and ACN (7.0% ACN up to 85.0% in 7 min), to afford 102.9 mg (52%) of the title compound as an off-white solid.

LC-MS: (ES, m/z): 367

¹H NMR (300 MHz, DMSO-d₆) δ 9.39 (s, 1H), 8.94 (s, 1H), 7.80 (d, J=3.0 Hz, 1H), 7.55 (dd, J=28.2, 8.7 Hz, 3H), 7.25-6.94 (m, 3H), 3.60 (dd, J=6.6, 3.7 Hz, 4H), 3.30 (dd, J=6.5, 3.8 Hz, 4H).

Example 15

N-(5-hydroxypyridin-2-yl)-4-(4-methoxyphenyl)piperazine-1-carboxamide

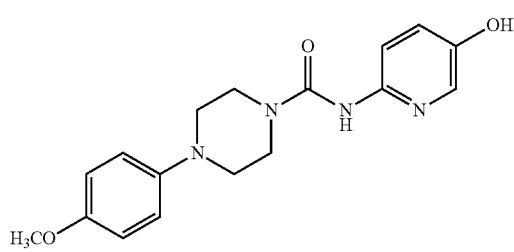

Step 1: Synthesis of N-[5-[(tert-butyldimethylsilyl)oxy]pyridin-2-yl]-4-(4-methoxyphenyl)piperazine-1-carboxamide

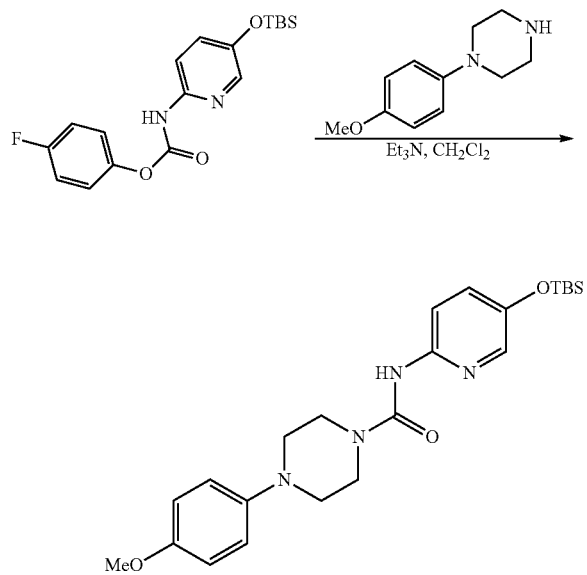

A solution of Intermediate "A" (200 mg, 0.55 mmol), 1-(4-methoxyphenyl)piperazine (318 mg, 1.65 mmol), and Et₃N (170 mg, 1.68 mmol) in CH₂Cl₂ (5 mL) was stirred for 16 h at RT, then extracted with 2×20 mL of CH₂Cl₂. The combined organic layers were concentrated under vacuum and purified with silica gel column chromatography using EtOAc/hexane (1:2) to afford 230 mg (94%) of the title compound as an off-white solid. LC-MS: (ES, m/z): 443.

Step 2: Synthesis of N-(5-hydroxypyridin-2-yl)-4-(4-methoxyphenyl)piperazine-1-carboxamide

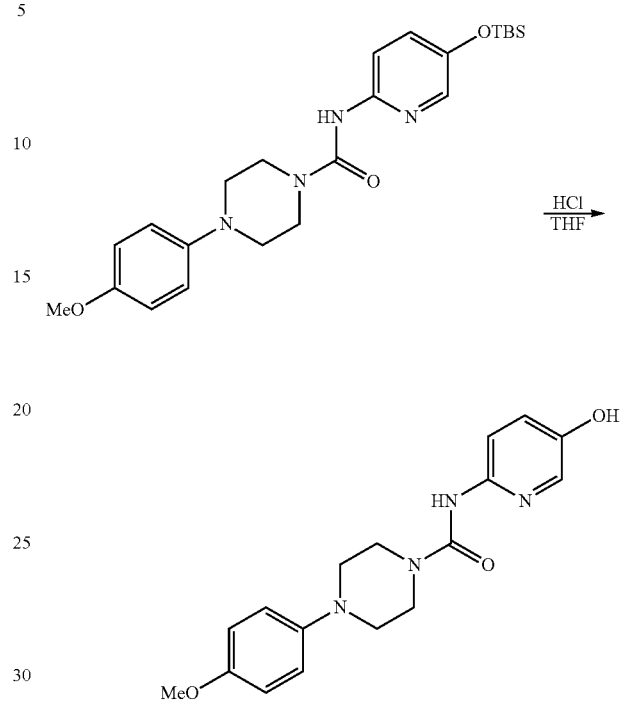

A solution of the product from the previous step (230 mg, 0.52 mmol) in 2 N aq. HCl (4 mL) and THF (2 mL) was stirred for 2 h at rt, then concentrated under vacuum. The crude product (230 mg) was purified with Prep-HPLC using the following conditions: Instrument "B"; Column "B"; mobile phase, 10 mM aq NH₄HCO₃ and ACN (5.0% ACN up to 70.0% in 7 min), to afford 84.2 mg (49%) of the title compound as an off-white solid.

LC-MS: (ES, m/z): 329

¹H NMR (300 MHz, DMSO-d₆) δ 9.37 (s, 1H), 8.89 (s, 1H), 7.79 (dd, J=2.9, 0.7 Hz, 1H), 7.59 (dd, J=9.0, 0.7 Hz, 1H), 7.13 (dd, J=9.0, 2.9 Hz, 1H), 6.99-6.88 (m, 2H), 6.88-6.78 (m, 2H), 3.68 (s, 3H), 3.58 (t, J=5.0 Hz, 4H), 2.98 (dd, J=6.0, 3.7 Hz, 4H).

Example 16

N-(5-hydroxypyridin-2-yl)-4-(pyrimidin-2-yl)piperazine-1-carboxamide

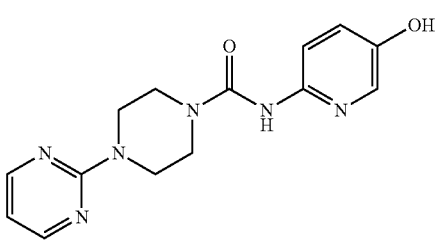 [SMILES: O=C(Nc1ccc(O)cn1)N1CCN(c2ncccn2)CC1]

Step 1: Synthesis of N-[5-[(tert-butyldimethylsilyl)oxy]pyridine-2-yl]-4-(pyrimidin-2-yl)piperazine-1-carboxamide

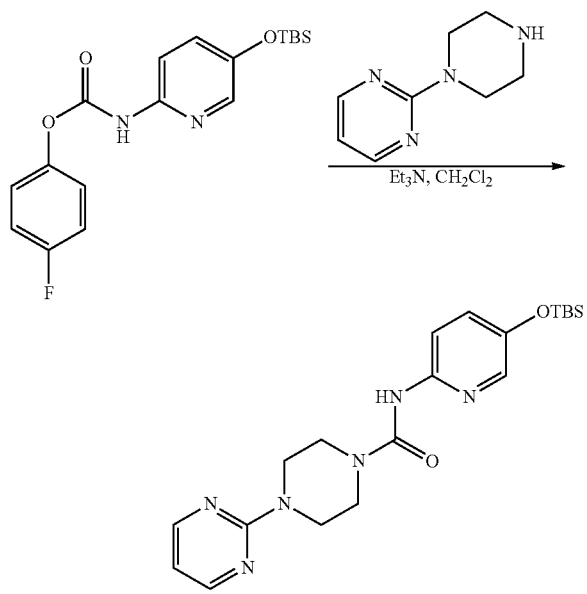

A solution of Intermediate "A" (200 mg, 0.55 mmol), 2-(piperazin-1-yl)pyrimidine (272 mg, 1.66 mmol), and Et₃N (170 mg, 3.00 eq) in CH₂Cl₂ (5 mL) was stirred for 16 h at rt, then extracted with 2×30 mL of CH₂Cl₂. The combined organic layers were concentrated under vacuum and purified with silica gel column chromatography using EtOAc/hexane (1:2) to afford 200 mg (87%) of the title compound as an off-white solid. LC-MS: (ES, m/z): 415.

Step 2: Synthesis of N-(5-hydroxypyridin-2-yl)-4-(pyrimidin-2-yl)piperazine-1-carboxamide

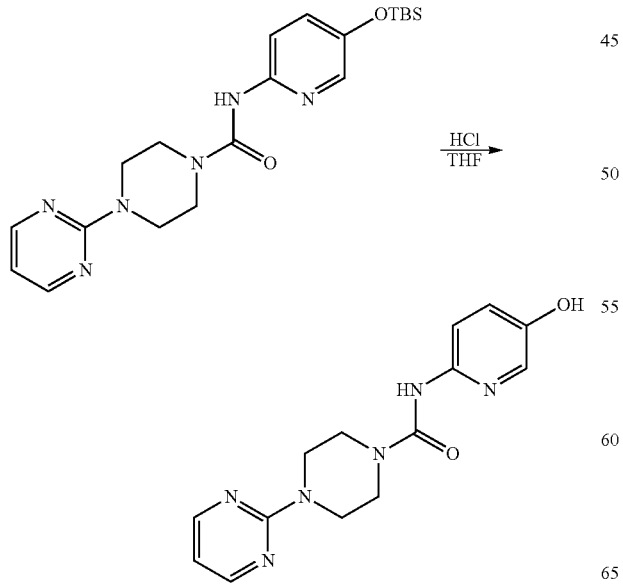

A solution of the product from the previous step (200 mg, 0.48 mmol) in 2N aq. HCl (2 mL) and THF (4 mL) was stirred for 2 h at rt. The crude product (200 mg) was purified with Prep-HPLC using the following conditions: Instrument "B"; Column "B"; mobile phase, 10 mM aq NH₄HCO₃ and ACN (7.0% ACN up to 60.0% in 7 min), to afford 77.2 mg (53%) of the title compound as an off-white solid.

LC-MS: (ES, m/z): 415

¹H NMR (300 MHz, Methanol-d₄) δ 8.36 (d, J=4.7 Hz, 2H), 7.83 (d, J=3.0 Hz, 1H), 7.52 (d, J=8.9 Hz, 1H), 7.21 (dd, J=8.9, 3.0 Hz, 1H), 6.64 (t, J=4.8 Hz, 1H), 3.94-3.83 (m, 4H), 3.68-3.58 (m, 4H).

Example 17

N-(5-hydroxypyridin-2-yl)-4-(pyridin-2-yl)piperazine-1-carboxamide

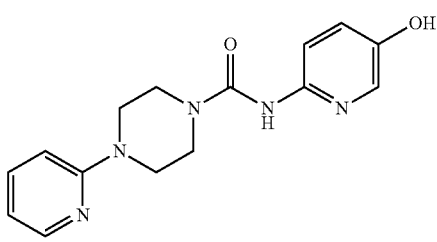 [SMILES: O=C(Nc1ccc(O)cn1)N1CCN(c2ccccn2)CC1]

Step 1: Synthesis of N-[5-[(tert-butyldimethylsilyl)oxy]pyridin-2-yl]-4-(pyridin-2-yl)piperazine-1-carboxamide

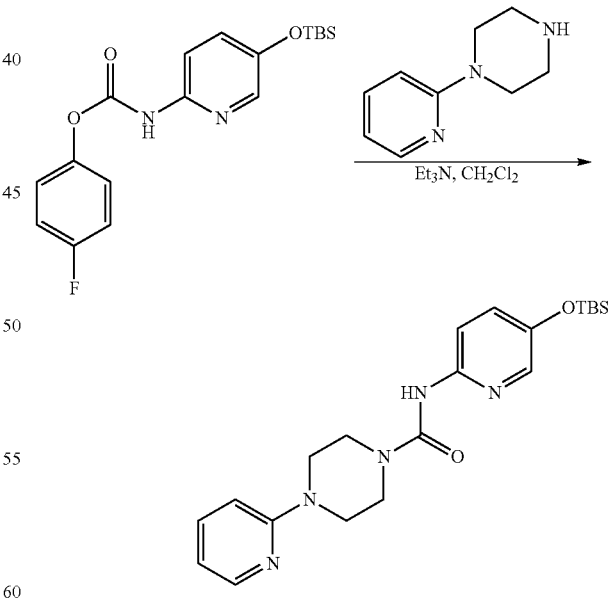

A solution of Intermediate "A" (200 mg, 0.55 mmol), 1.68 mmol), 1-(pyridin-2-yl)piperazine (270 mg, 1.65 mmol), and Et₃N (170 mg) in CH₂Cl₂ (5 mL) was stirred for 16 h at rt, then extracted with 2×20 mL of CH₂Cl₂. The combined organic layers were concentrated under vacuum and purified with silica gel column chromatography using EtOAc/hexane (1:2) to afford 220 mg (96%) of the title compound as an off-white solid. LC-MS: (ES, m/z): 414.

Step 2: Synthesis of N-(5-hydroxypyridin-2-yl)-4-(pyridin-2-yl) piperazine-1-carboxamide

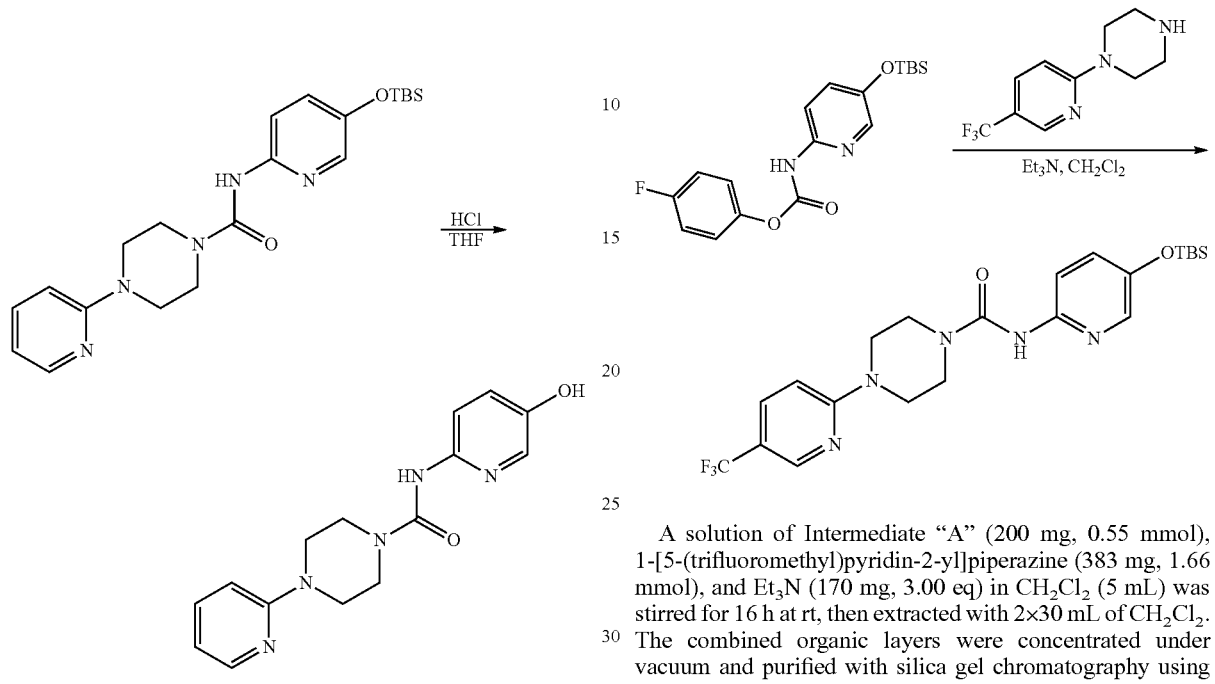

A solution of the product from the previous step (220 mg, 0.53 mmol) in 2 N aq. HCl (1 mL) and THF (2 mL) was stirred for 2 h at rt, then concentrated under vacuum. The crude product (220 mg) was purified by Prep-HPLC with the following conditions: Instrument "B"; Column "B"; mobile phase, 10 mM aq $NH_4HCO_3$ and ACN (7.0% ACN up to 60.0% in 7 min), to afford 90.5 mg (57%) of the title compound as an off-white solid.

LC-MS: (ES, m/z): 300

$^1$H NMR (300 MHz, DMSO-$d_6$) δ 9.41 (s, 1H), 8.89 (s, 1H), 8.12 (ddd, J=4.9, 2.0, 0.8 Hz, 1H), 7.79 (d, J=2.9 Hz, 1H), 7.64-7.48 (m, 2H), 7.13 (dd, J=8.9, 3.0 Hz, 1H), 6.85 (d, J=8.6 Hz, 1H), 6.70-6.60 (m, 1H), 3.52 (m, 8H).

Example 18

N-(5-hydroxypyridin-2-yl)-4-[5-(trifluoromethyl)pyridin-2-yl]piperazine-1-carboxamide

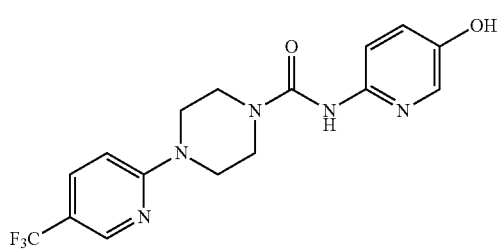

Step 1: Synthesis of N-[5-[(tert-butyldimethylsilyl)oxy]pyridin-2-yl]-4-[5-(trifluoromethyl)pyridin-2-yl]piperazine-1-carboxamide

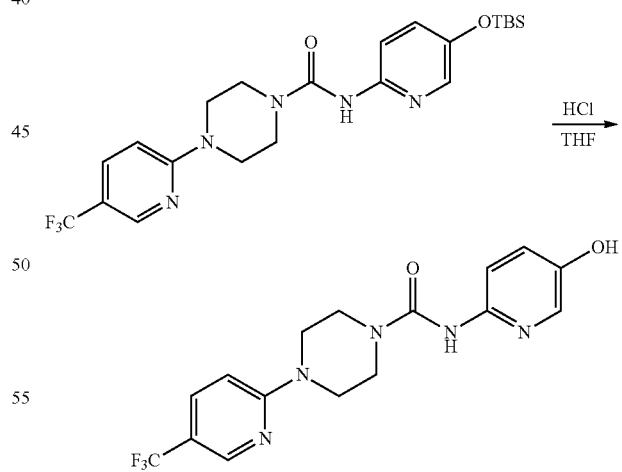

A solution of Intermediate "A" (200 mg, 0.55 mmol), 1-[5-(trifluoromethyl)pyridin-2-yl]piperazine (383 mg, 1.66 mmol), and $Et_3N$ (170 mg, 3.00 eq) in $CH_2Cl_2$ (5 mL) was stirred for 16 h at rt, then extracted with 2×30 mL of $CH_2Cl_2$. The combined organic layers were concentrated under vacuum and purified with silica gel chromatography using EtOAc/hexane (1:2) to afford 200 mg (75%) of the title compound as an off-white solid. LC-MS: (ES, m/z): 482.

Step 2: Synthesis of N-(5-hydroxypyridin-2-yl)-4-[5-(trifluoromethyl)pyridin-2-yl]piperazine-1-carboxamide A solution of the product from the previous step (200 mg, 0.42 mmol) in 2N aq. HCl (1 mL) and THF (2 mL) was stirred for 2 h at rt, then concentrated under vacuum. The crude product (200 mg) was purified with Prep-HPLC using the following conditions: Instrument "B"; Column "A"; mobile phase, 10 mM aq $NH_4HCO_3$ and ACN (20.0% ACN up to 55.0% in 7 min), to afford 80 mg (52%) of the title compound as an off-white solid LC-MS: (ES, m/z): 368
¹H NMR (300 MHz, DMSO-d₆) δ 9.44 (s, 1H), 8.92 (s, 1H), 8.42 (d, J=2.3 Hz, 1H), 7.80 (dd, J=7.6, 2.7 Hz, 2H), 7.60 (d, J=8.9 Hz, 1H), 7.14 (dd, J=8.9, 3.0 Hz, 1H), 6.98 (d, J=9.1 Hz, 1H), 3.71-3.51 (m, 8H).

Example 19

3-(5-hydroxypyridin-2-yl)-1-[(1r,4r)-4-phenylcyclohexyl]urea

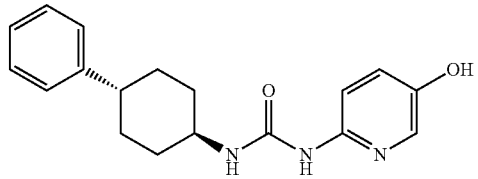 [SMILES: O=C(Nc1ccc(O)cn1)N[C@H]1CC[C@H](c2ccccc2)CC1]

Step 1: Synthesis of N-benzyl-4-phenylcyclohexan-1-amine

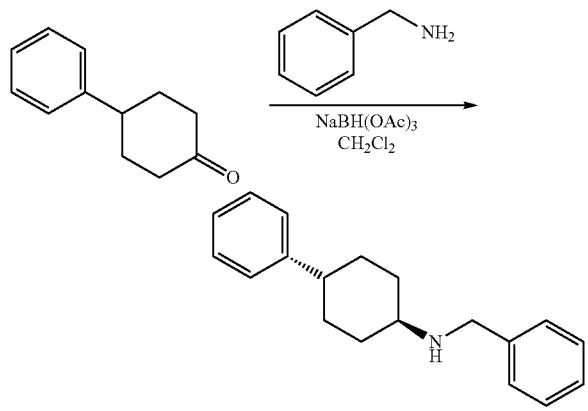

A solution of 4-phenylcyclohexan-1-one (8.1 g, 46.49 mmol, 1.00 eq), benzylamine (5 g, 46.66 mmol, 1.00 eq), and NaBH(OAc)₃ (19.8 g, 93.42 mmol, 2.00 eq) in CH₂Cl₂ (100 g) was stirred for 16 h at rt, then extracted with 2×300 mL of EtOAc. The combined organic layers were concentrated under vacuum and purified with silica gel chromatography using EtOAc/hexane (1:2) to afford 4 g (32%) of the title compound as an off-white solid. LC-MS: (ES, m/z): 266

Step 2: Synthesis of 4-phenylcyclohexan-1-amine

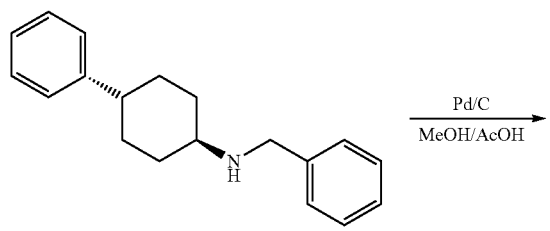

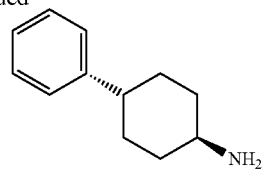

A solution of the product from the previous step (500 mg, 1.88 mmol, 1.00 eq) and AcOH (1 mg) in MeOH (10 mg) was stirred over Pd/C (100 mg) for 16 h at 30° C. The solids were removed by filtration, and the filtrate was concentrated under vacuum to afford 300 mg (91%) of the title compound as an off-white solid. LC-MS: (ES, m/z): 176.

Step 3: Synthesis of 3-[5-[(tert-butyldimethylsilyl)oxy]pyridin-2-yl]-1-[(1r,4r)-4-phenylcyclohexyl]urea

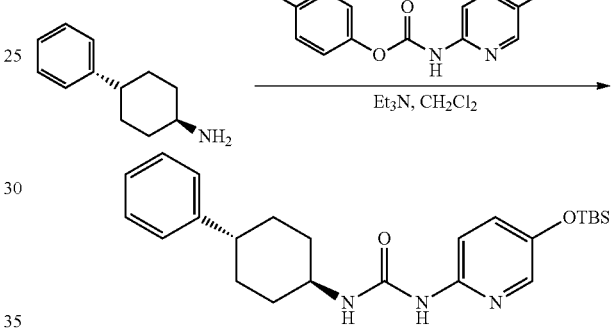

A solution of the product from the previous step (300 mg, 1.71 mmol), Intermediate "A" (186 mg, 0.51 mmol), and Et₃N (173 mg, 1.71 mmol) in CH₂Cl₂ (5 mL) was stirred for 16 h at rt, then extracted with 50 mL of EtOAc. The combined organic layers were concentrated under vacuum and purified with silica gel chromatography using EtOAc/hexane (1:1) to afford 220 mg (30%) of the title compound as an off-white solid. LC-MS: (ES, m/z): 426.

Step 4: Synthesis of 3-(5-hydroxypyridin-2-yl)-1-[(1r,4r)-4-phenylcyclohexyl]urea

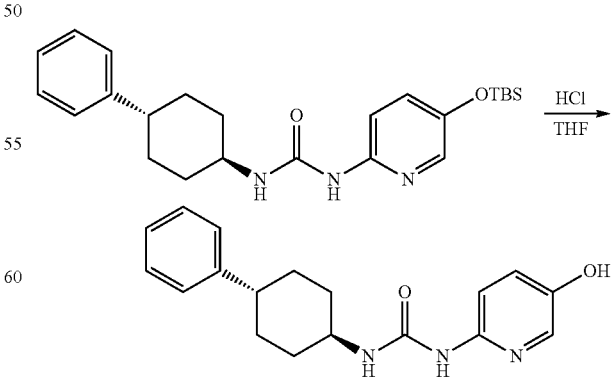

A solution of the product from the previous step (220 mg, 0.52 mmol) in 2 N aq. HCl (1 mL) and THF (2 mL) was stirred for 2 h at rt, then concentrated under vacuum. The crude product (220 mg) was purified by Prep-HPLC with the following conditions: Instrument "B"; Column "A"; mobile phase, 10 mM aq NH$_4$HCO$_3$ and ACN (25.0% ACN up to 60.0% in 7 min), affording 43.4 mg (26%) of the title compound as an off-white solid.

LC-MS: (ES, m/z): 312

$^1$H NMR (300 MHz, DMSO-d$_6$) δ 9.37 (s, 1H), 8.74 (s, 1H), 7.74 (t, J=5.7 Hz, 2H), 7.27 (p, J=7.2, 6.1 Hz, 7H), 7.23-7.09 (m, 1H), 3.57 (br, 1H), 2.51 (s, 1H), 2.02 (m, 2H), 1.83 m, 2H), 1.56 (br q, J=12.6 Hz, 2H), 1.32 (br q, J=12.8 Hz, 2H).

Example 20

3-(5-Hydroxypyridin-2-yl)-1-(oxan-4-yl)urea

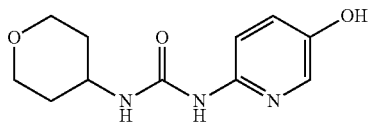 [SMILES: O=C(Nc1ccc(O)cn1)NC1CCOCC1]

Step 1: Synthesis of 3-[5-[(tert-butyldimethylsilyl)oxy]pyridin-2-yl]-1-(oxan-4-yl)urea

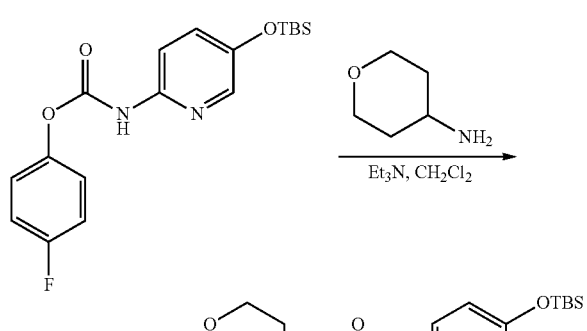

A solution of Intermediate "A" (200 mg, 0.55 mmol), oxan-4-amine (167 mg, 1.65 mmol), and Et$_3$N (170 mg) in CH$_2$Cl$_2$ (5 mL) was stirred for 16 h at rt, then extracted with 2×30 mL of CH$_2$Cl$_2$. The combined organic layers were concentrated under vacuum and purified with silica gel chromatography using EtOAc/hexane (1:2) to afford 190 mg (98%) of the title compound as an off-white solid. LC-MS: (ES, m/z): 352.

Step 2. Synthesis of 3-(5-hydroxypyridin-2-yl)-1-(oxan-4-yl)urea

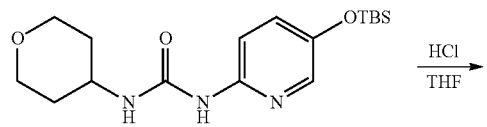

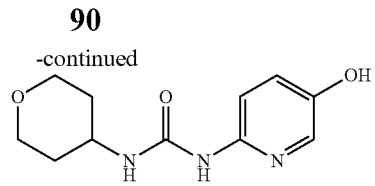

A solution of the product from the previous step (190 mg, 0.54 mmol) in 2 N aq. HCl (1 mL) and THF (2 mL) was stirred for 2 h at rt, then concentrated under vacuum. The crude product (190 mg) was purified by Prep-HPLC with the following conditions: Instrument "B"; Column "A"; mobile phase, 10 mM aq NH$_4$HCO$_3$ and ACN (5.0% ACN up to 25.0% in 7 min), affording 55 mg (43%) of the title compound as an off-white solid.

LC-MS: (ES, m/z): 238

$^1$H NMR (300 MHz, DMSO-d$_6$) δ 9.27 (s, 1H), 8.75 (s, 1H), 7.85 (d, J=7.3 Hz, 1H), 7.72 (d, J=2.9 Hz, 1H), 7.25 (d, J=8.9 Hz, 1H), 7.13 (dd, J=8.9, 2.9 Hz, 1H), 3.88-3.78 (m, 2H), 3.78-3.68 (m, 1H), 3.46-3.31 (m, 2H), 1.87-1.73 (m, 2H), 1.38 (m, 2H).

Example 21

1-cyclohexyl-3-(5-hydroxypyridin-2-yl)urea

Step 1. Synthesis of 3-[5-[(tert-butyldimethylsilyl)oxy]pyridin-2-yl]-1-cyclohexylurea

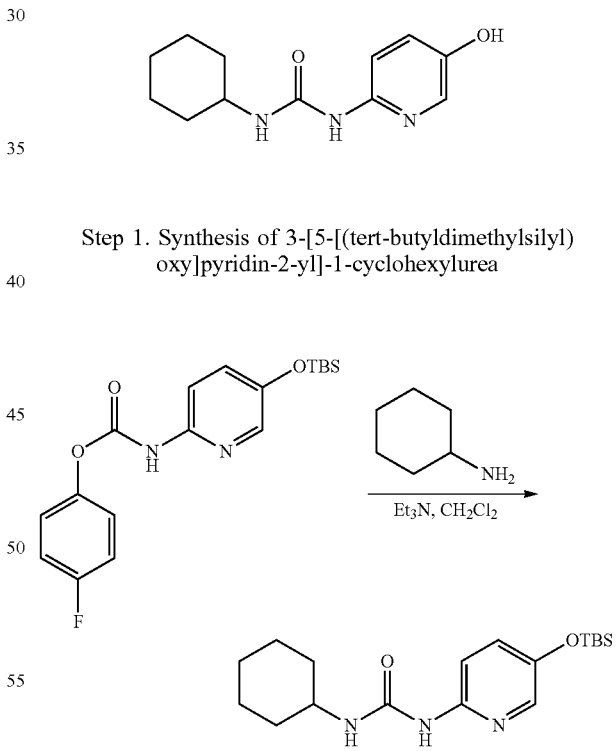

A solution of Intermediate "A" (200 mg, 0.55 mmol), cyclohexanamine (162 mg, 1.63 mmol), and Et$_3$N (170 mg) in CH$_2$Cl$_2$ (5 mL) was stirred for 16 h at rt, then extracted with 2×30 mL of CH$_2$Cl$_2$. The combined organic layers were concentrated under vacuum and purified with silica gel chromatography using EtOAc/hexane (1:2) to afford 180 mg (93%) of the title compound as an off-white solid. LC-MS: (ES, m/z): 350.

Step 2. Synthesis of 1-cyclohexyl-3-(5-hydroxypyridin-2-yl)urea

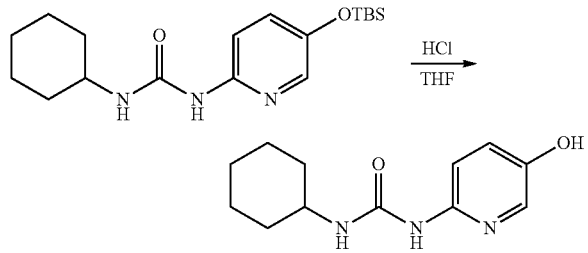

A solution of the product from the previous step (180 mg, 0.51 mmol) in 2 N aq. HCl (1 mL) and THF (2 mL) was stirred for 2 h at rt, then concentrated under vacuum. The crude product (180 mg) was purified by Prep-HPLC with the following conditions: Instrument "B"; Column "A"; mobile phase, 10 mM aq NH$_4$HCO$_3$ and ACN (10.0% ACN up to 52.0% in 7 min), affording 56 mg (46%) of the title compound as an off-white solid.

LC-MS: (ES, m/z): 236

$^1$H NMR (300 MHz, DMSO-d$_6$) δ 9.33 (s, 1H), 8.72 (s, 1H), 7.85-7.75 (m, 1H), 7.70 (d, J=2.9 Hz, 1H), 7.23 (d, J=8.9 Hz, 1H), 7.12 (dd, J=8.9, 2.9 Hz, 1H), 3.52 (tp, J=10.0, 3.7 Hz, 1H), 1.86-1.73 (m, 2H), 1.65 (m, 2H), 1.52 (dd, J=11.9, 5.8 Hz, 1H), 1.25 (m, 5H).

Example 22

4-(5-chloropyridin-2-yl)-N-(5-hydroxypyridin-2-yl)piperazine-1-carboxamide

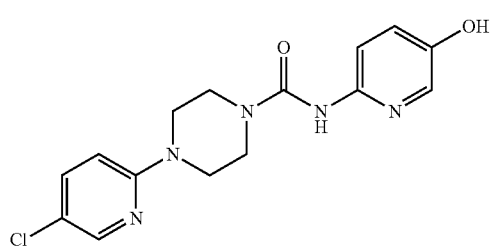

Step 1. Synthesis of N-[5-[(tert-butyldimethylsilyl)oxy]pyridin-2-yl]-4-(5-chloropyridin-2-yl)piperazine-1-carboxamide

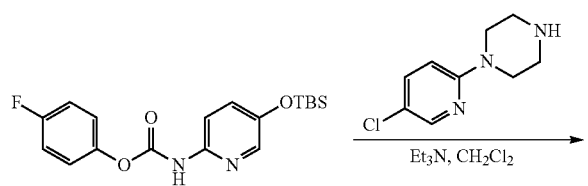

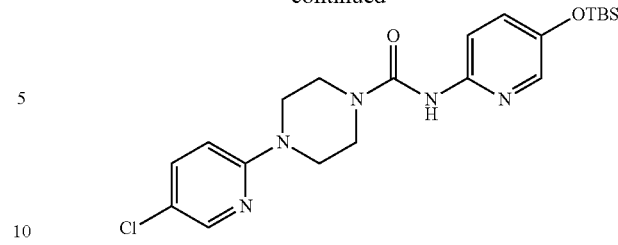

A solution of Intermediate "A" (150 mg, 0.41 mmol, 1.00 equiv), and 1-(5-chloropyridin-2-yl)piperazine (82 mg, 0.41 mmol, 1.00 equiv), and Et$_3$N (126 mg, 1.25 mmol, 3.00 equiv) in CH$_2$Cl$_2$ (5 mL) at 0° C. was allowed to warm to rt with stirring for 16, then concentrated under vacuum and purified with silica gel chromatography using with EtOAc/hexane (1/2) to afford 160 mg (86%) of the title compound as an off-white solid. LC-MS: (ES, m/z): 448.

Step 2. Synthesis of 4-(5-chloropyridin-2-yl)-N-(5-hydroxypyridin-2-yl)piperazine-1-carboxamide

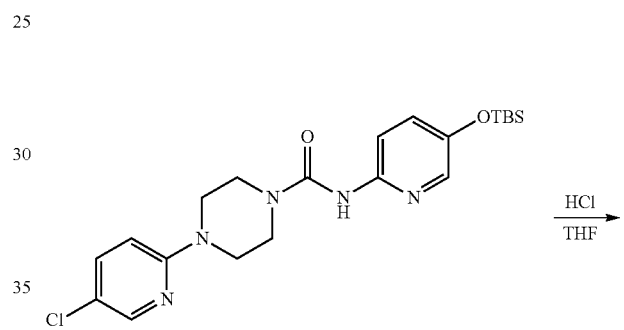

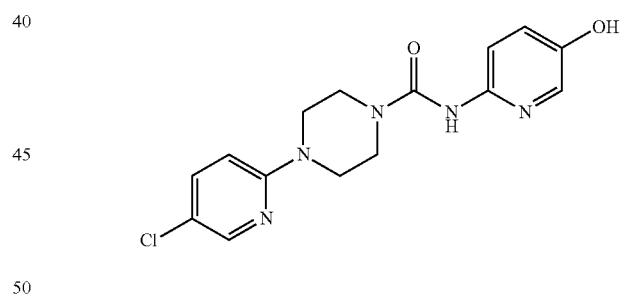

To a solution of the product from the previous step (160 mg, 0.36 mmol) in THF (2 mL) was added 2N HCl (1 mL) at rt. The resulting solution was stirred for 1 h at RT, then concentrated under vacuum. The crude product (160 mg) was purified by Prep-HPLC under the following conditions: Instrument "A"; Column "A"; mobile phase, 10 mM aq NH$_4$HCO$_3$ and ACN (31.0% ACN up to 32.0% in 7 min), to afford 74.3 mg (62%) of the title compound as an off-white solid.

LC-MS: (ES, m/z): 334

$^1$H NMR (400 MHz, DMSO-d$_6$) δ 9.45 (s, 1H), 8.89 (s, 1H), 8.12 (d, J=2.7 Hz, 1H), 7.79 (d, J=2.9 Hz, 1H), 7.68-7.53 (m, 2H), 7.14 (dd, J=8.9, 3.0 Hz, 1H), 6.90 (d, J=9.1 Hz, 1H), 3.63-3.46 (m, 8H).

Example 23

4-(2,4-dichlorophenyl)-N-(5-hydroxypyridin-2-yl)piperazine-1-carboxamide

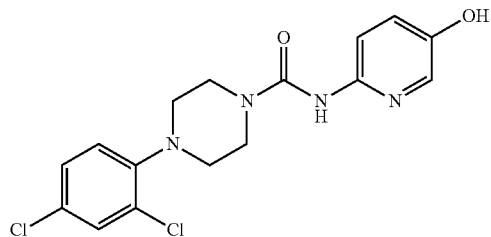

Step 1. Synthesis of tert-butyl 4-(2,4-dichlorophenyl)piperazine-1-carboxylate

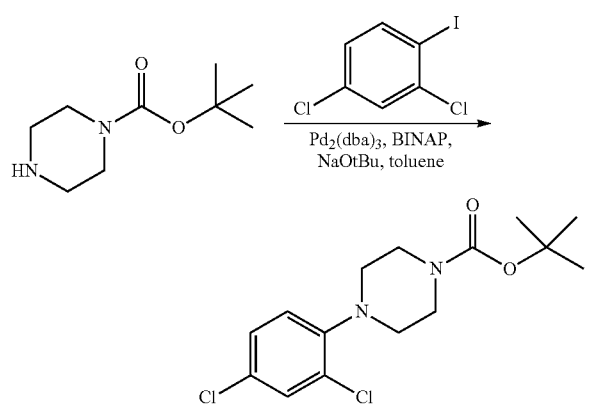

A solution of tert-butyl piperazine-1-carboxylate (2 g, 17.54 mmol), 1-bromo-3,5-dichlorobenzene (4 g, 17.71 mmol), NaOtBu (2.5 g), BINAP (108 mg, 0.17 mmol), Pd$_2$(dba)$_3$ (160 mg, 0.17 mmol, 0.01 equiv) in toluene (20 mL) was stirred under N$_2$ for 16 h at 80° C., then quenched by the addition of 50 mL of H$_2$O, and extracted with 2×60 mL of EtOAc. The combined organic layers were concentrated under vacuum and purified with silica gel chromatography using EtOAc/hexane (1/2) to afford 3.3 g (57%) of the title compound as an off-white solid.

LC-MS: (ES, m/z): 331

$^1$H NMR (400 MHz, DMSO-d$_6$) δ 7.56 (d, J=2.5 Hz, 1H), 7.37 (dd, J=8.7, 2.5 Hz, 1H), 7.17 (d, J=8.7 Hz, 1H), 3.47 (t, J=4.9 Hz, 4H), 2.90 (t, J=5.0 Hz, 4H), 1.42 (s, 9H).

Step 2. Synthesis of 1-(2,4-dichlorophenyl)piperazine

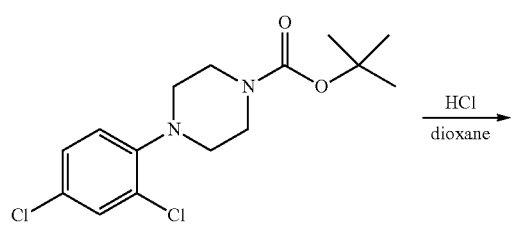

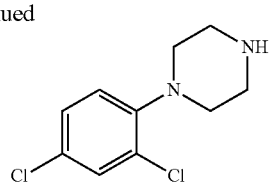

To a solution of the product from the previous step (1 g, 3.02 mmol) in 1,4-dioxane (6 mL) was added 4M HCl/dioxane (3 mL). The resulting solution was stirred for 6 h at rt, then concentrated under vacuum to afford 200 mg (29%) of the title compound as a light yellow solid.

LC-MS: (ES, m/z): 231

$^1$H NMR (400 MHz, DMSO-d$_6$) δ 7.52 (d, J=2.5 Hz, 1H), 7.35 (dd, J=8.7, 2.5 Hz, 1H), 7.13 (d, J=8.7 Hz, 1H), 2.85 (hept, J=3.3 Hz, 8H).

Step 3. Synthesis of N-[5-[(tert-butyldimethylsilyl)oxy]pyridin-2-yl]-4-(2,4-dichlorophenyl)piperazine-1-carboxamide

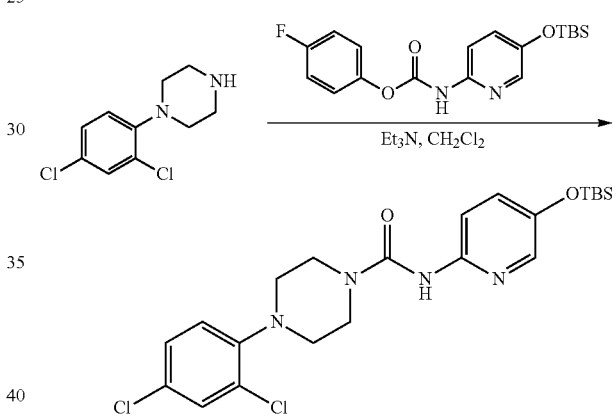

A solution of the product from the previous step (150 mg, 0.40 mmol), Et$_3$N (126 mg, 1.25 mmol), and 1-(2,4-dichlorophenyl)piperazine (114 mg, 0.49 mmol) in CH$_2$Cl$_2$ (5 mL) was stirred for 16 h at rt, then quenched by the addition of 20 mL H$_2$O and extracted with 2×20 mL of EtOAc. The combined organic layers were purified with silica gel column chromatography using EtOAc/hexane (1/2) to afford 180 mg (93%) of the title compound as an off-white solid.

LC-MS: (ES, m/z): 481.

Step 4. Synthesis of 4-(2,4-dichlorophenyl)-N-(5-hydroxypyridin-2-yl)piperazine-1-carboxamide

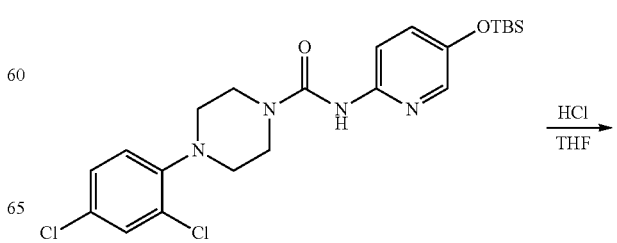

-continued

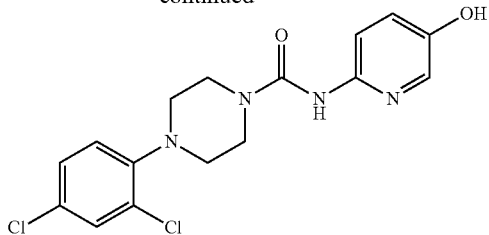

To a solution of the product from the previous step (180 mg, 0.37 mmol, 1.00 equiv) in THF (2 mL) was added 2N aq. HCl (1 mL) dropwise with stirring. The resulting solution was stirred for 1 h at rt, then concentrated under vacuum. The crude product (180 mg) was purified by Prep-HPLC with the following conditions: Instrument "A"; Column "A"; mobile phase, 10 mM aq $NH_4HCO_3$ and ACN (35.0% ACN up to 64.0% in 8 min); Detector, UV 254/220 nm, to afford 73.0 mg (53%) of the title compound as an off-white solid.

LC-MS: (ES, m/z): 367

$^1$H NMR (400 MHz, DMSO-$d_6$) δ 9.44 (s, 1H), 8.89 (s, 1H), 7.80 (d, J=3.0 Hz, 1H), 7.71-7.53 (m, 2H), 7.37 (dd, J=8.6, 2.5 Hz, 1H), 7.28-7.09 (m, 2H), 3.60 (m, 4H), 2.95 (m, 4H).

Example 24

4-(5-fluoropyridin-2-yl)-N-(5-hydroxypyridin-2-yl)piperazine-1-carboxamide

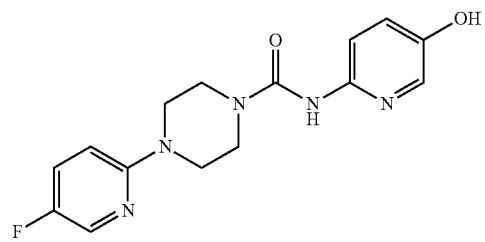

Step 1. Synthesis of N-[5-[(tert-butyldimethylsilyl)oxy]pyridin-2-yl]-4-(5-fluoropyridin-2-yl) piperazine-1-carboxamide

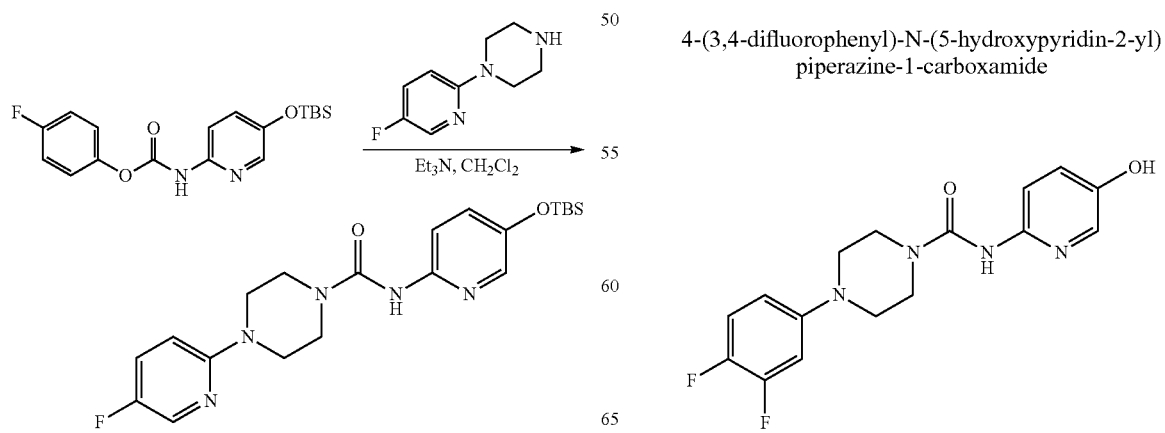

A solution of Intermediate "A" (150 mg, 0.41 mmol), 1-(5-fluoropyridin-2-yl)piperazine (75 mg, 0.41 mmol), and $Et_3N$ (126 mg, 1.25 mmol) in $CH_2Cl_2$ (5 mL) was stirred for 16 h at rt, then extracted with 2×20 mL of EtOAc. The combined organic layers were purified with silica gel chromatography using EtOAc/hexane (1/2) to afford 150 mg (84%) of the title compound as an off-white solid. LC-MS: (ES, m/z): 432

Step 2. Synthesis of 4-(5-fluoropyridin-2-yl)-N-(5-hydroxypyridin-2-yl)piperazine-1-carboxamide

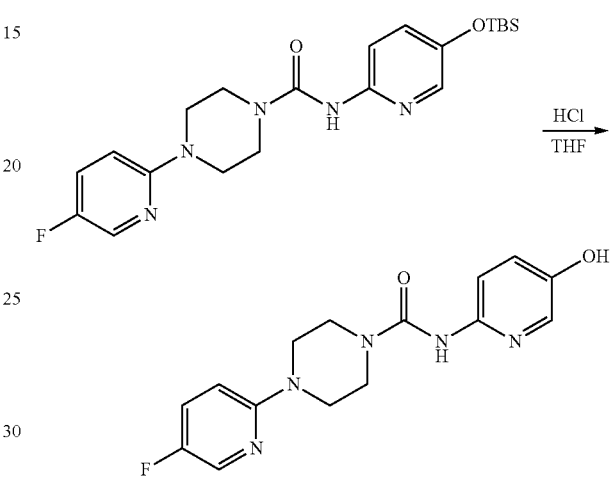

To a solution of the product from the previous step (150 mg, 0.35 mmol) in THF (2 mL) was added 2N aq. HCl (1 mL) at rt. The resulting solution was stirred for 1 h at rt, then concentrated under vacuum. The crude product (150 mg) was purified by Prep-HPLC with the following conditions: Instrument "A"; Column "B"; mobile phase, 10 mM aq $NH_4HCO_3$ and ACN (23.0% ACN up to 45.0% in 7 min), to afford 54.7 mg (50%) of the title compound as an off-white solid.

LC-MS: (ES, m/z): 318

$^1$H NMR (400 MHz, DMSO-$d_6$) δ 9.36 (br, 1H), 8.90 (s, 1H), 8.11 (d, J=3.1 Hz, 1H), 7.79 (d, J=2.9 Hz, 1H), 7.69-7.46 (m, 2H), 7.14 (dd, J=8.9, 3.0 Hz, 1H), 6.92 (dd, J=9.3, 3.5 Hz, 1H), 3.51 (m, 8H).

Example 25

4-(3,4-difluorophenyl)-N-(5-hydroxypyridin-2-yl)piperazine-1-carboxamide

Step 1. Synthesis of tert-butyl 4-(3,4-difluorophenyl)piperazine-1-carboxylate

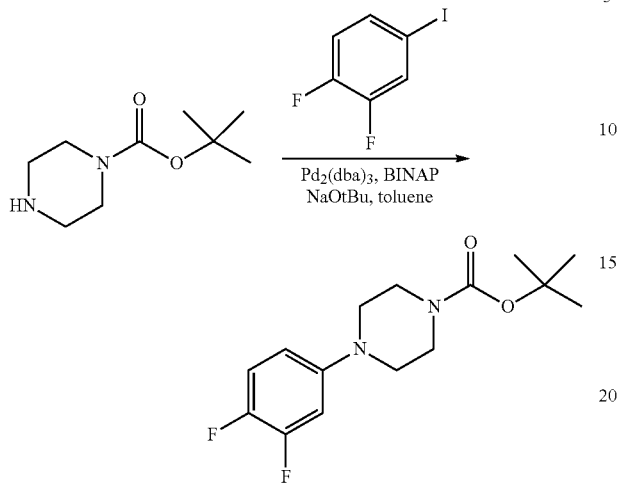

A solution of tert-butyl piperazine-1-carboxylate (2 g, 17.54 mmol) 1,2-difluoro-4-iodobenzene (4.2 g, 17.50 mmol), NaOtBu (2.5 g), BINAP (108 mg, 0.17 mmol, 0.01 equiv), and Pd$_2$(dba)$_3$ (160 mg, 0.17 mmol) in toluene (20 mL), at RT was stirred under N$_2$ for 16 h at 80° C. The reaction was then quenched by the addition of 40 mL H$_2$O, then extracted with 4×50 mL of EtOAc. The combined organic layers were concentrated under vacuum and purified with silica gel chromatography using EtOAc/hexane (1/2) to afford 3.2 g (61%) of the title compound as an off-white solid.

LC-MS: (ES, m/z): 299

$^1$H NMR (400 MHz, DMSO-d$_6$) δ 7.25 (dt, J=10.6, 9.3 Hz, 1H), 7.00 (ddd, J=14.2, 7.1, 3.0 Hz, 1H), 6.74 (dtd, J=9.1, 3.3, 1.4 Hz, 1H), 3.43 (t, J=5.2 Hz, 4H), 3.07 (dd, J=6.3, 4.2 Hz, 4H), 1.42 (s, 9H).

Step 2. Synthesis of 1-(3,4-difluorophenyl)piperazine

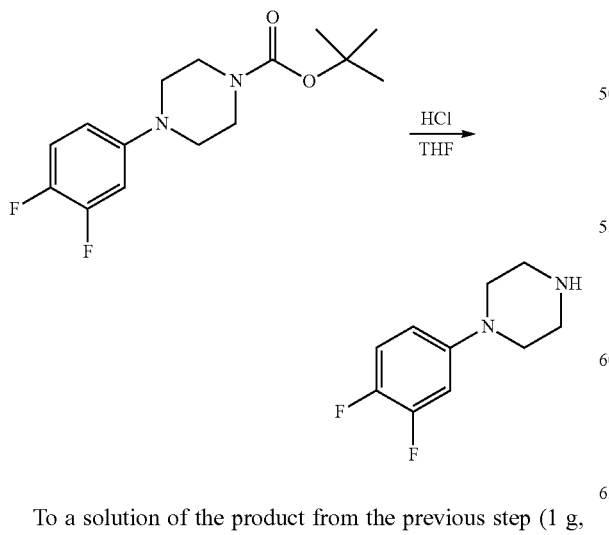

To a solution of the product from the previous step (1 g, 3.35 mmol) in 1,4-dioxane (6 mL) was added 4M HCl/dioxane (3 mL) dropwise with stirring. The resulting solution was stirred for 4 h at rt. The pH was adjusted to 7 with 2 N NaHCO$_3$. The resulting solution was extracted with 2×20 mL of EtOAc, and the combined organic layers were concentrated under vacuum to afford 640 mg (96%) of the title compound as an off-white solid.

LC-MS: (ES, m/z): 199

$^1$H NMR (400 MHz, DMSO-d$_6$) δ 7.22 (dt, J=10.6, 9.3 Hz, 1H), 6.94 (ddd, J=14.5, 7.1, 3.0 Hz, 1H), 6.69 (dtd, J=8.5, 3.3, 1.5 Hz, 1H), 3.06-2.93 (m, 4H), 2.87-2.72 (m, 4H).

Step 3. Synthesis of N-[5-[(tert-butyldimethylsilyl)oxy]pyridin-2-yl]-4-(3,4-difluorophenyl)piperazine-1-carboxamide

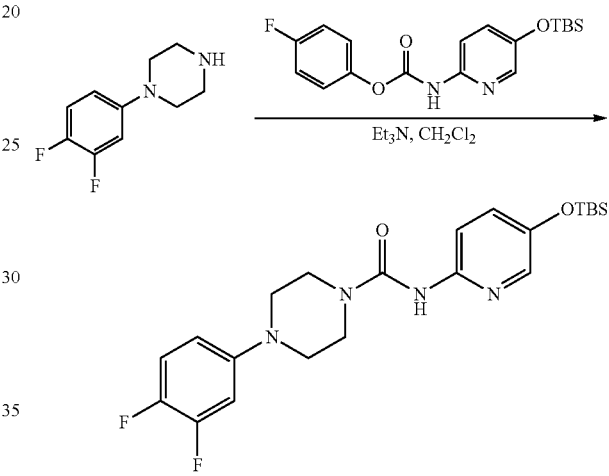

To a solution of the product from the previous step (150 mg, 0.41 mmol) and Et$_3$N (126 mg, 1.25 mmol) in CH$_2$Cl$_2$ (5 mL) was added of 1-(3,4-difluorophenyl)piperazine (98 mg, 0.49 mmol), in portions at rt. The resulting solution was stirred for 16 h at rt, then quenched by the addition of 20 mL H$_2$O. The resulting solution was extracted with 2×20 mL of EtOAc, and the combined organic layers were concentrated under vacuum and purified with silica gel chromatography using EtOAc/hexane (1/2) to afford 180 mg (97%) of the title compound as an off-white solid. LC-MS: (ES, m/z): 449

Step 4. Synthesis of 4-(3,4-difluorophenyl)-N-(5-hydroxypyridin-2-yl)piperazine-1-carboxamide

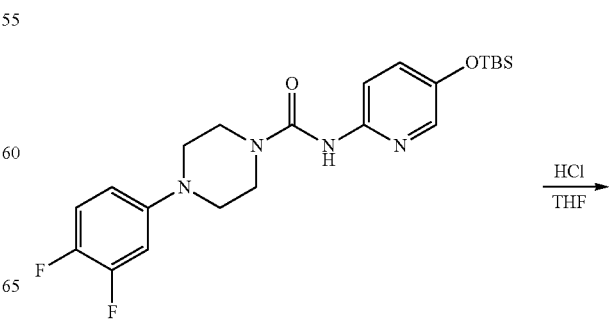

-continued

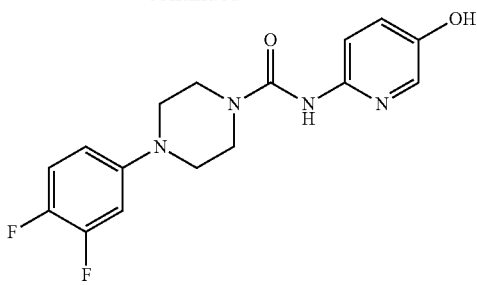

To a solution of the product from the previous step (180 mg, 0.40 mmol) in THF (2 mL) was added 2N aq. HCl (1 mL) dropwise with stirring at rt. The resulting solution was stirred for 1 h at rt, then concentrated under vacuum. The crude product (180 mg) was purified by Prep-HPLC with the following conditions: Instrument "A"; Column "A"; mobile phase, 10 mM aq NH$_4$HCO$_3$ and ACN (25.0% ACN up to 57.0% in 8 min), to afford 68.7 mg (51%) of the title compound as an off-white solid.

LC-MS: (ES, m/z): 335

$^1$H NMR (400 MHz, DMSO-d$_6$) δ 9.47 (s, 1H), 8.92 (s, 1H), 7.79 (d, J=2.9 Hz, 1H), 7.59 (d, J=8.9 Hz, 1H), 7.25 (q, J=9.7 Hz, 1H), 7.15 (d, J=3.1 Hz, 1H), 7.02 (ddd, J=14.2, 7.1, 3.0 Hz, 1H), 6.76 (dd, J=8.9, 4.1 Hz, 1H), 3.58 (m, 4H), 3.12 (m, 4H).

Example 26

4-(3,5-difluorophenyl)-N-(5-hydroxypyridin-2-yl)piperazine-1-carboxamide

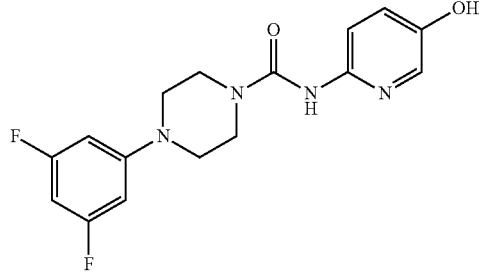

Step 1. Synthesis of tert-butyl 4-(3,5-difluorophenyl)piperazine-1-carboxylate

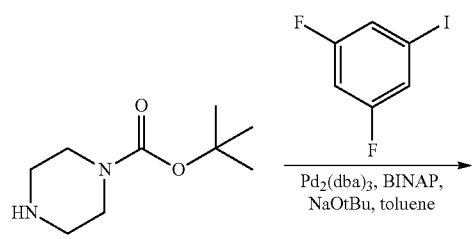

-continued

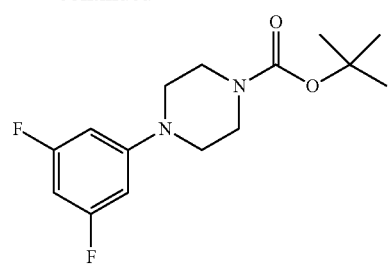

A solution of tert-butyl piperazine-1-carboxylate (2 g, 17.54 mmol), 1,3-difluoro-5-iodobenzene (4.2 g, 17.50 mmol), NaOtBu (2.5 g), BINAP (108 mg, 0.17 mmol), and Pd$_2$(dba)$_3$ (160 mg, 0.17 mmol) in toluene (20 mL) was stirred for 16 h at 80° C., then quenched by the addition of 40 mL H$_2$O. The resulting solution was extracted with 2×40 mL of EtOAc, and the combined organic layers were concentrated under vacuum and purified with silica gel chromatography using EtOAc/hexane (1/2) to afford 3.1 g (59%) of the title compound as an off-white solid.

LC-MS: (ES, m/z): 299

$^1$H NMR (400 MHz, DMSO-d$_6$) δ 6.69-6.57 (m, 2H), 6.49 (tt, J=9.3, 2.2 Hz, 1H), 3.42 (t, J=5.3 Hz, 4H), 3.26-3.13 (m, 4H), 1.42 (s, 9H).

Step 2. Synthesis of 1-(3,5-difluorophenyl)piperazine

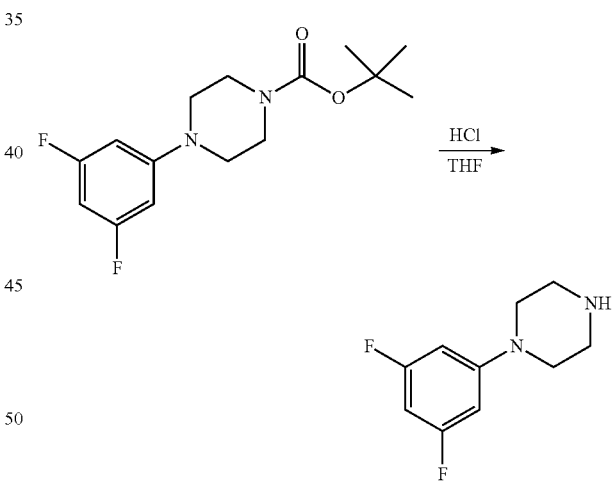

To a solution of the product from the previous step (1 g, 3.35 mmol) in 1,4-dioxane (6 mL) was added 4M HCl/dioxane (3 mL) dropwise with stirring. The resulting solution was stirred for 4 h at rt. The pH value was adjusted to 7 with 2 M NaHCO$_3$. The resulting solution was extracted with 2×40 mL of EtOAc, and the combined organic layers were concentrated under vacuum to afford 720 mg (108%) of the title compound as an off-white solid LC-MS: (ES, m/z): 199

$^1$H NMR (400 MHz, DMSO-d$_6$) δ 6.65-6.51 (m, 2H), 6.44 (tt, J=9.2, 2.2 Hz, 1H), 3.13-3.06 (m, 4H), 2.86-2.73 (m, 4H).

Step 3. Synthesis of N-[5-[(tert-butyldimethylsilyl) oxy]pyridin-2-yl]-4-(3,5-difluorophenyl)piperazine-1-carboxamide

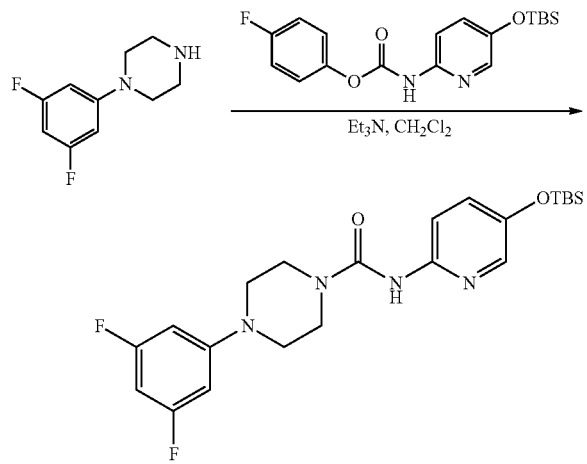

To a solution of the product from the previous step (150 mg, 0.41 mmol) and Et₃N (126 mg, 1.25 mmol) in CH₂Cl₂ (5 mL) was added 1-(3,5-difluorophenyl)piperazine (98 mg, 0.49 mmol), in portions at rt. The resulting solution was stirred for 16 h at rt, then then quenched by the addition of 20 mL H₂O and extracted with 2×20 mL of EtOAc. The combined organic layers were concentrated under vacuum and purified with silica gel chromatography using EtOAc/hexane (1/2) to afford 180 mg (97%) of the title compound as an off-white solid.

Step 4. Synthesis of 4-(3,5-difluorophenyl)-N-(5-hydroxypyridin-2-yl)piperazine-1-carboxamide

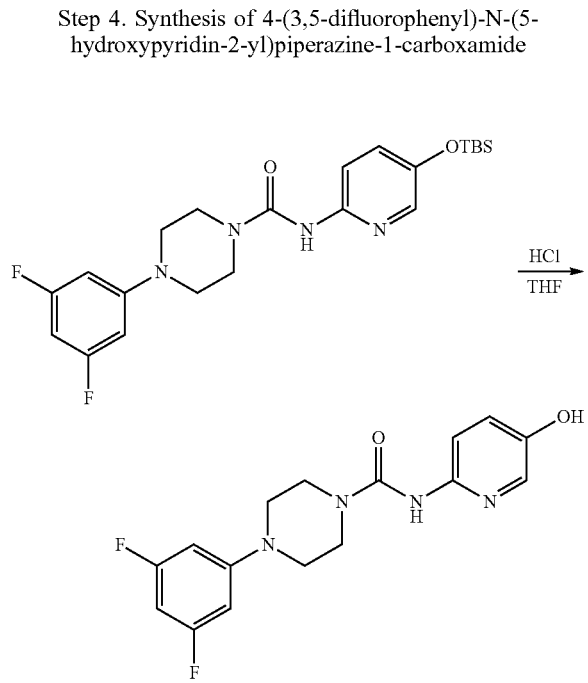

A solution of the product from the previous step (180 mg, 0.40 mmol) in 2N aq. HCl (1 mL) and THF (2 mL) was stirred for 1 h at rt, then concentrated under vacuum. The crude product (180 mg) was purified by Prep-HPLC with the following conditions: Instrument "A"; Column "A"; mobile phase, Water (10 mM NH₄HCO₃) and ACN (25.0% ACN up to 55.0% in 8 min), to afford 64 mg (48%) of the title compound as an off-white solid.

LC-MS: (ES, m/z): 335

¹H NMR (400 MHz, DMSO-d₆) δ 9.42 (s, 1H), 8.93 (s, 1H), 7.79 (d, J=2.9 Hz, 1H), 7.59 (d, J=8.9 Hz, 1H), 7.14 (dd, J=8.9, 3.0 Hz, 1H), 6.80-6.56 (m, 2H), 6.49 (tt, J=9.2, 2.2 Hz, 1H), 3.57 (m, 4H), 3.24 (m, 4H).

Example 27

4-(4-cyanophenyl)-N-(5-hydroxypyridin-2-yl)piperazine-1-carboxamide

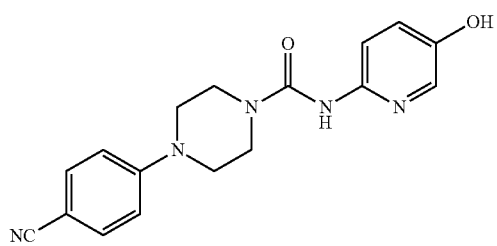

Step 1. Synthesis of N-[5-[(tert-butyldimethylsilyl)oxy]pyridin-2-yl]-4-(4-cyanophenyl)piperazine-1-carboxamide

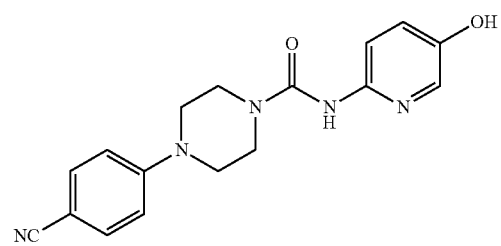

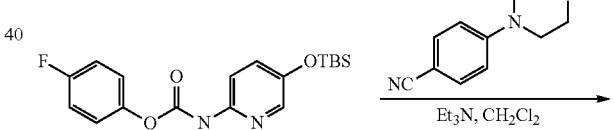

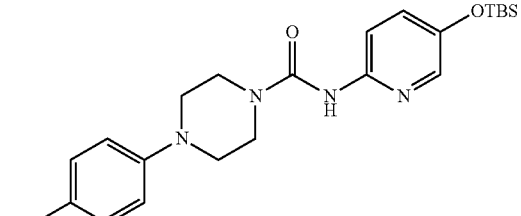

To a solution of Intermediate "A" (100 mg, 0.28 mmol) and Et₃N (84 mg, 0.83 mmol) in CH₂Cl₂ (5 mL) was added 4-(piperazin-1-yl)benzonitrile (52 mg, 0.28 mmol) at rt. The resulting solution was stirred for 16 h at rt, then quenched by the addition of H₂O and extracted with 2×mL of EtOAc. The combined organic layers were concentrated under vacuum and purified with silica gel chromatography using EtOAc/hexane (1/2) to afford 115 mg (95%) of the title compound as an off-white solid.

LC-MS: (ES, m/z): 438

Step 2. Synthesis of 4-(4-cyanophenyl)-N-(5-hydroxypyridin-2-yl)piperazine-1-carboxamide Step 1. Synthesis of N-[4-[(tert-butyldimethylsilyl)oxy]phenyl]-4-(2,4-difluorophenyl)piperazine-1-carboxamide

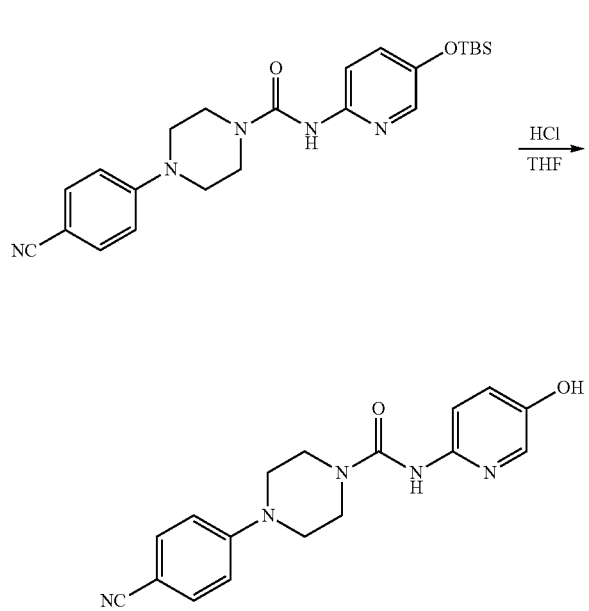 [SMILES: CC(C)(C)[Si](C)(C)Oc1ccc(NC(=O)N2CCN(c3ccc(C#N)cc3)CC2)nc1 ; Cl ; "THF" ; N#Cc1ccc(N2CCN(C(=O)Nc3ccc(O)cn3)CC2)cc1]

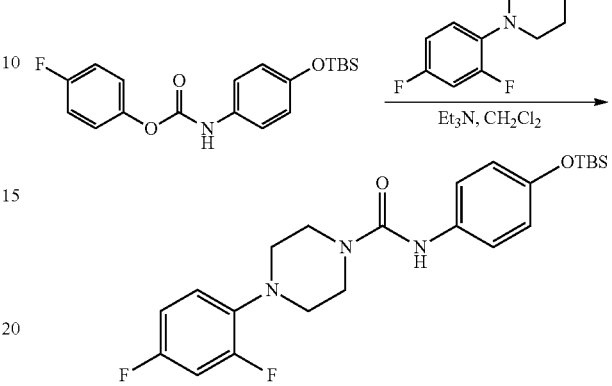

To a solution of the product from the previous step (150 mg, 0.41 mmol) in CH₂Cl₂ (5 mL) was added in portions Et₃N (126 mg, 1.25 mmol), followed by the addition in portions of 1-(2,4-difluorophenyl)piperazine (82 mg, 0.41 mmol, 1.00 equiv). The resulting solution was stirred for 16 h at rt, then quenched by the addition of 15 mL H₂O and extracted with 2×30 mL of EtOAc. The combined organic layers were concentrated under vacuum to afford 170 mg (92%) of the title compound as an off-white solid.

LC-MS: (ES, m/z): 448

Step 2. Synthesis of 4-(2,4-difluorophenyl)-N-(4-hydroxyphenyl)piperazine-1-carboxamide To a solution of the product from the previous step (115 mg, 0.26 mmol) in THF (2 mL) was added 2N HCl (1 mL) at rt. The resulting solution was stirred for 1 h at rt, then concentrated under vacuum. The crude product (115 mg) was purified by Prep-HPLC with the following conditions: Instrument "A"; Column "A"; mobile phase, 10 mM aq NH₄HCO₃ and ACN (20.0% ACN up to 45.0% in 8 min), to afford 41.2 mg (48%) of the title compound as an off-white solid.

LC-MS: (ES, m/z): 324

¹H NMR (400 MHz, DMSO-d₆) δ 9.45 (s, 1H), 8.91 (s, 1H), 7.79 (d, J=3.0 Hz, 1H), 7.59 (d, J=8.8 Hz, 3H), 7.14 (dd, J=9.0, 3.0 Hz, 1H), 7.12-7.00 (m, 2H), 3.59 (m, 4H), 3.38 (m, 4H).

Example 28

4-(2,4-difluorophenyl)-N-(4-hydroxyphenyl)piperazine-1-carboxamide

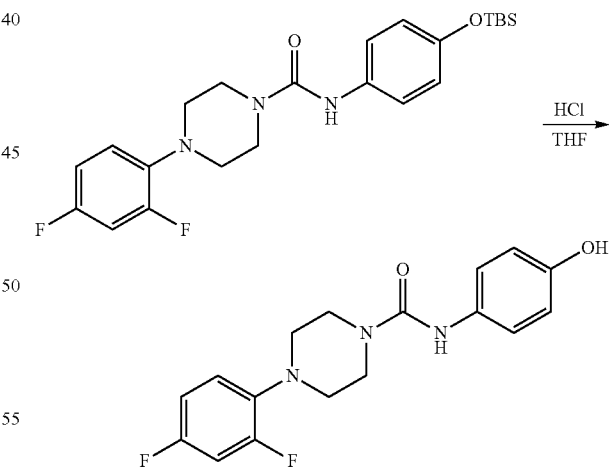

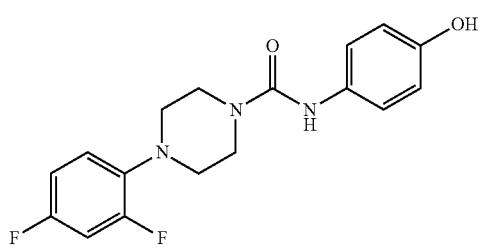

To a solution of the product from the previous step (170 mg, 0.38 mmol) in THF (2 mL) was added 2N aq. HCl (1 mL) dropwise with stirring. The resulting solution was stirred for 4 h at rt, then concentrated under vacuum. The crude product (170 mg) was purified by Prep-HPLC with the following conditions: Instrument "A"; Column "A"; mobile phase, Water (10 mM NH₄HCO₃) and ACN (20.0% ACN up to 58.0% in 7 min), to afford 80.1 mg (63%) of the title compound as an off-white solid.

LC-MS: (ES, m/z): 334

$^1$H NMR (300 MHz, DMSO-d$_6$) δ 9.03 (s, 1H), 8.31 (s, 1H), 7.29-6.93 (m, 5H), 6.67-6.58 (m, 2H), 3.54 (m, 4H), 2.93 (m, 4H).

Example 29

4-(4-fluorophenyl)-N-(4-hydroxyphenyl)piperazine-1-carboxamide

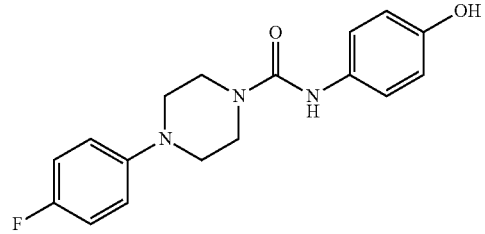

Step 1. Synthesis of N-[4-[(tert-butyldimethylsilyl)oxy]phenyl]-4-(4-fluorophenyl)piperazine-1-carboxamide

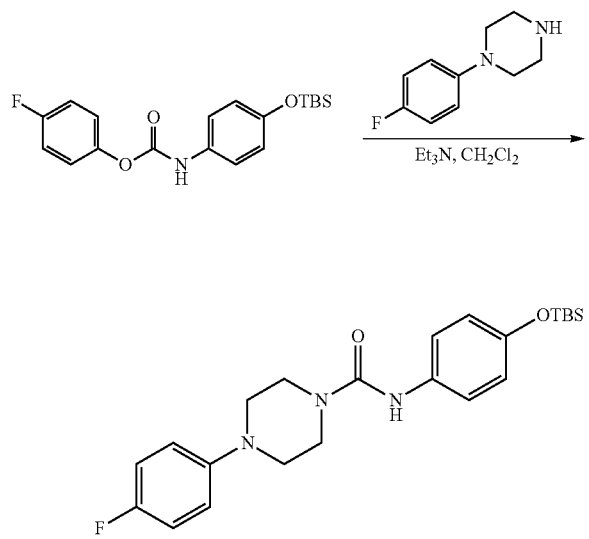

To a solution of Intermediate "B" (150 mg, 0.41 mmol) in CH$_2$Cl$_2$ (5 mL) was added Et$_3$N (126 mg, 1.25 mmol), in portions, followed by the addition of 1-(4-fluorophenyl)piperazine (75 mg, 0.42 mmol), in portions. The resulting solution was stirred for 16 h at rt, then quenched by the addition of 20 mL H$_2$O and extracted with 2×20 mL of EtOAc. The combined organic layers were concentrated under vacuum to afford 170 mg (95%) of the title compound as an off-white solid.

LC-MS: (ES, m/z): 430

Step 2. Synthesis of 4-(4-fluorophenyl)-N-(4-hydroxyphenyl)piperazine-1-carboxamide

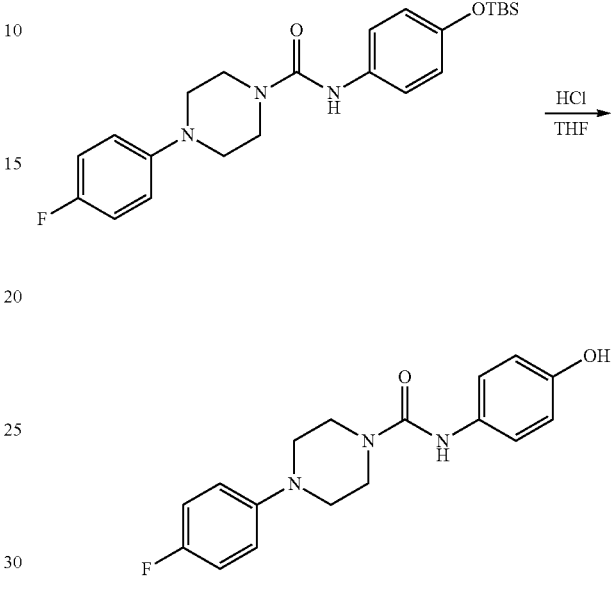

To a solution of the product from the previous step (170 mg, 0.40 mmol) in THF (2 mL) was added 2N aq. HCl (1 mL) dropwise with stirring. The resulting solution was stirred for 4 h at rt, then concentrated under vacuum. The crude product (170 mg) was purified by Prep-HPLC with the following conditions: Instrument "A"; Column "A"; mobile phase, Water (10 mM NH$_4$HCO$_3$) and ACN (20.0% ACN up to 58.0% in 8 min), to afford 76.2 mg (61%) of the title compound as an off-white solid.

LC-MS: (ES, m/z): 316

$^1$H NMR (300 MHz, DMSO-d$_6$) δ 9.01 (s, 1H), 8.32 (s, 1H), 7.23-7.13 (m, 2H), 7.11-6.92 (m, 4H), 6.68-6.57 (m, 2H), 3.53 (m, 4H), 3.06 (m, 4H).

Example 30

N-(4-hydroxyphenyl)-4-[4-(trifluoromethyl)phenyl]piperazine-1-carboxamide

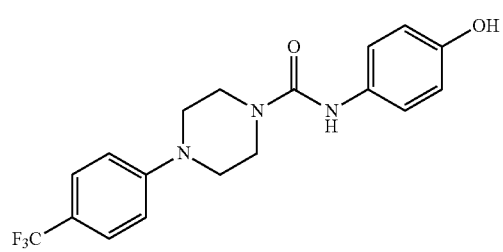

Step 1. Synthesis of N-[4-[(tert-butyldimethylsilyl)oxy]phenyl]-4-[4-(trifluoromethyl)phenyl]piperazine-1-carboxamide

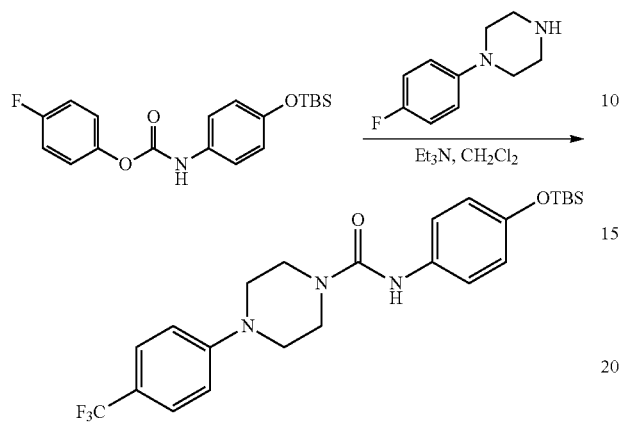

To a solution of Intermediate "B" (150 mg, 0.41 mmol) in CH₂Cl₂ (5 mL) was added Et₃N (126 mg, 1.25 mmol), in portions, followed by the addition of 1-[4-(trifluoro-methyl)phenyl]piperazine (96 mg, 0.42 mmol), in portions. The resulting solution was stirred for 16 h at rt, then quenched by the addition of 20 mL H₂O and extracted with 2×20 mL of EtOAc. The combined organic layers were concentrated under vacuum to afford 180 mg (90%) of the title compound as an off-white solid.

LC-MS: (ES, m/z): 480

Step 2. Synthesis of N-(4-hydroxyphenyl)-4-[4-(trifluoromethyl)phenyl]piperazine-1-carboxamide

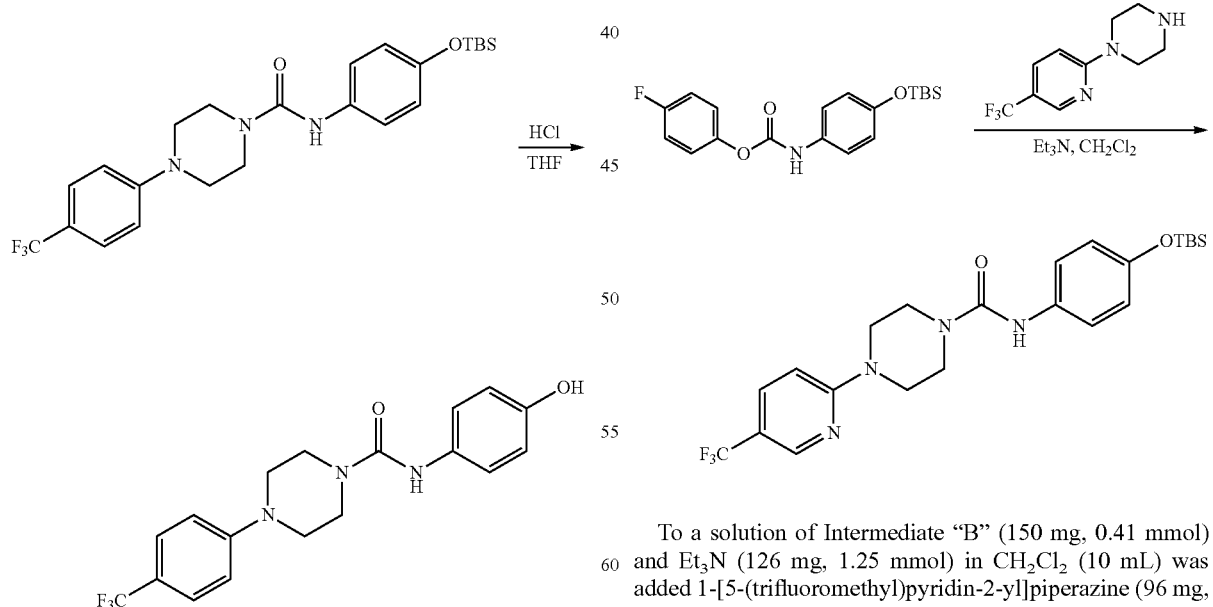

To a solution of the product from the previous step (180 mg, 0.38 mmol) in THF (2 mL) was added 2N aq. HCl (1 mL) dropwise with stirring. The resulting solution was stirred for 4 h at rt, then concentrated under vacuum. The crude product (180 mg) was purified by Prep-HPLC with the following conditions: Instrument "A"; Column "A"; mobile phase, Water (10 mM NH₄HCO₃) and ACN (28.0% ACN up to 62.0% in 7 min), to afford 91.4 mg (67%) of the title compound as an off-white solid.

LC-MS: (ES, m/z): 366

¹H NMR (300 MHz, DMSO-d₆) δ 9.02 (s, 1H), 8.34 (s, 1H), 7.50 (d, J=8.5 Hz, 2H), 7.23-7.12 (m, 2H), 7.08 (d, J=8.6 Hz, 2H), 6.68-6.58 (m, 2H), 3.55 (m, 4H), 3.30 (m, 4H).

Example 31

N-(4-hydroxyphenyl)-4-[5-(trifluoromethyl)pyridin-2-yl]piperazine-1-carboxamide

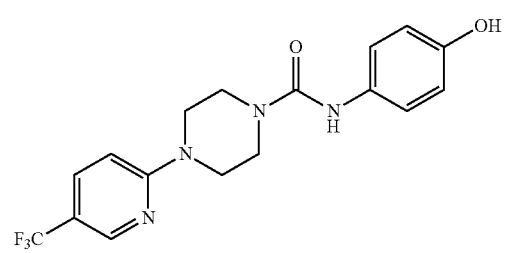

Step 1. Synthesis of N-[4-[(tert-butyldimethylsilyl)oxy]phenyl]-4-[5-(trifluoromethyl)pyridin-2-yl]piperazine-1-carboxamide To a solution of Intermediate "B" (150 mg, 0.41 mmol) and Et₃N (126 mg, 1.25 mmol) in CH₂Cl₂ (10 mL) was added 1-[5-(trifluoromethyl)pyridin-2-yl]piperazine (96 mg, 0.42 mmol), in portions. The resulting solution was stirred for 16 h at rt, then then quenched by the addition of 20 mL H₂O and extracted with 2×20 mL of EtOAc. The combined organic layers were concentrated under vacuum to afford 180 mg (90%) of the title compound as an off-white solid.

LC-MS: (ES, m/z): 481

Step 2. Synthesis of N-(4-hydroxyphenyl)-4-[5-(trifluoromethyl)pyridin-2-yl]piperazine-1-carboxamide

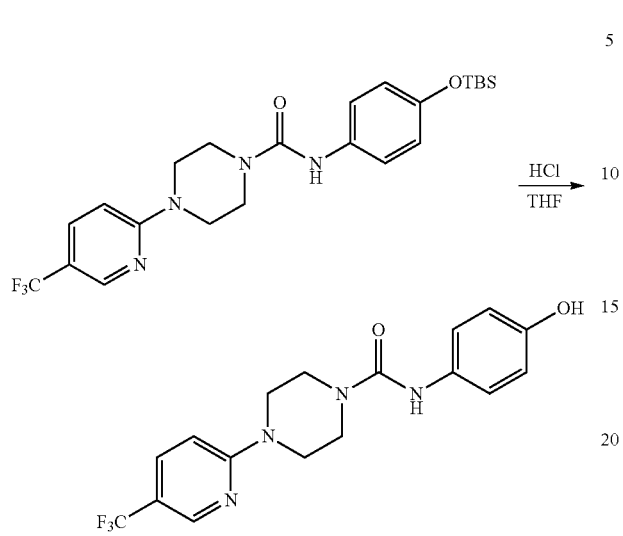

To a solution of the product from the previous step (180 mg, 0.37 mmol) in THF (2 mL) was added 2N aq. HCl (1 mL) dropwise with stirring. The resulting solution was stirred for 4 h at rt, then concentrated under vacuum. The crude product (180 mg) was purified by Prep-HPLC with the following conditions: Instrument "A"; Column "D"; mobile phase, Water (10 mM NH$_4$HCO$_3$) and ACN (25.0% ACN up to 55.0% in 7 min); Detector, UV 254/220 nm, to afford 85.2 mg (62%) of the title compound as an off-white solid.
LC-MS: (ES, m/z): 367
$^1$H NMR (300 MHz, DMSO-d$_6$) δ 9.02 (s, 1H), 8.45-8.38 (m, 1H), 8.33 (s, 1H), 7.80 (dd, J=9.2, 2.6 Hz, 1H), 7.23-7.12 (m, 2H), 6.97 (d, J=9.1 Hz, 1H), 6.69-6.58 (m, 2H), 3.66 (m, 4H), 3.52 (m, 4H).

Example 32

3-(5-hydroxypyridin-2-yl)-1-(1-phenylpiperidin-4-yl)urea

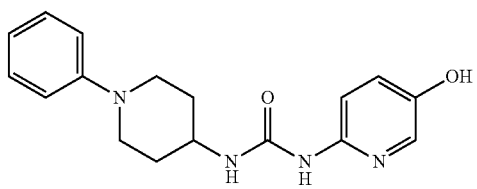

Step 1. Synthesis of 3-[5-[(tert-butyldimethylsilyl)oxy]pyridin-2-yl]-1-(1-phenylpiperidin-4-yl)urea

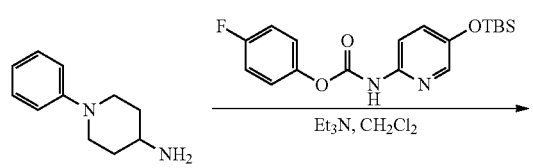

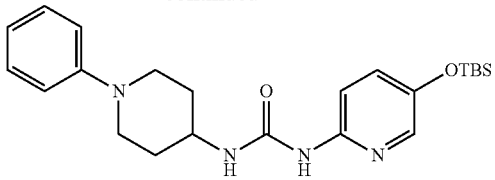

A solution of Intermediate "A" (200 mg, 0.55 mmol), 1-phenylpiperidin-4-amine (100 mg, 0.57 mmol, 1.00 equiv), and Et$_3$N (168 mg, 1.66 mmol) in CH$_2$Cl$_2$ (5 mL) was stirred overnight at rt, then quenched by the addition of H$_2$O and extracted with EtOAc. The combined organic layers were concentrated under vacuum to afford 150 mg (64%) of the title compound as a white solid.
LC-MS (ES, m/z): 427.5

Step 2. Synthesis of 3-(5-hydroxypyridin-2-yl)-1-(1-phenylpiperidin-4-yl)urea

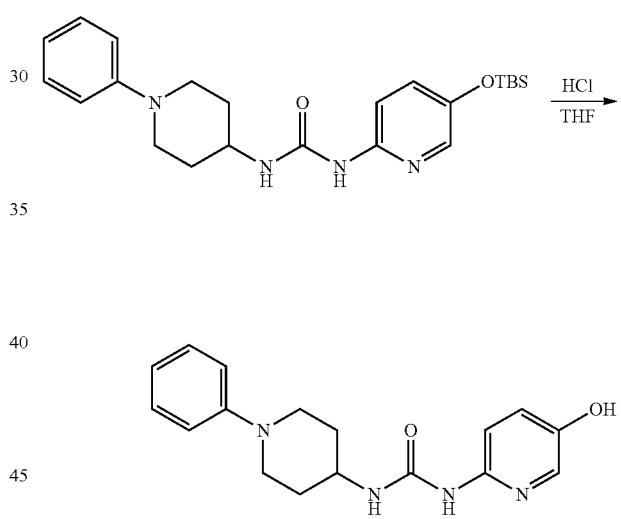

A solution of the product from the previous step (150 mg, 0.35 mmol) in 2N aq, HCl (1 mL) THF (2 mL) was stirred for 4 h at rt, then extracted with EtOAc. The combined organic layers were concentrated and purified by Prep-HPLC with the following conditions: Instrument "A"; Column "A"; mobile phase, 10 mM aq NH$_4$HCO$_3$ and ACN (20.0% ACN up to 52.0% in 8 min); Detector, UV 254/220 nm. mL product was obtained, to afford 42.3 mg (39%) of the title compound as a white solid.
LC-MS: (ES, m/z): 313.2
$^1$H NMR (400 MHz, DMSO-d$_6$) δ 9.42 (s, 1H), 8.78 (s, 1H), 7.91 (s, 1H), 7.71 (d, J=3.0 Hz, 1H), 7.29-7.10 (m, 4H), 6.95 (d, J=8.2 Hz, 2H), 6.75 (t, J=7.3 Hz, 1H), 3.76-3.66 (m, 1H), 3.59-3.49 (m, 2H), 2.94-2.82 (m, 2H), 1.98-1.88 (m, 2H), 1.57-1.43 (m, 2H).

Example 33

N-(5-hydroxypyridin-2-yl)-4-[4-(trifluoromethyl)pyridin-2-yl]piperazine-1-carboxamide

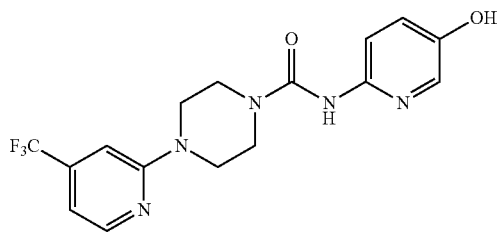

Step 1. Synthesis of N-[5-[(tert-butyldimethylsilyl)oxy]pyridin-2-yl]-4-[4-(trifluoromethyl)pyridin-2-yl]piperazine-1-carboxamide

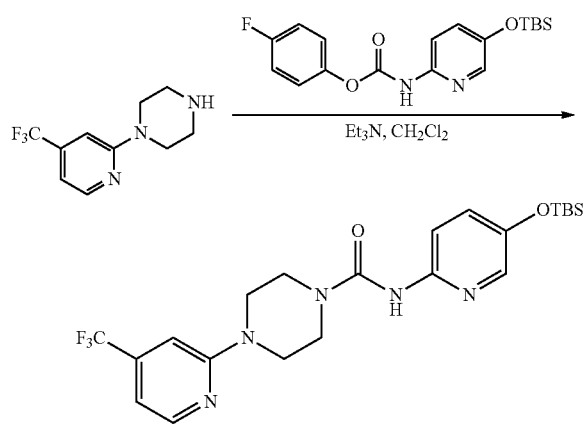

A solution of 4-fluorophenyl N-5-[(tert-butyldimethylsilyl)oxy]pyridin-2-ylcarbamate (100 mg, 0.28 mmol), 1-[4-(trifluoromethyl)pyridin-2-yl]piperazine (64 mg, 0.28 mmol), and Et₃N (84 mg, 0.83 mmol) in CH₂Cl₂ (5 mL) was stirred for 16 h at rt, then quenched by the addition of 20 mL H₂O and extracted with 2×20 mL of EtOAc. The combined organic layers were concentrated under vacuum and purified with silica gel chromatography using EtOAc/hexane (1/2) to afford 110 mg (83%) of the title compound as an off-white solid. LC-MS: (ES, m/z): 482

Step 2. Synthesis of N-(5-hydroxypyridin-2-yl)-4-[4-(trifluoromethyl)pyridin-2-yl]piperazine-1-carboxamide

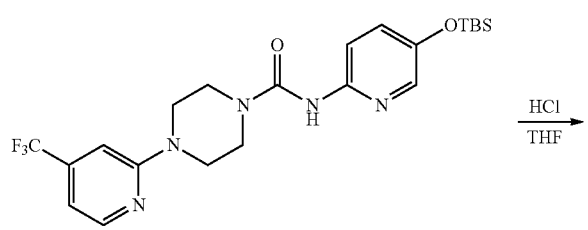

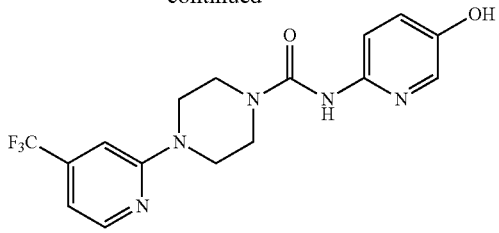

To a solution of the product from the previous step (110 g, 228.41 mmol) in THF (2 mL) was added 2N aq. HCl (1 mL) dropwise with stirring. The resulting solution was stirred for 2 h at rt, then concentrated under vacuum. The crude product (110 mg) was purified by Prep-HPLC with the following conditions: Instrument "A"; Column "A"; mobile phase, 10 mM aq NH₄HCO₃ and ACN (25.0% ACN up to 56.0% in 8 min); Detector, uv 254/220 nm, to afford 74.2 mg of the title compound as an off-white solid.

LC-MS: (ES, m/z): 368

¹H NMR (300 MHz, DMSO-d₆) δ 9.39 (s, 1H), 8.92 (s, 1H), 8.32 (d, J=5.2 Hz, 1H), 7.78 (d, J=2.9 Hz, 1H), 7.58 (d, J=8.9 Hz, 1H), 7.18-7.07 (m, 2H), 6.88 (dd, J=5.2, 1.3 Hz, 1H), 3.66-3.49 (m, 8H).

Example 34

4-(5-cyanopyridin-2-yl)-N-(5-hydroxypyridin-2-yl)piperazine-1-carboxamide

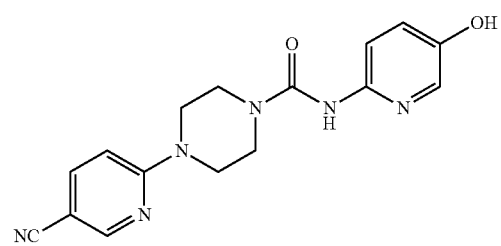

Step 1. Synthesis of N-[5-[(tert-butyldimethylsilyl)oxy]pyridin-2-yl]-4-(5-cyanopyridin-2-yl)piperazine-1-carboxamide

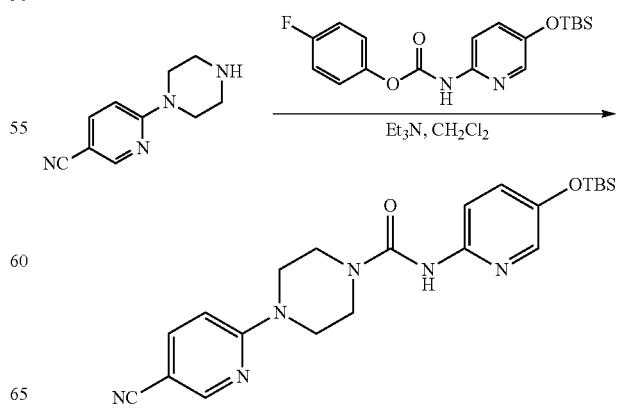

A solution of 4-fluorophenyl N-5-[(tert-butyldimethylsilyl)oxy]pyridin-2-ylcarbamate (100 mg, 0.28 mmol), 6-(piperazin-1-yl)pyridine-3-carbonitrile (52 mg, 0.28 mmol), and Et₃N (84 mg, 0.83 mmol) in CH₂Cl₂ (5 mL) was stirred for 16 h at rt, then quenched by the addition of 20 mL H₂O and extracted with 2×20 mL of EtOAc. The combined organic layers were concentrated under vacuum to afford 100 mg (83%) of the title compound as an off-white solid. LC-MS: (ES, m/z): 439

Step 2. Synthesis of 4-(5-cyanopyridin-2-yl)-N-(5-hydroxypyridin-2-yl)piperazine-1-carboxamide

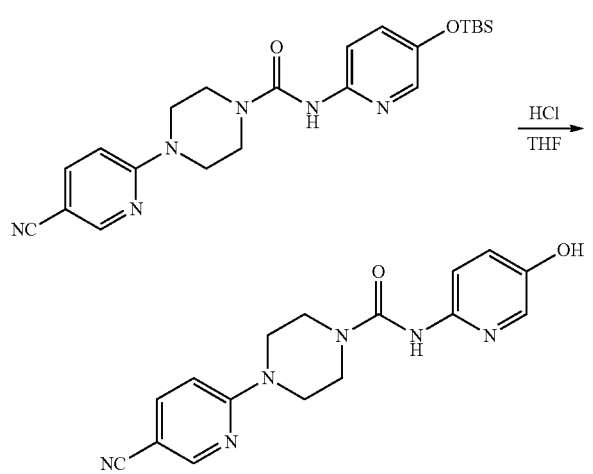

To a solution of the product from the previous step (100 mg, 0.23 mmol) in THF (2 mL) was added 2N HCl (1 mL) dropwise with stirring. The resulting solution was stirred for 2 h at rt, then concentrated under vacuum. The crude product (100 mg) was purified by Prep-HPLC with the following conditions: Instrument "A"; Column "A"; mobile phase, 10 mM aq NH₄HCO₃ and ACN (5.0% ACN up to 60.0% in 7 min); Detector, uv 254/220 nm, to afford 52.8 mg (71%) of the title compound as an off-white solid.

LC-MS: (ES, m/z): 325
¹H NMR (300 MHz, DMSO-d₆) δ 9.45 (s, 1H), 8.92 (s, 1H), 8.49 (d, J=2.3 Hz, 1H), 7.85 (dd, J=9.1, 2.4 Hz, 1H), 7.77 (d, J=2.9 Hz, 1H), 7.58 (d, J=8.9 Hz, 1H), 7.12 (dd, J=8.9, 3.0 Hz, 1H), 6.94 (d, J=9.1 Hz, 1H), 3.68 (m, 4H), 3.54 (m, 4H).

Example 35

4-(6-fluoropyridin-2-yl)-N-(5-hydroxypyridin-2-yl)piperazine-1-carboxamide

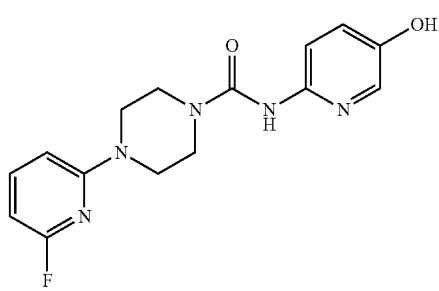 [SMILES: O=C(Nc1ccc(O)cn1)N1CCN(c2cccc(F)n2)CC1]

Step 1. Synthesis of N-[5-[(tert-butyldimethylsilyl)oxy]pyridin-2-yl]-4-(6-fluoropyridin-2-yl)piperazine-1-carboxamide

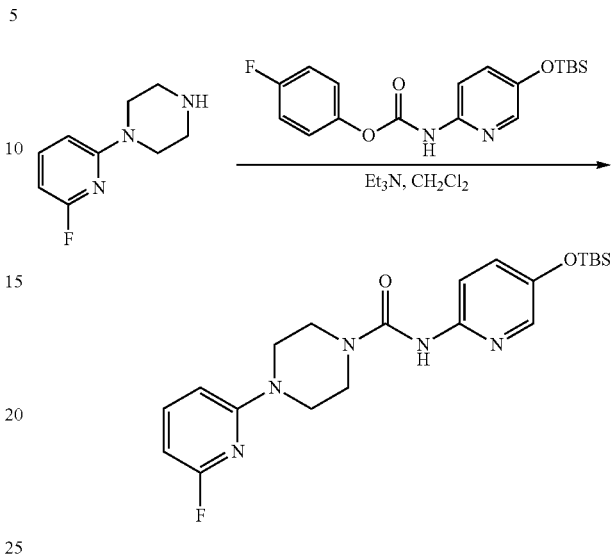

A solution of 4-fluorophenyl N-5-[(tert-butyldimethylsilyl)oxy]pyridin-2-ylcarbamate (100 mg, 0.28 mmol), Et₃N (84 mg, 0.83 mmol,), and 1-(6-fluoropyridin-2-yl)piperazine (58 mg, 0.32 mmol) in CH₂Cl₂ (5 mL). The resulting solution was stirred for 16 h at rt, then quenched by the addition of 20 mL H₂O and extracted with 2×20 mL of EtOAc. The combined organic layers were concentrated under vacuum, to afford 110 mg (80%) of as an off-white solid. LC-MS: (ES, m/z): 432

Step 2. Synthesis of 4-(6-fluoropyridin-2-yl)-N-(5-hydroxypyridin-2-yl)piperazine-1-carboxamide

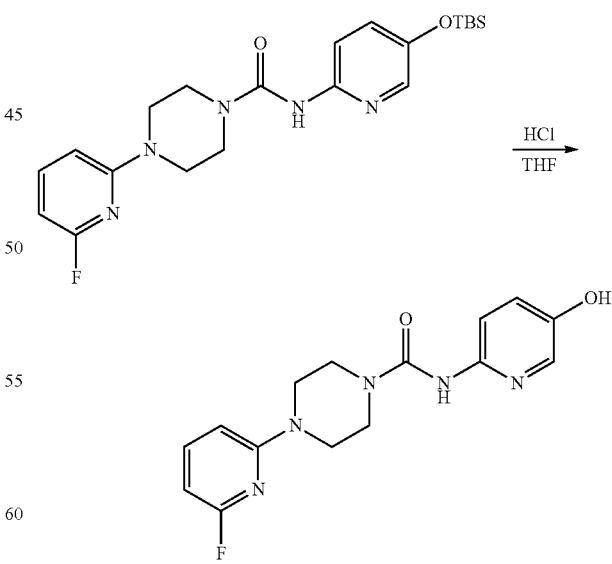

To a solution of the product from the previous step (110 mg, 0.25 mmol) in THF (2 mL) was added 2N aq. HCl (1 mL) with stirring. The reaction was stirred for 2 h at rt, then concentrated under vacuum and the crude product (110 mg)

was purified by Prep-HPLC with the following conditions: Instrument "A"; Column "A"; mobile phase, 10 mM aq NH₄HCO₃ and ACN (25.0% ACN up to 44.0% in 8 min), to afford 54.6 mg (68%) of the title compound as an off-white solid.

LC-MS (ES, m/z): 318

¹H NMR (300 MHz, DMSO-d₆) δ 9.45 (s, 1H), 8.91 (s, 1H), 7.78 (d, J=2.9 Hz, 1H), 7.66 (ddd, J=7.5, 8.3, 8.3 Hz, 1H), 7.58 (d, J=8.9 Hz, 1H), 7.12 (dd, J=8.9, 2.9 Hz, 1H), 6.70 (dd, J=8.3, 2.7 Hz, 1H), 6.27 (m, 1H), 3.51 (m, 8H).

Example 36

N-(5-hydroxypyridin-2-yl)-4-[6-(trifluoromethyl)pyridin-2-yl]piperazine-1-carboxamide

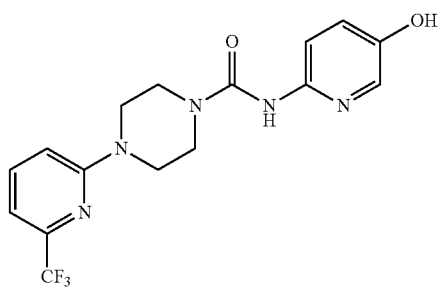 [SMILES: O=C(Nc1ccc(O)cn1)N1CCN(c2cccc(C(F)(F)F)n2)CC1]

Step 1. N-[5-[(tert-butyldimethylsilyl)oxy]pyridin-2-yl]-4-[6-(trifluoromethyl)pyridin-2-yl]piperazine-1-carboxamide

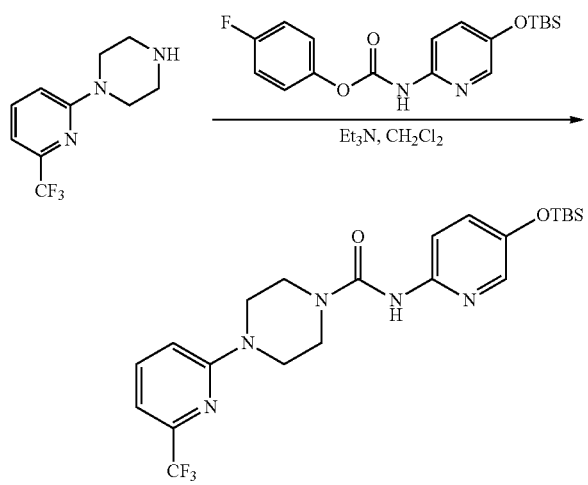

A solution of 4-fluorophenyl N-5-[(tert-butyldimethylsilyl)oxy]pyridin-2-ylcarbamate (100 mg, 0.28 mmol), 1-[6-(trifluoromethyl)pyridin-2-yl]piperazine (64 mg, 0.28 mmol), and Et₃N (84 mg, 0.83 mmol) in CH₂Cl₂ (5 mL) was stirred for 16 h at rt, then quenched by the addition of 20 mL H₂O and extracted with 2×20 mL of EtOAc. The combined organic layers were concentrated under vacuum and purified with silica gel chromatography using EtOAc/hexane (1/2) to afford 110 mg (83%) of the title compound as an off-white solid. LC-MS: (ES, m/z): 481.

Step 2. Synthesis of N-(5-hydroxypyridin-2-yl)-4-[6-(trifluoromethyl)pyridin-2-yl]piperazine-1-carboxamide

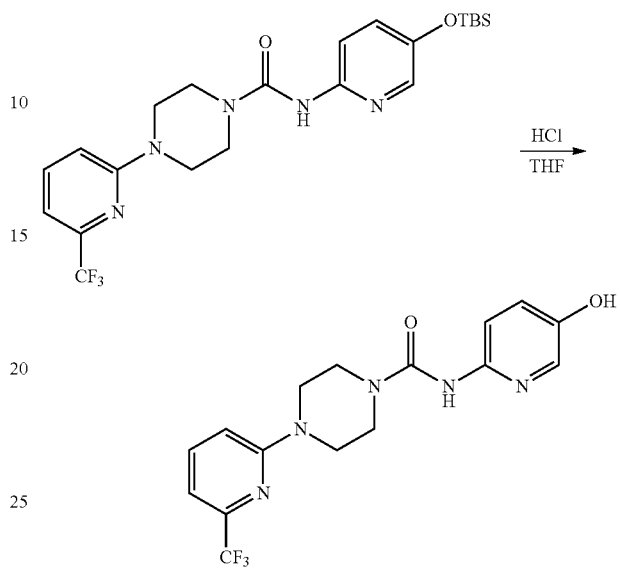

To a solution of the product from the previous step (150 mg, 0.31 mmol) in THF (2 mL) was added 2N aq. HCl (1 mL) dropwise with stirring. The resulting solution was stirred for 2 hr at rt, then concentrated under vacuum. The crude product (150 mg) was purified by Prep-HPLC with the following conditions: Instrument "A"; Column, SunFire C18 OBD Prep Column, 100& #65533; 5 µm, 19 mm×250 mm; mobile phase, 10 mM aq NH₄HCO₃ and ACN (35.0% ACN up to 66.0% in 8 min); Detector, UV 254/220 nm, to afford 46.5 mg (41%) of the title compound as an off-white solid.

LC-MS: (ES, m/z): 368

¹H NMR (300 MHz, DMSO-d₆) δ 9.40 (s, 1H), 8.92 (s, 1H), 7.82-7.68 (m, 2H), 7.59 (d, J=8.9 Hz, 1H), 7.13 (m, 2H), 7.04 (d, J=7.5 Hz, 1H), 3.56 (m, 8H).

Example 37

4-benzyl-N-(5-hydroxypyridin-2-yl)piperazine-1-carboxamide

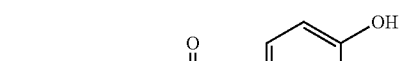
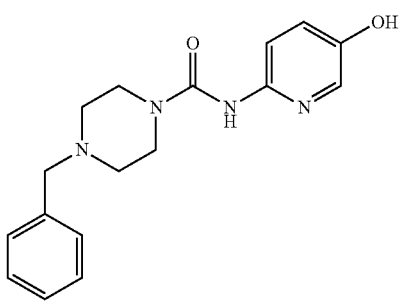 [SMILES: O=C(Nc1ccc(O)cn1)N1CCN(Cc2ccccc2)CC1]

Step 1. Synthesis of 4-benzyl-N-[5-[(tert-butyldimethylsilyl)oxy]pyridin-2-yl] piperazine-1-carboxamide

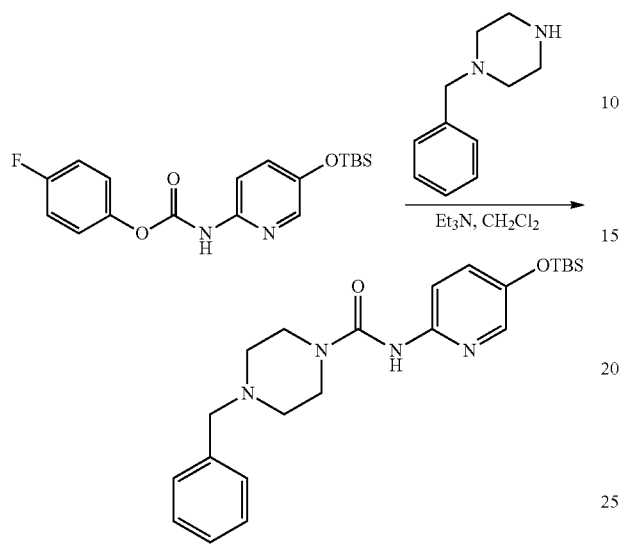

To a solution of Intermediate "A" (100 mg, 0.28 mmol) in CH$_2$Cl$_2$ (5 mL) was added Et$_3$N (3 eq) (84 mg) dropwise with stirring, followed by the addition of 1-benzylpiperazine (49 mg, 0.28 mmol). The resulting solution was stirred for 16 h at rt, then extracted with 2×20 mL of EtOAc. The combined organic layers were concentrated under vacuum to afford 94 mg (80%) of the title compound as a light yellow oil. LC-MS (ES, m/z): 427.1

Step 2. Synthesis of 4-benzyl-N-(5-hydroxypyridin-2-yl)piperazine-1-carboxamide

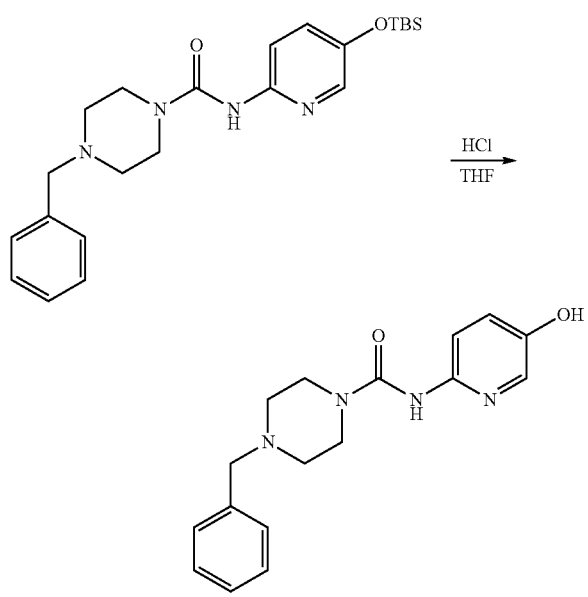

To a solution of the product from the previous step (94 mg, 0.22 mmol) in THF (4 mL) was added 2 N aq. HCl (2 mL) dropwise with stirring. The resulting solution was stirred for 2 h at rt, then concentrated under vacuum. The crude product (94 mg) was purified by Prep-HPLC with the following conditions: Instrument "A"; Column "B"; mobile phase, water (0.05% NH$_3$H$_2$O) and ACN (20.0% ACN up to 35.0% in 7 min); Detector, UV 254/220 nm, to afford 28.9 mg (42%) of s a brown solid.
LC-MS (ES, m/z): 313.0
$^1$H NMR (300 MHz, Methanol-d$_4$) δ 8.25 (s, 1H), 7.81 (d, J=2.9 Hz, 1H), 7.49 (d, J=8.9 Hz, 1H), 7.44-7.27 (m, 5H), 7.20 (dd, J=8.9, 2.8 Hz, 1H), 3.78 (s, 2H), 3.60 (m, 4H), 2.71 (m, 4H).

Example 38

4-[(4-Fluorophenyl)methyl]-N-(5-hydroxypyridin-2-yl)piperazine-1-carboxamide

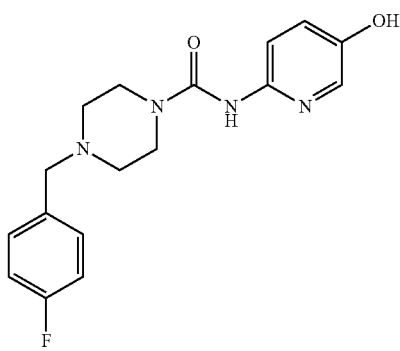 [SMILES: O=C(Nc1ccc(O)cn1)N1CCN(Cc2ccc(F)cc2)CC1]

Step 1. Synthesis of N-[5-[(tert-butyldimethylsilyl)oxy]pyridin-2-yl]-4-[(4-fluorophenyl)methyl]piperazine-1-carboxamide

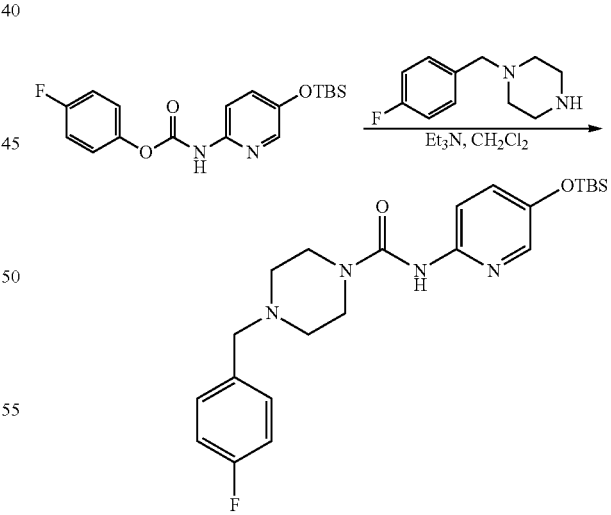

A solution of Intermediate "A" (100 mg, 0.28 mmol), 1-[(4-fluorophenyl)methyl]-piperazine (54 mg, 0.28 mmol), and Et$_3$N (3 eq) (84 mg) in CH$_2$Cl$_2$ (5 mL) was stirred for 16 h at rt, then extracted with 2×20 mL of EtOAc. The combined organic layers were concentrated under vacuum to afford 100 mg (82%) of the title compound as a light yellow oil. LC-MS (ES, m/z): 445.1

Step 2. Synthesis of 4-[(4-fluorophenyl)methyl]-N-(5-hydroxypyridin-2-yl)piperazine-1-carboxamide

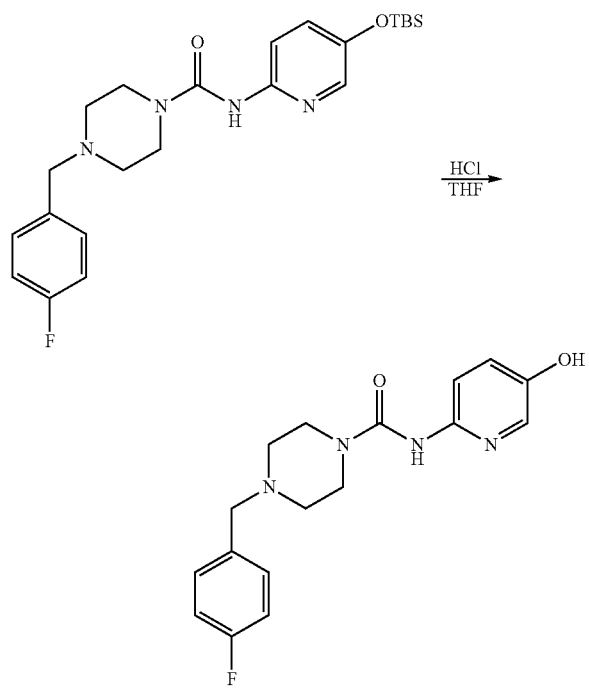

To a solution of the product from the previous step (100 mg, 0.22 mmol) in THF (4 mL) was added 2 N aq. HCl (2 mL) dropwise with stirring. The resulting solution was stirred for 2 h at rt, then concentrated under vacuum. The crude product (100 mg) was purified by Prep-HPLC with the following conditions: Instrument "A"; Column, Sunfire Prep C18 OBD Column, 10 um, 19*250 mm; mobile phase, water (0.1% FA) and ACN (2.0% ACN up to 8.0% in 10 min); Detector, UV, MASS 220/254 nm, to afford 49.9 mg (67%) of the title compound as light yellow oil.

LC-MS (ES, m/z): 331.0

$^1$H NMR (300 MHz, Methanol-$d_4$) δ 8.20 (s, 1H), 7.81 (d, J=2.9 Hz, 1H), 7.49 (d, J=8.9 Hz, 1H), 7.46-7.33 (m, 2H), 7.20 (dd, J=8.9, 2.9 Hz, 1H), 7.10 (t, J=8.7 Hz, 2H), 3.75 (s, 2H), 3.60 (m, 4H), 2.69 (m, 4H).

Example 39

1-[((5-Hydroxypyridin-2-yl)amino)carbonyl]-4-(pyridin-3-yl)piperazine

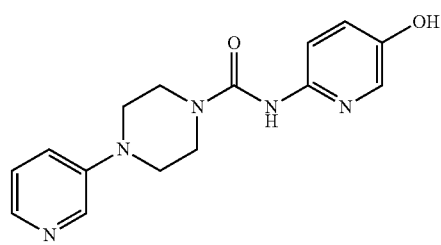 [SMILES: O=C(Nc1ccc(O)cn1)N1CCN(c2cccnc2)CC1]

This compound can be prepared using methods as disclosed elsewhere.

Step 1. Synthesis of N-[5-[(tert-butyldimethylsilyl)oxy]pyridin-2-yl]-4-(pyridin-3-yl)piperazine-1-carboxamide

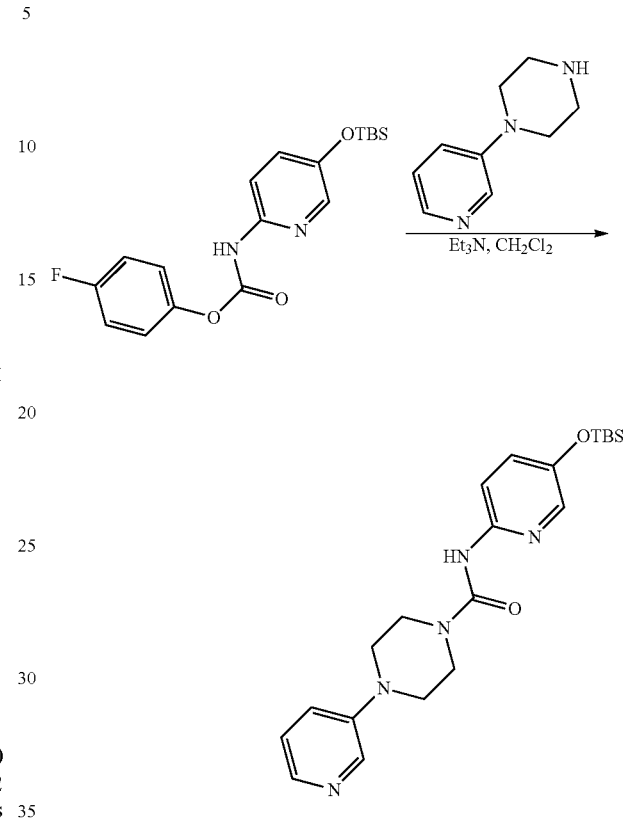

A solution of 4-fluorophenyl N-[5-[(tert-butyldimethylsilyl)oxy]pyridin-2-yl]carbamate (200 mg, 0.55 mmol), Et$_3$N (170 mg, 1.68 mmol), and 1-(pyridin-3-yl)piperazine (270 mg, 1.65 mmol) in CH$_2$Cl$_2$ (5 mL) was stirred for 16 h at rt, then extracted with 2×30 mL EtOAc. The combined organic layers were concentrated under vacuum and purified with silica gel column chromatography using EtOAc/hexane (1:2) to afford 140 mg (61%) of the title compound as an off-white solid. LC-MS: (ES, m/z): 414.

Step 2. Synthesis of 1-[((5-hydroxypyridin-2-yl)amino)carbonyl]-4-(pyridin-3-yl)piperazine

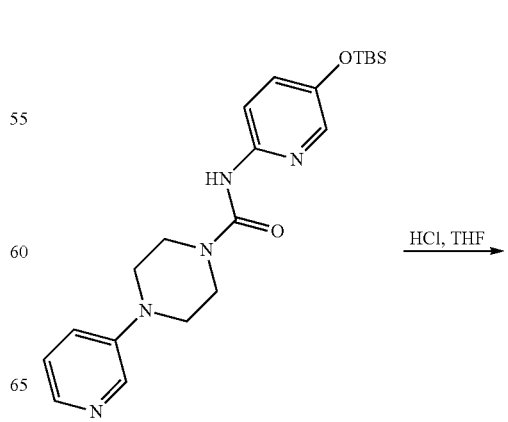

-continued

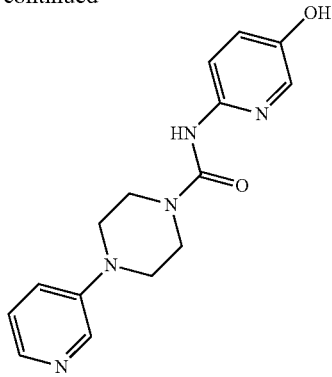

A solution of the product from the previous step (140 mg, 0.34 mmol) in aqueous 1 N HCl (1 mL) and THF (2 mL) was stirred for 2 h at rt, then concentrated under vacuum. The crude product (140 mg) was purified by Prep-HPLC with the following conditions: Instrument "A"; Column "B"; mobile phase, water (10 mM $NH_4HCO_3$) and ACN (5.0% ACN up to 40.0% in 7 min); Detector, uv 254/220 nm, to afford 49.7 mg (49%) of the title compound as an off-white solid.

LC-MS: (ES, m/z): 300.

$^1$H NMR (300 MHz, DMSO-$d_6$) δ 9.75-9.17 (m, 1H), 8.94 (s, 1H), 8.32 (d, J=2.9 Hz, 1H), 8.01 (dd, J=4.6, 1.3 Hz, 1H), 7.79 (d, J=2.9 Hz, 1H), 7.59 (d, J=8.9 Hz, 1H), 7.42-7.31 (m, 1H), 7.22 (dd, J=8.5, 4.5 Hz, 1H), 7.13 (dd, J=8.9, 3.0 Hz, 1H), 3.84-3.46 (m, 4H), 3.19 m, 4H).

Example 40

1-Hexyl-3-(5-hydroxypyridin-2-yl)urea

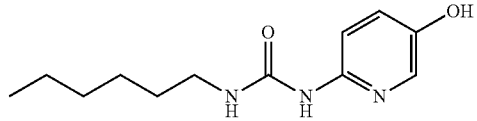 [SMILES: CCCCCCNC(=O)Nc1ccc(O)cn1]

Step 1: Synthesis of 1-[5-[(tert-butyldimethylsilyl)oxy]pyridine-2-yl]-3-hexylurea

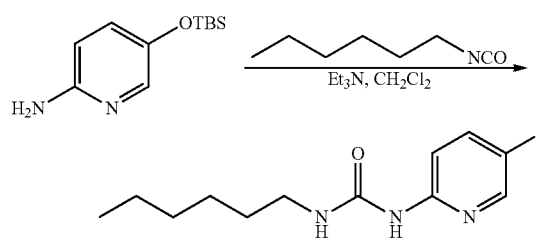

A solution of 5-[(tert-butyldimethylsilyl)oxy]pyridin-2-amine (224 mg, 1.00 mmol, 1.00 eq), 1-isocyanatohexane (127 mg, 1.00 mmol, 1.00 eq), and Et$_3$N (303.6 mg, 3.00 mmol, 3.00 eq) in CH$_2$Cl$_2$ (5 mL) was stirred for 18 h at rt. The resulting solution was extracted with 20 mL of CH$_2$Cl$_2$, and the combined organic layers were concentrated under vacuum and purified by prep-TLC (1:2), to afford 350 mg (100%) of the title compound as a solid. LC-MS: (ES, m/z): 352

Step 2: Synthesis of 3-hexyl-1-(5-hydroxypyridin-2-yl)urea

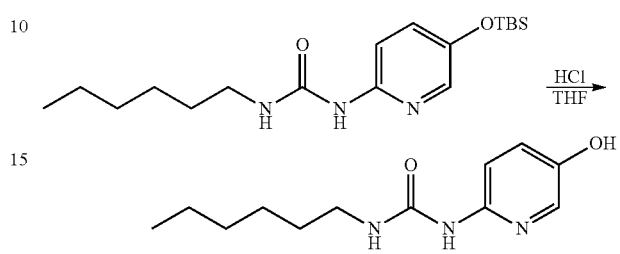

A solution of product from the previous step (350 mg, 1.00 mmol, 1.00 eq) in 2 N aq HCl (2 mL) and THF (4 mL) was stirred for 2 h at rt. The resulting mixture was concentrated under vacuum. The pH was adjusted to 7 with Et$_3$N. The crude product was purified by Prep-HPLC with the following conditions: Instrument "B"; Column "A"; mobile phase, water (0.1% FA) and ACN (10.0% ACN up to 50.0% in 7 min); Detector, UV 254/220 nm, to afford 140 mg (59%) of the title compound as a solid.

LC-MS: (ES, m/z): 238

$^1$H NMR (400 MHz, DMSO-$d_6$) δ 9.36 (s, 1H), 8.79 (s, 1H), 7.88 (s, 1H), 7.72 (d, J=2.9 Hz, 1H), 7.22 (d, J=8.9 Hz, 1H), 7.14 (dd, J=8.9, 2.9 Hz, 1H), 3.13 (q, J=6.5 Hz, 2H), 1.53-1.38 (m, 2H), 1.29 (dt, J=9.4, 3.5 Hz, 6H), 0.94-0.79 (m, 3H).

Example 41

Hexyl N-(5-hydroxypyridin-2-yl)carbamate

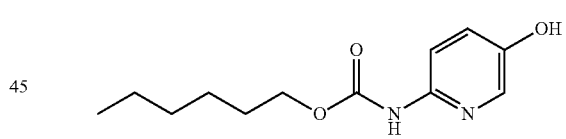

Step 1: Synthesis of hexyl N-[5-[(tert-butyldimethylsilyl)oxy]pyridin-2-yl]carbamate

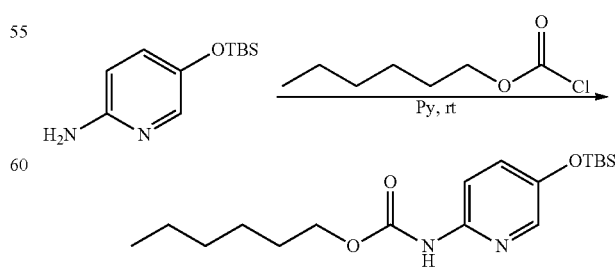

A solution of 5-[(tert-butyldimethylsilyl)oxy]pyridin-2-amine (336 mg, 1.50 mmol) and hexyl chloroformate (492 mg, 2.99 mmol) in pyridine (5 mL) was stirred for 2 h at rt, then extracted with 2×30 mL of EtOAc. The combined organic layers were purified with silica gel chromatography using EtOAc/hexane (1:2) to afford 500 mg (95%) of the title compound as a white solid. LC-MS: (ES, m/z): 353.

Step 2: Synthesis of hexyl N-(5-hydroxypyridin-2-yl)carbamate

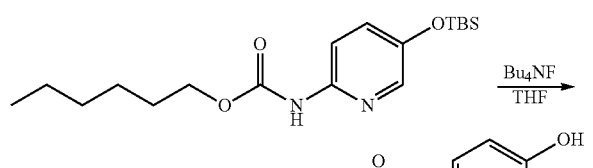

A solution of the product from the previous step (500 mg, 1.42 mmol, 1.00 eq) and $Bu_4NF$ (241 mg, 0.92 mmol, 2.00 eq) in THF (5 mL) was stirred for 2 h at rt, then concentrated under vacuum. The crude product was purified by Prep-HPLC with the following conditions: Instrument "B"; Column "E"; mobile phase, water (0.1% FA) and ACN (25.0% ACN up to 90.0% in 7 min); Detector, UV 254/220 nm, to afford 180 mg (53%) of the title compound as an off-white solid.

LC-MS: (ES, m/z): 239

$^1$H NMR (300 MHz, DMSO-$d_6$) δ 9.72 (s, 1H), 9.53 (s, 1H), 7.82 (d, J=2.9 Hz, 1H), 7.62 (d, J=8.9 Hz, 1H), 7.19 (d, J=8.9, 3.0 Hz, 1H), 4.06 (t, J=6.6 Hz, 2H), 1.59 (q, J=6.8 Hz, 2H), 1.44-1.20 (m, 6H), 0.96-0.82 (m, 3H).

Example 42

Cyclohexyl N-(5-hydroxypyridin-2-yl)carbamate

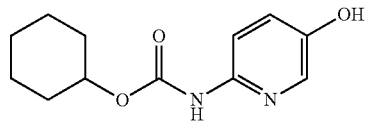 [SMILES: O=C(Nc1ccc(O)cn1)OC1CCCCC1]

Step 1: Synthesis of cyclohexyl N-[5-[(tert-butyldimethylsilyl)oxy]pyridin-2-yl]carbamate

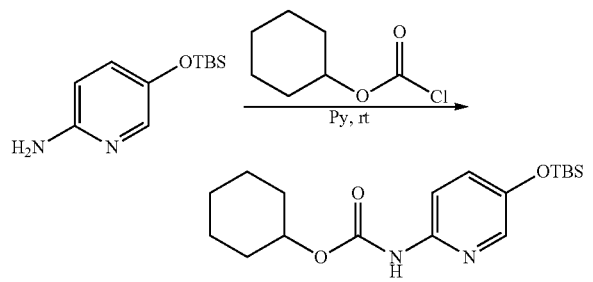

A solution of 5-[(tert-butyldimethylsilyl)oxy]pyridin-2-amine (22 mg, 0.10 mmol, 1.00 eq) and cyclohexyl chloroformate (486 mg, 2.99 mmol, 3.00 eq) in pyridine (3 mL) was stirred for 2 h at rt, then extracted with 2×20 mL of EtOAc. The combined organic layers were concentrated under vacuum and purified with silica gel column chromatography using $CH_2Cl_2$/MeOH (20:1) to afford 300 mg (873%) of the title compound as a white solid. LC-MS: (ES, m/z): 351.

Step 2: Synthesis of cyclohexyl N-(5-hydroxypyridin-2-yl)carbamate

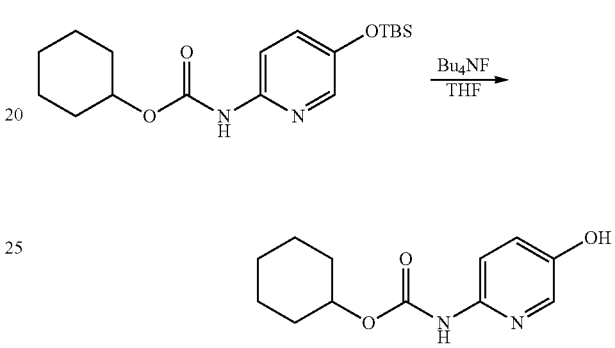

A solution of the product from the previous step (300 mg, 0.86 mmol, 1.00 eq) and $Bu_4NF$ (447 mg, 2.00 eq) in THF (3 mL) was stirred for 2 h at rt, then concentrated under vacuum. The residue was purified first with silica gel chromatography using $CH_2Cl_2$/MeOH (20:1), then with Prep-HPLC under the following conditions: Instrument "A"; Column "E"; mobile phase, water (0.1% FA) and ACN (33.0% ACN up to 74.0% in 7 min); Detector, UV 254/220 nm, to afford 125.2 mg (62%) of the title compound as a white solid.

LC-MS: (ES, m/z): 237

$^1$H NMR (300 MHz, DMSO-$d_6$) δ 9.70 (s, 1H), 9.60 (s, 1H), 7.81 (d, J=2.9 Hz, 1H), 7.59 (d, J=8.9 Hz, 1H), 7.21 (d, J=8.9, 3.0 Hz, 1H), 4.62 (m, 1H), 1.78 (m, 4H), 1.58-1.13 (m, 6H).

Scheme V

Example 43

(1r,4r)-4-Phenylcyclohexyl N-(5-hydroxypyridin-2-yl)carbamate

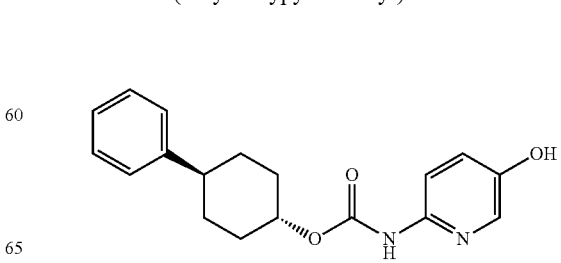

Step 1: Synthesis of 4-phenylcyclohexan-1-ol

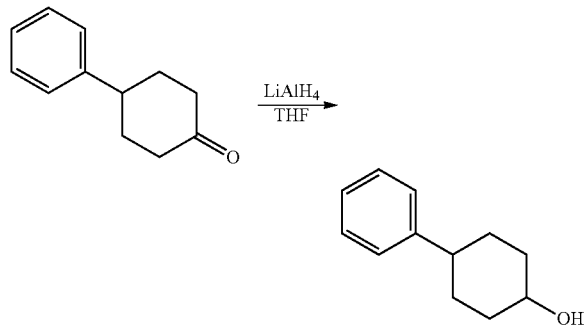

A mixture of 4-phenylcyclohexan-1-one (500 mg, 2.87 mmol, 1.00 eq) and LiAlH₄ (220 mg, 5.80 mmol, 2.00 eq) in THF (8 mL) was stirred for 16 h at rt. The resulting solids were removed by filtration, and the filtrate was concentrated under vacuum, to afford 500 mg (99%) of the title compound as an off-white solid. LC-MS: (ES, m/z): 159.

Step 2: Synthesis of (1r,4r)-4-phenylcyclohexan-1-ol

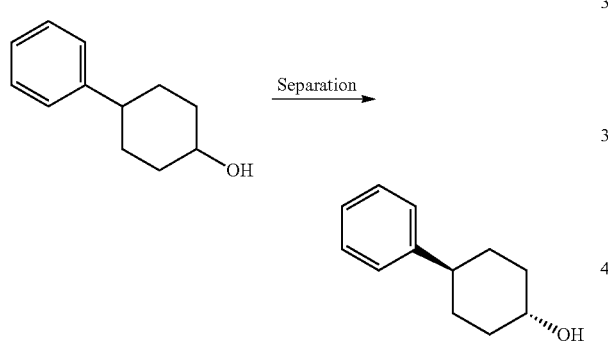

The crude product from the previous step (500 mg) was purified by Prep-HPLC under the following conditions: Instrument "B"; Column "B"; mobile phase, 10 mM aq NH₄HCO₃ and ACN (45.0% ACN up to 51.0% in 7 min); Detector, UV 254/220 nm, to afford 108 mg (22%) of the title compound as a white solid.

LC-MS–: (ES, m/z): 159

Step 3: Synthesis of (1r,4r)-4-phenylcyclohexyl N-[5-[(tert-butyldimethylsilyl)oxy]pyridin-2-yl]carbamate

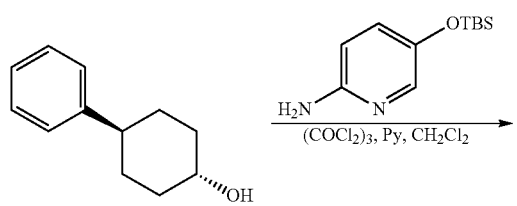

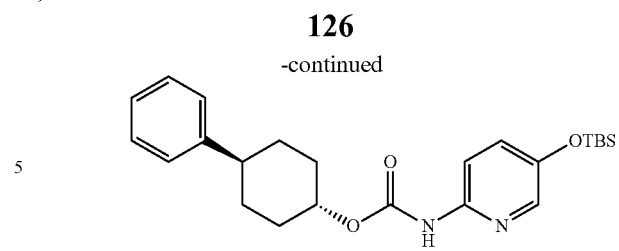

A solution of the product from the previous step (300 mg, 1.70 mmol, 1.00 eq), triphosgene (256 mg, 0.85 mmol, 0.50 eq), and 5-[(tert-butyldimethylsilyl)oxy]pyridin-2-amine (382 mg, 1.70 mmol, 1.00 eq) in pyridine (1 mL) and CH₂Cl₂ (5 mL) was stirred for 16 h at rt. The resulting solution was extracted with 2×30 mL of CH₂Cl₂, and the combined organic layers were concentrated under vacuum and purified with silica gel chromatography using EtOAc/hexane (1:2) to afford 300 mg (41%) of the title compound as an off-white solid. LC-MS: (ES, m/z): 427

Step 4: Synthesis of (1r,4r)-4-phenylcyclohexyl N-(5-hydroxypyridin-2-yl)carbamate

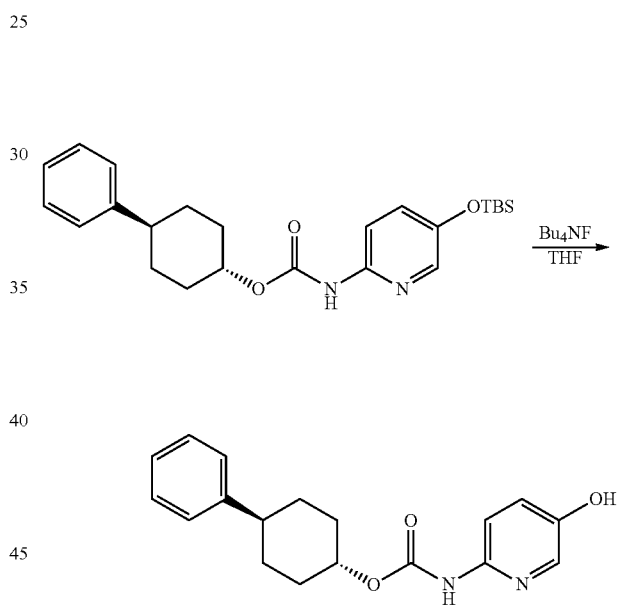

A solution of the product from the previous step (200 mg, 0.47 mmol, 1.00 eq) and Bu₄NF (245 mg, 0.94 mmol, 2.00 eq) in THF (3 mL) was stirred for 2 h at rt, then concentrated under vacuum. The crude product (200 mg) was purified by Prep-HPLC under the following conditions: Instrument "B"; Column "A"; mobile phase, 10 mM aq NH₄HCO₃ and ACN (36.0% ACN up to 63.0% in 7 min); Detector, UV 254/220 nm, to afford 91.1 mg (62%) of the title compound as an off-white solid.

LC-MS: (ES, m/z): 313

¹H NMR (300 MHz, DMSO-d₆) 7.79 (d, J=2.9 Hz, 1H), 7.59 (d, J=8.9 Hz, 1H), 7.34-7.11 (m, 6H), 4.67 (m, 1H), 2.56 (dt, J=11.6, 3.6 Hz, 1H), 2.08 (dd, J=9.8, 5.1 Hz, 2H), 1.84 (d, J=11.5 Hz, 2H), 1.70-1.36 (m, 4H).

Example 44

1-Phenylpiperidin-4-yl N-(5-hydroxypyridin-2-yl)carbamate

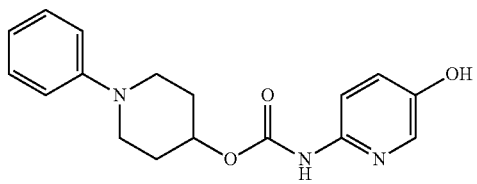 [SMILES: O=C(Nc1ccc(O)cn1)OC1CCN(c2ccccc2)CC1]

Step 1: Synthesis of 1-phenylpiperidin-4-yl N-[5-[(tert-butyldimethylsilyl) oxy]pyridin-2-yl]carbamate

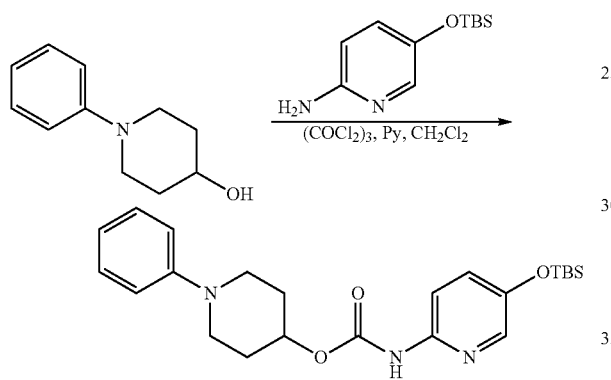

To a solution of triphosgene (300 mg) in CH$_2$Cl$_2$ (5 mL) was added 1-phenylpiperidin-4-ol (352 mg, 1.99 mmol) over 3 hr, followed by the addition of a solution of 5-[(tert-butyldimethylsilyl)oxy]pyridin-2-amine (448 mg, 2.00 mmol, 1.00 eq) in pyridine (1 mL) over 16 hr. The resulting solution was stirred an additional 16 h at rt, then extracted with 2×30 mL of CH$_2$Cl$_2$. The combined organic layers were concentrated under vacuum and purified with silica gel chromatography using CH$_2$Cl$_2$/MeOH (20:1) to afford 270 mg (32%) of the title compound as an off-white solid. LC-MS: (ES, m/z): 428.

Step 2: Synthesis of 1-phenylpiperidin-4-yl N-(5-hydroxypyridin-2-yl)carbamate

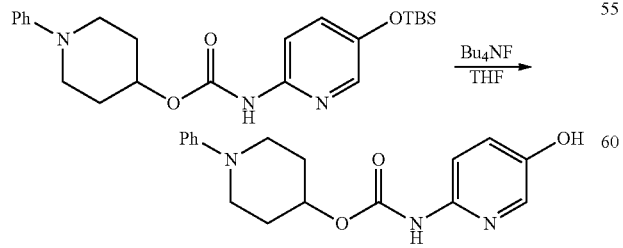

A solution of the product from the previous step (270 mg, 0.63 mmol, 1.00 eq) and Bu$_4$NF (330 mg, 1.26 mmol, 2.00 eq) in THF (5 mL) was stirred for 2 h at rt, then concentrated under vacuum. The crude product (270 mg) was purified by Prep-HPLC with the following conditions: Instrument "B"; Column "D"; mobile phase, water (0.1% FA) and ACN (5.0% ACN up to 37.0% in 7 min), to afford 67.9 mg (34%) of the title compound as an off-white solid.

LC-MS: (ES, m/z): 314

$^1$H NMR (300 MHz, DMSO-d$_6$) δ 9.71 (s, 1H), 9.55 (s, 1H), 7.80 (d, J=2.9 Hz, 1H), 7.60 (d, J=8.9 Hz, 1H), 7.27-7.12 (m, 3H), 7.01-6.89 (m, 2H), 6.75 (tt, J=7.2, 1.1 Hz, 1H), 4.81 (m, 1H), 3.51 (m, 2H), 3.02 (m, 2H), 1.97 m, 2H), 1.68 (m, 2H).

Scheme VI

Example 45

N-(5-hydroxypyridin-2-yl)-4-(5-methoxypyridin-2-yl)piperazine-1-carboxamide

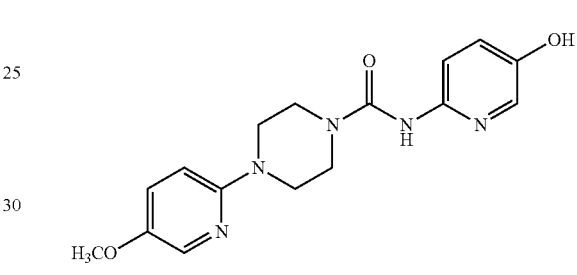

Step 1. Synthesis of tert-butyl 4-(5-methoxypyridin-2-yl)piperazine-1-carboxylate

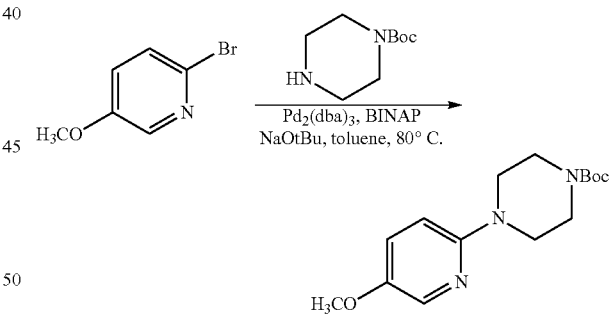

A solution of tert-butyl piperazine-1-carboxylate (2 g, 10.74 mmol), 2-bromo-5-methoxypyridine (2 g, 10.64 mmol), Pd$_2$(dba)$_3$ (98 mg, 0.11 mmol), BINAP (67 mg, 0.11 mmol), and NaOtBu (1.5 g, 15.62 mmol) in toluene (20 mL) was stirred for 16 h at 80° C., then quenched by the addition of H$_2$O and extracted with EtOAc. The combined organic layers were concentrated under vacuum and purified with silica gel chromatography using EtOAc/petroleum ether (1:3) to afford 2 g (63%) of the title compound as a white solid.

LC-MS: (ES, m/z): 294.3

$^1$HNMR (300 MHz, DMSO-d$_6$) δ 7.87 (dd, J=3.1, 0.6 Hz, 1H), 7.26 (dd, J=9.1, 3.1 Hz, 1H), 6.82 (dd, J=9.2, 0.7 Hz, 1H), 3.71 (s, 3H), 3.44-3.27 (m, 8H), 1.40 (s, 9H).

Step 2. Synthesis of 1-(5-methoxypyridin-2-yl)piperazine

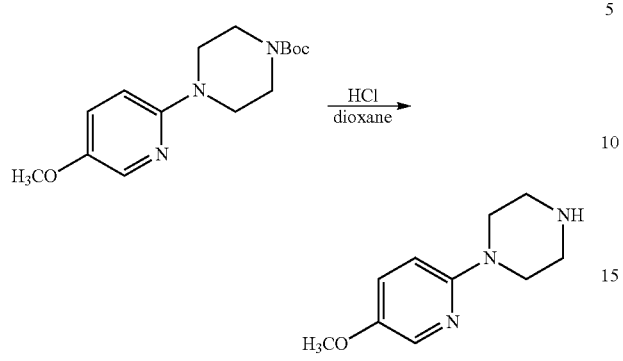

A solution of the product from the previous step (1 g, 3.41 mmol) in dioxane (5 mL), 4N HCl/dioxane (3 mL) was stirred for 2 h at rt, then concentrated under vacuum. The pH was adjusted to 8-9 with NaHCO$_3$. The resulting solution was extracted with EtOAc, and the combined organic layers were concentrated to afford 1 g crude of the title compound as a yellow oil.

Step 3. Synthesis of N-[5-[(tert-butyldimethylsilyl)oxy]pyridin-2-yl]-4-(5-methoxypyridin-2-yl)piperazine-1-carboxamide

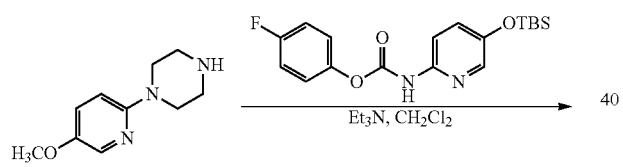

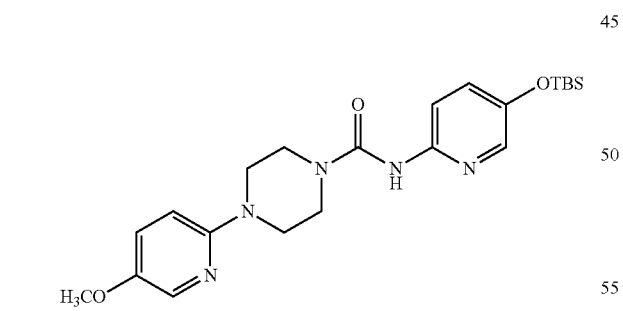

A solution of the product from the previous step (100 mg, 0.52 mmol), Intermediate "A" (200 mg, 0.55 mmol), and Et$_3$N (160 mg) in CH$_2$Cl$_2$ (20 mL) was stirred for 16 h at rt, then concentrated under vacuum and purified with silica gel chromatography using EtOAc/petroleum ether (1:3) to afford 150 mg (65%) of the title compound as a white solid.

LC-MS: (ES, m/z): 444.5

Step 4. Synthesis of N-(5-hydroxypyridin-2-yl)-4-(5-methoxypyridin-2-yl)piperazine-1-carboxamide A solution of the product from the previous step (150 mg, 0.34 mmol) in 2N aq. HCl (2 mL) and THF (5 mL) was stirred for 4 h at rt, then concentrated under vacuum. The crude product was purified by Prep-HPLC with the following conditions: Instrument "A"; Column "A"; mobile phase, 10 mM aq NH$_4$HCO$_3$ and ACN (10.0% ACN up to 46.0% in 8 min); Detector, UV 254/220 nm, to afford 26.6 mg (24%) of the title compound as a white solid.

LC-MS: (ES, m/z): 330.0

$^1$H NMR (300 MHz, DMSO-d$_6$) δ 9.48 (s, 1H), 8.88 (s, 1H), 7.88 (d, J=3.1 Hz, 1H), 7.77 (d, J=2.9 Hz, 1H), 7.57 (d, J=8.9 Hz, 1H), 7.26 (dd, J=9.1, 3.1 Hz, 1H), 7.12 (dd, J=9.0, 3.0 Hz, 1H), 6.85 (d, J=9.1 Hz, 1H), 3.71 (s, 3H), 3.53 (m, 4H), 3.40-3.31 (m, 4H).

Example 46

N-(5-hydroxypyridin-2-yl)-4-[5-(trifluoromethoxy)pyridin-2-yl]piperazine-1-carboxamide

Step 1. Synthesis of tert-butyl 4-[5-(trifluoromethoxy)pyridin-2-yl]piperazine-1-carboxylate

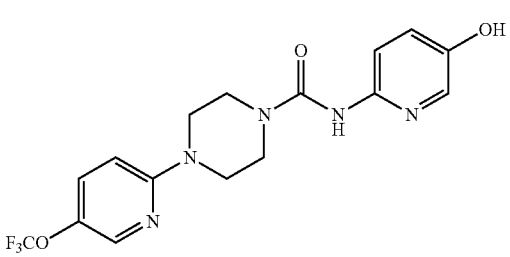 [SMILES: O=C(Nc1ccc(O)cn1)N1CCN(c2ccc(OC(F)(F)F)cn2)CC1]

-continued

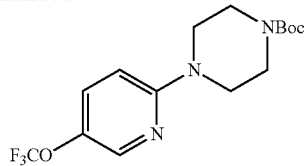

A solution of 2-bromo-5-(trifluoromethoxy)pyridine (500 mg, 2.07 mmol), tert-butyl piperazine-1-carboxylate (386 mg, 2.07 mmol), NaOtBu (299 mg), BINAP (65 mg), and Pd$_2$(dba)$_3$ (95 mg, 0.10 mmol) in toluene (10 mL) was stirred for 16 h at 80° C., then quenched by the addition of 30 mL H$_2$O. The resulting solution was extracted with 2×60 mL of EtOAc, and the combined organic layers were concentrated under vacuum and purified with silica gel chromatography using EtOAc/hexane (1/2) to afford 200 mg (28%) of the title compound as an off-white solid. LC-MS: (ES, m/z): 348

Step 2. Synthesis of 1-[5-(trifluoromethoxy)pyridin-2-yl]piperazine

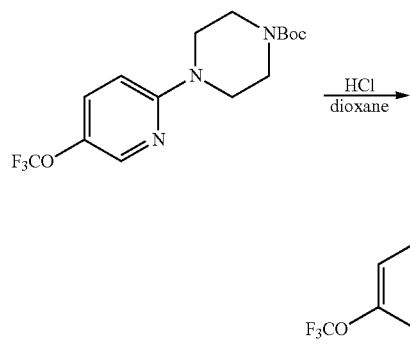

To a solution of the product from the previous step (200 mg, 0.58 mmol) in dioxane (3 mL) was added 4M aq. HCl in dioxane (1 mL) dropwise with stirring. The resulting solution was stirred for 4 h at rt. The pH was adjusted to 7 with 2 N NaHCO$_3$. The resulting solution was extracted with 50 mL of EtOAc, and the combined organic layers were concentrated under vacuum and purified with silica gel chromatography using EtOAc/hexane (2:1) to afford 100 mg (70%) of the title compound as an off-white solid. LC-MS: (ES, m/z): 248

Step 3. Synthesis of N-[5-[(tert-butyldimethylsilyl)oxy]pyridin-2-yl]-4-[5-(trifluoromethoxy)pyridin-2-yl]piperazine-1-carboxamide

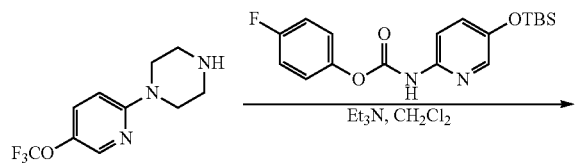

-continued

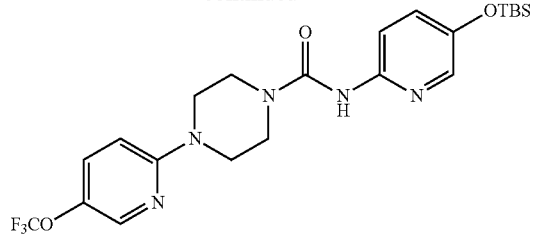

A solution of the product from the previous step (68 mg, 0.28 mmol), 4-fluorophenyl N-5-[(tert-butyldimethylsilyl)oxy]pyridin-2-ylcarbamate (100 mg, 0.28 mmol), and Et$_3$N (84 mg, 0.83 mmol) in CH$_2$Cl$_2$ (5 mL) was stirred for 16 h at rt, then quenched by the addition of 20 mL H$_2$O and extracted with 2×50 mL of EtOAc. The combined organic layers were concentrated under vacuum and purified with silica gel chromatography using EtOAc/hexane (1/2) to afford 116 mg (85%) of the title compound as an off-white solid. LC-MS: (ES, m/z): 498.

Step 4. Synthesis of N-(5-hydroxypyridin-2-yl)-4-[5-(trifluoromethoxy)pyridin-2-yl]piperazine-1-carboxamide

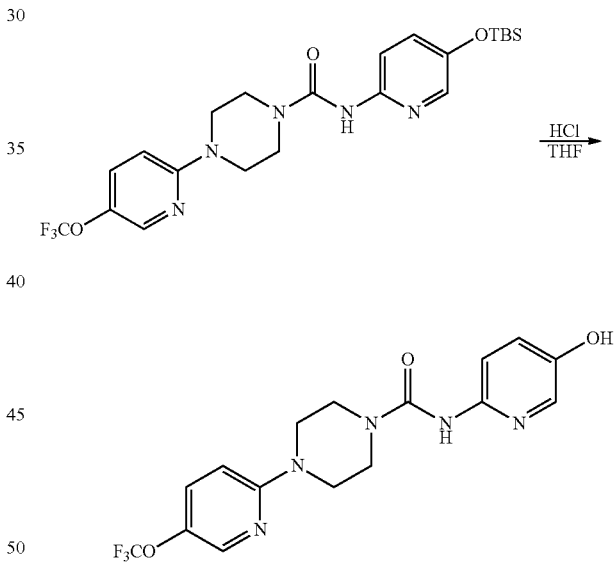

To a solution of the product from the previous step (116 mg, 0.30 mmol) in THF (2 mL) was added 2N aq. HCl (1 mL) dropwise with stirring. The resulting solution was stirred for 2 h at rt, then concentrated under vacuum. The crude product (150 mg) was purified by Prep-HPLC with the following conditions: Instrument "A"; Column "A"; mobile phase, 10 mM aq NH$_4$HCO$_3$ and ACN (30.0% ACN up to 52.0% in 8 min); Detector, UV 254/220 nm, to afford 64.6 mg (43%) of the title compound as an off-white solid.

LC-MS: (ES, m/z): 384

$^1$H NMR (300 MHz, DMSO-d$_6$) δ 9.44 (s, 1H), 8.91 (s, 1H), 8.15 (m, 1H), 7.78 (m, 1H), 7.65-7.53 (m, 2H), 7.12 (dd, J=8.9, 3.0 Hz, 1H), 6.95 (d, J=9.3 Hz, 1H), 3.53 (br s, 8H).

Example 47

1-[1-(4-fluorophenyl)piperidin-3-yl]-3-(5-hydroxypyridin-2-yl)urea

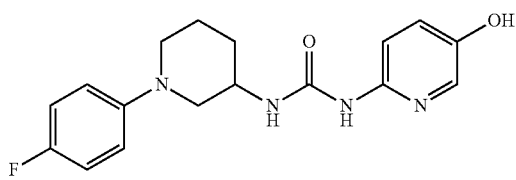 [SMILES: O=C(Nc1ccc(O)cn1)NC1CCCN(c2ccc(F)cc2)C1]

Step 1. Synthesis of tert-butyl N-[1-(4-fluorophenyl)piperidin-3-yl]carbamate

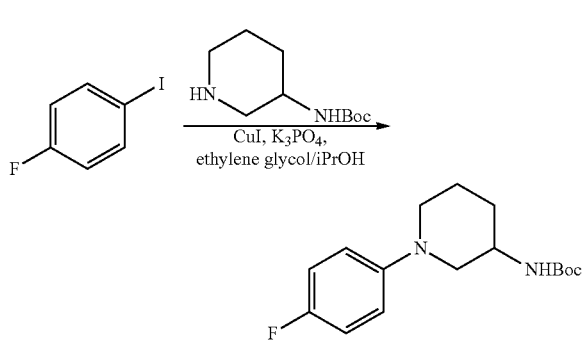

A solution of 1-fluoro-4-iodobenzene (1 g, 4.50 mmol), CuI (86 mg, 0.45 mmol), $K_3PO_4$ (1.9 g, 8.95 mmol), and tert-butyl N-(piperidin-3-yl)carbamate (900 mg, 4.49 mmol) in ethylene glycol/isopropanol (1/10 mL) was stirred for 16 h at 90° C., then cooled to rt and diluted with water (100 mL). The resulting solution was extracted with 3×50 mL of EtOAc. The combined organic layers were washed with brine, dried over $Na_2SO_4$, concentrated under vacuum, and purified with silica gel chromatography using EtOAc/petroleum ether (1/4) to afford 550 mg (41%) of the title compound as a light yellow oil. LC-MS (ES, m/z): 295.20.

Step 2. Synthesis of 1-(4-fluorophenyl)piperidin-3-amine

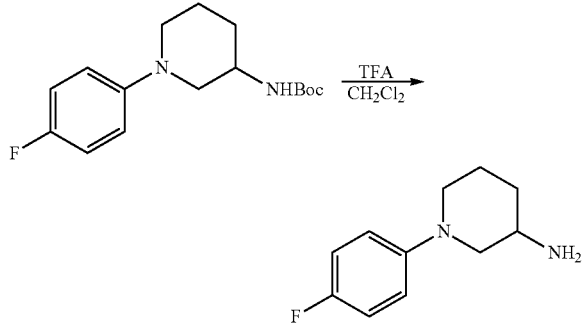

A solution of the product from the previous step (550 mg, 1.87 mmol) in $CF_3COOH/CH_2Cl_2$ (5/5 mL) was stirred for 2 h at rt, then concentrated under vacuum, taken up in 90 mL of EtOAc, and washed with saturated aq. $NaHCO_3$. The combined organic layers were washed with brine, dried over anhydrous $Na_2SO_4$ and concentrated under vacuum, to afford 200 mg (55%) of the title compound as a light yellow oil. LC-MS (ES, m/z): 195.15

Step 3. Synthesis of 3-[5-[(tert-butyldimethylsilyl)oxy]pyridin-2-yl]-1-[1-(4-fluorophenyl)piperidin-3-yl]urea

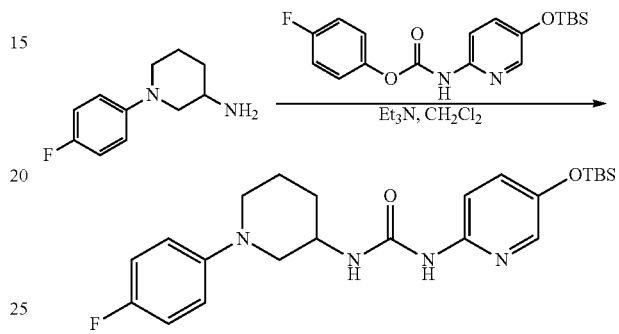

A solution of the product from the previous step (200 mg, 1.03 mmol), $Et_3N$ (0.297 mL), 4-fluorophenyl N-5-[(tert-butyldimethylsilyl)oxy]pyridin-2-ylcarbamate (373 mg, 1.03 mmol) in $CH_2Cl_2$ (10 mL) was stirred for 16 h at rt, then extracted with 3×30 mL of EtOAc. The combined organic layers were dried over $Na_2SO_4$, concentrated under vacuum, and purified with silica gel chromatography using EtOAc/petroleum ether (1/4) to afford 200 mg (44%) of the title compound as light yellow oil. LC-MS (ES, m/z): 445.35

Step 4. Synthesis of 1-[1-(4-fluorophenyl)piperidin-3-yl]-3-(5-hydroxypyridin-2-yl)urea

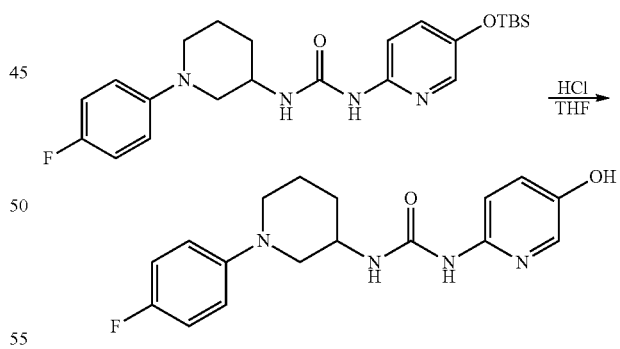

A solution of the product from the previous step (200 mg, 0.45 mmol) in 2N aq. HCl (2 mL) and THF (6 mL) was stirred for 2 h at rt, then concentrated under vacuum. The crude product was purified by Prep-HPLC with the following conditions: Instrument "A"; Column "A"; mobile phase, water (0.05% $NH_3H_2O$) and ACN (35.0% ACN up to 40.0% in 7 min); Detector, UV 254; 220 nm, affording 45.7 mg (31%) of as an off-white solid.

LC-MS (ES, m/z): 331.0

$^1$H NMR (300 MHz, DMSO-$d_6$) δ 9.37 (s, 1H), 8.84 (s, 1H), 8.03 (s, 1H), 7.69 (d, J=2.9 Hz, 1H), 7.28 (d, J=8.9 Hz,

1H), 7.14 (dd, J=8.9, 2.9 Hz, 1H), 7.09-7.00 (m, 2H), 7.00-6.91 (m, 2H), 3.90-3.73 (m, 1H), 3.40 (dd, J=11.9, 3.5 Hz, 1H), 3.21 (d, J=12.6 Hz, 1H), 2.95 (t, J=9.6 Hz, 1H), 2.80 (dd, J=11.7, 7.7 Hz, 1H), 1.78 (s, 2H), 1.70-1.56 (m, 1H), 1.48 (d, J=8.6 Hz, 1H).

Example 48

1-[1-(4-chlorophenyl)piperidin-3-yl]-3-(5-hydroxypyridin-2-yl)urea

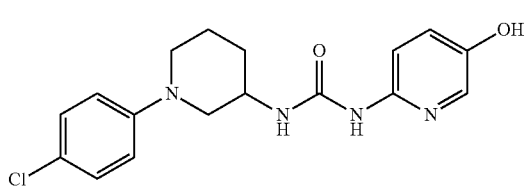 [SMILES: O=C(Nc1ccc(O)cn1)NC1CCCN(c2ccc(Cl)cc2)C1]

Step 1. Synthesis of tert-butyl N-[1-(4-chlorophenyl)piperidin-3-yl]carbamate

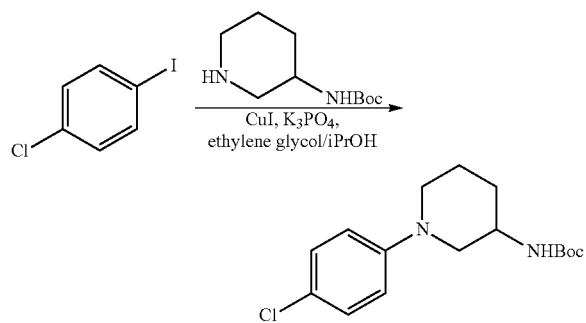

A solution of 1-chloro-4-iodobenzene (1 g, 4.19 mmol), CuI (80 mg, 0.42 mmol), K₃PO₄ (1.8 g, 8.48 mmol), and tert-butyl N-(piperidin-3-yl)carbamate (800 mg, 3.99 mmol) in ethylene glycol/isopropanol (1/10 mL) was stirred for 16 h at 90° C., then cooled to rt and diluted with H₂O (100 mL). The resulting mixture was extracted with 3×50 mL of EtOAc. The combined organic layers were washed with brine, dried over Na₂SO₄ concentrated under vacuum, and purified with silica gel chromatography using EtOAc/petroleum ether (1/4) to afford 0.5 g (38%) of the title compound as light yellow oil. LC-MS (ES, m/z): 311.15

Step 2. Synthesis of 1-(4-chlorophenyl)piperidin-3-amine

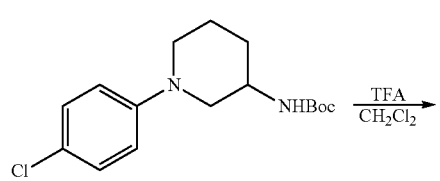

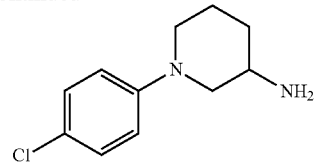

A solution of the product from the previous step (500 mg, 1.61 mmol) in CF₃COOH (5 mL)/CH₂Cl₂ (5 mL) was stirred for 2 h at rt, then concentrated under vacuum. The residue was taken up in 3×30 mL of EtOAc, and washed with aq. NaHCO₃. The combined organic layers were concentrated under vacuum to afford 200 mg (59%) of the title compound as light yellow oil. LC-MS (ES, m/z): 211.15

Step 3. Synthesis of 3-[5-[(tert-butyldimethylsilyl)oxy]pyridin-2-yl]-1-[1-(4-chlorophenyl)piperidin-3-yl]urea

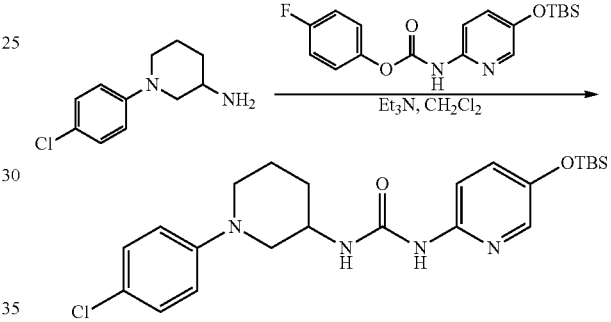

A solution of the product from the previous step (200 mg, 0.95 mmol), Et₃N (0.275 mL), and 4-fluorophenyl N-5-[(tert-butyldimethylsilyl)oxy]pyridin-2-ylcarbamate (345 mg, 0.95 mmol) in CH₂Cl₂ (10 mL) was stirred for 16 h at rt, then extracted with 3×30 mL EtOAc. The combined organic layers were dried over Na₂SO₄, concentrated under vacuum, and purified with prep-TLC using EtOAc/petroleum ether (1/4) to afford 200 mg (46%) of the title compound as a light yellow oil.

Step 4. Synthesis of 1-[1-(4-chlorophenyl)piperidin-3-yl]-3-(5-hydroxypyridin-2-yl)urea

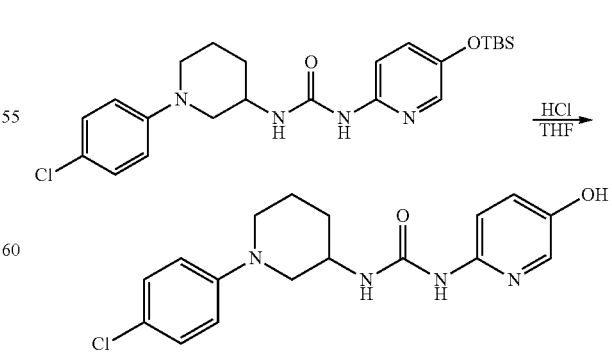

A solution of the product from the previous step (200 mg, 0.43 mmol), 2 N aq. HCl (2 mL) and THF (6 mL) was stirred for 2 h at rt, then concentrated under vacuum and purified by Prep-HPLC with the following conditions: Instrument "A"; Column "A"; mobile phase, water (0.05% NH₃H₂O) and ACN (35.0% ACN up to 40.0% in 7 min); Detector, UV 254; 220 nm, to afford 65.3 mg (43%) of the title compound an off-white solid.

LC-MS (ES, m/z): 347.0

¹H NMR (300 MHz, DMSO-d₆) δ 9.37 (s, 1H), 8.84 (s, 1H), 8.00 (s, 1H), 7.68 (d, J=2.9 Hz, 1H), 7.40-7.08 (m, 4H), 7.04-6.87 (m, 2H), 3.78 (d, J=9.4 Hz, 1H), 3.50 (dd, J=11.9, 3.5 Hz, 1H), 3.30 (s, 1H), 3.00 (t, J=9.3 Hz, 1H), 2.85 (dd, J=12.1, 7.9 Hz, 1H), 1.82 (d, J=12.3 Hz, 2H), 1.69-1.42 (m, 2H).

Example 49

1-[1-(5-fluoropyridin-2-yl)piperidin-4-yl]-3-(5-hydroxypyridin-2-yl)urea

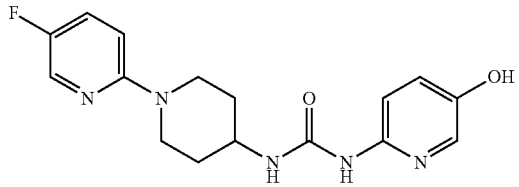 [SMILES: O=C(Nc1ccc(O)cn1)NC1CCN(c2ccc(F)cn2)CC1]

Step 1. Synthesis of tert-butyl N-[1-(5-fluoropyridin-2-yl)piperidin-4-yl] carbamate

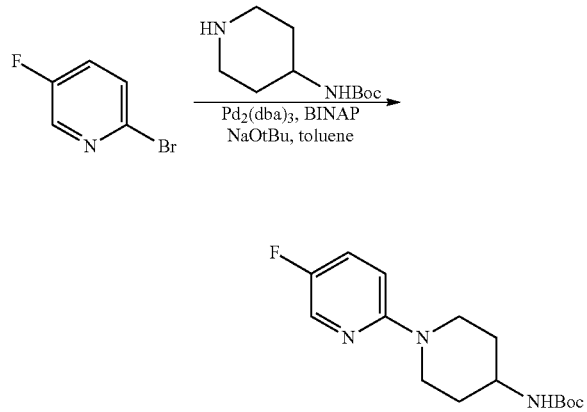

A solution of 2-bromo-5-fluoropyridine (1 g, 5.68 mmol), NaOtBu (0.8 g), BINAP (0.133 g), tert-butyl N-(piperidin-4-yl)carbamate (1.1 g, 5.49 mmol), and Pd₂(dba)₃ (260 mg, 0.28 mmol) in toluene (20 mL) was stirred for 16 h at 80° C., then extracted with 2×30 mL of EtOAc. The combined organic layers were concentrated under vacuum and purified with silica gel chromatography using EtOAc/hexane (1/2) to afford 700 mg (42%) of the title compound as an off-white solid. LC-MS (ES, m/z): 296.

Step 2. Synthesis of 1-(5-fluoropyridin-2-yl)piperidin-4-amine

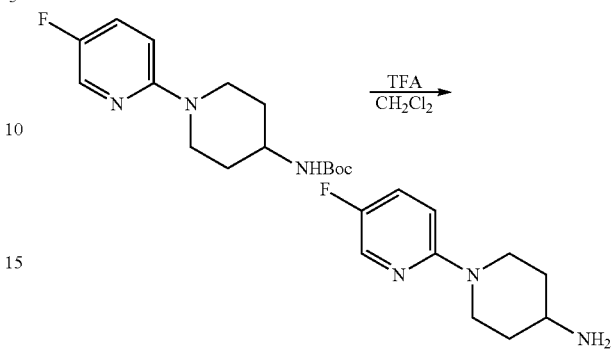

To a solution of the product from the previous step (700 mg, 2.37 mmol) in CH₂Cl₂ (6 mL) was added CF₃COOH (3 mL) dropwise with stirring. The resulting solution was stirred for 4 h at rt. The pH was adjusted to 8 with aq. NaHCO₃. The resulting solution was extracted with 30 mL of EtOAc, and the combined organic layers were concentrated under vacuum, to afford 300 mg (65%) of the title compound as an off-white solid. LC-MS (ES, m/z): 196

Step 3. Synthesis of 3-[5-[(tert-butyldimethylsilyl)oxy]pyridin-2-yl]-1-[1-(5-fluoropyridin-2-yl)piperidin-4-yl]urea

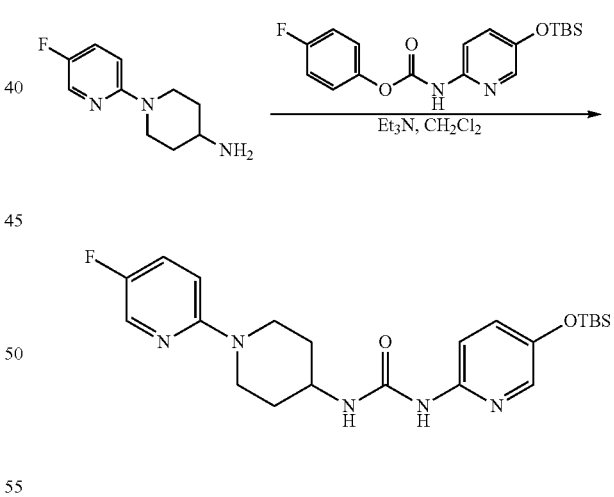

To a solution of the product from the previous step (54 mg, 0.28 mmol) in CH₂C₁₂ (5 mL) was added Et₃N (84 mg, 0.83 mmol), in portions, followed by the addition of 5-fluoropyridin-2-yl N-5-[(tert-butyldimethylsilyl)oxy]pyridin-2-ylcarbamate (100 mg, 0.28 mmol), in portions. The resulting solution was stirred for 16 h at rt, then extracted with 2×30 mL CH₂Cl₂. The combined organic layers concentrated under vacuum and purified with silica gel chromatography using EtOAc/hexane (1/2) to afford 100 mg (81%) of the title compound as an off-white solid. LC-MS (ES, m/z): 446.

Step 4. Synthesis of 1-[1-(5-fluoropyridin-2-yl)piperidin-4-yl]-3-(5-hydroxypyridin-2-yl)urea

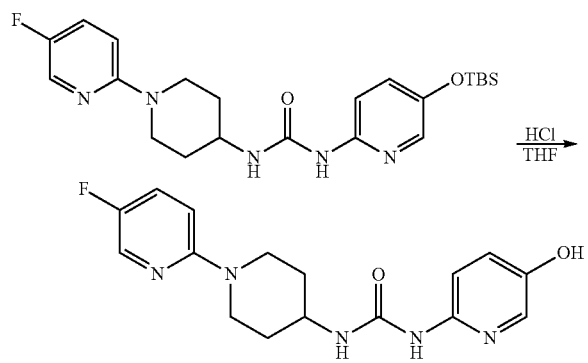

To a solution of the product from the previous step (100 mg, 0.22 mmol) in THF (4 mL) was added 2N aq. HCl (2 mL) dropwise with stirring. The resulting solution was stirred for 2 h at rt, then concentrated under vacuum. The crude product (100 mg) was purified by Prep-HPLC under the following conditions: Instrument "A"; Column "A"; mobile phase, water (0.05% $NH_3H_2O$) and ACN (20.0% ACN up to 35.0% in 7 min); Detector, UV 254; 220 nm, to afford 51.8 mg (70%) of the title compound as light yellow oil.

LC-MS (ES, m/z): 332

$^1$H NMR (300 MHz, Methanol-$d_4$) δ 8.00 (s, 1H), 7.77 (s, 1H), 7.41 (d, J=9.0 Hz, 1H), 7.22 (d, J=8.9 Hz, 1H), 7.02 (d, J=9.0 Hz, 1H), 6.87 (dd, J=9.6, 3.5 Hz, 1H), 3.98 (m, 3H), 3.43-3.03 (m, 2H), 2.11-2.00 (m, 2H), 1.59 (m, 2H).

Example 50

4-(6-fluoropyridin-3-yl)-N-(5-hydroxypyridin-2-yl)piperazine-1-carboxamide

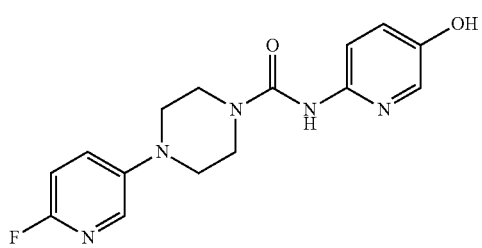 [SMILES: O=C(Nc1ccc(O)cn1)N1CCN(c2ccc(F)nc2)CC1]

Step 1. Synthesis of benzyl 4-(6-fluoropyridin-3-yl)piperazine-1-carboxylate

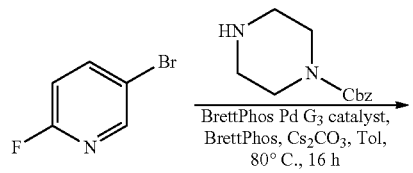

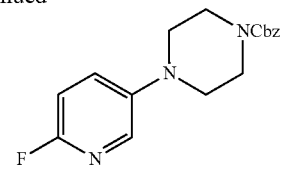

A solution of 5-bromo-2-fluoropyridine (200 mg, 1.14 mmol), benzyl piperazine-1-carboxylate (251 mg, 1.14 mmol), $Cs_2CO_3$ (1.1 g, 3.38 mmol), BrettPhos (6 mg), and BrettPhos Pd G3 catalyst (10 mg) in toluene (5 mL) was stirred for 16 h at 80° C., then extracted with 2×30 mL of EtOAc. The combined organic layers were concentrated under vacuum and purified with silica gel column chromatography using EtOAc/hexane (1/2) to afford 90 mg (25%) of the title compound as an off-white solid. LC-MS (ES, m/z): 315.95

Step 2. Synthesis of 1-(6-fluoropyridin-3-yl)piperazine

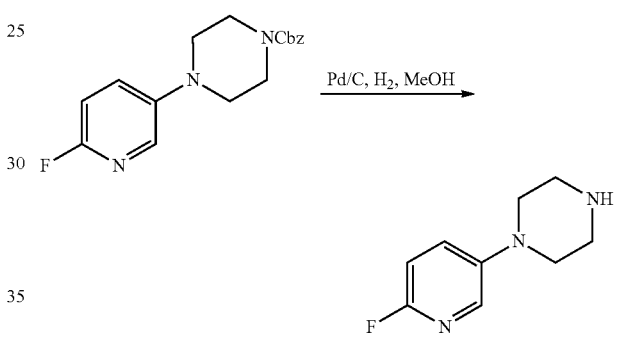

A solution of the product from the previous step (90 mg, 0.29 mmol) in MeOH (5 mL) was stirred for 16 h under $H_2$ and over Pd/C (10 mg) at rt. The solids were removed by filtration, and the filtrate was concentrated under vacuum to afford 40 mg (77%) of the title compound as an off-white solid. LC-MS (ES, m/z): 182.2

Step 3. Synthesis of N-[5-[(tert-butyldimethylsilyl)oxy]pyridin-2-yl]-4-(6-fluoropyridin-3-yl)piperazine-1-carboxamide

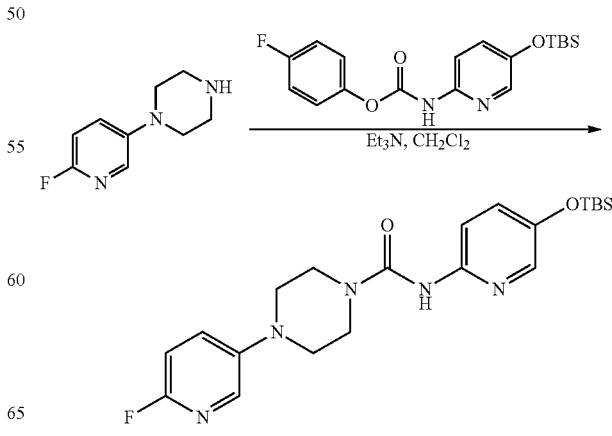

A solution of the product from the previous step (40 mg, 0.22 mmol), 5-fluoro-pyridin-2-yl N-5-[(tert-butyldimethylsilyl)oxy]pyridin-2-ylcarbamate (80 mg, 0.22 mmol), and Et₃N (67 mg, 0.66 mmol) in CH₂Cl₂ (5 mL) was stirred for 16 h at rt, then extracted with 2×30 mL of EtOAc. The combined organic layers were concentrated under vacuum and purified with silica gel column chromatography using EtOAc EtOAc/hexane (1/2) to afford 80 mg (84%) of the title compound as an off-white solid. LC-MS (ES, m/z): 432.2.

Step 4. Synthesis of 4-(6-fluoropyridin-3-yl)-N-(5-hydroxypyridin-2-yl) piperazine-1-carboxamide

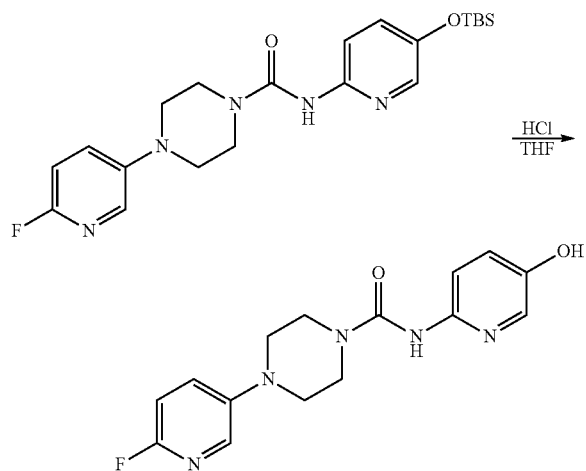

To a solution of the product from the previous step (80 mg, 0.19 mmol) in THF (2 mL) was added 2N aq. HCl (1 mL) dropwise with stirring. The resulting solution was stirred for 2 h at rt, then concentrated under vacuum. The crude product (80 mg) was purified by Prep-HPLC with the following conditions: Instrument "A"; Column "D"; mobile phase, water (0.1% FA) and ACN (3.0% ACN up to 28.0% in 7 min); Detector, UV 254/220 nm, affording 28.1 mg (48%) of the title compound as an off-white solid.

LC-MS (ES, m/z): 318.0

¹H NMR (300 MHz, DMSO-d₆) δ 9.42 (s, 1H), 8.93 (s, 1H), 7.84 (t, J=2.5 Hz, 1H), 7.78 (d, J=3.0 Hz, 1H), 7.68-7.52 (m, 2H), 7.14 (dd, J=8.9, 3.0 Hz, 1H), 7.02 (dd, J=8.9, 3.5 Hz, 1H), 3.59 (m, 4H), 3.13 m, 4H).

Example 51

1-[1-(4-fluorophenyl)piperidin-4-yl]-3-(5-hydroxypyridin-2-yl)urea

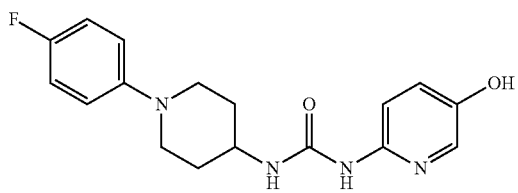 [SMILES: O=C(Nc1ccc(O)cn1)NC1CCN(c2ccc(F)cc2)CC1]

Step 1. Synthesis of tert-butyl N-[1-(4-fluorophenyl)piperidin-4-yl]carbamate

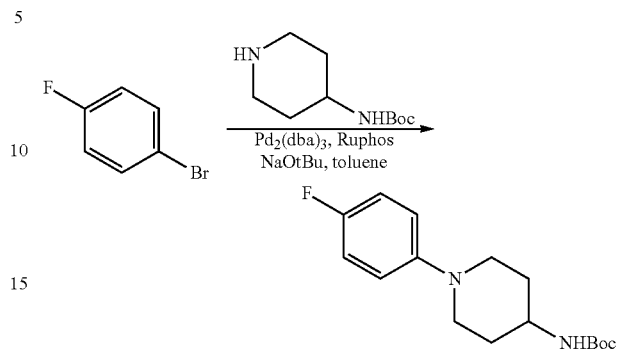

A solution of 1-bromo-4-fluorobenzene (1 g, 5.71 mmol), tert-butyl N-(piperidin-4-yl)carbamate (2.3 g, 11.48 mmol), NaOtBu (1.66 g, 1.50 equiv), Ruphos (268 mg), and Pd₂(dba)₃ (526 mg, 0.57 mmol) in toluene (20 mL) was stirred under N₂ for 16 h at 80° C., then quenched by the addition of 60 mL H₂O and extracted with 2×60 mL of EtOAc. The combined organic layers were concentrated under vacuum and purified with silica gel chromatography using EtOAc/hexane (1/2) to afford 590 mg (35%) of the title compound as an off-white solid. LC-MS (ES, m/z): 295.

Step 2. Synthesis of 1-(4-fluorophenyl)piperidin-4-amine

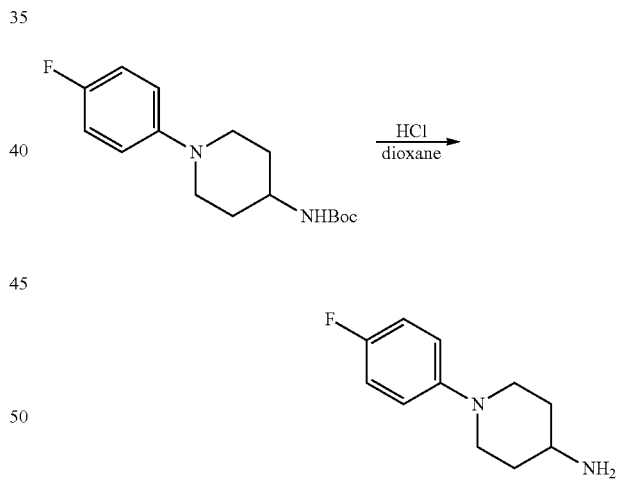

To a solution of the product from the previous step (590 mg, 2.00 mmol) in 1,4-dioxane (10 mL) was added 4M HCl/dioxane (4 mL) dropwise with stirring at rt over 2 min. The resulting solution was stirred for 4 h at rt. The pH was adjusted to 7 with 2 N NaHCO₃. The resulting solution was extracted with 2×50 mL of EtOAc, and the combined organic layers were concentrated under vacuum to afford 190 mg (49%) of the title compound as an off-white solid.

LC-MS: (ES, m/z): 195

¹H NMR (400 MHz, DMSO-d₆) δ 7.10-6.97 (m, 2H), 6.97-6.90 (m, 2H), 3.55-3.44 (m, 2H), 2.65 (td, J=11.9, 2.7 Hz, 3H), 1.76 (d, J=12.7 Hz, 2H), 1.39-1.22 (m, 2H).

Step 3. Synthesis of 3-[5-[(tert-butyldimethylsilyl)oxy]pyridin-2-yl]-1-[1-(4-fluorophenyl) piperidin-4-yl]urea

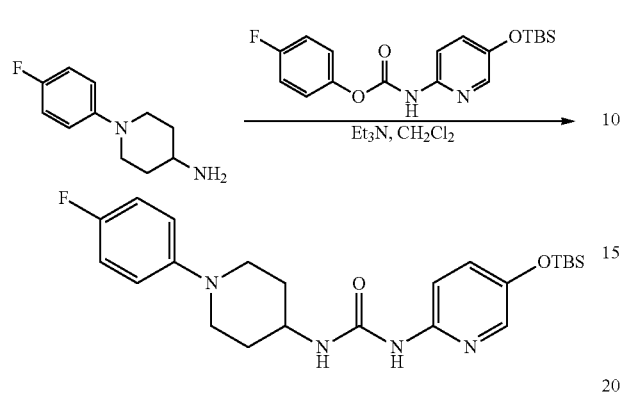

To a 40-mL vial containing the product from the previous step (150 mg, 0.41 mmol) was added Et₃N (126 g), in portions, followed by the addition of a solution of 1-(4-fluorophenyl)piperidin-4-amine (80 mg, 0.41 mmol) in CH₂Cl₂ (5 mL). The resulting solution was stirred for 16 h at rt, then quenched by the addition of 20 mL H₂O and extracted with 2×20 mL of EtOAc. The combined organic layers were concentrated under vacuum to afford 180 mg (98%) of the title compound as an off-white solid. LC-MS (ES, m/z): 445

Step 4. Synthesis of 1-[1-(4-fluorophenyl)piperidin-4-yl]-3-(5-hydroxypyridin-2-yl)urea

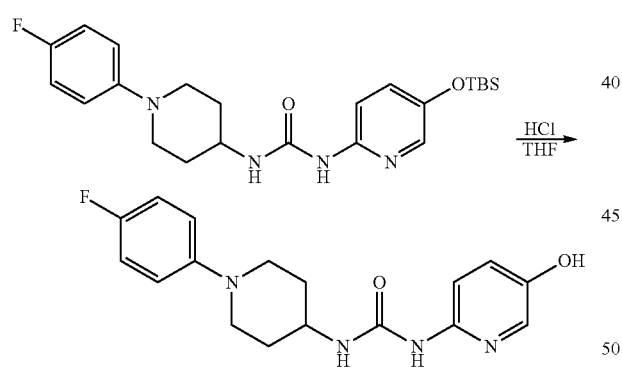

To a solution of the product from the previous step (180 mg, 0.40 mmol) in THF (2 mL) was added 2N aq. HCl (1 mL) dropwise with stirring. The resulting solution was stirred for 2 h at rt, then concentrated under vacuum. The crude product (180 mg) was purified by Prep-HPLC with the following conditions: Instrument "A"; Column "A"; mobile phase, 10 mM aq NH₄HCO₃ and ACN (25.0% ACN up to 54.0% in 8 min); Detector, UV 254/220 nm, to afford 50.5 mg (38%) of the title compound as an off-white solid.

LC-MS: (ES, m/z): 331
¹H NMR (300 MHz, DMSO-d₆) δ 9.38 (s, 1H), 8.76 (s, 1H), 7.89 (s, 1H), 7.69 (d, J=2.8 Hz, 1H), 7.24 (d, J=8.8 Hz, 1H), 7.12 (dd, J=8.9, 2.9 Hz, 1H), 7.08-6.88 (m, 4H), 3.67 (s, 1H), 3.42 (m, 2H), 2.82 (m, 2H), 1.91 (m, 2H), 1.58-1.44 (m, 2H).

Example 52

1-[1-(4-chlorophenyl)piperidin-4-yl]-3-(5-hydroxypyridin-2-yl)urea

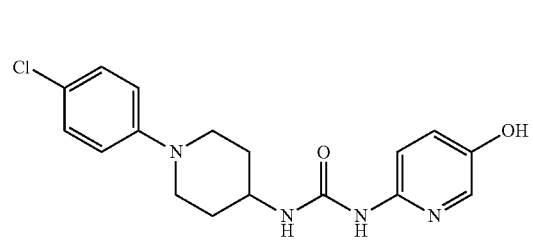 [SMILES: O=C(Nc1ccc(O)cn1)NC1CCN(c2ccc(Cl)cc2)CC1]

Step 1. Synthesis of tert-butyl N-[1-(4-chlorophenyl) piperidin-4-yl]carbamate

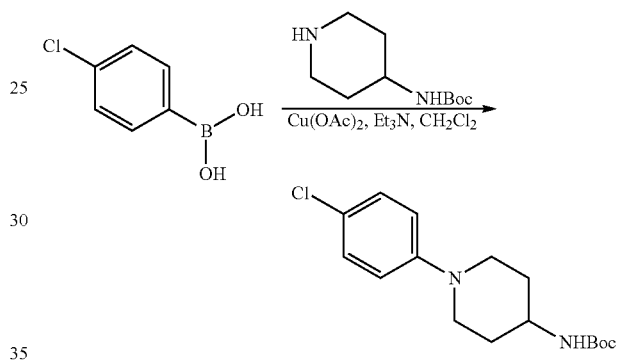

A solution of (4-chlorophenyl)boronic acid (1.56 g, 9.98 mmol), Cu(OAc)₂ (1.81 g, 9.97 mmol), tert-butyl N-(piperidin-4-yl)carbamate (1 g, 4.99 mmol), and Et₃N (4.04 g, 39.92 mmol) in CH₂Cl₂ (20 mL) was stirred for 16 h at rt, then quenched by the addition of 50 mL H₂O and extracted with 2×50 mL of EtOAc. The combined organic layers were concentrated under vacuum and purified with silica gel chromatography using EtOAc/hexane (1:5) to afford 2.5 g (161%) of the title compound as an off-white solid. LC-MS: (ES, m/z): 311.

Step 2. Synthesis of 1-(4-chlorophenyl)piperidin-4-amine

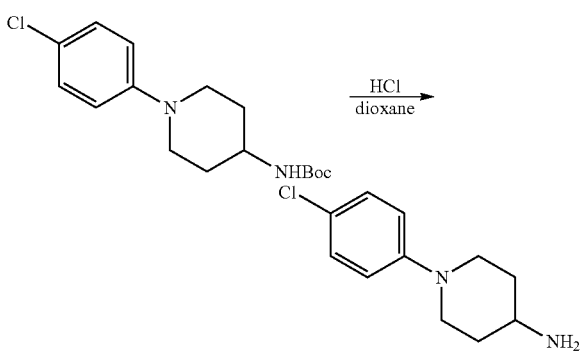

A solution of the product from the previous step (1 g, 3.22 mmol) in 4N HCl/dioxane (4 mL) and 1,4-dioxane (10 mL) was stirred for 4 h at rt. The pH was adjusted to 7 with 2 N NaHCO₃. The resulting solution was extracted with 2×50 mL of EtOAc, and the combined organic layers were concentrated under vacuum to afford 200 mg (30%) of the title compound as an off-white solid. LC-MS: (ES, m/z): 211

Step 3: Synthesis of 3-[5-[(tert-butyldimethylsilyl)oxy]pyridin-2-yl]-1-[1-(4-chlorophenyl)piperidin-4-yl]urea

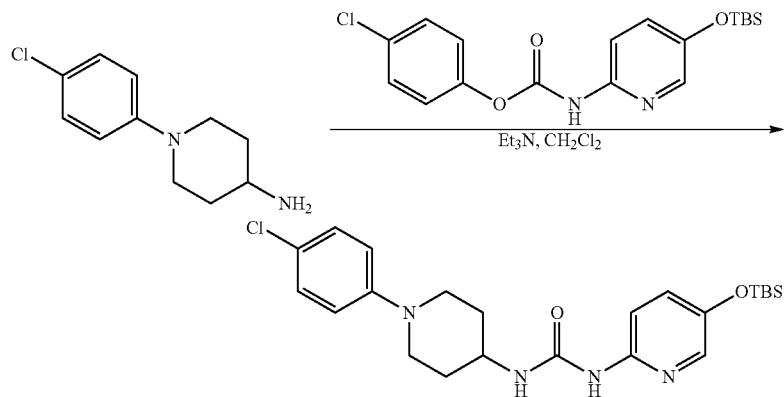

A solution of the product from the previous step (150 mg, 0.41 mmol), 1-(4-chlorophenyl)piperidin-4-amine (87 mg, 0.41 mmol, 1.00 equiv), and Et₃N (126 mg, 1.25 mmol) in CH₂Cl₂ (5 mL) was stirred for 16 h at rt, then quenched by the addition of 20 mL H₂O and extracted with 2×20 mL of EtOAc. The combined organic layers were concentrated under vacuum to afford 180 mg (95%) of the title compound as an off-white solid.

LC-MS: (ES, m/z): 461

Step 4. Synthesis of 1-[1-(4-chlorophenyl)piperidin-4-yl]-3-(5-hydroxypyridin-2-yl)urea

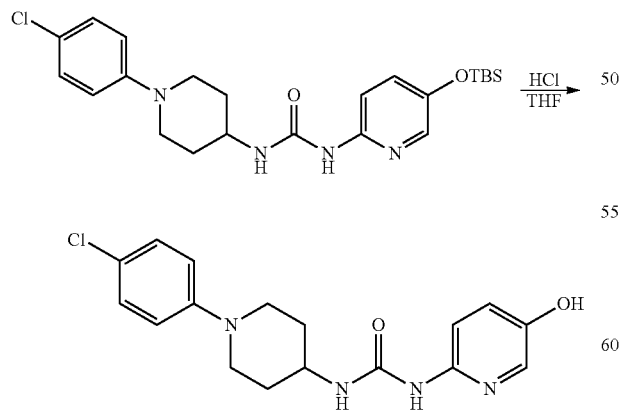

To a solution of the product from the previous step (180 mg, 0.39 mmol) in THF (2 mL) was added 2N aq. HCl (1 mL) dropwise with stirring. The resulting solution was stirred for 2 h at rt, then concentrated under vacuum. The crude product (180 mg) was purified by Prep-HPLC with the following conditions: Instrument "A"; Column "A"; mobile phase, Water (10 mM NH₄HCO₃) and ACN (30.0% ACN up to 57.0% in 8 min); Detector, UV 254/220 nm, to afford 82.8 mg (61%) of the title compound as an off-white solid.

LC-MS: (ES, m/z): 347

¹H NMR (300 MHz, DMSO-d₆) δ 9.37 (s, 1H), 8.77 (s, 1H), 7.89 (s, 1H), 7.69 (d, J=2.9 Hz, 1H), 7.32-7.10 (m, 4H), 6.94 (d, J=8.7 Hz, 2H), 3.69 (s, 1H), 3.52 (m, 2H), 2.87 (m, 2H), 1.90 (m, 2H), 1.46 (m, 2H).

Scheme VII

Example 53

1-(4-fluorophenyl)piperidin-4-yl N-(5-hydroxypyridin-2-yl)carbamate

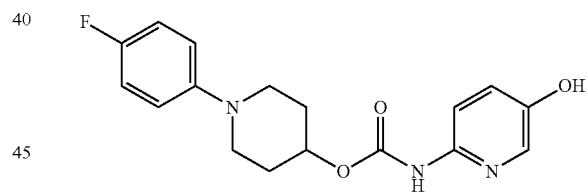

Step 1. Synthesis of 1-(4-fluorophenyl)piperidin-4-ol

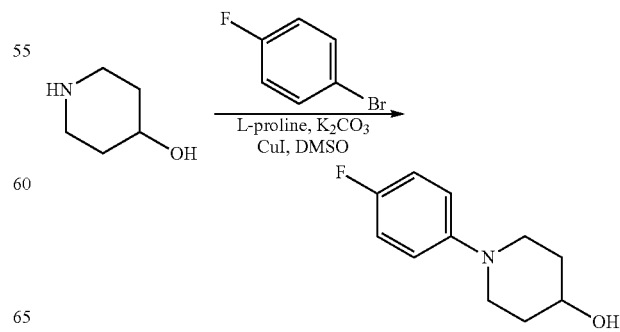

A solution of piperidin-4-ol (1 g, 9.89 mmol), 1-bromo-4-fluorobenzene (1.74 g, 9.94 mmol), L-proline (1.15 g), K₂CO₃ (2.76 g, 19.97 mmol), and CuI (190 mg, 1.00 mmol) in DMSO (20 mL) was stirred for 16 h under N₂ at 80° C., then cooled and extracted with 2×60 mL of EtOAc. The combined organic layers were concentrated under vacuum and purified with silica gel column chromatography using EtOAc/hexane (2:1) to afford 500 mg (26%) of the title compound as an off-white solid.

LC-MS: (ES, m/z): 196

¹H NMR (300 MHz, DMSO-d₆) δ 7.09-6.97 (m, 2H), 6.97-6.87 (m, 2H), 4.65 (d, J=4.2 Hz, 1H), 4.09 (q, J=5.3 Hz, 1H), 3.41 (dt, J=11.7, 4.3 Hz, 2H), 3.16 (d, J=5.1 Hz, 2H), 2.76 (ddd, J=12.7, 10.1, 3.1 Hz, 2H), 1.46 (dtd, J=13.0, 9.9, 3.8 Hz, 2H).

Step 2. Synthesis of 1-(4-fluorophenyl)piperidin-4-yl N-[5-[(tert-butyldimethylsilyl)oxy]pyridin-2-yl]carbamate

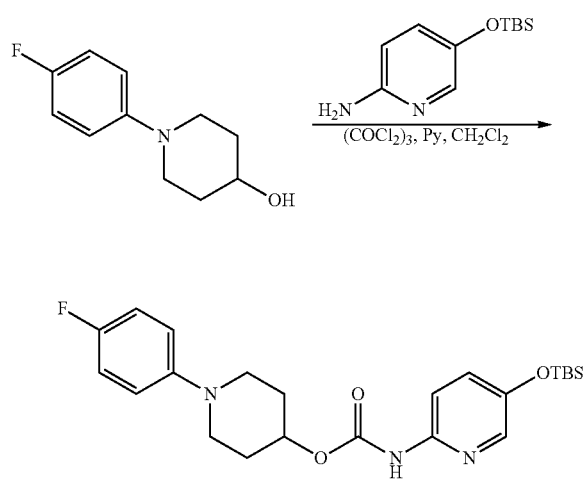

To a flask containing stirred triphosgene (385 mg, 0.50 equiv) was added a solution of the product from the previous step (500 mg, 2.56 mmol, 1.00 equiv) in CH₂Cl₂ (10 mL) dropwise at 0° C. over 1 min, followed by the addition of a mixture of pyridine (1 mL) and CH₂Cl₂ (1 mL) dropwise with stirring at 0° C. over 2 min. The temperature of the mixture was allowed to rise slowly to rt and stirring was continued for 2 h. To the mixture was added 5-[(tert-butyldimethylsilyl)oxy]pyridin-2-amine (574 mg, 2.56 mmol, 1.00 equiv). The resulting solution was stirred for 16 h at rt, then extracted with 2×50 mL of EtOAc. The combined organic layers were concentrated under vacuum and purified with silica gel column chromatography using EtOAc/hexane (1/2) to afford 200 mg (18%) of the title compound as an off-white solid.

LC-MS: (ES, m/z): 446

¹H NMR (400 MHz, DMSO-d₆) δ 9.91 (s, 1H), 7.88 (dd, J=3.0, 0.6 Hz, 1H), 7.71 (d, J=8.9 Hz, 1H), 7.32 (dd, J=8.9, 3.0 Hz, 1H), 7.01 (ddt, J=19.6, 6.9, 2.4 Hz, 4H), 4.83 (dq, J=8.5, 4.1 Hz, 1H), 3.43 (d, J=6.2 Hz, 1H), 2.99 (ddd, J=12.4, 8.9, 3.2 Hz, 3H), 1.99 (d, J=4.5 Hz, 2H), 1.82-1.65 (m, 2H), 0.96 (s, 9H), 0.19 (s, 6H).

Step 3. Synthesis of 1-(4-fluorophenyl)piperidin-4-yl N-(5-hydroxypyridin-2-yl)carbamate

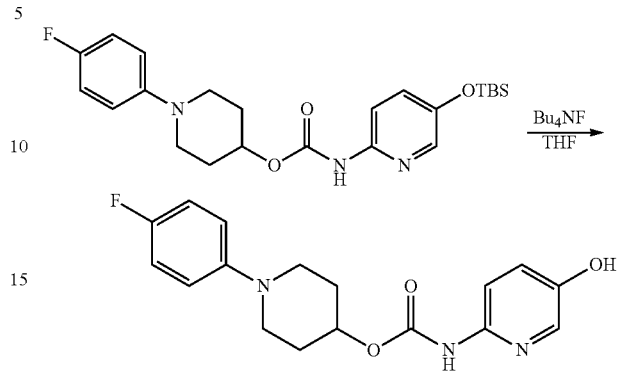

A solution of the product from the previous step (200 mg, 0.45 mmol) and Bu₄NF (234 mg, 7.13 mmol) in THF (5 mL) was stirred for 1 h at rt, then extracted with 20 mL of EtOAc. The combined organic layers were concentrated under vacuum. The crude product (200 mg) was purified by Prep-HPLC with the following conditions: Instrument "B"; Column "A"; mobile phase, 10 mM aq NH₄HCO₃ and ACN (25.0% ACN up to 58.0% in 7 min), to afford 75 mg (50%) of the title compound as an off-white solid.

LC-MS: (ES, m/z): 332

¹H NMR (300 MHz, DMSO-d₆) δ 9.69 (s, 1H), 9.51 (s, 1H), 7.79 (dd, J=3.0, 0.7 Hz, 1H), 7.59 (d, J=8.8 Hz, 1H), 7.16 (dd, J=8.9, 3.0 Hz, 1H), 7.08-6.89 (m, 4H), 4.79 (dq, J=8.5, 4.2 Hz, 1H), 3.47-3.35 (m, 2H), 2.95 (ddd, J=12.4, 9.1, 3.2 Hz, 2H), 1.95 (s, 2H), 1.69 (dtd, J=12.5, 8.8, 3.7 Hz, 2H).

Example 54

1-(2,4-difluorophenyl)piperidin-4-yl N-(5-hydroxypyridin-2-yl)carbamate

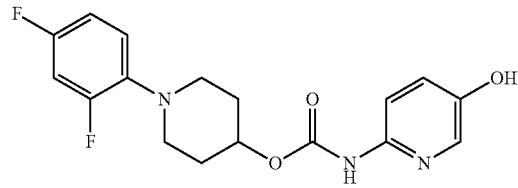 [SMILES: O=C(Nc1ccc(O)cn1)OC1CCN(c2ccc(F)cc2F)CC1]

Step 1. Synthesis of 1-(2,4-difluorophenyl)piperidin-4-ol

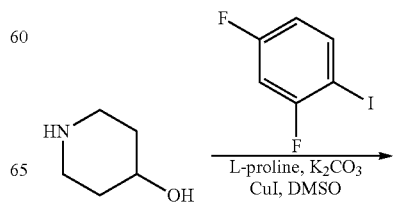

-continued

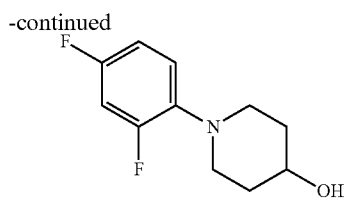

A solution of piperidin-4-ol (1 g, 9.89 mmol), L-proline (1.15 g), K₂CO₃ (2.76 g, 19.97 mmol), 2,4-difluoro-1-iodobenzene (2.4 g, 10.00 mmol), and CuI (190 mg, 1.00 mmol) in DMSO (20 mL) was stirred for 16 h under N₂ at 80° C., the cooled. The resulting solids were removed by filtration and washed with EtOAc. The combined filtrates were concentrated under vacuum and purified with silica gel chromatography using EtOAc/hexane (2:1) to afford 800 mg (38%) of the title compound as an off-white solid.

LC-MS: (ES, m/z): 214

¹H NMR (300 MHz, DMSO-d₆) δ 7.21-6.91 (m, 3H), 4.68 (d, J=4.2 Hz, 1H), 3.59 (dq, J=8.7, 4.4 Hz, 1H), 3.14 (dt, J=10.1, 4.2 Hz, 2H), 2.75-2.67 (m, 2H), 1.86-1.80 (m, 2H), 1.53 (ddt, J=12.7, 9.2, 4.7 Hz, 2H).

Step 2. Synthesis of 1-(2,4-difluorophenyl)piperidin-4-yl N-[5-[(tert-butyldimethylsilyl)oxy]pyridin-2-yl]carbamate

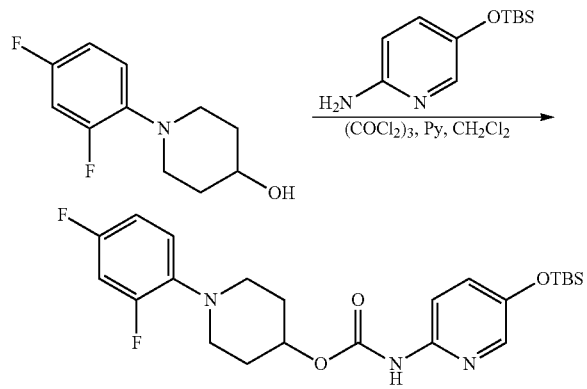

To a solution of triphosgene (352 mg) and the product from the previous step (500 mg, 2.34 mmol) in CH₂Cl₂ (10 mL) was added a solution of pyridine (1 mL) in CH₂Cl₂ (1 mL) at 0° C. The temperature of the mixture was allowed to rise slowly to rt, and stirring was continued for 2 h. To this was added 5-[(tert-butyldimethylsilyl)oxy]pyridin-2-amine (525 mg, 2.34 mmol). The resulting solution was stirred for 16 h at rt. The resulting solution was quenched by water and extracted with 2×50 mL of EtOAc. The combined organic layers were concentrated under vacuum and purified with silica gel chromatography using EtOAc/hexane (1/2) to afford 720 mg (66%) of the title compound as an off-white solid.

LC-MS: (ES, m/z): 464

¹H NMR (300 MHz, DMSO-d₆) δ 9.92 (s, 1H), 7.86 (dd, J=3.0, 0.7 Hz, 1H), 7.73-7.64 (m, 1H), 7.30 (dd, J=8.9, 3.0 Hz, 1H), 7.25-6.93 (m, 3H), 4.79 (dt, J=8.4, 4.3 Hz, 1H), 3.25-3.11 (m, 2H), 2.87 (t, J=9.2 Hz, 2H), 1.99 (s, 2H), 1.77 (td, J=8.8, 4.0 Hz, 2H), 0.93 (s, 9H), 0.17 (s, 6H).

Step 3. Synthesis of 1-(2,4-difluorophenyl)piperidin-4-yl N-(5-hydroxypyridin-2-yl)carbamate

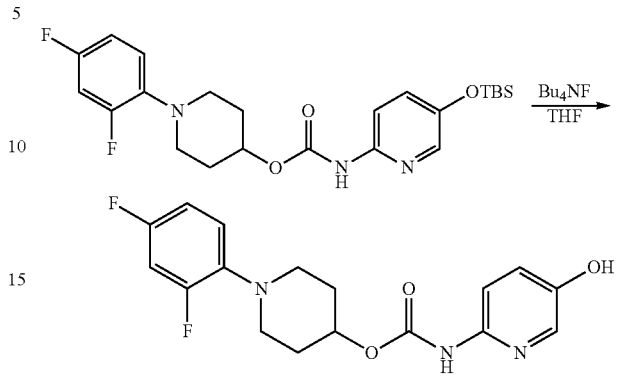

A solution of the product from the previous step (300 mg, 0.65 mmol) and Bu₄NF (337 mg, 10.27 mmol) in THF (5 mL) was stirred for 1 h at rt, then extracted with 20 mL of EtOAc. The combined organic layers were concentrated under vacuum and purified with silica gel chromatography using CH₂Cl₂/MeOH (20:1). The crude product (300 mg) was purified by Prep-HPLC with the following conditions: Instrument "B"; Column "A"; mobile phase, Water (10 mM NH₄HCO₃) and ACN (38.0% ACN up to 55.0% in 7 min); Detector, UV 254/220 nm, to afford 45.2 mg (20%) of the title compound as an off-white solid.

LC-MS: (ES, m/z): 350

¹H NMR (400 MHz, DMSO-d₆) δ 9.71 (s, 1H), 9.55 (s, 1H), 7.81 (d, J=2.9 Hz, 1H), 7.60 (d, J=8.9 Hz, 1H), 7.26-7.16 (m, 2H), 7.16-7.09 (m, 1H), 7.09-6.93 (m, 1H), 4.79 (tt, J=8.2, 3.9 Hz, 1H), 3.19 (dt, J=11.0, 4.4 Hz, 2H), 2.89 (td, J=8.9, 4.6 Hz, 2H), 2.02 (d, J=12.1 Hz, 2H), 1.76 (dtd, J=12.4, 8.6, 3.6 Hz, 2H).

Example 55

1-(4-chlorophenyl)piperidin-4-yl N-(5-hydroxypyridin-2-yl)carbamate

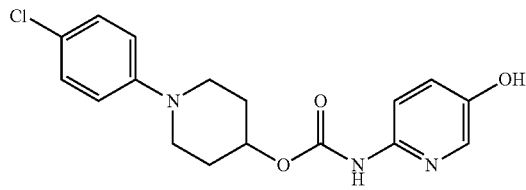 [SMILES: O=C(Nc1ccc(O)cn1)OC1CCN(c2ccc(Cl)cc2)CC1]

Step 1. Synthesis of 1-(4-chlorophenyl)piperidin-4-ol

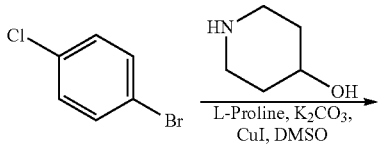

-continued

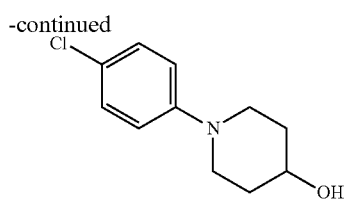

A solution of 1-bromo-4-chlorobenzene (760 mg, 3.97 mmol), K$_2$CO$_3$ (1.1 g, 7.96 mmol), piperidin-4-ol (404 mg, 3.99 mmol), L-proline (460 mg), and CuI (76 mg, 0.40 mmol) in DMSO (20 mL) was stirred for 16 h under N$_2$ at 80° C., then cooled and extracted with 2×60 mL EtOAc. The combined organic layers were concentrated under vacuum and purified with silica gel chromatography using EtOAc/hexane (2:1) to afford 560 mg (67%) of the title compound as an off-white solid.

LC-MS: (ES, m/z): 212
$^1$H NMR (300 MHz, DMSO-d$_6$) δ 7.29-7.10 (m, 2H), 7.03-6.85 (m, 2H), 4.76-4.56 (m, 1H), 4.09 (s, 1H), 3.49 (dt, J=12.7, 4.4 Hz, 2H), 2.83 (ddd, J=12.9, 10.0, 3.1 Hz, 2H), 1.89-1.71 (m, 2H), 1.43 (dtd, J=13.0, 9.8, 3.8 Hz, 2H).

Step 2. Synthesis of 1-(4-chlorophenyl)piperidin-4-yl N-[5-[(tert-butyldimethylsilyl)oxy]pyridin-2-yl] carbamate

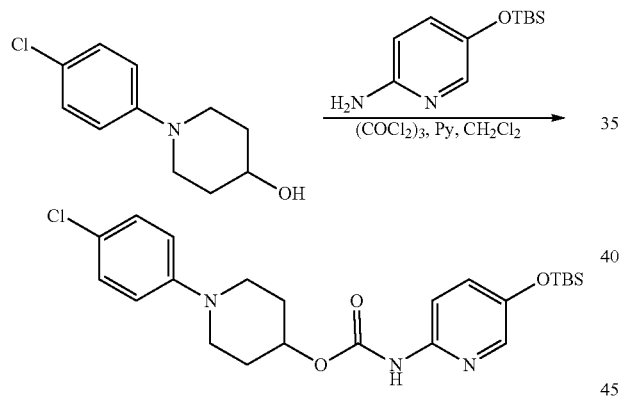

To a solution of triphosgene (398 mg) in CH$_2$Cl$_2$ (10 mL) was added a solution of the product from the previous step (560 mg, 2.65 mmol) in CH$_2$Cl$_2$ (15 mL) dropwise with stirring over 1 min, followed by the addition of a solution of pyridine (1 ml) in CH$_2$Cl$_2$ (1 mL) dropwise with stirring over 2 min. The temperature of the mixture was allowed to rise slowly to rt and stirring was continued for 2 h, then 5-[(tert-butyldimethylsilyl)oxy]pyridin-2-amine (300 mg, 1.34 mmol) was added, and stirring was continued for 16 h at rt. The resulting solution was extracted with 2×20 mL of EtOAc, and the combined organic layers were concentrated under vacuum and purified with silica gel chromatography using EtOAc/hexane (1/2) to afford 280 mg (23%) of the title compound as an off-white solid.

LC-MS: (ES, m/z): 462
$^1$H NMR (400 MHz, DMSO-d$_6$) δ 9.92 (s, 1H), 7.88 (d, J=2.9 Hz, 1H), 7.71 (d, J=8.9 Hz, 1H), 7.32 (dd, J=9.0, 3.0 Hz, 1H), 7.23 (d, J=2.2 Hz, 1H), 7.21 (m, 1H), 6.97 (td, J=4.8, 2.5 Hz, 2H), 4.85 (dt, J=8.4, 4.4 Hz, 1H), 3.57-3.48 (m, 2H), 3.25-2.82 (m, 2H), 1.98 (d, J=9.4 Hz, 2H), 1.92-1.47 (m, 2H), 0.95 (s, 9H), 0.19 (s, 6H).

Step 3. Synthesis of 1-(4-chlorophenyl)piperidin-4-yl N-(5-hydroxypyridin-2-yl)carbamate

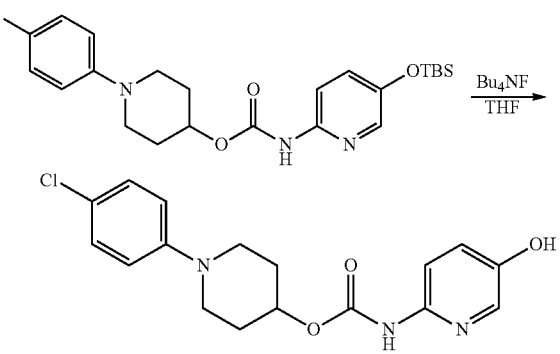

A solution of the product from the previous step (280 mg, 0.61 mmol) and Bu$_4$NF (317 mg, 1.21 mmol) in THF (5 mL) was stirred for 1 h at rt, then extracted with 20 mL of EtOAc. The combined organic layers combined and concentrated unver vacuum. The crude product (280 mg) was purified by Prep-HPLC with the following conditions: Instrument "B"; Column "A"; mobile phase, water (0.1% FA) and ACN (35.0% ACN up to 64.0% in 7 min); Detector, UV 254/220 nm, to afford 81.2 mg (39%) of the title compound as an off-white solid.

LC-MS: (ES, m/z): 348
$^1$H NMR (300 MHz, DMSO-d$_6$) δ 9.69 (s, 1H), 9.53 (s, 1H), 7.82-7.75 (m, 1H), 7.59 (d, J=8.9 Hz, 1H), 7.26-7.11 (m, 3H), 7.01-6.90 (m, 2H), 4.80 (dt, J=8.4, 4.3 Hz, 1H), 3.54-3.42 (m, 2H), 3.10-2.95 (m, 2H), 1.93 (m, 2H), 1.68 (td, J=8.8, 4.0 Hz, 2H).

Example 56

1-(5-fluoropyridin-2-yl)piperidin-4-yl N-(5-hydroxy-pyridin-2-yl)

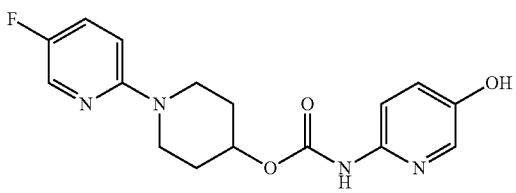 [SMILES: O=C(Nc1ccc(O)cn1)OC1CCN(c2ccc(F)cn2)CC1]

Step 1. Synthesis of 1-(5-fluoropyridin-2-yl)piperidin-4-ol

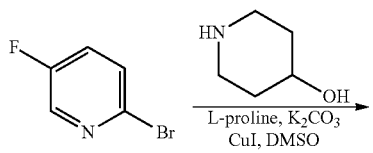

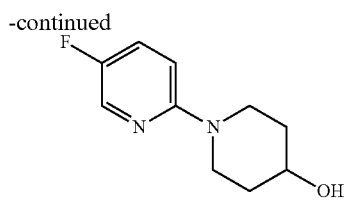

A solution of 2-bromo-5-fluoropyridine (900 mg, 5.11 mmol), CuI (100 mg, 0.53 mmol), proline (600 mg), K₂CO₃ (1.38 g, 9.98 mmol), and piperidin-4-ol (516 mg, 5.11 mmol) in DMSO (20 mL) was stirred for 16 h at 80° C., then extracted with 2×60 mL of EtOAc. The combined organic layers were concentrated under vacuum and purified with silica gel chromatography using EtOAc/hexane (2:1) to afford 300 mg (30%) of the title compound as an off-white solid. LC-MS: (ES, m/z): 197

Step 2. Synthesis of 1-(5-fluoropyridin-2-yl)piperidin-4-yl N-[5-[(tert-butyldimethylsilyl)oxy]pyridin-2-yl]carbamate

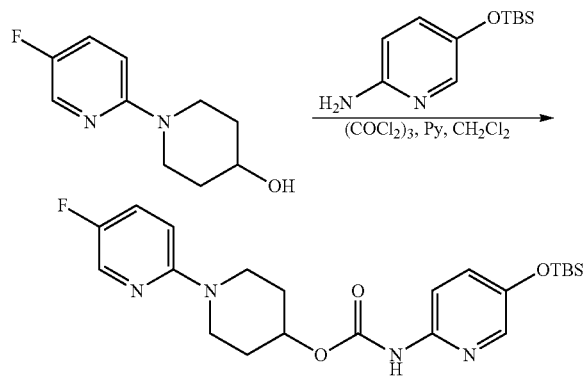

To a solution of triphosgene (0.5 eq) (300 mg) in CH₂Cl₂ (5 mL) was added a solution of the product from the previous step (300 mg, 1.53 mmol) in CH₂Cl₂ (2 mL) dropwise with stirring at 0° C. over 1 min, followed by the addition of a solution of pyridine (1 mL) in CH₂Cl₂ (2 mL) dropwise with stirring at 0° C. over 2 min. The temperature of the mixture was allowed to rise slowly to rt, and stirring was continued for 2 h. To the mixture was added 5-[(tert-butyldimethylsilyl)oxy]pyridin-2-amine (171 mg, 0.76 mmol). The resulting solution was stirred for 16 h at rt, then quenched by the addition of 30 mL H₂O and extracted with 2×40 mL of EtOAc. The combined organic layers were concentrated under vacuum and purified with silica gel chromatography using EtOAc/hexane (1/2) to afford 200 mg (29%) of the title compound as an off-white solid. LC-MS: (ES, m/z): 447

Step 3. Synthesis of 1-(5-fluoropyridin-2-yl)piperidin-4-yl N-(5-hydroxypyridin-2-yl)carbamate

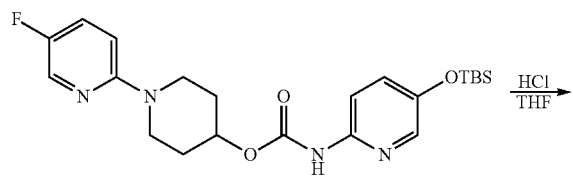

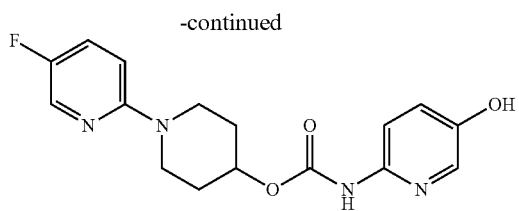

To a solution of the product from the previous step (200 mg, 0.45 mmol) in THF (2 mL) was added 2N aq. HCl (1 mL), in portions at rt. The resulting solution was stirred for 2 h at rt, then concentrated under vacuum. The crude product (200 mg) was purified by Prep-HPLC with the following conditions: Instrument "A"; Column "A"; mobile phase, 10 mM aq NH₄HCO₃ and ACN (25.0% ACN up to 56.0% in 8 min); Detector, UV 254/220 nm, to afford 31.9 mg (21%) of the title compound as an off-white solid.

LC-MS: (ES, m/z): 333.3

¹H NMR (300 MHz, DMSO-d₆) δ 9.70 (s, 1H), 9.55 (s, 1H), 8.06 (d, J=3.1 Hz, 1H), 7.78 (d, J=2.9 Hz, 1H), 7.59 (d, J=8.9 Hz, 1H), 7.47 (ddd, J=9.3, 8.3, 3.2 Hz, 1H), 7.16 (dd, J=8.9, 3.0 Hz, 1H), 6.89 (dd, J=9.4, 3.4 Hz, 1H), 4.85 (dt, J=8.6, 4.5 Hz, 1H), 3.92-3.80 (m, 2H), 3.28-3.22 (m, 2H), 1.95-1.84 (m, 2H), 1.59-1.54 (m, 2H).

Example 57

1-[4-(trifluoromethyl)phenyl] piperidin-4-yl N-(5-hydroxypyridin-2-yl) carbamate

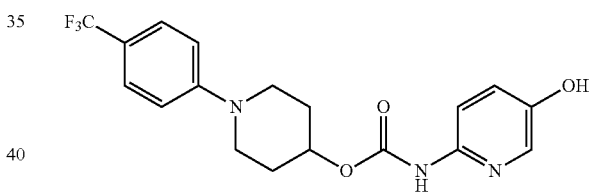

Step 1. Synthesis of 1-[4-(trifluoromethyl)phenyl] piperidin-4-ol

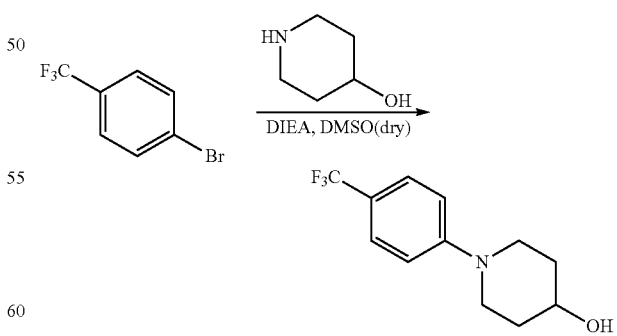

A solution of 1-fluoro-4-(trifluoromethyl)benzene (820 mg, 5.00 mmol), piperidin-4-ol (505 mg, 4.99 mmol), and DIEA (1.29 g, 9.98 mmol) in dry DMSO (20 mL) was stirred for 16 h at 80° C., then cooled to rt and extracted with 2×60 mL of EtOAc. The combined organic layers were concentrated under vacuum and purified with silica gel chromatography using EtOAc/hexane (2:1) to afford 460 mg (38%) of the title compound as an off-white solid.

LC-MS: (ES, m/z): 246

$^1$H NMR (300 MHz, DMSO-$d_6$) δ 7.52-7.42 (m, 2H), 7.03 (d, J=8.8 Hz, 2H), 4.70 (d, J=4.3 Hz, 1H), 4.09 (q, J=5.3 Hz, 1H), 3.66 (dd, J=8.7, 4.4 Hz, 2H), 2.99 (ddd, J=13.1, 9.9, 3.1 Hz, 2H), 1.86-1.68 (m, 2H), 1.41 (dtd, J=12.9, 9.5, 3.8 Hz, 2H).

Step 2. Synthesis of 1-[4-(trifluoromethyl)phenyl]piperidin-4-yl N-[5-[(tert-butyldimethylsilyl)oxy]pyridin-2-yl]carbamate

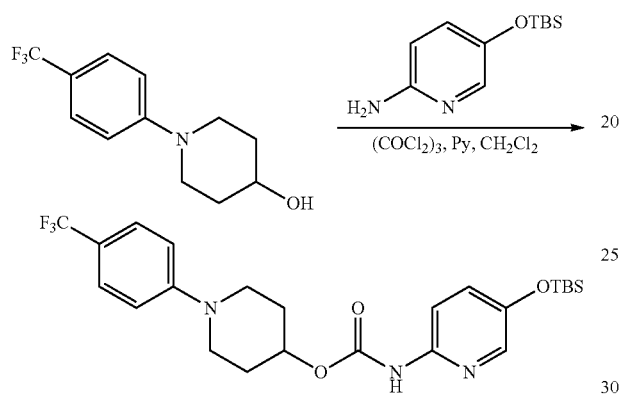

To a solution of triphosgene (280 mg) in CH$_2$Cl$_2$ (5 mL) was added a solution of the product from the previous step (460 mg, 1.88 mmol) in CH$_2$Cl$_2$ (2 mL) dropwise with stirring at 0° C. over 1 min, followed by the addition of a mixture of pyridine (1 mL) and CH$_2$Cl$_2$ (1 mL) dropwise with stirring at 0° C. over 2 min. The temperature of the mixture was allowed to rise slowly to rt and stirring was continued for 2 h. To the mixture was added 5-[(tert-butyldimethylsilyl)oxy]pyridin-2-amine (224 mg, 1.00 mmol, 0.60 eq). The resulting solution was stirred for 16 h at rt, then extracted with 2×60 mL of CH$_2$Cl$_2$. The combined organic layers were concentrated under vacuum and purified with silica gel chromatography using EtOAc/hexane (1/2) to afford 260 mg (28%) of the title compound as an off-white solid. LC-MS: (ES, m/z): 496.

Step 3. Synthesis of 1-[4-(trifluoromethyl)phenyl]piperidin-4-yl N-(5-hydroxypyridin-2-yl) carbamate

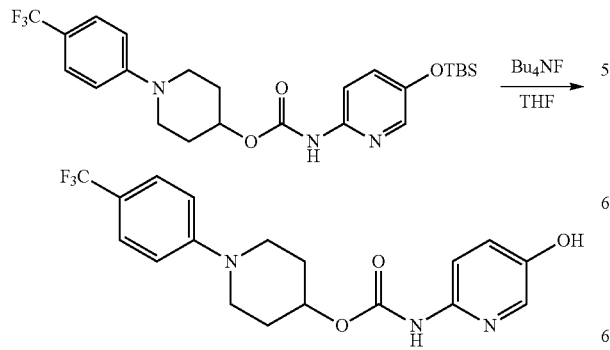

To a solution of the product from the previous step (260 mg, 0.52 mmol) in THF (5 mL) was added Bu$_4$NF (274 mg) at rt. The resulting solution was stirred for 2 h at rt, then extracted with 20 mL of EtOAc. The combined organic layers were concentrated under vacuum. The crude product (260 mg) was purified by Prep-HPLC with the following conditions: Instrument "B"; Column "A"; mobile phase, 10 mM aq NH$_4$HCO$_3$ and ACN (35.0% ACN up to 65.0% in 7 min); Detector, uv 254/220 nm, to afford 54.8 mg (27%) of the title compound as an off-white solid.

LC-MS: (ES, m/z): 382

$^1$H NMR (300 MHz, DMSO-$d_6$) δ 9.71 (s, 1H), 9.53 (s, 1H), 7.79 (d, J=3.0 Hz, 1H), 7.59 (d, J=8.9 Hz, 1H), 7.47 (d, J=8.5 Hz, 2H), 7.17 (dd, J=8.9, 3.0 Hz, 1H), 7.06 (d, J=8.6 Hz, 2H), 4.86 (dt, J=8.2, 4.8 Hz, 1H), 3.70-3.58 (m, 2H), 3.27-3.12 (m, 2H), 1.93 (s, 2H), 1.64 (m, 2H).

Example 58

1-(2,4-dichlorophenyl)piperidin-4-yl N-(5-hydroxypyridin-2-yl)carbamate

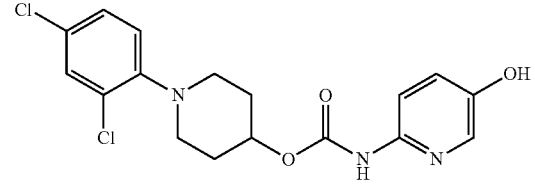 [SMILES: O=C(Nc1ccc(O)cn1)OC1CCN(c2ccc(Cl)cc2Cl)CC1]

Step 1. Synthesis of 1-(2,4-dichlorophenyl)piperidin-4-ol

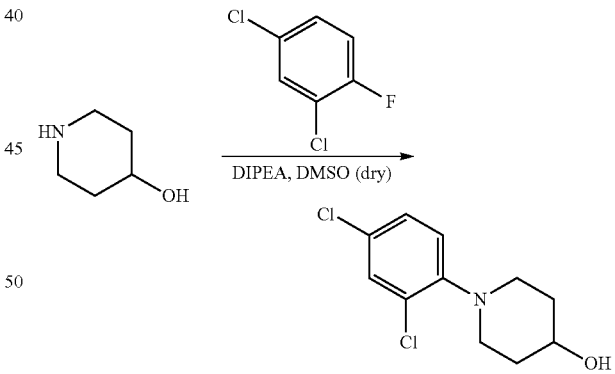

A solution of piperidin-4-ol (1.01 g, 9.99 mmol), 2,4-dichloro-1-fluorobenzene (1.65 g, 10.00 mmol), and DIEA (2.58 g) in dry DMSO (20 mL) was stirred for 16 h at 80° C., then cooled and extracted with 2×50 mL of EtOAc. The combined organic layers were concentrated under vacuum and purified with silica gel chromatography using EtOAc/hexane (2:1) to afford 110 mg (4%) of the title compound as an off-white solid.

LC-MS: (ES, m/z): 246

$^1$H NMR (300 MHz, DMSO-$d_6$) δ 7.50 (d, J=2.5 Hz, 1H), 7.32 (dd, J=8.6, 2.5 Hz, 1H), 7.14 (d, J=8.7 Hz, 1H), 4.70 (d, J=4.2 Hz, 1H), 3.61 (tt, J=8.6, 4.3 Hz, 1H), 3.13 (dt, J=10.2, 4.2 Hz, 2H), 2.70 (ddd, J=12.1, 9.7, 2.9 Hz, 2H), 1.91-1.72 (m, 2H), 1.54 (dtd, J=12.7, 9.2, 3.6 Hz, 2H).

Step 2. Synthesis of 1-(2,4-dichlorophenyl)piperidin-4-yl N-[5-[(tert-butyldimethylsilyl)oxy]pyridin-2-yl] carbamate

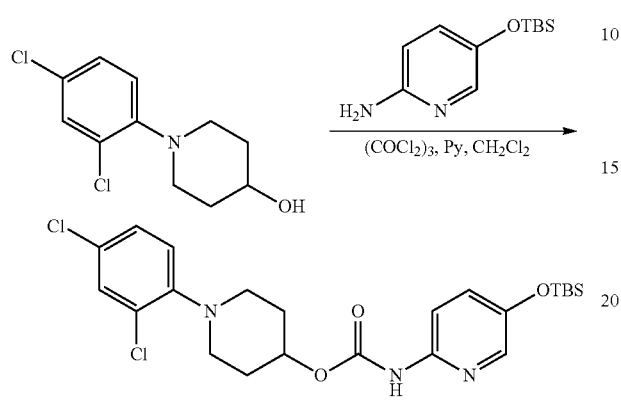

To a solution of triphosgene (67 mg) in CH$_2$Cl$_2$ (5 mL) was added a solution of the product from the previous step (110 mg, 0.45 mmol) in CH$_2$Cl$_2$ (1 mL) dropwise with stirring over 1 min, followed by the addition of a solution of pyridine (0.5 mL) in CH$_2$Cl$_2$ (0.5 mL) dropwise with stirring over 1 min. The temperature of the mixture was allowed to rise slowly to rt, and stirring was continued for 2 h. To the mixture was added 5-[(tert-butyldimethylsilyl)oxy]pyridin-2-amine (100 mg, 0.45 mmol). The resulting solution was stirred for 16 h at rt, then extracted with 2×20 mL of EtOAc. The combined organic layers were concentrated under vacuum and purified with silica gel column chromatography using EtOAc/hexane (1/2) to afford 160 mg (72%) of the title compound as an off-white solid. LC-MS: (ES, m/z): 496.

Step 3. Synthesis of 1-(2,4-dichlorophenyl)piperidin-4-yl N-(5-hydroxypyridin-2-yl)carbamate

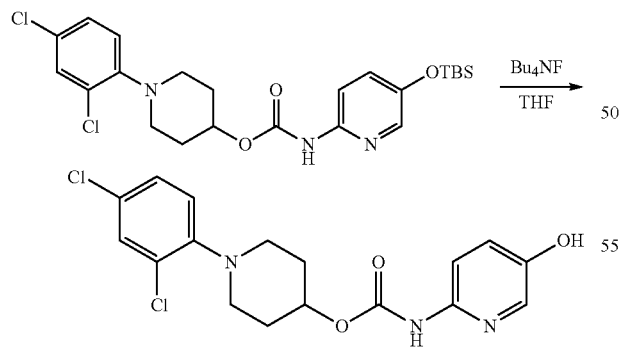

A solution of the product from the previous step (160 mg, 0.32 mmol) and Bu$_4$NF (169 mg, 0.65 mmol) in THF (5 mL) was stirred for 1 h at rt, then diluted with 20 mL of H$_2$O and extracted with 2×30 mL of EtOAc. The combined organic layers were dried over Na$_2$SO$_4$ and concentrated under vacuum. The crude product (160 mg) was purified by Prep-HPLC with the following conditions: Instrument "A"; Column "E"; mobile phase, water (0.05% TFA) and ACN (5.0% ACN up to 37.0% in 7 min); Detector, UV 254/220 nm, to afford 58.3 mg (47%) of the title compound as an off-white solid.

LC-MS: (ES, m/z): 382

$^1$H NMR (300 MHz, DMSO-d$_6$) δ 9.72 (s, 1H), 9.55 (s, 1H), 7.79 (d, J=2.9 Hz, 1H), 7.59 (d, J=8.9 Hz, 1H), 7.52 (d, J=2.5 Hz, 1H), 7.35 (dd, J=8.6, 2.5 Hz, 1H), 7.25-7.08 (m, 2H), 4.80 (tt, J=8.1, 3.9 Hz, 1H), 3.23-3.09 (m, 2H), 2.86 (ddd, J=11.8, 8.6, 3.1 Hz, 2H), 2.00 (ddt, J=10.0, 6.9, 4.2 Hz, 2H), 1.75 (dtd, J=12.2, 8.4, 3.5 Hz, 2H).

Example 59

1-(pyridin-2-yl)piperidin-4-yl N-(5-hydroxypyridin-2-yl)carbamate

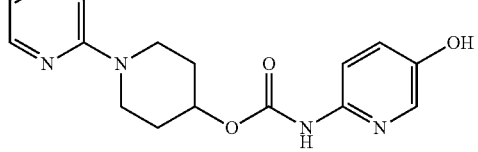

Step 1. Synthesis of 1-(pyridin-2-yl)piperidin-4-ol

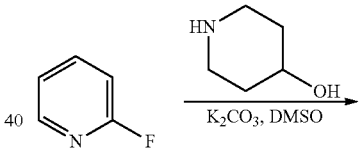

A mixture of 2-fluoropyridine (970 mg, 9.99 mmol), piperidin-4-ol (1.01 g, 9.99 mmol), and K$_2$CO$_3$ (2.76 g, 19.97 mmol) in DMSO (30 mL) was stirred for 16 h at rt, then extracted with 2×100 mL of EtOAc. The combined organic layers were concentrated under vacuum and purified with silica gel chromatography using EtOAc/hexane (2:1) to afford 690 mg (39%) of the title compound as an off-white solid.

LC-MS: (ES, m/z): 179

$^1$H NMR (400 MHz, DMSO-d$_6$) δ 8.08 (ddd, J=4.9, 2.1, 0.9 Hz, 1H), 7.49 (ddd, J=8.9, 7.1, 2.1 Hz, 1H), 6.81 (dd, J=8.6, 0.9 Hz, 1H), 6.57 (ddd, J=7.1, 4.8, 0.8 Hz, 1H), 4.67 (d, J=4.3 Hz, 1H), 4.04-3.93 (m, 2H), 3.69 (tq, J=8.5, 4.1 Hz, 1H), 3.05 (ddd, J=13.3, 10.2, 3.1 Hz, 2H), 1.76 (dqd, J=10.0, 3.6, 1.7 Hz, 2H), 1.40-1.29 (m, 2H).

Step 2. Synthesis of 1-(pyridin-2-yl)piperidin-4-yl N-[5-[(tert-butyldimethylsilyl)oxy]pyridin-2-yl] carbamate

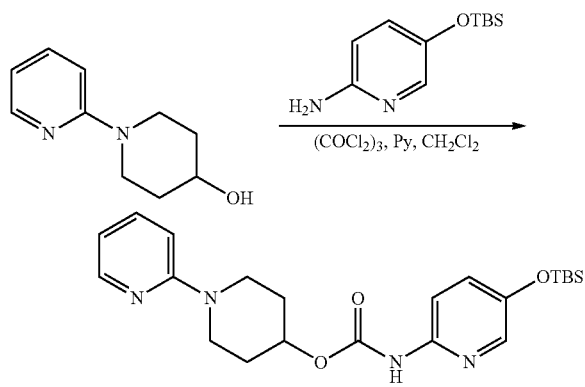

To a solution of triphosgene (581 mg) in CH$_2$Cl$_2$ (10 mL) was added a solution of the product from the previous step (690 mg, 3.87 mmol) in CH$_2$Cl$_2$ (2 mL) dropwise with stirring over 1 min, followed by the addition of a solution of pyridine (1 mL) in CH$_2$Cl$_2$ (1 mL) dropwise with stirring over 2 min. The temperature of the mixture was allowed to rise slowly to rt and stirring was continued for 2 h. To the mixture was added 5-[(tert-butyldimethylsilyl)oxy]pyridin-2-amine (300 mg, 1.34 mmol). The resulting solution was stirred for 16 h at rt. The resulting solution was extracted with 2×50 mL of CH$_2$Cl$_2$, and the combined organic layers were concentrated under vacuum and purified with silica gel chromatography using EtOAc/hexane (1/2), to afford 500 mg (30%) of the title compound as an off-white solid.

LC-MS: (ES, m/z): 429

$^1$H NMR (300 MHz, DMSO-d$_6$) δ 9.89 (s, 1H), 8.09 (ddd, J=4.9, 2.1, 0.8 Hz, 1H), 7.94-7.81 (m, 1H), 7.77-7.66 (m, 1H), 7.50 (ddd, J=8.9, 7.1, 2.0 Hz, 1H), 7.38-7.28 (m, 1H), 6.85 (d, J=8.6 Hz, 1H), 6.59 (ddd, J=7.1, 4.9, 0.8 Hz, 1H), 4.88 (dt, J=8.5, 4.4 Hz, 1H), 4.02-3.86 (m, 2H), 3.31 (m, 2H), 1.92 (d, J=12.9 Hz, 2H), 1.57 (dtd, J=12.7, 8.8, 3.8 Hz, 2H), 0.93 (d, J=2.7 Hz, 9H), 0.17 (d, J=3.6 Hz, 6H).

Step 3. Synthesis of 1-(pyridin-2-yl)piperidin-4-yl N-(5-hydroxypyridin-2-yl)carbamate

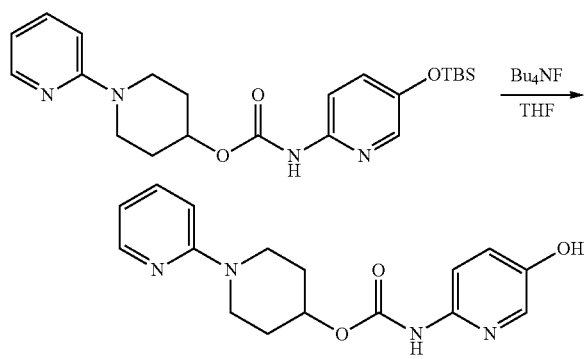

A solution of the product from the previous step (250 mg, 0.58 mmol) and Bu$_4$NF (304 g, 1.16 mol) THF (6 mL) was stirred for 1 h at rt, then extracted with 30 mL of EtOAc. The combined organic layers were concentrated under vacuum and purified with silica gel chromatography using CH$_2$Cl$_2$/MeOH (20:1). The crude product (250 mg) was further purified by Prep-HPLC with the following conditions: Instrument "B"; Column "D"; mobile phase, 10 mM aq NH$_4$HCO$_3$ and ACN (8.0% ACN up to 50.0% in 7 min); Detector, UV 254/220 nm, to afford 83 mg (45%) of the title compound as an off-white solid.

LC-MS: (ES, m/z): 315

$^1$H NMR (300 MHz, DMSO-d$_6$) δ 9.70 (s, 1H), 9.52 (s, 1H), 8.09 (ddd, J=4.9, 2.0, 0.8 Hz, 1H), 7.79 (d, J=2.9 Hz, 1H), 7.59 (d, J=8.9 Hz, 1H), 7.50 (ddd, J=8.9, 7.1, 2.1 Hz, 1H), 7.16 (dd, J=8.9, 3.0 Hz, 1H), 6.89-6.79 (m, 1H), 6.59 (ddd, J=7.1, 4.8, 0.8 Hz, 1H), 4.87 (tt, J=8.3, 3.9 Hz, 1H), 3.94 (dt, J=13.3, 4.8 Hz, 2H), 3.36-3.21 (m, 2H), 1.98-1.83 (m, 2H), 1.56 (dtd, J=12.7, 8.8, 3.7 Hz, 2H).

Example 60

1-[5-(trifluoromethyl)pyridin-2-yl]piperidin-4-yl N-(5-hydroxypyridin-2-yl)carbamate

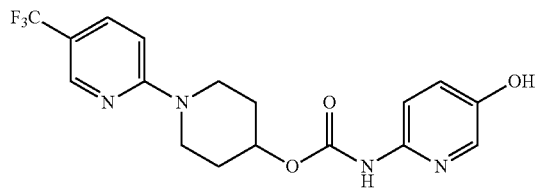 [SMILES: O=C(Nc1ccc(O)cn1)OC1CCN(c2ccc(C(F)(F)F)cn2)CC1]

Step 1. Synthesis of 1-[5-(trifluoromethyl)pyridin-2-yl]piperidin-4-ol

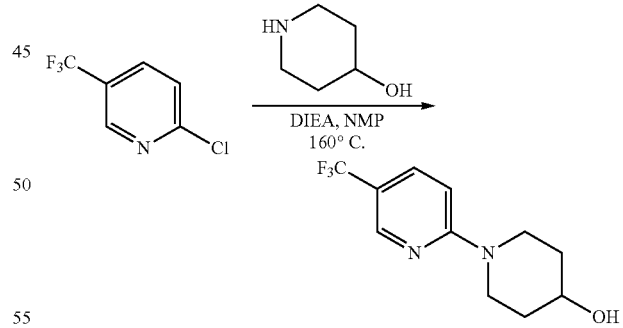

A solution of 2-chloro-5-(trifluoromethyl)pyridine (1.8 g, 9.92 mmol), piperidin-4-ol (1 g, 9.89 mmol), and DIEA (2.6 g, 20.12 mmol), in NMP (10 mL) was stirred for 1.5 h at 160° C. The reaction mixture was cooled, and water was added. The mixture was then extracted with 2×50 mL of EtOAc, and the combined organic layers combined were concentrated under vacuum and purified with silica gel chromatography using EtOAc/hexane (2:1) to afford 1.2 g (49%) of the title compound as a solid. LC-MS: (ES, m/z): 247

Step 2. Synthesis of 1-[5-(trifluoromethyl)pyridin-2-yl]piperidin-4-yl N-[5-[(tert-butyldimethylsilyl)oxy] pyridine-2-yl]carbamate

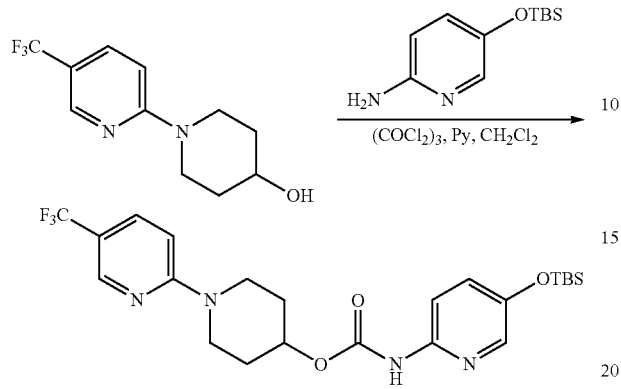

To a solution of triphosgene (0.5 eq) (300 mg, 1.00 mmol) in CH$_2$Cl$_2$ (5 mL) was added a solution of the product from the previous step (492 mg, 2.00 mmol) in CH$_2$Cl$_2$ (5 mL) dropwise with stirring at 0° C., followed by the addition of pyridine (1 mL) in CH$_2$Cl$_2$ (5 mL) dropwise with stirring at 0° C., followed by the addition of 5-[(tert-butyldimethylsilyl)-oxy]pyridin-2-amine (224 mg, 1.00 mmol). The resulting solution was stirred for 16 h at rt, then quenched by the addition of 10 mL H$_2$O and extracted with 2×20 mL of EtOAc. The combined organic layers were concentrated under vacuum and purified with silica gel chromatography using EtOAc/hexane (2:1) to afford 100 mg (10%) of the title compound as an off-white solid. LC-MS: (ES, m/z): 497

Step 3. Synthesis of 1-[5-(trifluoromethyl)pyridin-2-yl]piperidin-4-yl N-(5-hydroxypyridin-2-yl)carbamate

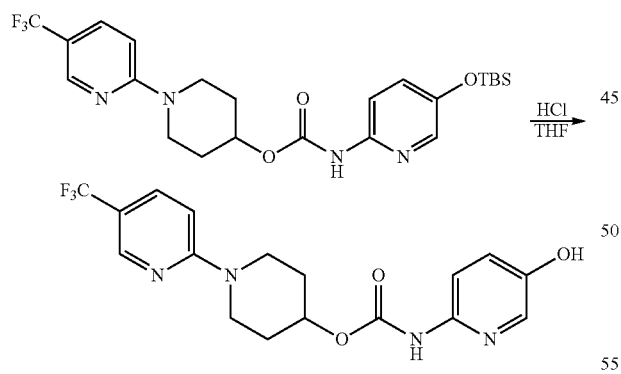

A solution of the product from the previous step (100 mg, 0.20 mmol) in 2N aq. HCl (1 mL) and THF (2 mL) was stirred for 2 h at rt, then concentrated under vacuum. The crude product (100 mg) was purified by Prep-HPLC with the following conditions: Instrument "A"; Column "A"; mobile phase, 10 mM aq NH$_4$HCO$_3$ and ACN (30.0% ACN up to 57.0% in 8 min); Detector, UV 254/220 nm, affording 23 mg (30%) of the title compound as an off-white solid.
LC-MS: (ES, m/z): 383.0
$^1$H NMR (300 MHz, DMSO-d$_6$) δ 9.72 (s, 1H), 9.54 (s, 1H), 8.39 (s, 1H), 7.79-7.76 (m, 2H), 7.59 (d, J=8.9 Hz, 1H), 7.16 (dd, J=8.9, 3.0 Hz, 1H), 6.99 (d, J=9.1 Hz, 1H), 4.91 (dt, J=8.0, 4.5 Hz, 1H), 4.00 (d, J=13.6 Hz, 2H), 3.55-3.42 (m, 2H), 1.99-1.91 (m, 2H), 1.64-1.50 (m, 2H).

Scheme VIII

Example 61

N-(5-Hydroxypyridin-2-yl)-4-(propan-2-yl)benzene-1-sulfonamide

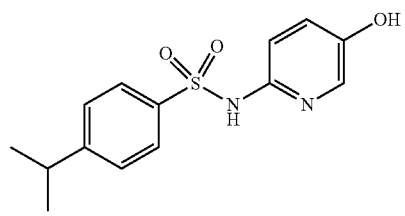 [SMILES: CC(C)c1ccc(S(=O)(=O)Nc2ccc(O)cn2)cc1]

Step 1: Synthesis of N-[5-[(tert-butyldimethylsilyl)oxy]pyridin-2-yl]-4-(propan-2-yl)benzene-1-sulfonamide

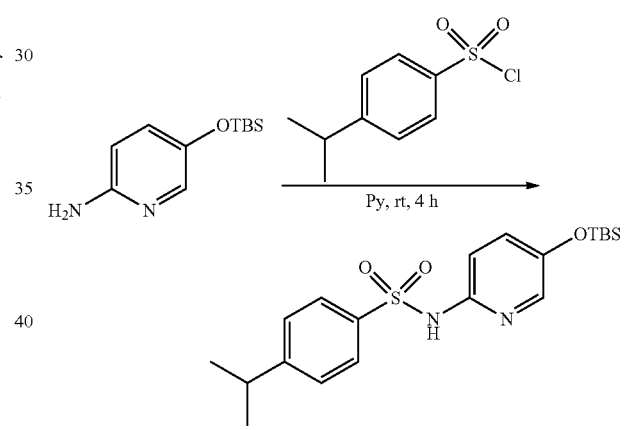

A solution of 5-[(tert-butyldimethylsilyl) oxy]pyridin-2-amine (224 mg, 1.00 mmol, 1.00 eq), 4-(propan-2-yl)benzene-1-sulfonyl chloride (218 mg, 1.00 mmol, 1.00 eq), and pyridine (4 mL) was stirred for 4 h at rt. The resulting mixture was concentrated under vacuum and purified with silica gel chromatography using EtOAc/hexane (1:2) to afford 300 mg (74%) of the title compound as a white solid. LC-MS (ES, m/z): 406.

Step 2: Synthesis of N-(5-hydroxypyridin-2-yl)-4-(propan-2-yl)benzene-1-sulfonamide

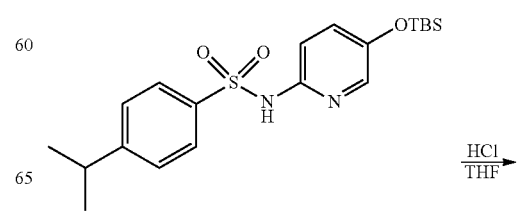

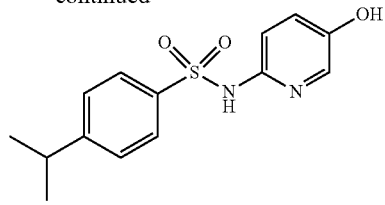

A solution of product from the previous step (300 mg, 0.74 mmol, 1.00 eq) in 2 N aq HCl (2 mL) and THF (4 mL) was stirred for 2 h at rt, then concentrated under vacuum and purified with Prep-HPLC using the following conditions: Instrument "B"; Column, SunFire C18 OBD Prep Column, 100& #65533; 5 μm, 19 mm×250 mm; mobile phase, water (0.1% FA) and ACN (35.0% ACN up to 68.0% in 7 min); Detector, uv 254/220 nm, to afford 137 mg (64%) of the title compound as a white solid.

LC-MS: (ES, m/z): 292

$^1$H NMR (300 MHz, DMSO-$d_6$) δ 10.55 (s, 1H), 9.64 (s, 1H), 7.79-7.70 (m, 3H), 7.41 (d, J=8.3 Hz, 2H), 7.15 (d, J=8.8, 3.0 Hz, 1H), 7.04 (d, J=8.8 Hz, 1H), 2.94 (m, 1H), 1.19 (d, J=6 Hz, 6H).

Example 62

4-tert-Butyl-N-(5-hydroxypyridin-2-yl)benzene-1-sulfonamide

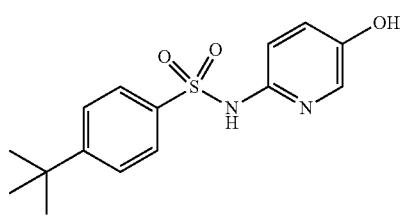 [SMILES: CC(C)(C)c1ccc(S(=O)(=O)Nc2ccc(O)cn2)cc1]

Step 1: Synthesis of 4-tert-butyl-N-[5-[(tert-butyldimethylsilyl)oxy]pyridin-2-yl]benzene-1-sulfonamide

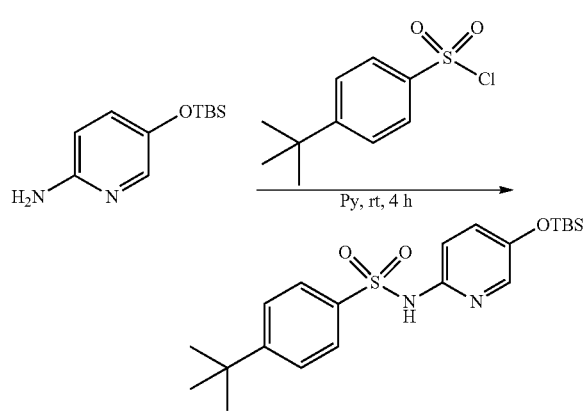

A solution of 5-[(tert-butyldimethylsilyl)oxy]pyridin-2-amine (224 mg, 1.00 mmol, 1.00 eq) and 4-tert-butylbenzene-1-sulfonyl chloride (232 mg, 1.00 mmol, 1.00 eq) in pyridine (5 mL) was stirred for 4 h at rt. The resulting mixture was concentrated under vacuum, and purified with silica gel chromatography using EtOAc/hexane (1:2) to afford 230 mg (55%) of the title compound as a white solid.

LC-MS: (ES, m/z): 421.

Step 2: Synthesis of 4-tert-butyl-N-(5-hydroxypyridin-2-yl)benzene-1-sulfonamide

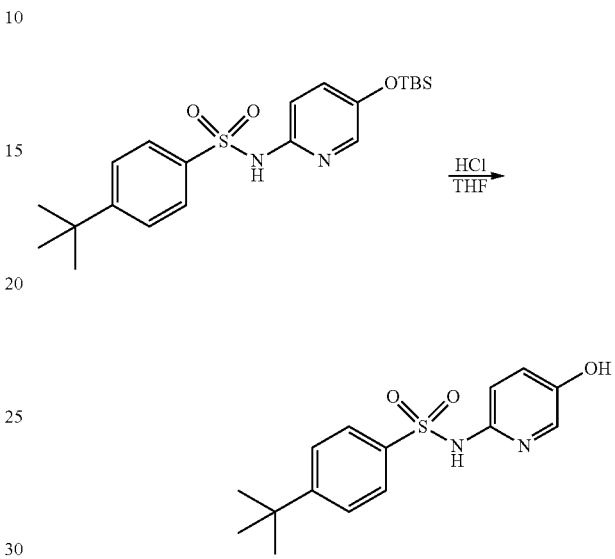

A solution of the product from the previous step (230 mg, 0.55 mmol, 1.00 eq) in 2N HCl (2 mL) and THF (4 mL) was stirred for 2 h at rt, then concentrated under vacuum. The crude product was purified by Prep-HPLC with the following conditions: Instrument "B"; Column, SunFire C18 OBD Prep Column, 100& #65533; 5 μm, 19 mm×250 mm; mobile phase, water (0.1% FA) and ACN (30.0% ACN up to 80.0% in 7 min); Detector, uv 254/220 nm, to afford 128.2 mg (77%) of the title compound as a white solid.

LC-MS: (ES, m/z): 306

$^1$H NMR (300 MHz, DMSO-$d_6$) δ 10.55 (s, 1H), 9.64 (s, 1H), 7.78-7.72 (m, 2H), 7.61-7.54 (m, 2H), 7.15 (dd, J=8.8, 3.0 Hz, 1H), 7.04 (d, J=8.8 Hz, 1H), 1.27 (s, 9H).

Example 63

Benzyl 4-[(5-hydroxypyridin-2-yl)sulfamoyl]piperidine-1-carboxylate

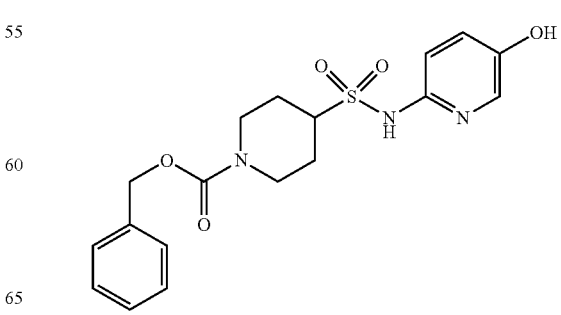

Step 1. Synthesis of benzyl 4-([5-[(tert-butyldimethylsilyl)oxy]pyridin-2-yl]sulfamoyl) piperidine-1-carboxylate

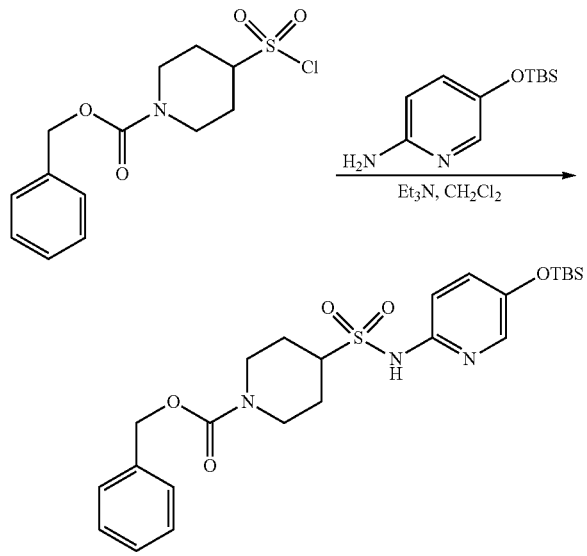

To a solution of 5-[(tert-butyldimethylsilyl)oxy]pyridin-2-amine (105 mg, 0.47 mmol) Et₃N (150 mg, 1.48 mmol) in CH₂Cl₂ (5 mL) was added benzyl 4-(chlorosulfonyl)-piperidine-1-carboxylate (150 mg, 0.47 mmol), in portions at 0° C. The resulting solution was stirred for 2 h at rt, then extracted with 2×20 mL of EtOAc. The combined organic layers were concentrated under vacuum and purified with silica gel column chromatography using EtOAc/hexane (1/2) to afford 180 mg (75%) of the title compound as an off-white solid. LC-MS: (ES, m/z): 506

Step 2. Synthesis of benzyl 4-[(5-hydroxypyridin-2-yl)sulfamoyl]piperidine-1-carboxylate

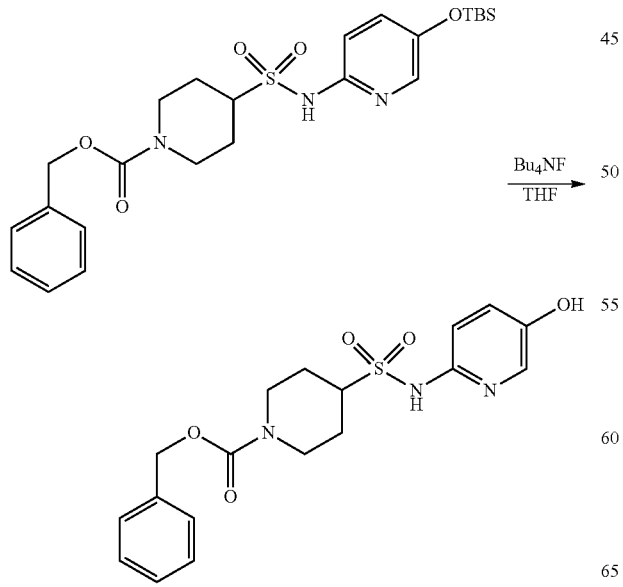

A solution of the product from the previous step (180 mg, 0.36 mmol) and Bu₄NF (186 mg, 0.71 mmol) in THF (5 mL) was stirred for 1 h at rt, then extracted with 20 mL of EtOAc. The combined organic layers were concentrated under vacuum. The crude product (180 mg) was purified by Prep-HPLC with the following conditions: Instrument "A"; Column "A"; mobile phase, Water (10 mM NH₄HCO₃) and ACN (28.0% ACN up to 46.0% in 8 min), to afford 71.5 mg of the title compound as an off-white solid.

LC-MS: (ES, m/z): 392

$^1$H NMR (300 MHz, DMSO-$d_6$) δ 9.80 (s, 2H), 7.80 (d, J=2.9 Hz, 1H), 7.42-7.24 (m, 5H), 7.16 (dd, J=8.8, 3.0 Hz, 1H), 6.92 (d, J=8.7 Hz, 1H), 5.06 (s, 2H), 4.06 (d, J=13.2 Hz, 2H), 3.64-3.56 (m, 1H), 2.84 (s, 2H), 1.99 m, 2H), 1.51 (m, 2H).

Example 64

N-(5-hydroxypyridin-2-yl)-1-phenylpiperidine-4-sulfonamide

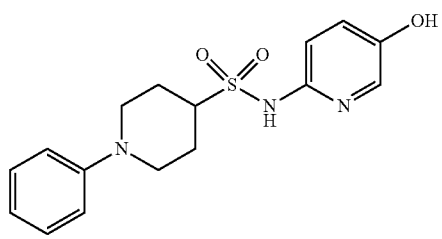 [SMILES: O=S(=O)(Nc1ccc(O)cn1)C1CCN(c2ccccc2)CC1]

Step 1. Synthesis of benzyl 4-([5-[(tert-butyldimethylsilyl)oxy]pyridin-2-yl]sulfamoyl)piperidine-1-carboxylate

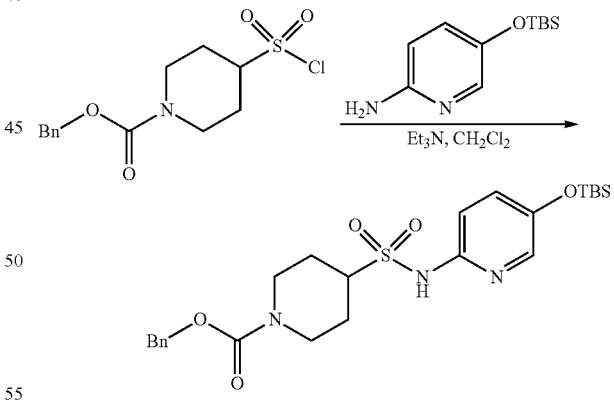

To a mixture of 5-[(tert-butyldimethylsilyl)oxy]pyridin-2-amine (2.1 g, 9.36 mmol) and Et₃N (2.88 g, 28.46 mmol) was added a solution of benzyl 4-(chlorosulfonyl)piperidine-1-carboxylate (3 g, 9.44 mmol) in CH₂Cl₂ (30 mL) at 0° C. over 2 min. The resulting solution was stirred for 2 h at 0° C., then quenched by the addition of 50 mL H₂O and extracted with 2×100 mL of EtOAc. The combined organic layers were concentrated under vacuum and purified with silica gel column chromatography using EtOAc/hexane (1/1) to afford 3.2 g (67%) of the title compound as an off-white solid. LC-MS: (ES, m/z): 506.

Step 2. Synthesis of N-[5-[(tert-butyldimethylsilyl)oxy]pyridin-2-yl]piperidine-4-sulfonamide

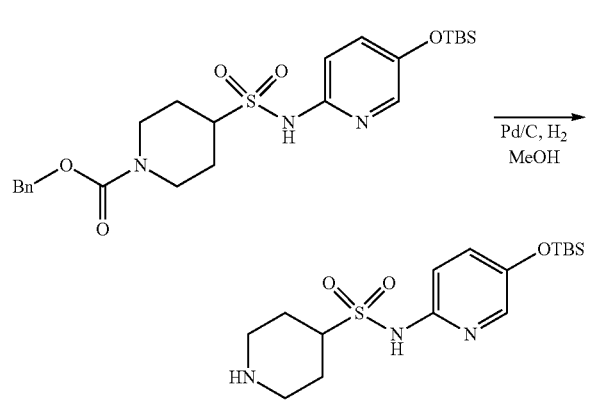

A solution of the product from the previous step (3.2 g, 6.33 mmol) in MeOH (30 mL) was stirred for 2 hr over Pd/C (300 mg) under an H₂ atmosphere, then concentrated under vacuum and purified with silica gel chromatography using $CH_2Cl_2$/MeOH (20:1) to afford 1.26 g (54%) of the title compound as a light brown solid.

LC-MS: (ES, m/z): 372

$^1$H NMR (300 MHz, DMSO-$d_6$) δ 7.86 (d, J=2.9 Hz, 1H), 7.28 (dd, J=8.8, 3.0 Hz, 1H), 6.95 (d, J=8.8 Hz, 1H), 3.53 (t, J=11.9 Hz, 1H), 3.20-2.99 (m, 2H), 2.59-2.51 (m, 2H), 1.93 (d, J=12.5 Hz, 2H), 1.60 (qd, J=12.1, 3.9 Hz, 2H), 0.93 (s, 9H), 0.17 (s, 6H).

Step 3. Synthesis of N-[5-[(tert-butyldimethylsilyl)oxy]pyridin-2-yl]-1-phenylpiperidine-4-sulfonamide

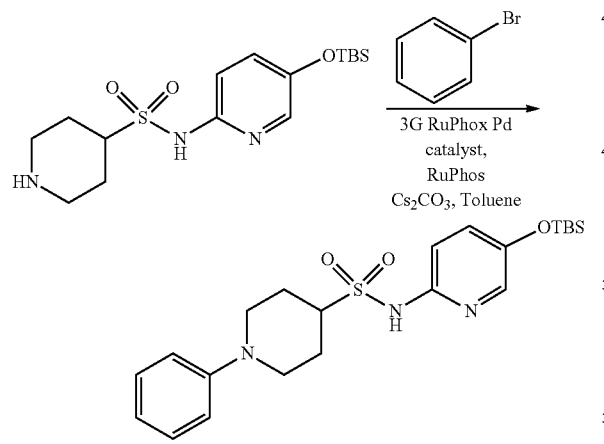

A mixture of the product from the previous step (200 mg, 0.54 mmol), $Cs_2CO_3$ (352 mg, 1.08 mmol), bromobenzene (1.68 g, 10.70 mmol), RuPhos (26 g), and 3G RuPhox Pd catalysis (45 mg) in toluene (5 mL) was stirred for 16 h at 100° C., then quenched by the addition of 20 mL $H_2O$ and extracted with 2×60 mL of EtOAc. The combined organic layers were concentrated under vacuum and purified with silica gel column chromatography using EtOAc/hexane (1/2) to afford 30 mg (12%) of the title compound as an off-white solid. LC-MS: (ES, m/z): 448.

Step 4. Synthesis of N-(5-hydroxypyridin-2-yl)-1-phenylpiperidine-4-sulfonamide

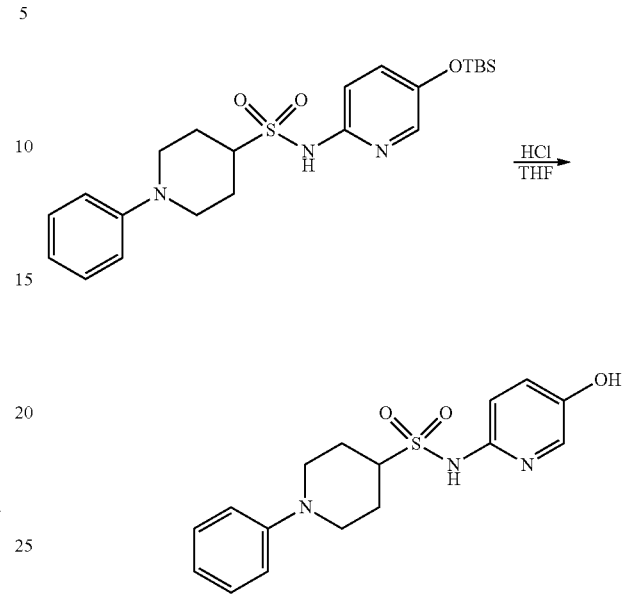

A solution of the product from the previous step (30 mg, 0.07 mmol) in 2N HCl (1 mL) and THF (2 mL) was stirred for 2 h at rt, then concentrated under vacuum. The crude product (30 mg) was purified by Prep-HPLC with the following conditions: Instrument "A"; Column "E"; mobile phase, 10 mM aq $NH_4HCO_3$ and ACN (20.0% ACN up to 50.0% in 7 min), to afford 8.7 mg (39%) of the title compound as an off-white solid.

LC-MS: (ES, m/z): 334

$^1$H NMR (300 MHz, Methanol-$d_4$) δ 7.78 (d, J=2.9 Hz, 1H), 7.28-7.11 (m, 3H), 7.05 (dd, J=8.8, 0.7 Hz, 1H), 7.02-6.92 (m, 2H), 6.82 (t, J=7.4 Hz, 1H), 3.77 (d, J=12.6 Hz, 2H), 3.45 (tt, J=12.0, 3.8 Hz, 1H), 2.70 (m, 2H), 2.19 (d, J=12.6 Hz, 2H), 1.94 (m, 2H).

Example 65

1-benzyl-N-(5-hydroxypyridin-2-yl)piperidine-4-sulfonamide

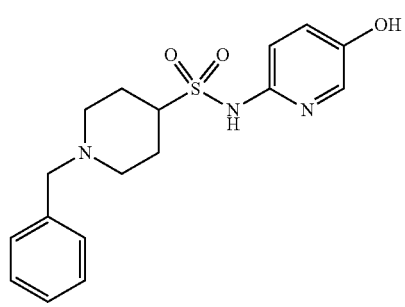 [SMILES: O=S(=O)(Nc1ccc(O)cn1)C1CCN(Cc2ccccc2)CC1]

Step 1. Synthesis of 1-benzyl-N-[5-[(tert-butyldimethylsilyl)oxy]pyridin-2-yl]piperidine-4-sulfonamide

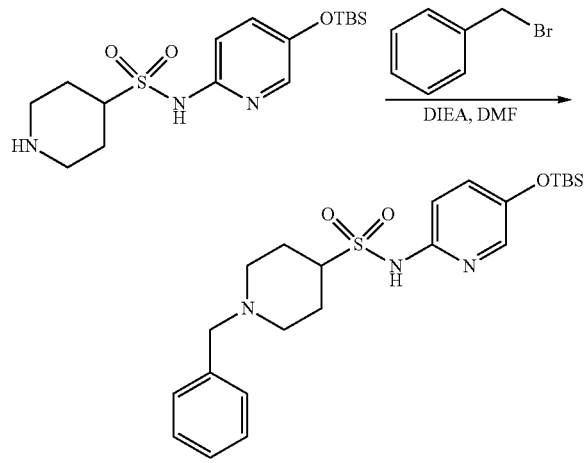

A solution of N-[5-[(tert-butyldimethylsilyl)oxy]pyridin-2-yl]piperidine-4-sulfonamide (600 mg, 1.61 mmol, 1.00 equiv), (bromomethyl)benzene (247 mg, 1.44 mmol, 0.90 equiv), and DIEA (208 mg, 1.61 mmol, 1.00 equiv) in DMF (10 mL) was stirred for 2 h at 0° C., then quenched with H$_2$O and extracted with 2×30 mL of EtOAc. The combined organic layers were concentrated under vacuum and purified with silica gel column chromatography using EtOAc/hexane (1/2) to afford 670 mg (90%) of the title compound as an off-white solid.

LC-MS: (ES, m/z): 462

$^1$H NMR (400 MHz, DMSO-d$_6$) δ 10.23 (s, 1H), 7.95 (s, 1H), 7.92-7.86 (m, 1H), 7.36-7.19 (m, 6H), 6.97 (dd, J=8.7, 0.6 Hz, 1H), 3.45 (s, 2H), 2.73 (d, J=0.6 Hz, 4H), 1.92 (s, 2H), 1.74-1.60 (m, 2H), 0.94 (s, 9H), 0.19 (s, 6H).

Step 2. Synthesis of 1-benzyl-N-(5-hydroxypyridin-2-yl)piperidine-4-sulfonamide

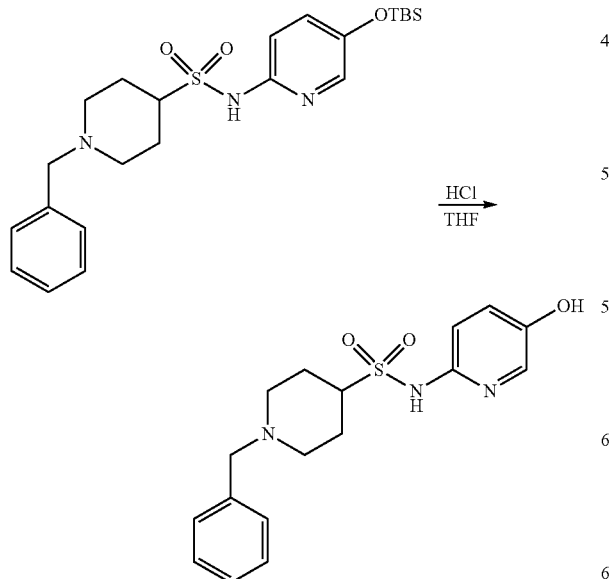

A solution of the product from the previous step (200 mg, 0.43 mmol, 1.00 equiv) in 2N HCl (2 mL) and THF (4 mL) was stirred for 1 h at rt, then concentrated under vacuum. The crude product (200 mg) was purified by Prep-HPLC with the following conditions: Instrument "A"; Column "A"; mobile phase, 10 mM aq NH$_4$HCO$_3$ and ACN (20.0% ACN up to 47.0% in 8 min); Detector, UV 254/220 nm, to afford 78.2 mg (52%) of the title compound as an off-white solid.

LC-MS: (ES, m/z): 348

$^1$H NMR (400 MHz, DMSO-d$_6$) δ 9.70 (br, 2H), 7.82 (d, J=2.9 Hz, 1H), 7.39-7.21 (m, 5H), 7.16 (dd, J=8.8, 2.9 Hz, 1H), 6.93 (d, J=8.8 Hz, 1H), 3.45 (s, 2H), 3.31 (m, 1H), 2.88 (m, 2H), 1.91 (m, 4H), 1.65 (m, 2H).

Example 66

1-(4-fluorophenyl)-N-(5-hydroxypyridin-2-yl)piperidine-4-sulfonamide

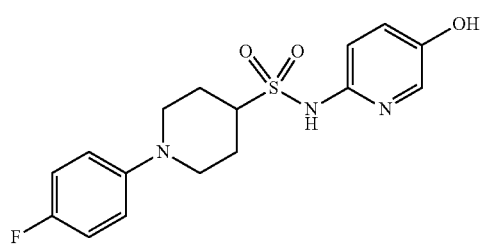 [SMILES: O=S(=O)(Nc1ccc(O)cn1)C1CCN(c2ccc(F)cc2)CC1]

Step 1. Synthesis of benzyl 4-([5-[(tert-butyldimethylsilyl)oxy]pyridin-2-yl]sulfamoyl)piperidine-1-carboxylate

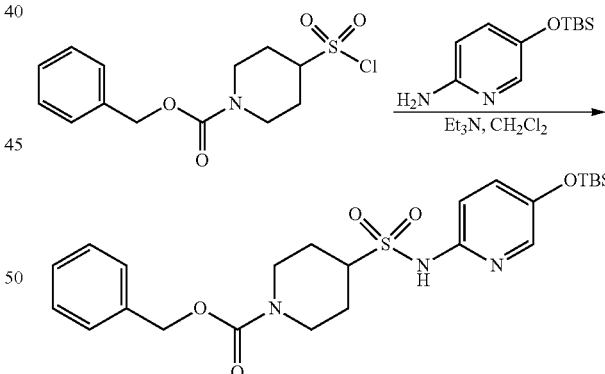

To a solution of 5-[(tert-butyldimethylsilyl)oxy]pyridin-2-amine (4.38 g, 19.52 mmol) and Et$_3$N (5.9 g, 58.31 mmol) in CH$_2$Cl$_2$ (80 mL) was added a solution of benzyl 4-(chlorosulfonyl)piperidine-1-carboxylate (6.2 g, 19.51 mmol) in CH$_2$Cl$_2$ (20 mL) dropwise with stirring at 0° C. over 3 min. The resulting solution was stirred for 2 h at 0° C., then concentrated under reduced pressure and purified with silica gel chromatography using EtOAc/hexane (1/2). The resulting solution was extracted with 2×200 mL of CH$_2$Cl$_2$, and the organic layers were combined and concentrated under vacuum. This resulted in 6.2 g (63%) of the title compound as an off-white solid. LC-MS (ES, m/z): 506

Step 2. Synthesis of N-[5-[(tert-butyldimethylsilyl)oxy]pyridin-2-yl]piperidine-4-sulfonamide Step 4. Synthesis of 1-(4-fluorophenyl)-N-(5-hydroxypyridin-2-yl)piperidine-4-sulfonamide

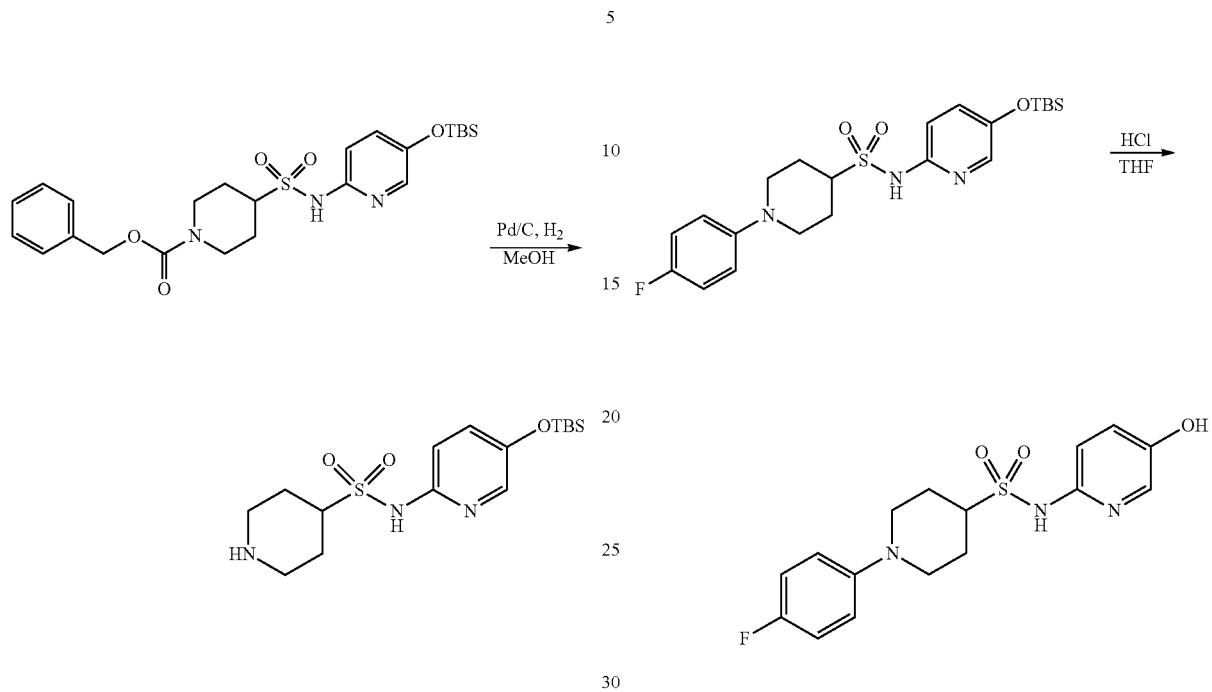

A solution of the product from the previous step (6 g, 11.86 mmol) in MeOH (60 mL) was stirred for 1 h at rt under H₂ over Pd/C (600 mg). The solids were removed by filtration, and the filtrate was concentrated under vacuum to afford 3.5 g (79%) of the title compound as a light brown solid. LC-MS (ES, m/z): 372

Step 3. Synthesis of

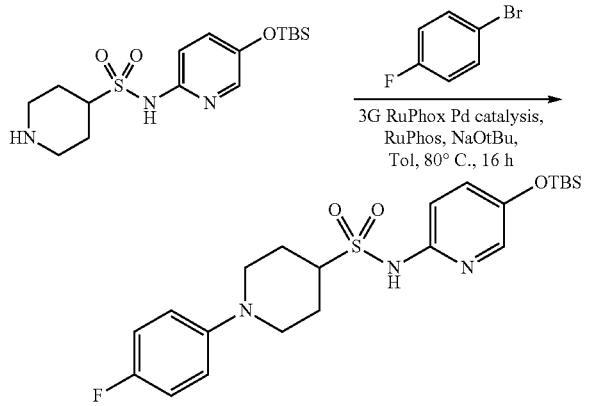

A solution of the product from the previous step (200 mg, 0.54 mmol), 1-bromo-4-fluorobenzene (94 mg, 0.54 mmol), NaOtBu (156 mg), RuPhos (2.5 mg), and 3G RuPhox Pd catalysis (4.5 mg) in toluene (5 mL) was stirred for 16 h at 80° C., then extracted with 2×30 mL EtOAc. The combined organic layers concentrated under vacuum and purified with silica gel chromatography using EtOAc/hexane (1/2) to afford 130 mg (52%) of the title compound as a light yellow solid. LC-MS (ES, m/z): 466

To a solution of the product from the previous step (130 mg, 0.27 mmol) in THF (3 mL) was added 2N aq. HCl (3 mL) dropwise with stirring. The resulting solution was stirred for 2 h at rt, then concentrated under vacuum. The crude product (100 mg) was purified by Prep-HPLC with the following conditions: Instrument "A"; Column "D"; mobile phase, 10 mM aq NH₄HCO₃— and ACN (20.0% ACN up to 55.0% in 7 min); Detector, UV 254/220 nm, to afford 62.4 mg (63%) of the title compound as an off-white solid.
LC-MS (ES, m/z): 352
¹H NMR (300 MHz, Methanol-d₄) δ 7.83 (dd, J=3.0, 0.7 Hz, 1H), 7.22 (dd, J=8.8, 3.0 Hz, 1H), 7.08 (dd, J=8.8, 0.7 Hz, 1H), 7.04-6.89 (m, 4H), 3.67 (d, J=12.4 Hz, 2H), 3.46 (m, 1H), 2.69 (m, 2H), 2.22 (d, J=12.6 Hz, 2H), 2.09-1.87 (m, 2H).

Example 67

1-(5-chloropyridin-2-yl)-N-(5-hydroxypyridin-2-yl)piperidine-4-sulfonamide

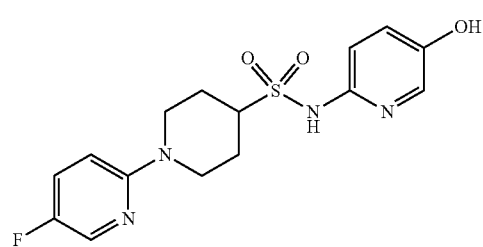 [SMILES: O=S(=O)(Nc1ccc(O)cn1)C1CCN(c2ccc(F)cn2)CC1]

Step 1. Synthesis of N-[5-[(tert-butyldimethylsilyl)oxy]pyridin-2-yl]-1-(5-chloropyridin-2-yl)piperidine-4-sulfonamide

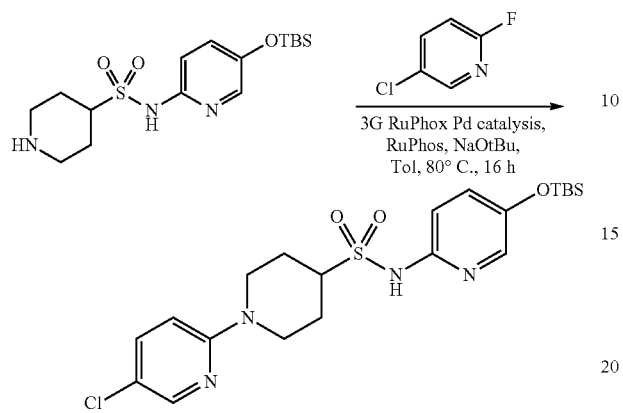

A solution of N-[5-[(tert-butyldimethylsilyl)oxy]pyridin-2-yl]piperidine-4-sulfonamide (200 mg, 0.54 mmol), DIEA (139 mg, 1.08 mmol), and 5-chloro-2-fluoropyridine (142 mg, 1.08 mmol) in DMSO (5 mL) was stirred for 16 h at 80° C., then extracted with 2×30 mL EtOAc. The combined organic layers were concentrated under vacuum and purified with silica gel chromatography using EtOAc/hexane (1/2) to afford 170 mg (65%) of the title compound as a light yellow solid.

Step 2. Synthesis of 1-(5-chloropyridin-2-yl)-N-(5-hydroxypyridin-2-yl)piperidine-4-sulfonamide

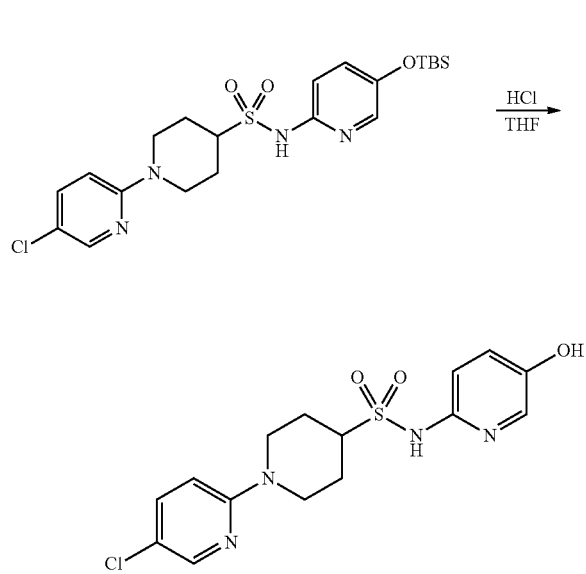

A solution of the product from the previous step (170 mg, 0.35 mmol) in 3N aq. HCl (3 mL) and THF (3 mL) stirred for 2 h at rt, then concentrated under vacuum. The crude product (170 mg) was purified by Prep-HPLC with the following conditions: Instrument "A"; Column "D"; mobile phase, 10 mM aq NH$_4$HCO$_3$ and ACN (20.0% ACN up to 62.0% in 7 min); Detector, UV 254/220 nm, to afford 78.3 mg (60%) of the title compound as an off-white solid.

LC-MS (ES, m/z): 318

$^1$H NMR (300 MHz, DMSO-d$_6$) δ 9.89 (br, 2H), 8.10 (d, J=2.8 Hz, 1H), 7.83 (d, J=3.0 Hz, 1H), 7.58 (dd, J=9.2, 2.8 Hz, 1H), 7.19 (dd, J=8.8, 3.0 Hz, 1H), 6.93 (m, 2H), 4.35 (d, J=13.2 Hz, 2H), 3.68 (tt, J=12.3, 3.7 Hz, 1H), 2.88 (t, J=12.6 Hz, 2H), 2.11-1.96 (m, 2H), 1.60 (qd, J=12.6, 3.9 Hz, 2H).

Example 68

1-(4-chlorophenyl)-N-(5-hydroxypyridin-2-yl)piperidine-4-sulfonamide

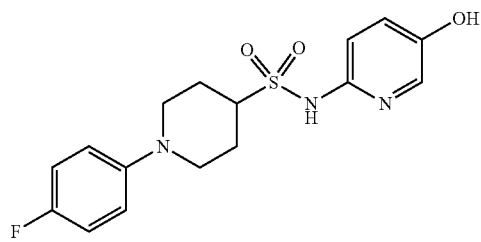 [SMILES: O=S(=O)(Nc1ccc(O)cn1)C1CCN(c2ccc(F)cc2)CC1]

Step 1. Synthesis of N-[5-[(tert-butyldimethylsilyl)oxy]pyridin-2-yl]-1-(4-chlorophenyl) piperidine-4-sulfonamide

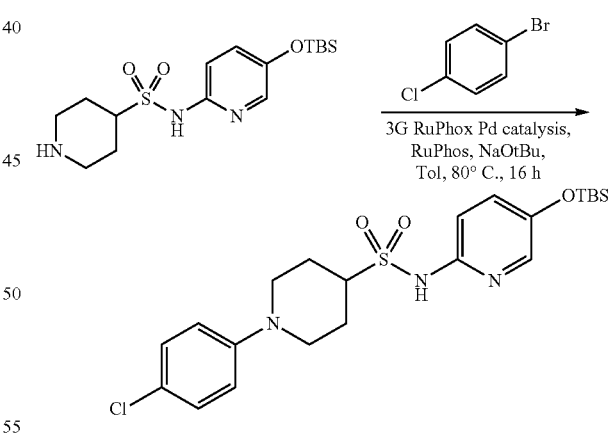

A solution of N-[5-[(tert-butyldimethylsilyl)oxy]pyridin-2-yl]piperidine-4-sulfonamide (200 mg, 0.54 mmol), 1-bromo-4-chlorobenzene (205 mg, 1.07 mmol), NaOtBu (156 mg), RuPhos (2.5 mg), and 3G RuPhox Pd catalysis (4.5 mg) in toluene (5 mL) was stirred for 16 hr at 80° C. in an oil bath. The resulting solution was extracted with 2×30 mL of EtOAc, and the combined organic layers were concentrated under vacuum and purified with silica gel chromatography using EtOAc/hexane (1/2) to afford 180 mg (69%) of the title compound as a light yellow solid. LC-MS (ES, m/z): 482

Step 2. Synthesis of 1-(4-chlorophenyl)-N-(5-hydroxypyridin-2-yl)piperidine-4-sulfonamide

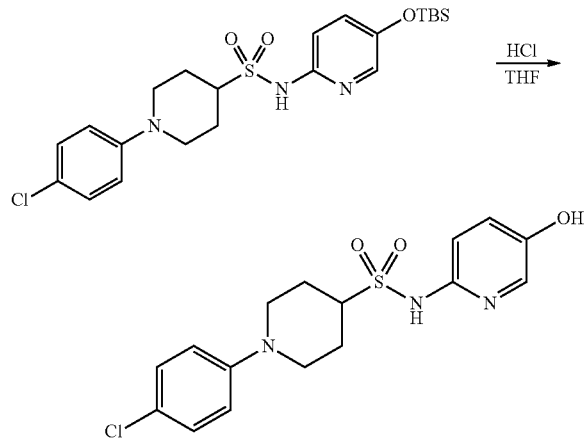

A solution of the product from the previous step (180 mg, 0.37 mmol) in 2 N aq. HCl (3 mL) and THF (3 mL) was stirred for 2 h at rt, then concentrated under vacuum. The crude product (180 mg) was purified by Prep-HPLC with the following conditions: Instrument "A"; Column "D"; mobile phase, 10 mM aq $NH_4HCO_3$ and ACN (hold 25.0% ACN in 7 min); Detector, UV 254/220 nm, to afford 98 mg (71%) of the title compound as an off-white solid.
LC-MS (ES, m/z): 368
$^1$H NMR (300 MHz, DMSO-$d_6$) δ 9.88 (br, 2H), 7.84 (d, J=2.9 Hz, 1H), 7.28-7.14 (m, 3H), 7.02-6.88 (m, 3H), 3.80 (m, 2H), 3.57 (m, 1H), 2.73 (m, 2H), 2.11-1.96 (m, 2H), 1.73 (m, 2H).

Example 69

N-(5-hydroxypyridin-2-yl)-1-[4-(trifluoromethyl)phenyl]piperidine-4-sulfonamide

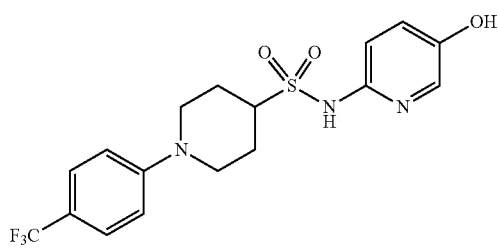 [SMILES: O=S(=O)(Nc1ccc(O)cn1)C1CCN(c2ccc(C(F)(F)F)cc2)CC1]

Step 1. Synthesis of N-[5-[(tert-butyldimethylsilyl)oxy]pyridin-2-yl]-1-[4-(trifluoromethyl)phenyl] piperidine-4-sulfonamide

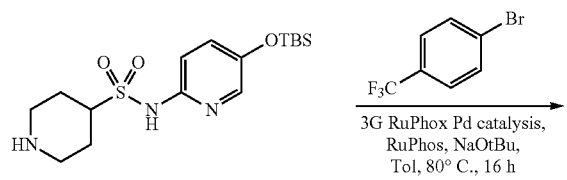

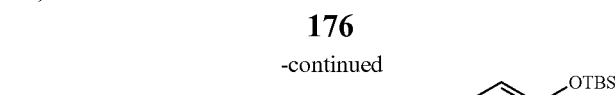

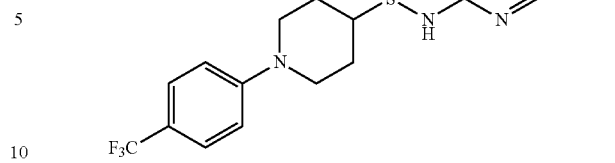

A solution of N-[5-[(tert-butyldimethylsilyl)oxy]pyridin-2-yl]piperidine-4-sulfonamide (200 mg, 0.54 mmol), 1-bromo-4-(trifluoromethyl)benzene (215 mg, 0.96 mmol), NaOtBu (156 mg), RuPhos (2.5 mg), 3G RuPhox Pd catalysis (4.5 mg), and toluene (5 mL) was stirred for 16 h at 80° C., then extracted with 2×30 mL of EtOAc. The combined organic layers were concentrated under vacuum and purified with silica gel chromatography using EtOAc/hexane (1/2) to afford 115 mg (41%) of the title compound as a light yellow solid. LC-MS: (ES, m/z): 516

Step 2. Synthesis of N-(5-hydroxypyridin-2-yl)-1-[4-(trifluoromethyl)phenyl]piperidine-4-sulfonamide

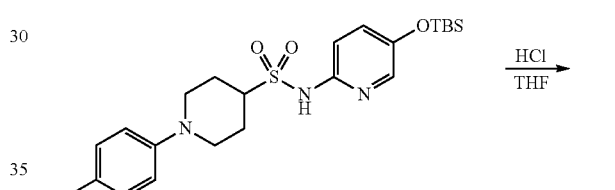

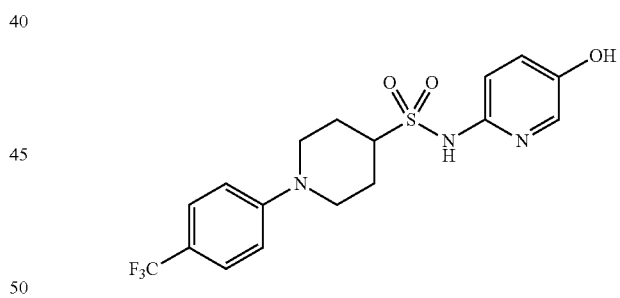

To a solution of the product from the previous step (115 mg, 0.22 mmol) in THF (3 mL) was added 2N aq. HCl (3 mL) dropwise with stirring. The resulting solution was stirred for 2 h at rt, then concentrated under vacuum. The crude product (115 mg) was purified by Prep-HPLC under the following conditions: Instrument "A"; Column "D"; mobile phase, Water (10 mM $NH_4HCO_3$) and ACN (25.0% ACN up to 75.0% in 7 min); Detector, UV 254/220 nm, to afford 56.5 mg (63%) of the title compound as an off-white solid.

LC-MS (ES, m/z): 402
$^1$H NMR (300 MHz, DMSO-$d_6$) δ 9.86 (br, 2H), 7.84 (d, J=2.9 Hz, 1H), 7.49 (d, J=8.5 Hz, 2H), 7.20 (dd, J=8.8, 3.0 Hz, 1H), 7.02 (m, 3H), 3.99 (m, 2H), 3.66 m, 1H), 2.88 m, 2H), 2.11-1.98 (m, 2H), 1.70 (m, 2H).

Example 70

N-(5-Hydroxypyridin-2-yl)-6-methylheptane-1-sulfonamide

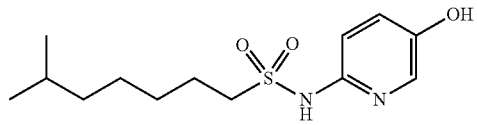 [SMILES: CC(C)CCCCCS(=O)(=O)Nc1ccc(O)cn1]

Step 1. Synthesis of 6-methylheptane-1-thiol

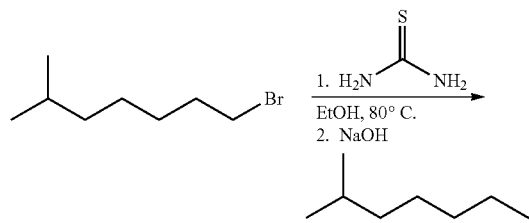

To a solution of 1-bromo-6-methylheptane (900 mg, 4.66 mmol) in EtOH (9 mL) was added $CH_4N_2S$ (372 mg, 4.89 mmol) over 16 hr. Aq. NaOH (9 mL) was then added over 2 hr. The resulting solution was extracted with 2×20 mL of petroleum ether, and the combined organic layers were concentrated under vacuum to afford 680 mg (100%) of the title compound as a colorless oil.

Step 2. Synthesis of 6-methylheptane-1-sulfonyl chloride

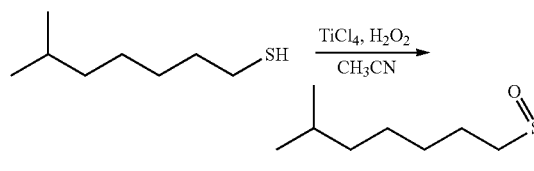

A solution of the product from the previous step (680 mg, 4.65 mmol), $H_2O_2$ (1.4 mL), and $TiCl_4$ (4.65 mL) in $CH_3CN$ (10 mL) was stirred for 4 h at rt, then extracted with 3×20 mL of EtOAc. The combined organic layers were concentrated under vacuum to afford 500 mg (51%) of the title compound as a yellow oil.

Step 3. Synthesis of N-[5-[(tert-butyldimethylsilyl)oxy]pyridin-2-yl]-6-methylheptane-1-sulfonamide

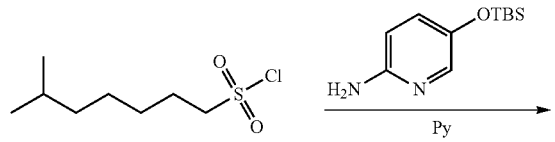

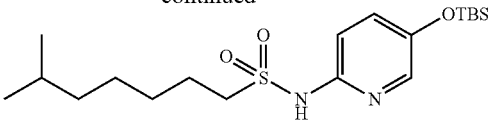

A solution of 5-[(tert-butyldimethylsilyl)oxy]pyridin-2-amine (528 mg, 2.35 mmol) and the product from the previous step (500 g, 2.35 mol) in pyridine (5 mL) was stirred for 16 h at rt, then concentrated under vacuum and purified with silica gel column chromatography using EtOAc/hexane (1:5) to afford 260 mg of the title compound as a yellow solid. LC-MS: (ES, m/z): 401.

Step 4. Synthesis of N-(5-hydroxypyridin-2-yl)-6-methylheptane-1-sulfonamide

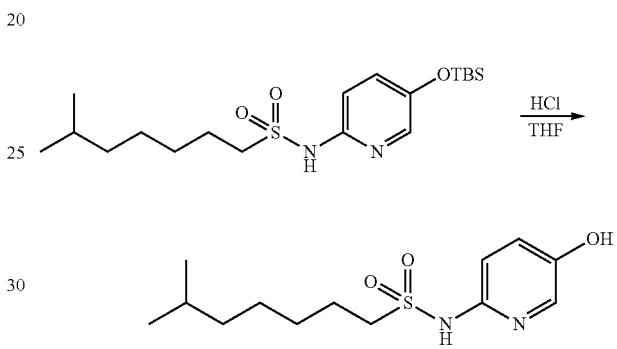

A solution of the product from the previous step (260 mg, 0.65 mmo) in 2N aq. HCl (2 mL) and THF (4 mL) was stirred for 2 h at rt, then concentrated under vacuum. The crude product (260 mg) was purified by Prep-HPLC with the following conditions: Instrument "A"; Column "A"; mobile phase, Water (10 mM NH4HCO3) and ACN (20.0% ACN up to 50.0% in 7 min); Detector, uv 254/220 nm, to afford 82.9 mg (45%) of the title compound as an off-white solid.

LCMS: (ES, m/z): 287.

$^1$H NMR (300 MHz, Methanol-$d_4$) δ 7.84 (d, J=3.0 Hz, 1H), 7.20 (dd, J=8.8, 3.0 Hz, 1H), 6.99 (d, J=8.8 Hz, 1H), 3.31 (m, 2H), 1.80 (m, 2H), 1.51 (m, 1H), 1.45-1.23 (m, 4H), 1.17 (dd, J=8.4, 5.9 Hz, 2H), 0.87 (d, J=6.6 Hz, 6H).

Example 71

4-(4-chlorophenyl)-N-(5-hydroxypyridin-2-yl)piperidine-1-sulfonamide

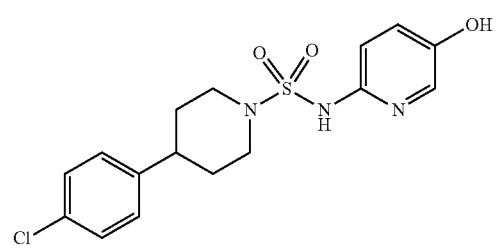 [SMILES: O=S(=O)(Nc1ccc(O)cn1)N1CCC(c2ccc(Cl)cc2)CC1]

Step 1. Synthesis of 4-(4-chlorophenyl)piperidine-1-sulfonyl chloride

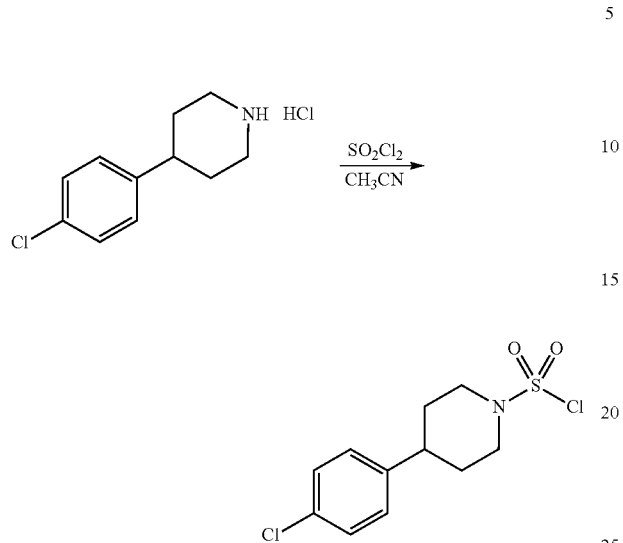

To a solution of 4-(4-chlorophenyl)piperidine (500 mg, 2.56 mmol) in ACN (5 mL) was added SO$_2$Cl$_2$ (2.06 g) dropwise at 0° C. The resulting solution was stirred for 16 h at rt, then concentrated under vacuum to afford 500 mg (67%) of the title compound as an off-white solid.

Step 2. Synthesis of N-[5-[(tert-butyldimethylsilyl)oxy]pyridin-2-yl]-4-(4-chlorophenyl) piperidine-1-sulfonamide

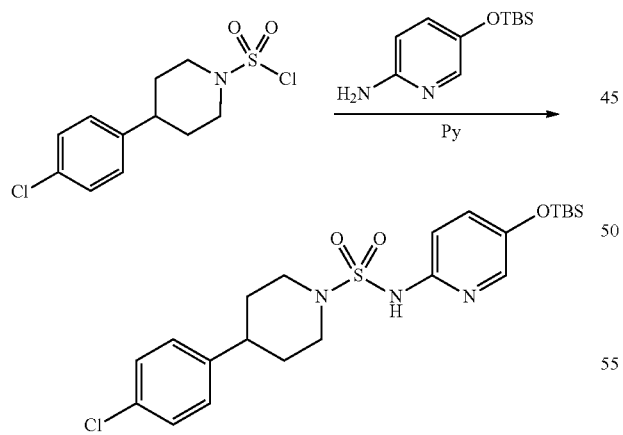

To a solution of the product from the previous step (244 mg, 1.09 mmol) in pyridine (5 mL) was added 4-(4-chlorophenyl)piperidine-1-sulfonyl chloride (500 mg, 1.70 mmol) dropwise with stirring at 0° C. The resulting solution was stirred for 2 h at rt, then concentrated under vacuum and purified with silica gel chromatography using EtOAc/hexane (1:1) to afford 80 mg (15%) of the title compound as an off-white solid. LC-MS: (ES, m/z): 482

Step 3. Synthesis of 4-(4-chlorophenyl)-N-(5-hydroxypyridin-2-yl)piperidine-1-sulfonamide

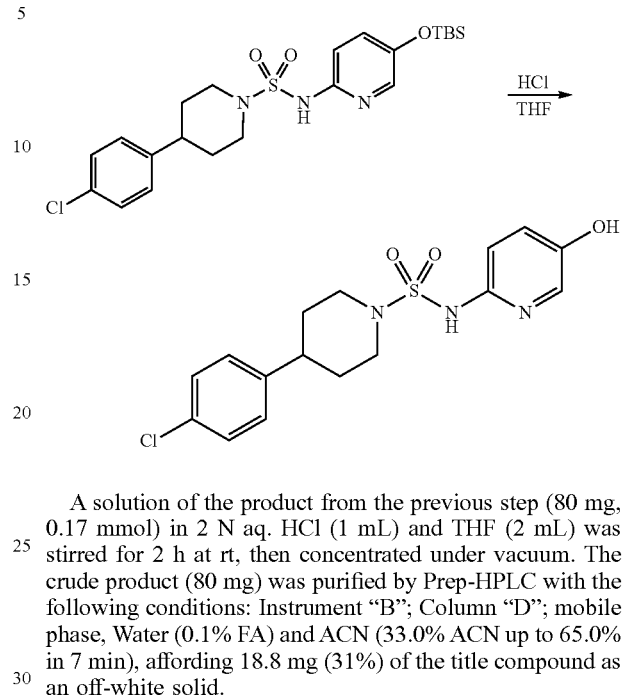

A solution of the product from the previous step (80 mg, 0.17 mmol) in 2 N aq. HCl (1 mL) and THF (2 mL) was stirred for 2 h at rt, then concentrated under vacuum. The crude product (80 mg) was purified by Prep-HPLC with the following conditions: Instrument "B"; Column "D"; mobile phase, Water (0.1% FA) and ACN (33.0% ACN up to 65.0% in 7 min), affording 18.8 mg (31%) of the title compound as an off-white solid.

LC-MS: (ES, m/z): 368

$^1$H NMR (300 MHz, DMSO-d$_6$) δ 10.33-9.38 (m, 2H), 7.84 (d, J=2.9 Hz, 1H), 7.39-7.31 (m, 2H), 7.25-7.18 (m, 3H), 7.06 (d, J=8.8 Hz, 1H), 3.81-3.63 (m, 2H), 2.80 (m, 2H), 2.60 (m, 1H), 1.86-1.67 (m, 2H), 1.48 (m, 2H).

Scheme X

Example 72

N-(5-hydroxypyridin-2-yl)-2-(4-(4-(trifluoromethyl)phenyl)piperazin-1-yl)acetamide

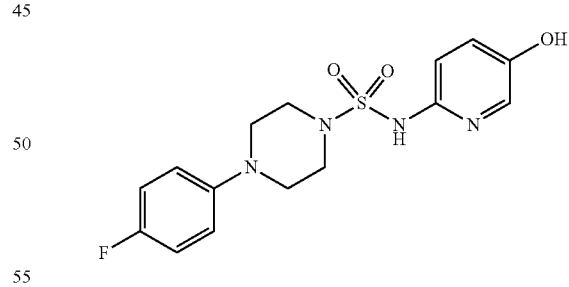

Step 1. Synthesis of N-(5-(tert-butyldimethylsilyloxy)pyridin-2-yl)-2-oxooxazolidine-3-sulfonamide

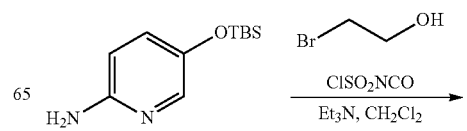

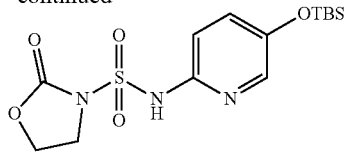

To a solution of chlorosulfonyl isocyanate (282 mg, 2 mmol) in DCM (15 mL) was added 2-bromoethanol (248 mg, 2 mmol) dropwise at 0° C. The mixture was stirred 0.5 h, then a solution of 5-(tert-butyldimethylsilyloxy)pyridin-2-amine (448 mg, 2 mmol) and Et₃N (600 mg, 6 mmol) in DCM (15 mL) was added dropwise at 0° C. The resulting solution was stirred for 2 h at rt, then concentrated under vacuum and purified with silica gel chromatography using EtOAc/MeOH (15/1) to afford the title compound as a light yellow solid (500 mg, 67%). LC-MS: (ES, m/z): 374.2

Step 2. Synthesis of N-(5-(tert-butyldimethylsilyloxy)pyridin-2-yl)-4-(4-fluorophenyl)piperazine-1-sulfonamide

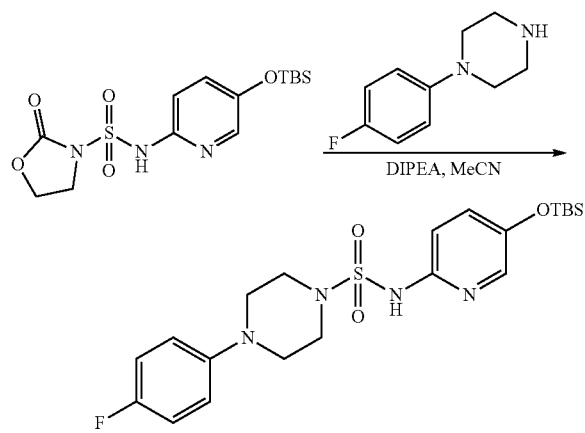

A solution of the product from the previous step (115 mg, 0.3 mmol), 1-(4-fluorophenyl)piperazine (108 mg, 0.6 mmol) and DIPEA (0.6 mL) in MeCN (1.5 mL) was heated to 130° C. using microwave heating for 0.5 h. The mixture was then cooled to rt, concentrated under vacuum, and purified with silica gel column chromatography using CH₂Cl₂/EtOAc (10/1) to afford 70 mg (50%) of the title compound as a light yellow solid. LC-MS: (ES, m/z): 467.1.

Step 3. Synthesis of N-(5-hydroxypyridin-2-yl)-2-(4-(4-(trifluoromethyl)phenyl)piperazin-1-yl)acetamide

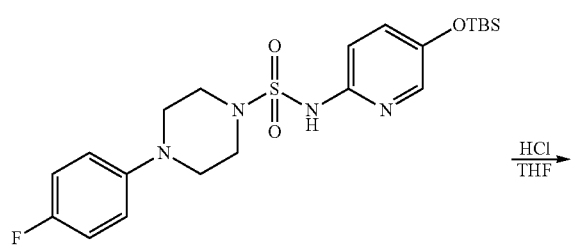

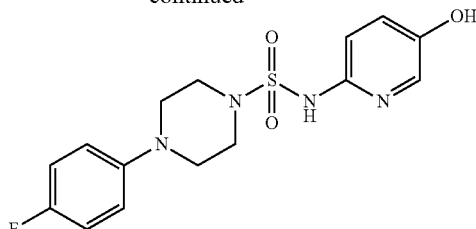

To a solution of the product from the previous step (70 mg, 0.15 mmol) in THF (2 mL) was added conc. HCl (1 mL) at 0° C. The resulting solution was stirred for 2 h at rt, then concentrated under vacuum. The residue was purified by Prep-HPLC with the following conditions: Instrument "A"; Column "A"; mobile phase, 10 mM aq NH₄HCO₃ and ACN (20.0% ACN up to 49.0% in 8 min); Detector, UV 254/220 nm, to afford 17.9 mg (24%) of the title compound as a white solid.

LC-MS: (ES, m/z): 353.1

¹H NMR (400 MHz, DMSO-d₆) δ 9.74 (s, 2H), 7.80 (d, J=2.9 Hz, 1H), 7.19 (dd, J=8.8, 3.0 Hz, 1H), 7.09-7.00 (m, 3H), 6.97-6.90 (m, 2H), 3.27-3.18 (m, 4H), 3.11-3.02 (m, 4H).

Example 73

4-(5-Chloropyridin-2-yl)-N-(5-hydroxypyridin-2-yl)piperazine-1-sulfonamide

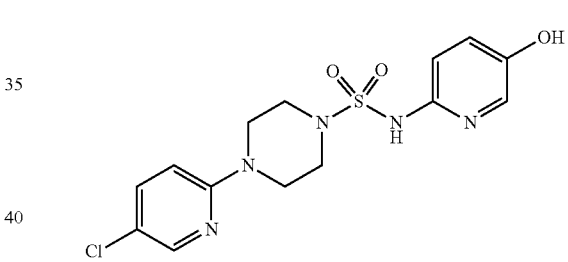

Step 1. Synthesis of N-(5-(tert-butyldimethylsilyloxy)pyridin-2-yl)-4-(5-chloropyridin-2-yl)piperazine-1-sulfonamide

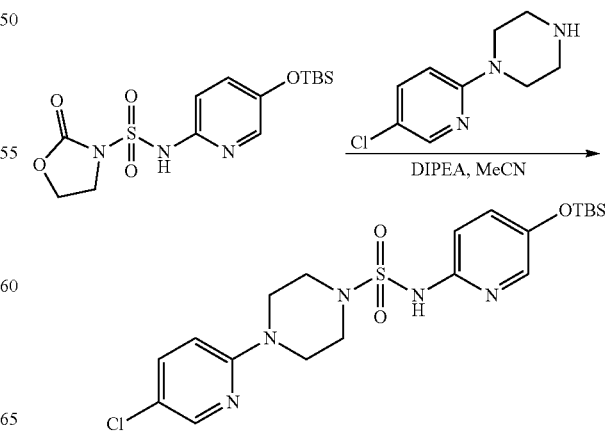

A solution of N-(5-(tert-butyldimethylsilyloxy)pyridin-2-yl)-2-oxooxazolidine-3-sulfonamide (165 mg, 0.45 mmol), 1-(5-chloropyridin-2-yl)piperazine (180 mg, 0.9 mmol) and DIPEA (0.6 mL) in MeCN (1.5 mL) was heated to 130° C. using microwave heating for 0.5 h. The mixture was then cooled to rt, concentrated under vacuum, and purified with silica gel chromatography using $CH_2Cl_2$/EtOAc (10/1) to afford 150 mg (72%) of the title compound as a light yellow foam. LC-MS: (ES, m/z): 484.3.

Step 2. Synthesis of 4-(5-chloropyridin-2-yl)-N-(5-hydroxypyridin-2-yl)piperazine-1-sulfonamide

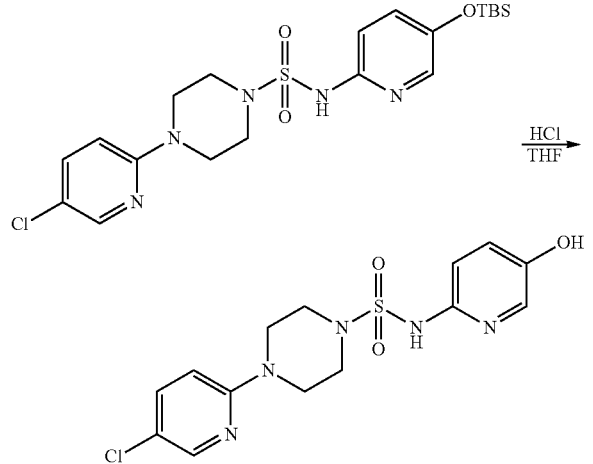

To a solution of the product from the previous step (150 mg, 0.3 mmol) in THF (2 mL) was added conc. HCl (1 mL) at 0° C. The resulting solution was stirred for 2 h at rt, then concentrated under vacuum and purified by Prep-HPLC with the following conditions: Instrument "A"; Column "A"; mobile phase, 10 mM aq $NH_4HCO_3$ and ACN (20.0% ACN up to 49.0% in 8 min); Detector, UV 254/220 nm, to afford 82.1 mg (72%) of the title compound as a white solid.

LC-MS: (ES, m/z): 370.1

$^1$H NMR (400 MHz, DMSO-$d_6$) δ 9.91 (br, 2H), 8.11 (d, J=2.7 Hz, 1H), 7.76 (d, J=2.9 Hz, 1H), 7.62 (dd, J=9.1, 2.7 Hz, 1H), 7.17 (dd, J=8.8, 2.9 Hz, 1H), 7.03 (d, J=8.8 Hz, 1H), 6.88 (d, J=9.1 Hz, 1H), 3.49 (m, 4H), 3.18 (m, 4H).

Example 74

4-(4-chlorophenyl)-N-(5-hydroxypyridin-2-yl)piperazine-1-sulfonamide

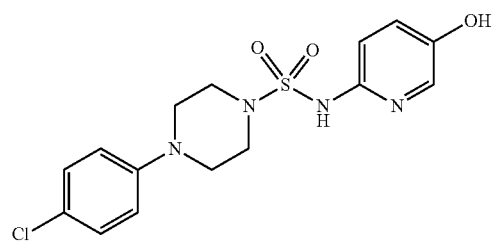 [SMILES: O=S(=O)(Nc1ccc(O)cn1)N1CCN(c2ccc(Cl)cc2)CC1]

Step 1. Synthesis of N-(5-(tert-butyldimethylsilyloxy)pyridin-2-yl)-4-(4-chlorophenyl)piperazine-1-sulfonamide

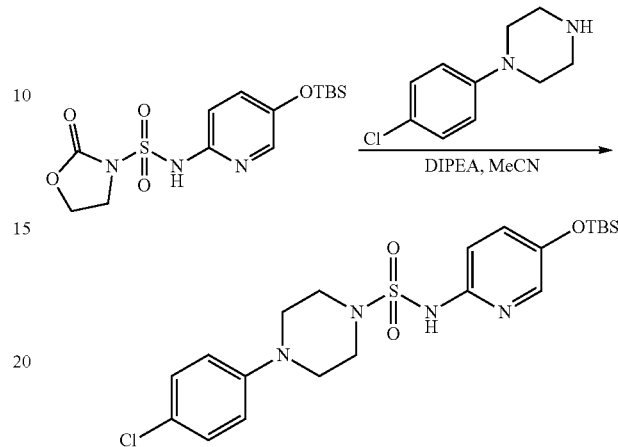

A solution of N-(5-(tert-butyldimethylsilyloxy)pyridin-2-yl)-2-oxooxazolidine-3-sulfonamide (165 mg, 0.45 mmol), 1-(4-chlorophenyl)piperazine (180 mg, 0.9 mmol) and DIPEA (0.6 mL) in MeCN (1.5 mL) was heated to 130° C. using microwave heating for 0.5 h, then cooled to rt, concentrated under vacuum, and purified with silica gel chromatography using $CH_2Cl_2$/EtOAc (10/1) to afford 150 mg (72%) of the title compound as a light yellow foam. LC-MS: (ES, m/z): 483.2

Step 2. Synthesis of 4-(4-chlorophenyl)-N-(5-hydroxypyridin-2-yl)piperazine-1-sulfonamide

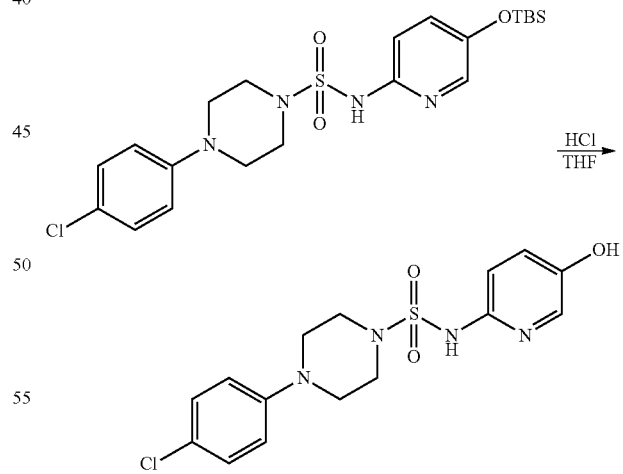

To a solution of the product from the previous step (150 mg, 0.3 mmol) in THF (2 mL) was added conc. HCl (1 mL) at 0° C. The resulting solution was stirred for 2 h at rt, then concentrated under vacuum and purified by Prep-HPLC with the following conditions: Instrument "A"; Column "A"; mobile phase, Water (10 mM $NH_4HCO_3$) and ACN (20.0% ACN up to 49.0% in 8 min); Detector, UV 254/220 nm, to afford 77.5 mg (68%) of the title compound as a white solid.

LC-MS: (ES, m/z): 369.1

$^1$H NMR (400 MHz, DMSO-d$_6$) δ 10.18 (s, 1H), 9.72 (s, 1H), 7.80 (d, J=3.0 Hz, 1H), 7.26-7.21 (m, 2H), 7.19 (dd, J=8.8, 3.0 Hz, 1H), 7.05 (d, J=8.8 Hz, 1H), 6.97-6.91 (m, 2H), 3.26-3.19 (m, 4H), 3.15-3.07 (m, 4H).

Example 75

N-(5-hydroxypyridin-2-yl)-4-(4-(trifluoromethyl)phenyl)-piperazine-1-sulfonamide

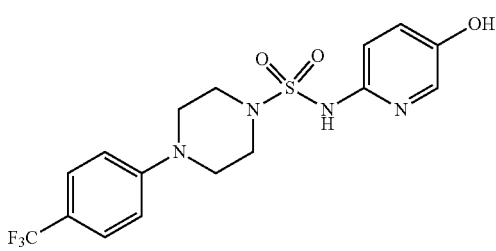 [SMILES: O=S(=O)(Nc1ccc(O)cn1)N1CCN(c2ccc(C(F)(F)F)cc2)CC1]

Step 1. Synthesis of N-(5-(tert-butyldimethylsilyloxy)pyridin-2-yl)-4-(4-(trifluoromethyl)phenyl)piperazine-1-sulfonamide

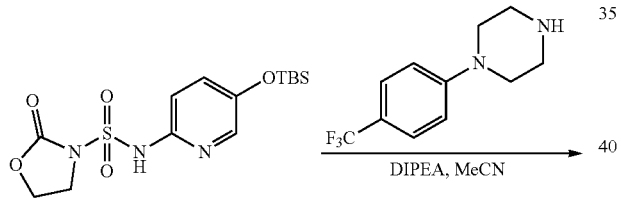

A solution of N-(5-(tert-butyldimethylsilyloxy)pyridin-2-yl)-2-oxooxazolidine-3-sulfonamide (165 mg, 0.45 mmol), 1-(4-(trifluoromethyl)phenyl)piperazine (205 mg, 0.9 mmol) and DIPEA (0.6 mL) in MeCN (1.5 mL) was heated to 130° C. using microwave heating for 0.5 h, then cooled to rt, concentrated under vacuum, and purified with silica gel column chromatography using CH$_2$Cl$_2$/EtOAc (10/1) to afford 150 mg (68%) of the title compound as a light yellow foam. LC-MS: (ES, m/z): 517.3.

Step 2. Synthesis of N-(5-hydroxypyridin-2-yl)-4-(4-(trifluoromethyl)phenyl)piperazine-1-sulfonamide

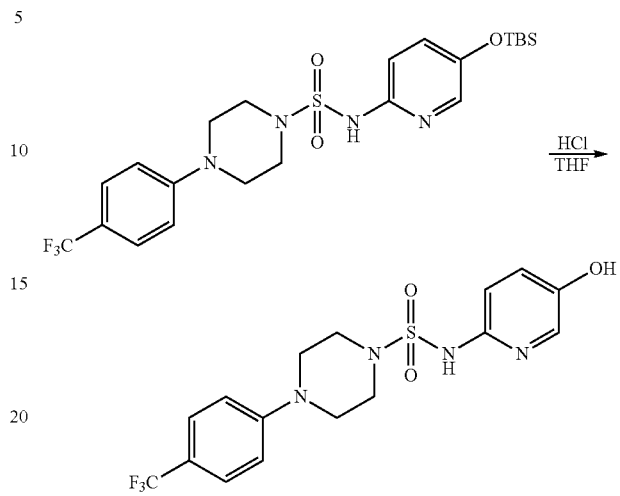

To a solution of the product from the previous step (150 mg, 0.29 mmol) in THF (2 mL) was added conc. HCl (1 mL) at 0. The resulting solution was stirred for 2 h at rt, then concentrated under vacuum and purified by Prep-HPLC with the following conditions: Instrument "A"; Column "A"; mobile phase, 10 mM aq NH$_4$HCO$_3$ and ACN (20.0% ACN up to 49.0% in 8 min); Detector, UV 254/220 nm, to obtain 71.8 mg (61%) of the title compound as a white solid.

LC-MS: (ES, m/z): 403.2.

$^1$H NMR (400 MHz, DMSO-d$_6$) δ 10.18 (s, 1H), 9.73 (s, 1H), 7.79 (d, J=2.9 Hz, 1H), 7.51 (d, J=8.7 Hz, 2H), 7.19 (dd, J=8.8, 3.0 Hz, 1H), 7.08-7.04 (m, 3H), 3.31-3.26 (m, 4H), 3.26-3.21 (m, 4H).

Example 76

1-[(4-chlorophenyl)methyl]-3-(5-hydroxypyridin-2-yl)urea

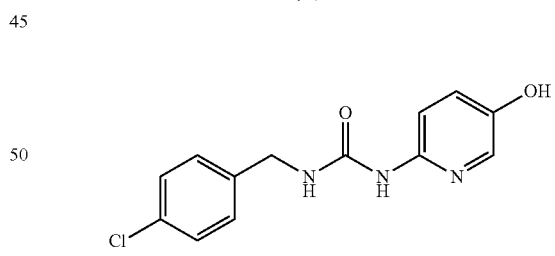

Step 1. Synthesis of 3-[5-[(tert-butyldimethylsilyl)oxy]pyridin-2-yl]-1-[(4-chlorophenyl) methyl]urea

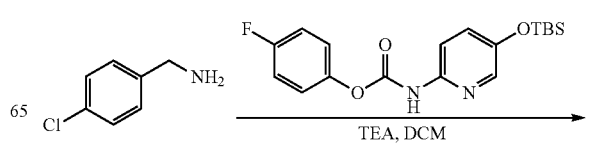

187
-continued

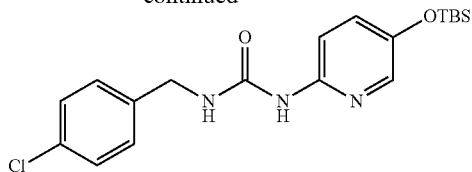

A solution of 1-(4-chlorophenyl)methanamine (24 mg, 0.17 mmol, 1.20 eq.), TEA (42 mg, 0.42 mmol, 3.00 eq.), and 4-fluorophenyl N-5-[(tert-butyldimethylsilyl)oxy]pyridin-2-ylcarbamate (50 mg, 0.14 mmol, 1.00 eq.) in CH$_2$Cl$_2$ (5 mL) in a 40-mL vial was stirred for 16 h at room temperature. The mixture was then extracted with 2×20 mL of CH$_2$Cl$_2$, and the combined organic layers were dried over Na$_2$SO$_4$ and concentrated in vacuo. The residue was purified by prep-TLC using EtOAc/hexane (1/2) to afford 50 mg (92%) of the title compound as an off-white solid. LC-MS: (ES, m/z): 392

Step 2. Synthesis of 1-[(4-chlorophenyl)methyl]-3-(5-hydroxypyridin-2-yl)urea

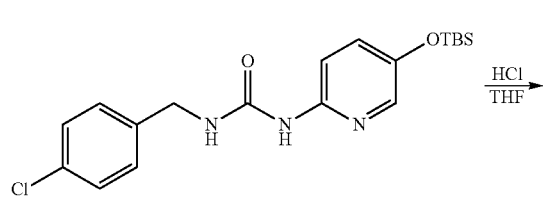

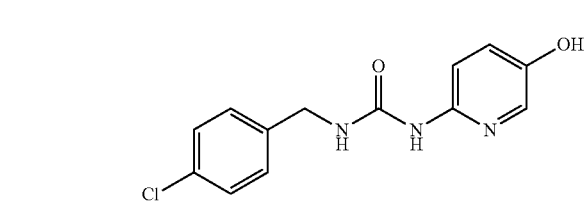 [SMILES: O=C(NCc1ccc(Cl)cc1)Nc1ccc(O)cn1]

To a solution of the product from the previous step (50 mg, 0.13 mmol, 1.00 eq.) in THF (4 mL) in a 100-mL round-bottom flask was added 2 M aqueous HCl (2 mL) dropwise with stirring. The resulting solution was stirred for 2 h at room temperature, then concentrated in vacuo. The crude product (50 mg) was purified by Prep-HPLC with the following conditions: Instrument "A"; Column "A"; mobile phase, water (10 mM NH$_4$HCO$_3$) and ACN (25.0% ACN up to 54.0% in 8 min); Detector, UV 254/220 nm, to afford 32 mg (90%) of the title compound as an off-white solid.

LC-MS: (ES, m/z): 277.8

$^1$H NMR (300 MHz, DMSO-d$_6$) δ 9.35 (s, 1H), 8.96 (s, 1H), 8.35 (s, 1H), 7.71 (dd, J=2.8, 0.7 Hz, 1H), 7.44-7.07 (m, 6H), 4.34 (d, J=6.0 Hz, 2H).

188
Example 77

4-[(3,4-difluorophenyl)methyl]-N-(5-hydroxypyridin-2-yl)piperazine-1-carboxamide

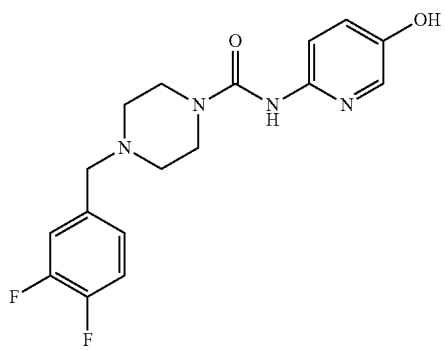 [SMILES: O=C(Nc1ccc(O)cn1)N1CCN(Cc2ccc(F)c(F)c2)CC1]

Step 1. Synthesis of N-[5-[(tert-butyldimethylsilyl)oxy]pyridin-2-yl]-4-[(3,4-difluorophenyl)methyl]piperazine-1-carboxamide

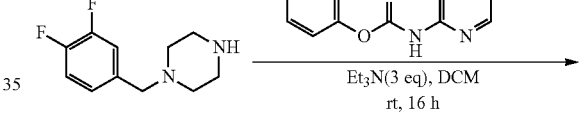

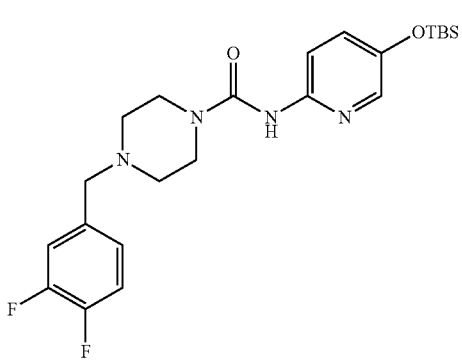

A solution of 4-fluorophenyl N-[5-[(tert-butyldimethylsilyl)oxy]pyridin-2-yl]-carbamate (100 mg, 0.28 mmol, 1.00 eq.), Et$_3$N (84 mg, 3.00 eq.), and 1-[(3,4-difluorophenyl)methyl]piperazine (59 mg, 0.28 mmol, 1.00 eq.) in CH$_2$Cl$_2$ (5 mL) was stirred for 16 h at room temperature. It was then extracted with 2×30 mL EtOAc, and the organic layers were combined and concentrated in vacuo. The residue was purified by silica gel column chromatography using EtOAc/hexane (1/1) to afford 96 mg (75%) of the title compound as an off-white solid.

Step 2. Synthesis of 4-[(3,4-difluorophenyl)methyl]-N-(5-hydroxypyridin-2-yl)piperazine-1-carboxamide

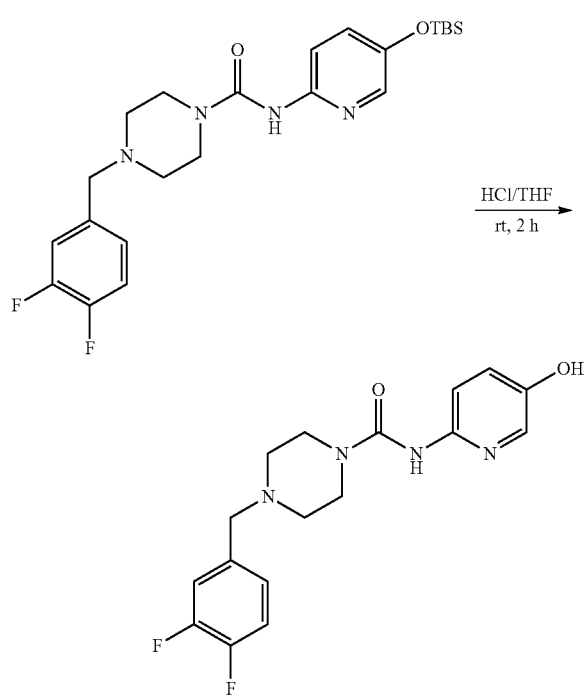

To a solution of the product from the previous step (96 mg, 0.21 mmol, 1.00 eq.) in THF (4 mL) was added 2N aq. HCl (2 mL) dropwise with stirring. The resulting solution was stirred for 2 h at room temperature, then concentrated in vacuo. The crude product (96 mg) was purified by Prep-HPLC with the following conditions: Instrument "A"; Column "D"; mobile phase, water (0.1% FA) and ACN (1.0% ACN up to 18.0% in 7 min); Detector, UV 254/220 nm, to afford 38.6 mg (53%) of the title compound as an off-white solid.

LC-MS: (ES, m/z): 349

$^1$H NMR (300 MHz, DMSO-d$_6$) δ 8.75 (s, 1H), 8.13 (s, 1H), 7.76 (d, J=2.9 Hz, 1H), 7.55 (d, J=8.9 Hz, 1H), 7.43-7.27 (m, 2H), 7.17-7.10 (m, 2H), 3.53-3.43 (m, 6H), 2.33 (m, 4H).

Example 78

4-(4-fluoropyridin-2-yl)-N-(5-hydroxypyridin-2-yl)piperazine-1-carboxamide

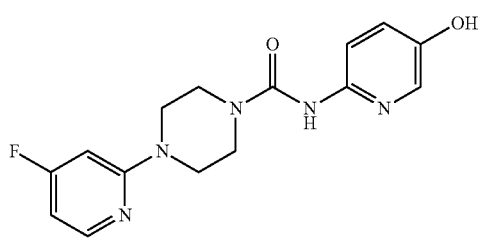 [SMILES: O=C(Nc1ccc(O)cn1)N1CCN(c2cc(F)ccn2)CC1]

Step 1. Synthesis of benzyl 4-(4-fluoropyridin-2-yl)piperazine-1-carboxylate

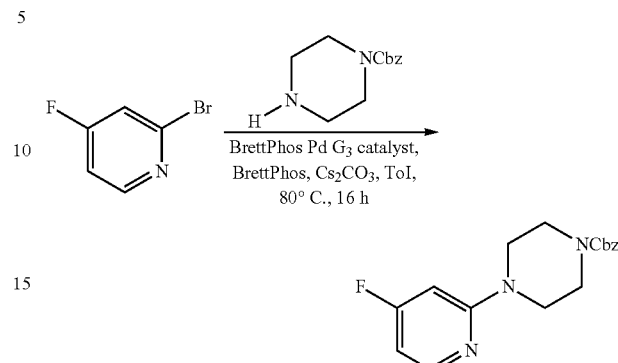

A mixture of 2-bromo-4-fluoropyridine (600 mg, 3.41 mmol, 1.00 eq.), benzyl piperazine-1-carboxylate (754 mg, 3.42 mmol, 1.00 eq.), Cs$_2$CO$_3$ (3.3 g, 3.00 eq.), Brettphos (18 mg, 0.01 eq.), Brettphos Pd G3 catalyst (31 mg, 0.01 eq.) in toluene (10 mL) was stirred in a 30 mL sealed tube for 16 h at 80° C. in an oil bath. The resulting mixture was cooled, diluted with water, and extracted with 2×30 mL EtOAc. The organic layers were combined and concentrated in vacuo. The residue was purified by silica gel column chromatography using EtOAc/hexane (1/1) to afford 110 mg (10%) of the title compound as an off-white solid. LC-MS: (ES, m/z): 316

Step 2. Synthesis of 1-(4-fluoropyridin-2-yl)piperazine

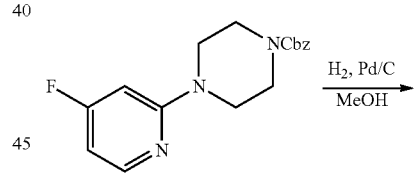

A solution of the product from the previous step (110 mg, 0.35 mmol, 1.00 eq.) in MeOH (5 mL) was stirred for 4 h under H$_2$ over Pd/C (10% on carbon, 11 mg) in a 100 mL round-bottom flask at room temperature. The solids were removed by filtration. The resulting solution was concentrated in vacuo, affording 60 mg (95%) of the title compound as an off-white solid. LC-MS: (ES, m/z): 182

Step 3. Synthesis of N-[5-[(tert-butyldimethylsilyl)oxy]pyridin-2-yl]-4-(4-fluoropyridin-2-yl)piperazine-1-carboxamide

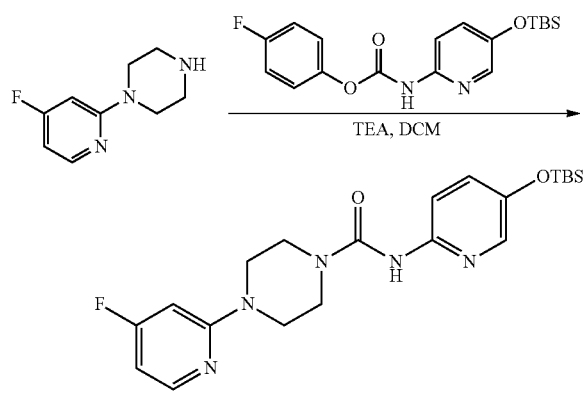

A solution of the product from the previous step (60 mg, 0.33 mmol, 1.20 eq.), TEA (84 mg, 0.83 mmol, 3.00 eq.) and 4-fluorophenyl N-5-[(tert-butyldimethylsilyl)-oxy]pyridin-2-ylcarbamate (100 mg, 0.28 mmol, 1.00 eq.) in CH$_2$Cl$_2$ (5 mL) was stirred for 16 h in a 40 mL vial at room temperature, then extracted with 2×30 mL EtOAc, and the organic layers were combined and concentrated in vacuo. The residue was purified by silica gel column chromatography using EtOAc/hexane (1/1), to afford 100 mg (84%) of the title compound as an off-white solid. LC-MS: (ES, m/z): 432

Step 4. Synthesis of 4-(4-fluoropyridin-2-yl)-N-(5-hydroxypyridin-2-yl)piperazine-1-carboxamide

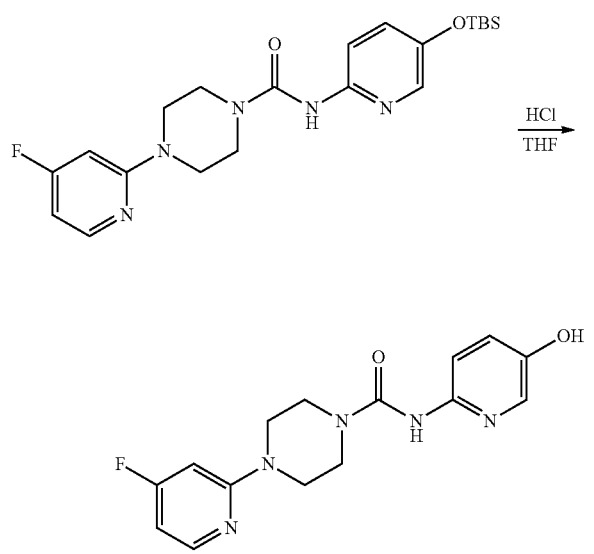

To a solution of the product from the previous step (100 mg, 0.23 mmol, 1.00 eq.) in THF (4 mL) in a 100 mL round-bottom flask was added 2 N HCl (2 mL) with stirring. The resulting solution was stirred for 2 h at room temperature, then concentrated in vacuo. The crude product (100 mg) was purified by Prep-HPLC with the following conditions: Instrument "A"; Column "A"; mobile phase, water (10 mM NH$_4$HCO$_3$) and ACN (15.0% ACN up to 39.0% in 8 min); Detector, UV 254/220 nm, to afford 24.1 mg (33%) of the title compound as an off-white solid.

LC-MS: (ES, m/z): 318

$^1$H NMR (300 MHz, DMSO-d$_6$) δ 9.42 (br, 1H), 8.89 (s, 1H), 8.10 (dd, J=9.8, 5.7 Hz, 1H), 7.77 (d, J=2.9 Hz, 1H), 7.58 (d, J=8.9 Hz, 1H), 7.12 (dd, J=8.9, 2.9 Hz, 1H), 6.71 (dd, J=13.2, 2.2 Hz, 1H), 6.53 (ddd, J=8.1, 5.7, 2.1 Hz, 1H), 3.56-3.53 (m, 8H).

Example 79

4-(3,5-difluoropyridin-2-yl)-N-(5-hydroxypyridin-2-yl) piperazine-1-carboxamide

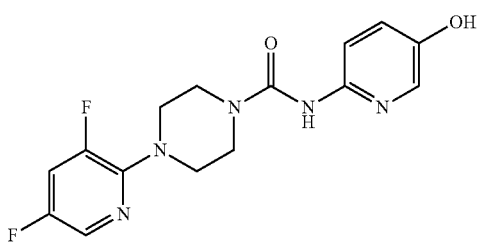

Step 1. Synthesis of tert-butyl 4-(3,5,6-trifluoropyridin-2-yl)piperazine-1-carboxylate

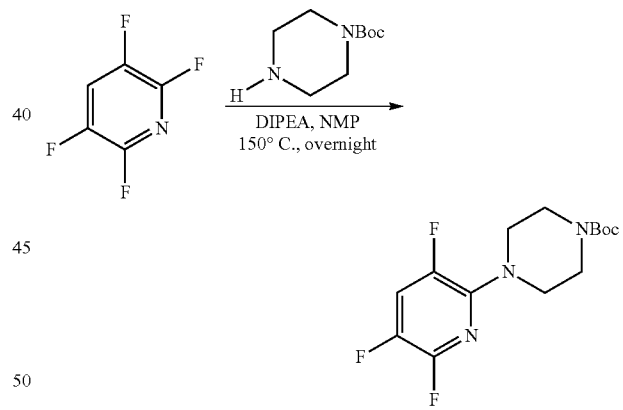

A solution of 2,3,5,6-tetrafluoropyridine (1.5 g, 9.93 mmol, 1.00 eq.), tert-butyl piperazine-1-carboxylate (1.0 g, 5.37 mmol, 0.54 eq.), and DIPEA (2 mL) in NMP (10 mL) was stirred overnight in a 40-mL sealed tube at 150° C. The reaction was then quenched by the addition of water. The resulting solution was extracted with EtOAc, and the organic layers were combined, washed with brine, concentrated in vacuo, and purified by silica gel column chromatography using EtOAc/petroleum ether (1:10) to afford 1.2 g (38%) of the title compound as a white solid.

LC-MS: (ES, m/z): 218.0

$^1$H NMR (400 MHz, DMSO-d$_6$) δ 8.20-8.08 (m, 1H), 3.44 (t, J=5.0 Hz, 4H), 3.35-3.28 (t, J=5.0 Hz, 4H), 1.42 (s, 9H).

Step 2. Synthesis of tert-butyl 4-(3,5-difluoropyridin-2-yl)piperazine-1-carboxylate

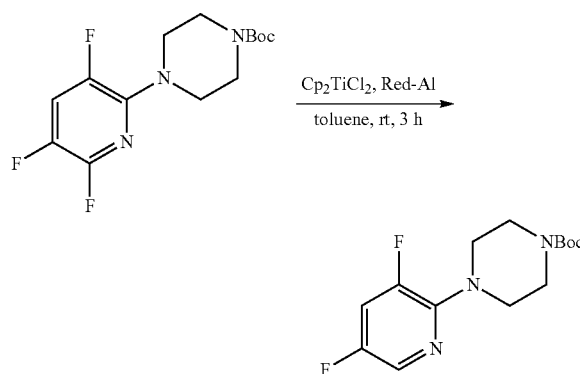

A solution of the product from the previous step (1.2 g, 3.78 mmol, 1.00 eq.), Cp$_2$TiCl$_2$ (100 mg, 0.40 mmol, 0.11 eq.), and RED-AL® in toluene (2.2 mL) in toluene (10 mL) was stirred in a 100-mL round-bottom flask overnight at room temperature, then quenched by the addition of water. The resulting solution was extracted with EtOAc, and the organic layers were combined and concentrated in vacuo. The residue was purified by silica gel column chromatography using EtOAc/petroleum ether (10:1), to afford 800 mg of the title compound as a yellow solid. LC-MS: (ES, m/z): 200.3

Step 3. Synthesis of 1-(3,5-difluoropyridin-2-yl)piperazine

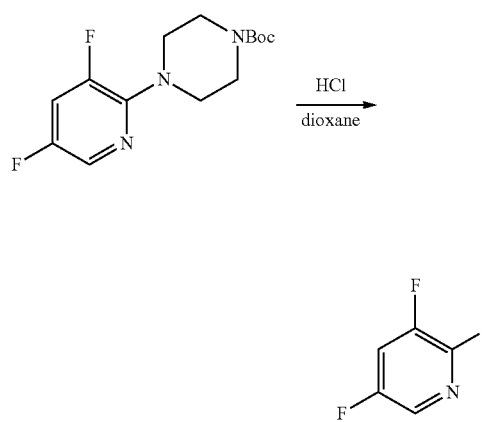

A solution of the product from the previous step (crude, 800 mg, 2.67 mmol, 1.00 eq.) in 4 N HCl/dioxane (10 mL) was stirred for 2 h at room temperature. The resulting mixture was concentrated in vacuo. The pH value of the solution was adjusted to pH 8-9 with NaHCO$_3$ solution. The resulting solution was extracted with CH$_2$Cl$_2$, and the organic layers were combined. The solvent was removed to afford 300 mg of the title compound as a yellow oil. LC-MS: (ES, m/z): 200.0

Step 4. Synthesis of N-[5-[(tert-butyldimethylsilyl)oxy]pyridin-2-yl]-4-(3,5-difluoropyridin-2-yl)piperazine-1-carboxamide

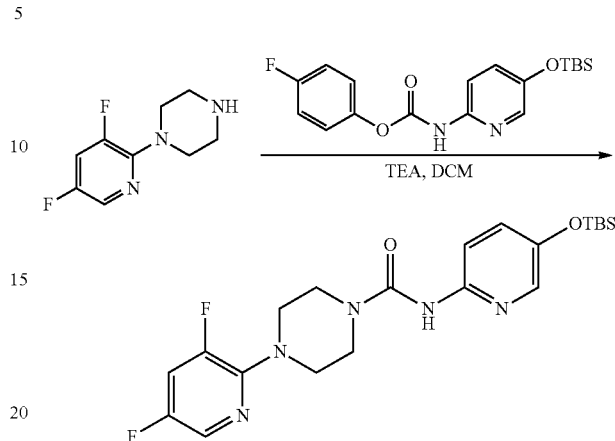

A solution of the product from the previous step (150 mg, 0.75 mmol, 1.82 eq.), 4-fluorophenyl N-[5-[(tert-butyldimethylsilyl)oxy]pyridin-2-yl]carbamate (150 mg, 0.41 mmol, 1.00 eq.), and Et$_3$N (300 mg, 2.97 mmol, 7.18 eq.) in CH$_2$Cl$_2$ (10 mL) was stirred overnight at room temperature. The reaction was then quenched by the addition of water. The resulting solution was extracted with CH$_2$Cl$_2$, and the organic layers were combined and concentrated in vacuo. The residue was purified by silica gel column chromatography using EtOAc/petroleum ether (1:6) to afford 80 mg (43%) of the title compound as a yellow solid. LC-MS: (ES, m/z): 450.1

Step 5. Synthesis of 4-(3,5-difluoropyridin-2-yl)-N-(5-hydroxypyridin-2-yl) piperazine-1-carboxamide

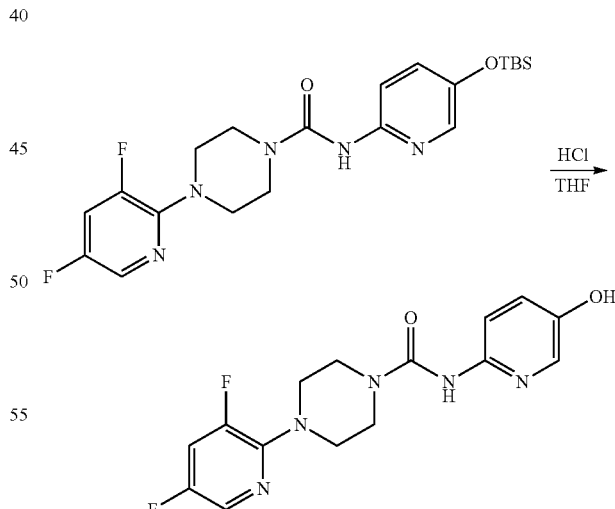

A solution of the product from the previous step (80 mg, 0.18 mmol, 1.00 eq.) in 2 N aq. HCl (2 mL) and THF (5 mL) was stirred for 2 h at room temperature, then concentrated in vacuo. The crude product (100 mg) was purified by Prep-HPLC with the following conditions: Instrument "A"; Column "B"; mobile phase, water (10 mM NH$_4$HCO$_3$+0.1% NH$_3$·H$_2$O) and ACN (30.0% ACN up to 60.0% in 8 min);

Detector, UV 254/220 nm, to afford 28.1 mg (47%) of the title compound as a white solid.

LC-MS: (ES, m/z): 336.3

$^1$H NMR (400 MHz, DMSO-$d_6$) δ 9.37 (br, 1H), 8.90 (s, 1H), 8.13 (d, J=2.5 Hz, 1H), 7.89-7.77 (m, 2H), 7.60 (d, J=8.9 Hz, 1H), 7.14 (dd, J=8.9, 3.0 Hz, 1H), 3.63-3.55 (m, 4H), 3.35-3.27 (m, 4H).

Example 80

N-(5-hydroxypyridin-2-yl)-4-(1-phenyl-1H-pyrazol-4-yl)piperazine-1-carboxamide

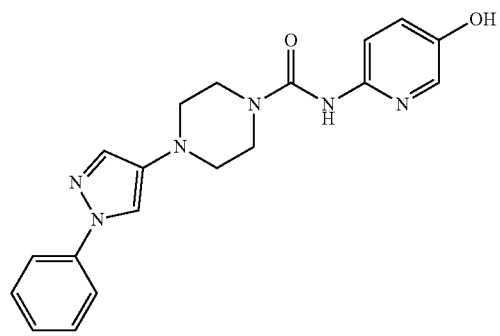 [SMILES: O=C(Nc1ccc(O)cn1)N1CCN(c2cnn(-c3ccccc3)c2)CC1]

Step 1. Synthesis of tert-butyl 4-(1-phenyl-1H-pyrazol-4-yl) piperazine-1-carboxylate

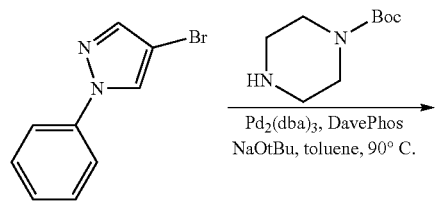

A solution of 4-bromo-1-phenyl-1H-pyrazole (500 mg, 2.24 mmol, 1.00 eq.), tert-butyl piperazine-1-carboxylate (419 mg, 2.25 mmol, 1.00 eq.), NaOtBu (324 mg, 1.50 eq.), DavePhos (45 mg, 0.05 eq.), and Pd$_2$(dba)$_3$ (105 mg, 0.11 mmol, 0.05 eq.) in toluene (10 mL) was stirred in a 30-mL sealed tube under N$_2$ for 16 h at 90° C. in an oil bath. The resulting solution was extracted with 2×30 mL EtOAc, and the organic layers were combined and concentrated in vacuo. The residue was purified by silica gel column chromatography using EtOAc/petroleum ether (1/1) to afford 600 mg (82%) of the title compound as an off-white solid. LC-MS: (ES, m/z): 329.1

Step 2. Synthesis of 1-(1-phenyl-1H-pyrazol-4-yl)piperazine

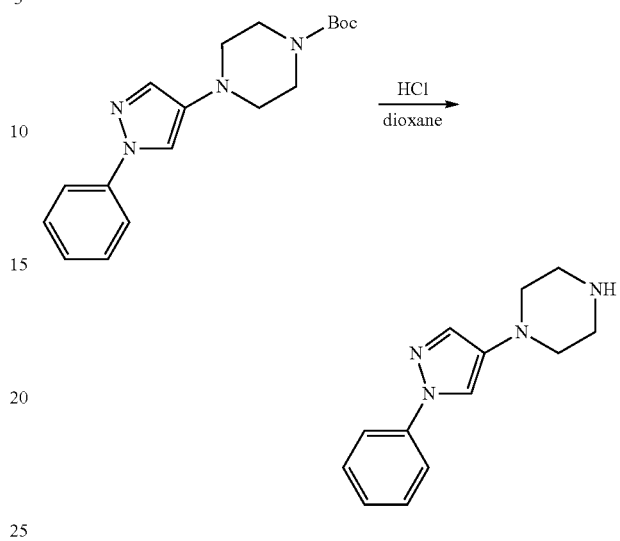

To a solution of the product from the previous step (600 mg, 1.83 mmol, 1.00 eq.) in dioxane (6 mL) was added a solution of 2 N aq. HCl (3 mL) dropwise with stirring. The resulting solution was stirred for 4 h at room temperature. The pH value of the solution was adjusted to 7 with NaHCO$_3$ (2 M). The resulting solution was extracted with 2×30 mL EtOAc, and the combined organic layers were combined and concentrated in vacuo, to afford 110 mg (26%) of the title compound as an off-white solid. LC-MS: (ES, m/z): 229.00

Step 3. Synthesis of N-[5-[(tert-butyldimethylsilyl)oxy]pyridin-2-yl]-4-(1-phenyl-1H-pyrazol-4-yl)piperazine-1-carboxamide

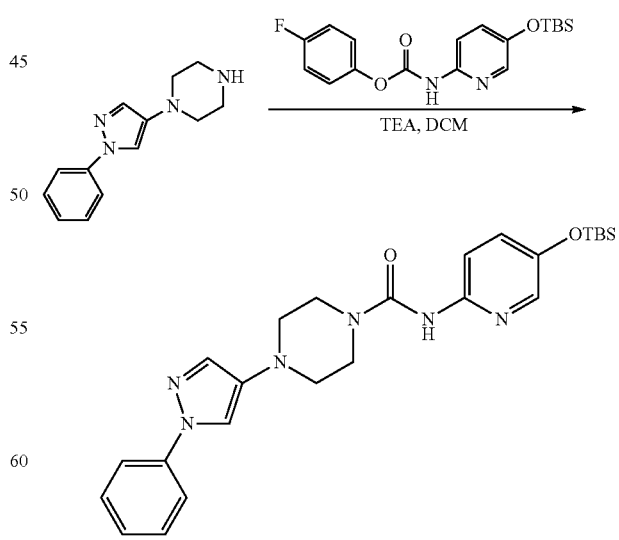

A solution of the product from the previous step (100 mg, 0.44 mmol, 1.50 eq.), 4-fluorophenyl N-5-[(tert-butyldimethylsilyl)oxy]pyridin-2-ylcarbamate (100 mg, 0.28 mmol, 1.00 eq.), and TEA (84 mg, 0.83 mmol, 3.00 eq.) in CH$_2$Cl$_2$ (5 mL) was stirred for 16 h at room temperature. The resulting solution was extracted with 2×20 mL of CH$_2$Cl$_2$, and the organic layers were combined and concentrated in vacuo. The residue was purified by silica gel column chromatography using EtOAc/hexane (1/1) to afford 110 mg (83%) of the title compound as an off-white solid. LC-MS (ES, m/z): 479.10

Step 4. Synthesis of N-(5-hydroxypyridin-2-yl)-4-(1-phenyl-1H-pyrazol-4-yl)piperazine-1-carboxamide

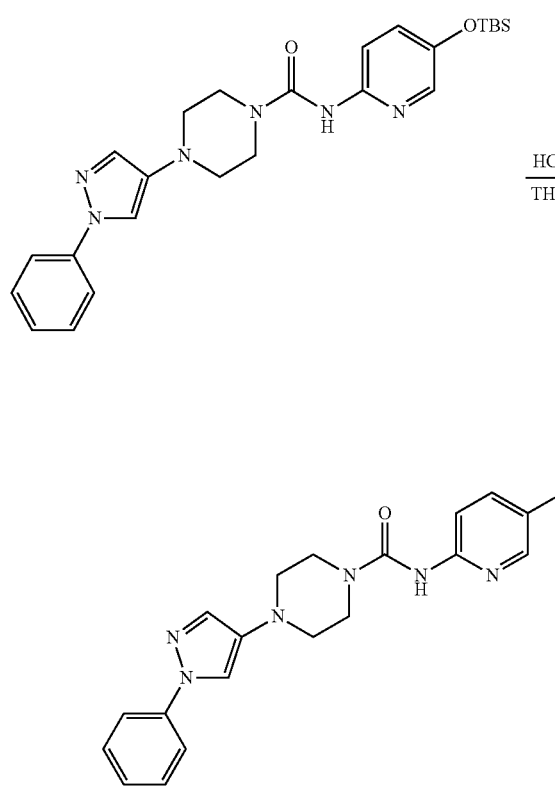

To a solution of the product from the previous step (110 mg, 0.23 mmol, 1.00 eq.) in THF (4 mL) was added 2 N aq HCl (2 mL) dropwise with stirring. The resulting solution was stirred for 2 h at room temperature, then concentrated in vacuo. The crude product (110 mg) was purified by Prep-HPLC with the following conditions: Instrument "A"; Column "A"; mobile phase, water (10 mM NH$_4$HCO$_3$) and ACN (20.0% ACN up to 49.0% in 8 min); Detector, UV 254/220 nm, to afford 58.3 mg (70%) of the title compound as an off-white solid.

LC-MS: (ES, m/z): 365.3

$^1$H NMR (300 MHz, DMSO-d$_6$) δ 9.43 (br, 1H), 8.91 (s, 1H), 8.08 (s, 1H), 7.82-7.70 (m, 3H), 7.63-7.53 (m, 2H), 7.43 (t, J=7.9 Hz, 2H), 7.21 (t, J=7.4 Hz, 1H), 7.12 (dd, J=8.9, 3.0 Hz, 1H), 3.58 (m, 4H), 2.95 (m, 4H).

Example 81

N-(5-hydroxypyridin-2-yl)-4-(1-methyl-1H-indazol-4-yl)piperazine-1-carboxamide

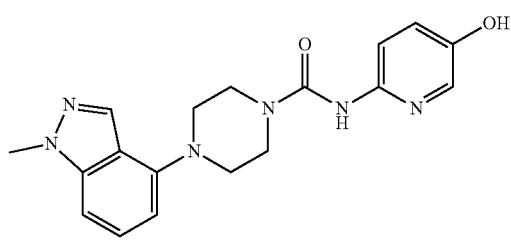 [SMILES: Cn1ncc2c(N3CCN(C(=O)Nc4ccc(O)cn4)CC3)cccc21]

Step 1. Synthesis of tert-butyl 4-(1-methyl-1H-indazol-4-yl)piperazine-1-carboxylate

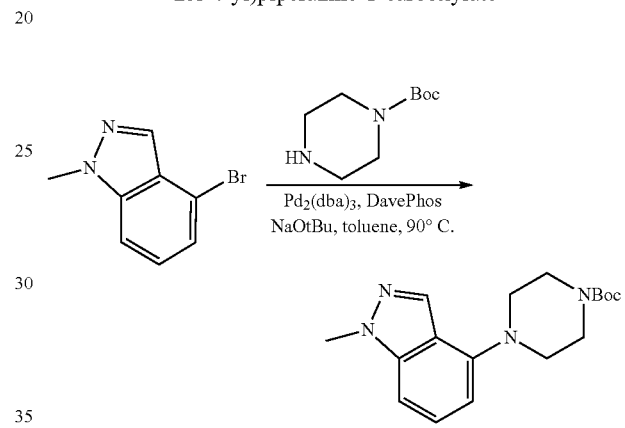

A solution of 4-bromo-1-methyl-1H-indazole (500 mg, 2.37 mmol, 1.00 eq.), tert-butyl piperazine-1-carboxylate (443 mg, 2.38 mmol, 1.00 eq.), NaOtBu (343 mg, 1.50 eq.), DavePhos (9 mg, 0.01 eq.), and Pd$_2$(dba)$_3$ (22 mg, 0.02 mmol, 0.01 eq.) in toluene (10 mL) was stirred for 16 h in a 30-mL sealed tube under N$_2$ at 90° C. in an oil bath. The resulting solution was cooled, water was added, and the mixture was extracted with 2×30 mL EtOAc. The combined organic layers were concentrated in vacuo and purified by silica gel column chromatography using EtOAc/hexane (1/1) to afford 500 mg (67%) of the title compound as an off-white solid. LC-MS: (ES, m/z): 317

Step 2. Synthesis of 1-methyl-4-(piperazin-1-yl)-1H-indazole

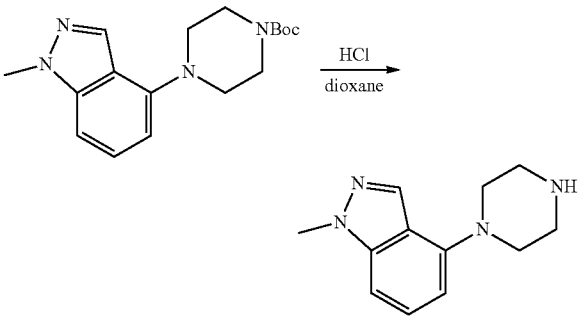

To a solution of the product from the previous step (500 mg, 1.58 mmol, 1.00 eq.) in dioxane (10 mL) was added 4 N HCl/dioxane (5 mL) dropwise with stirring. The resulting solution was stirred for 4 h at room temperature. The pH value of the solution was adjusted to pH 7 with NaHCO₃ solution. The resulting solution was extracted with 2×30 mL of CH₂Cl₂, and the organic layers were combined and concentrated in vacuo to afford 300 mg (88%) of the title compound as an off-white solid. LC-MS: (ES, m/z): 217

Step 3. Synthesis of N-[5-[(tert-butyldimethylsilyl)oxy]pyridin-2-yl]-4-(1-methyl-1H-indazol-4-yl)piperazine-1-carboxamide

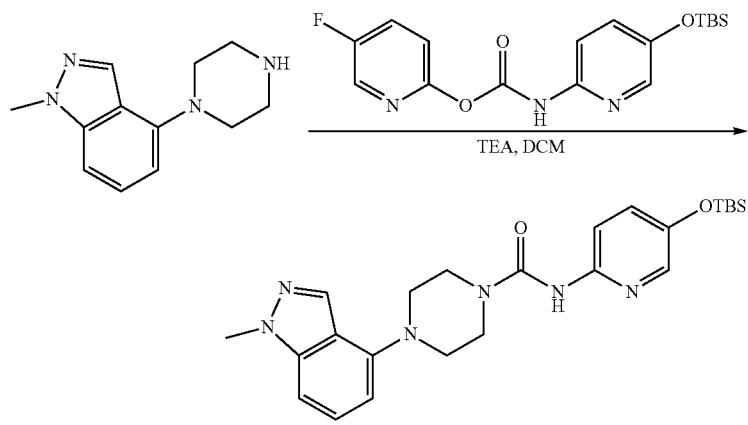

A solution of the product from the previous step (60 mg, 0.28 mmol, 1.00 eq.), 5-fluoropyridin-2-yl N-5-[(tert-butyldimethylsilyl)oxy]pyridin-2-ylcarbamate (100 mg, 0.28 mmol, 1.00 eq.), and TEA (84 mg, 0.83 mmol, 3.00 eq.), in CH₂Cl₂ (5 mL) was stirred for 16 h in a 40-mL vial at room temperature. To the resulting solution was added water, and the mixture was extracted with 2×30 mL of CH₂Cl₂. The organic layers were combined and concentrated in vacuo. The residue was purified by silica gel column chromatography using EtOAc/hexane (1/1) to afford 110 mg (85%) of the title compound as an off-white solid. LC-MS (ES, m/z): 467

Step 4. Synthesis of N-(5-hydroxypyridin-2-yl)-4-(1-methyl-1H-indazol-4-yl)piperazine-1-carboxamide

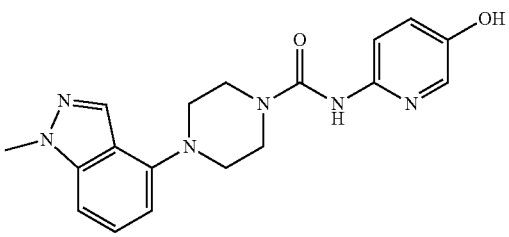

To a solution of the product from the previous step (110 mg, 0.24 mmol, 1.00 eq.) in THF (4 mL) was added 2 N aq. HCl (2 mL) dropwise with stirring. The resulting solution was stirred for 2 h at room temperature, then concentrated in vacuo. The crude product (110 mg) was purified by Prep-HPLC with the following conditions: Instrument "A"; Column "A"; mobile phase, water (10 mM NH₄HCO₃) and ACN (20.0% ACN up to 50.0% in 8 min); Detector, UV 254/220 nm, to afford 59.0 mg (71%) of the title compound as an off-white solid.

LC-MS: (ES, m/z): 353

¹H NMR (300 MHz, DMSO-d₆) δ 9.40 (s, 1H), 8.91 (s, 1H), 8.10 (d, J=0.9 Hz, 1H), 7.79 (d, J=2.9 Hz, 1H), 7.59 (d, J=8.9 Hz, 1H), 7.29-7.17 (m, 1H), 7.14-7.13 (m, 2H), 6.47 (d, J=7.4 Hz, 1H), 3.98 (s, 3H), 3.67 (m, 4H), 3.21 m, 4H).

Example 82

N-(5-hydroxypyridin-2-yl)-4-(1-methyl-1H-indazol-6-yl)piperazine-1-carboxamide

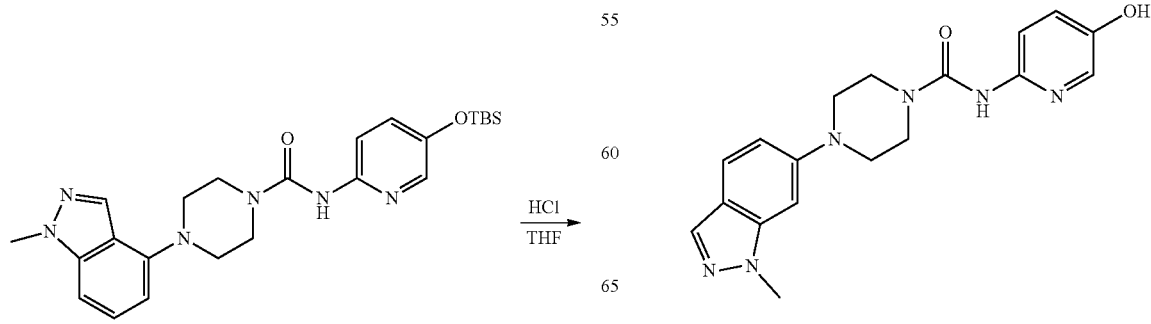

Step 1. Synthesis of tert-butyl 4-(1-methyl-1H-indazol-6-yl)piperazine-1-carboxylate

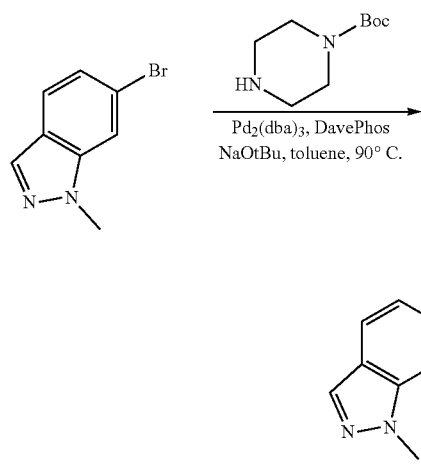

A solution of 6-bromo-1-methyl-1H-indazole (500 mg, 2.37 mmol, 1.00 eq.), tert-butyl piperazine-1-carboxylate (443 mg, 2.38 mmol, 1.00 eq.), NaOtBu (343 mg, 1.50 eq.), DavePhos (9 mg, 0.01 eq.), and Pd$_2$(dba)$_3$ (22 mg, 0.02 mmol, 0.01 eq.) in toluene (10 mL) was stirred for 16 h in a 30-mL sealed tube under N$_2$ at 90° C. in an oil bath. The resulting solution was extracted with 2×30 mL EtOAc, and the organic layers were combined and concentrated in vacuo. The residue was purified by silica gel column chromatography using EtOAc/hexane (1/1), to afford 600 mg (80%) of the title compound as white solid. LC-MS: (ES, m/z): 317

Step 2. Synthesis of 1-methyl-6-(piperazin-1-yl)-1H-indazole

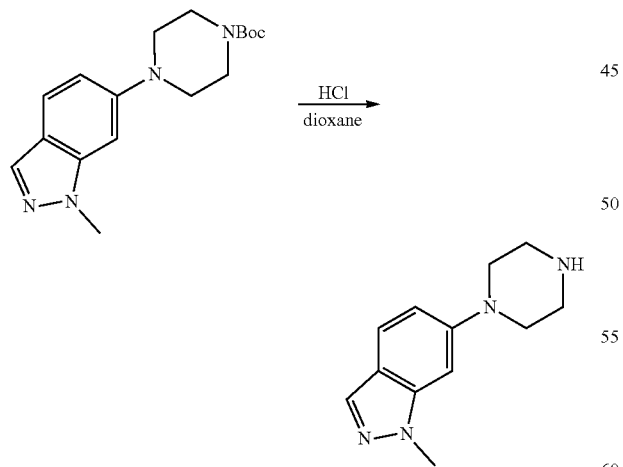

To a solution of the product from the previous step (600 mg, 1.90 mmol, 1.00 eq.) in dioxane (10 mL) was added 4 N HCl/dioxane (5 mL) with stirring. The resulting solution was stirred for 4 h at room temperature. The pH value of the solution was adjusted to pH 7 with NaHCO$_3$ solution. The resulting solution was extracted with 2×30 mL EtOAc, and the organic layers were combined and concentrated in vacuo, to afford 100 mg (24%) of the title compound as an off-white solid. LC-MS (ES, m/z): 217

Step 3. Synthesis of N-[5-[(tert-butyldimethylsilyl)oxy]pyridin-2-yl]-4-(1-methyl-1H-indazol-6-yl)piperazine-1-carboxamide

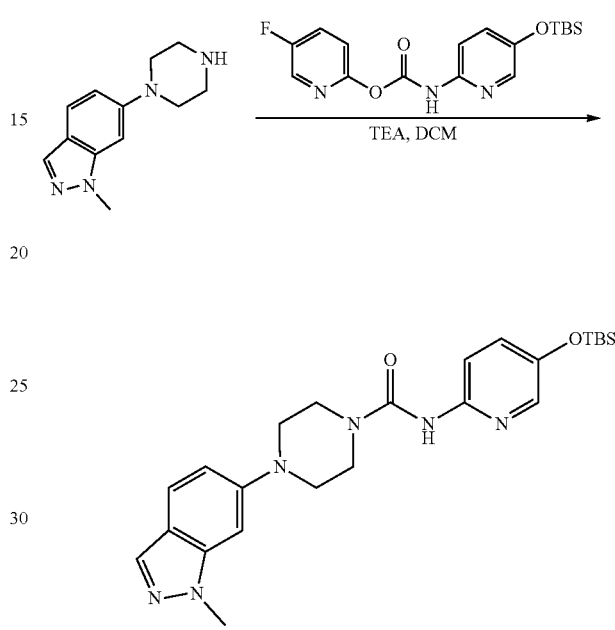

A solution of the product from the previous step (100 mg, 0.46 mmol, 1.00 eq.), 5-fluoropyridin-2-yl N-5-[(tert-butyldimethylsilyl)oxy]pyridin-2-ylcarbamate (100 mg, 0.28 mmol, 1.00 eq.), and TEA (84 mg, 0.83 mmol, 3.00 eq.), in CH$_2$Cl$_2$ (5 mL) was stirred for 16 h a 40-mL vial at room temperature. To the resulting solution was added water, and the mixture was extracted with 2×30 mL EtOAc. The combined organic layers were concentrated in vacuo. The residue was purified by silica gel column chromatography using EtOAc/hexane (1/2), to afford 105 mg (49%) of the title compound as an off-white solid. LC-MS (ES, m/z): 467

Step 4. Synthesis of N-(5-hydroxypyridin-2-yl)-4-(1-methyl-1H-indazol-6-yl)piperazine-1-carboxamide

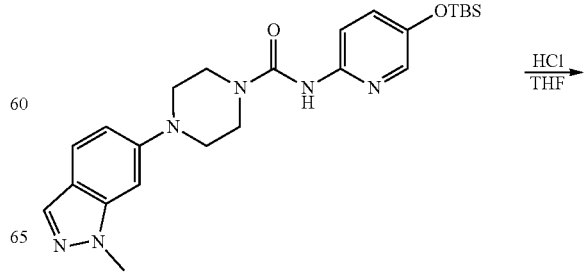

-continued

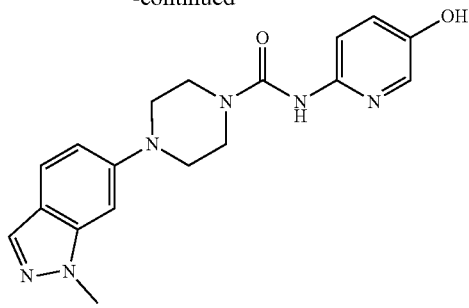

To a solution of the product from the previous step (105 mg, 0.23 mmol, 1.00 eq.) in THF (4 mL) was added 2 N aq. HCl (2 mL) dropwise with stirring. The resulting solution was stirred for 2 h at room temperature. The resulting mixture was concentrated in vacuo. The crude product (105 mg) was purified by Prep-HPLC with the following conditions: Instrument "A"; Column "A"; mobile phase, water (10 mM NH$_4$HCO$_3$) and ACN (10.0% ACN up to 45.0% in 8 min); Detector, UV 254/220 nm, to afford 56.9 mg (72%) of the title compound as an off-white solid.

LC-MS (ES, m/z): 353

$^1$H NMR (300 MHz, DMSO-d$_6$) δ 9.43 (s, 1H), 8.93 (s, 1H), 7.84-7.75 (m, 2H), 7.57 (m, 2H), 7.13 (m, 1H), 6.95 (m, 2H), 3.93 (s, 3H), 3.62 (m, 4H), 3.21 (m, 4H).

Example 83

N-(5-hydroxypyridin-2-yl)-4-(3,5,6-trifluoropyridin-2-yl) piperazine-1-carboxamide

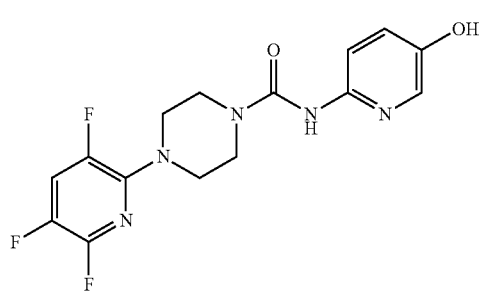 [SMILES: O=C(Nc1ccc(O)cn1)N1CCN(c2nc(F)c(F)cc2F)CC1]

Step 1. Synthesis of 4-(3,5,6-trfluoropyridin-2-yl)-N-(5-hydroxypyridin-2-yl) piperazine-1-carboxamide

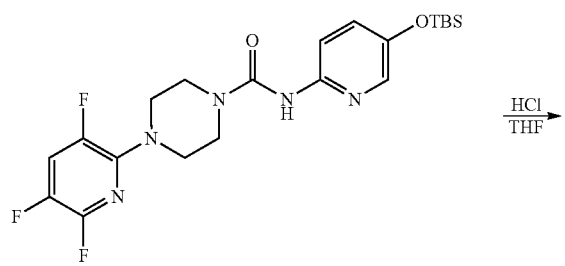

-continued

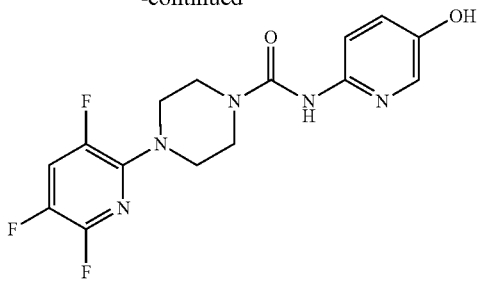

A solution of N-[5-[(tert-butyldimethylsilyl)oxy]pyridin-2-yl]-4-(3,5,6-trifluoro-pyridin-2-yl)piperazine-1-carboxamide (prepared analogously to the synthesis of Example 79; 100 mg, 0.21 mmol, 1.00 eq.) in 2 N aq. HCl (2 mL) and THF (5 mL) was stirred for 2 h at room temperature. The resulting mixture was concentrated in vacuo. The crude product (120 mg) was purified by Prep-HPLC under the following conditions: Instrument "A"; Column "B"; mobile phase, water (10 mM NH$_4$HCO$_3$+0.1% NH$_3$·H$_2$O) and ACN (30.0% ACN up to 60.0% in 8 min); Detector, UV 254/220 nm, to afford 48.7 mg (64%) of the title compound as a white solid.

LC-MS (ES, m/z): 353.9

$^1$H NMR (300 MHz, Methanol-d$_4$) δ 7.84 (d, J=2.9 Hz, 1H), 7.70 (dt, J=11.0, 7.8 Hz, 1H), 7.53 (d, J=8.9 Hz, 1H), 7.22 (dd, J=8.9, 2.9 Hz, 1H), 3.68 (m, 4H), 3.49 (m, 4H).

Example 84

4-(5-fluoropyridin-2-yl)-N-(5-hydroxypyridin-2-yl)-1,4-diazepane-1-carboxamide

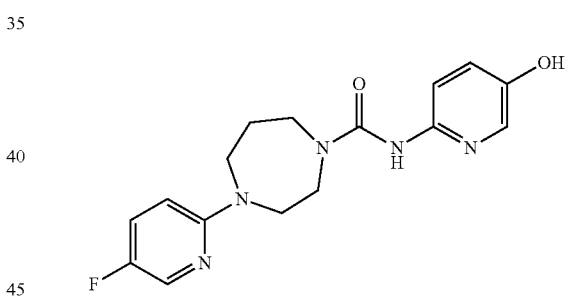

Step 1. Synthesis of tert-butyl 4-(5-fluoropyridin-2-yl)-1,4-diazepane-1-carboxylate

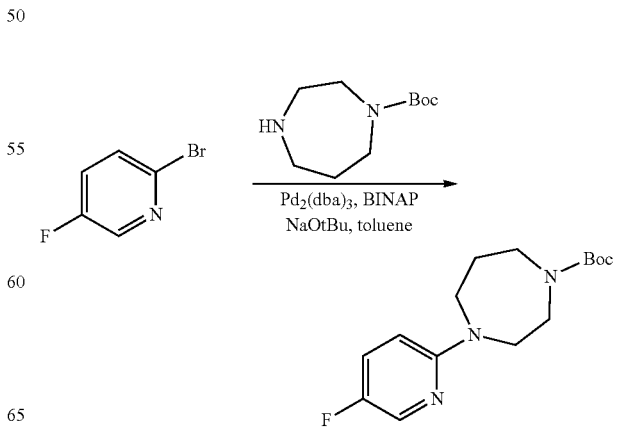

A solution of 2-bromo-5-fluoropyridine (1 g, 5.68 mmol, 1.14 eq.), tert-butyl 1,4-diazepane-1-carboxylate (1 g, 4.99 mmol, 1.00 eq.), Pd$_2$(dba)$_3$ (46 mg, 0.05 mmol, 0.01 eq.), BINAP (31 mg, 0.05 mmol, 0.01 eq.), NaOtBu (2 g, 20.83 mmol, 4.17 eq.) in toluene (10 mL) was stirred overnight at 90° C. in a 30-mL sealed tube. The reaction was then quenched by the addition of water. The resulting solution was extracted with EtOAc, and the organic layers were combined and concentrated in vacuo. The residue was purified by silica gel chromatography using EtOAc/petroleum ether (1:6) to afford 1.1 g (75%) of the title compound as a yellow oil.

LC-MS: (ES, m/z): 296.3

$^1$H NMR (300 MHz, DMSO-d$_6$) δ 8.05-7.96 (m, 1H), 7.42 (tt, J=8.8, 2.8 Hz, 1H), 6.66 (dd, J=9.3, 3.3 Hz, 1H), 3.67 (q, J=6.5 Hz, 2H), 3.57 (t, J=6.0 Hz, 2H), 3.46 (dt, J=17.2, 5.7 Hz, 2H), 3.20 (dt, J=20.5, 5.9 Hz, 2H), 1.75 (dt, J=21.8, 5.9 Hz, 2H), 1.29-1.21 (m, 9H).

Step 2. Synthesis of 1-(5-fluoropyridin-2-yl)-1,4-diazepane

A solution of the product from the previous step (1.1 g, 3.72 mmol, 1.00 eq.) in 4 N HCl/dioxane (5 mL) was stirred for 2 h in a 50-mL round-bottom flask at room temperature. The resulting mixture was concentrated in vacuo. The pH was adjusted to pH 8-9 with NaHCO$_3$ solution. The resulting solution was extracted with CH$_2$Cl$_2$, and the organic layers were combined. The solvent was removed to afford 480 mg (66%) of the title compound as a yellow oil. LC-MS: (ES, m/z): 196.2

Step 3. Synthesis of N-[5-[(tert-butyldimethylsilyl)oxy]pyridin-2-yl]-4-(5-fluoropyridin-2-yl)-1,4-diazepane-1-carboxamide

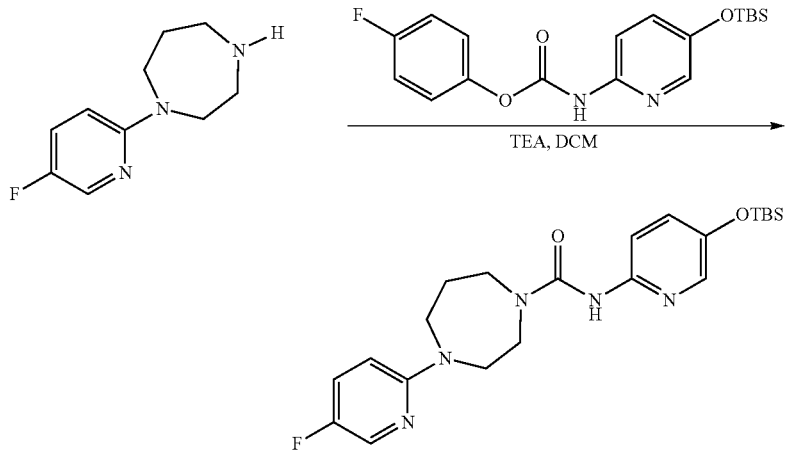

A solution of the product from the previous step (65 mg, 0.33 mmol, 1.21 eq.), 4-fluorophenyl N-5-[(tert-butyldimethylsilyl)oxy]pyridin-2-ylcarbamate (100 mg, 0.28 mmol, 1.00 eq.), and Et$_3$N (200 mg, 1.98 mmol, 7.18 eq.) in CH$_2$Cl$_2$ (10 mL) was stirred overnight in a 50-mL round-bottom flask at room temperature. The reaction was then quenched by the addition of water. The resulting solution was extracted with CH$_2$Cl$_2$, and the organic layers were combined and concentrated in vacuo, to afford 110 mg (89%) of the title compound as a white solid. LC-MS: (ES, m/z): 446.2

Step 4. Synthesis of 4-(5-fluoropyridin-2-yl)-N-(5-hydroxypyridin-2-yl)-1,4-diazepane-1-carboxamide

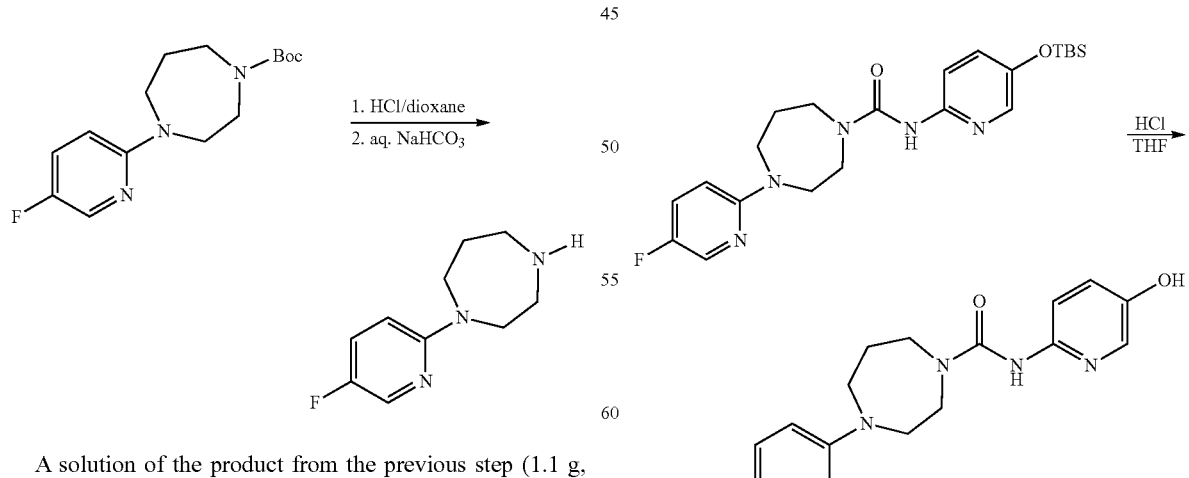

A solution of the product from the previous step (110 mg, 0.25 mmol, 1.00 eq.) in 2 N HCl (2 mL) and THF (5 mL)

was stirred in a 50-mL round-bottom flask for 2 h at room temperature. The resulting mixture was concentrated in vacuo. The crude product was purified by Prep-HPLC with the following conditions: Instrument "A"; Column "D"; mobile phase, water (0.1% FA) and ACN (2.0% ACN up to 25.0% in 7 min); Detector, UV 254/220 nm, to afford 42.4 mg (52%) of the title compound as a white solid.

LC-MS (ES, m/z): 332.3

$^1$H NMR (300 MHz, DMSO-$d_6$) δ 9.38 (s, 1H), 8.48 (s, 1H), 7.99 (d, J=3.1 Hz, 1H), 7.75 (d, J=2.9 Hz, 1H), 7.53-7.34 (m, 2H), 7.08 (dd, J=8.9, 3.0 Hz, 1H), 6.68 (dd, J=9.4, 3.4 Hz, 1H), 3.70 (m, 2H), 3.59 (m, 4H), 3.38 (m, 2H), 1.83 (m, 2H).

Example 85

4-(5-chloropyridin-2-yl)-N-(5-hydroxypyridin-2-yl)-1,4-diazepane-1-carboxamide

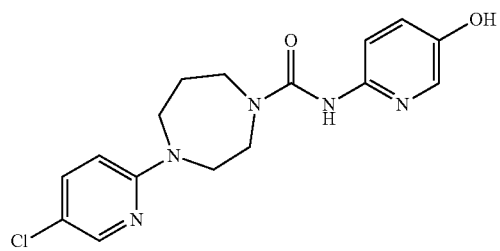 [SMILES: O=C(Nc1ccc(O)cn1)N1CCCN(c2ccc(Cl)cn2)CC1]

Step 1. Synthesis of tert-butyl 4-(5-chloropyridin-2-yl)-1,4-diazepane-1-carboxylate

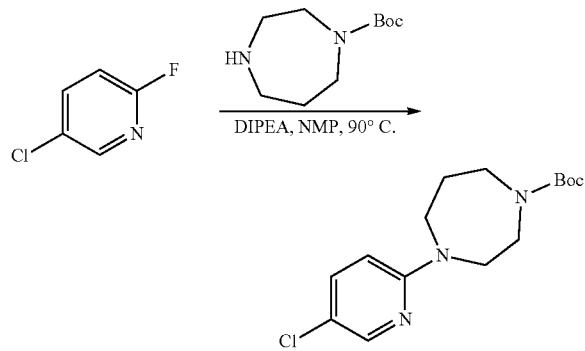

A solution of 5-chloro-2-fluoropyridine (1.31 g, 9.96 mmol, 1.00 eq.), tert-butyl 1,4-diazepane-1-carboxylate (2 g, 9.99 mmol, 1.00 eq.), and DIPEA (2 mL) in NMP (5 mL) was stirred overnight at 90° C. in a 30-mL sealed tube. The reaction was then quenched by the addition of water. The resulting solution was extracted with EtOAc, and the organic layers were combined. The resulting mixture was concentrated in vacuo. The residue was purified by silica gel column chromatography using EtOAc/petroleum ether (1:6) to afford 1.4 g (45%) of the title compound as a white solid.

LC-MS (ES, m/z): 312.0

$^1$H NMR (300 MHz, DMSO-$d_6$) δ 8.03 (d, J=2.8 Hz, 1H), 7.51 (dt, J=9.1, 2.1 Hz, 1H), 6.69 (dd, J=9.1, 0.7 Hz, 1H), 3.75-3.62 (m, 2H), 3.58 (t, J=6.0 Hz, 2H), 3.46 (dt, J=17.9, 5.8 Hz, 2H), 3.33-3.12 (m, 2H), 1.74 (dt, J=16.8, 5.7 Hz, 2H), 1.25 (d, J=23.5 Hz, 9H).

Step 2. Synthesis of 1-(5-chloropyridin-2-yl)-1,4-diazepane

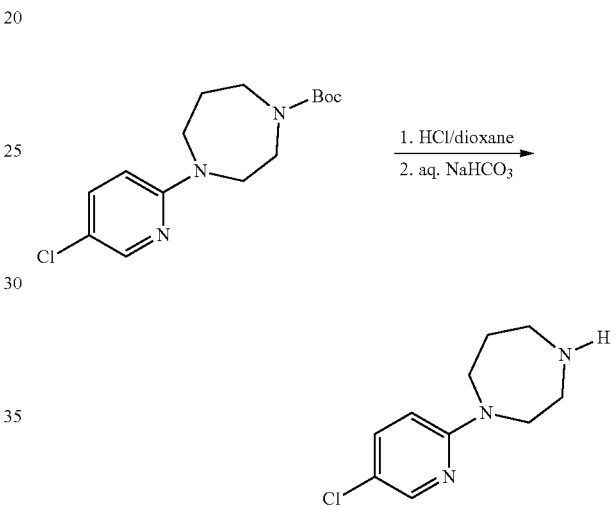

A solution of the product from the previous step (1.4 g, 4.49 mmol, 1.00 eq.) in 4 N HCl/dioxane (10 mL) was stirred in a 50-mL round-bottom flask for 2 h at room temperature. The resulting mixture was concentrated in vacuo. The pH value of the solution was adjusted to pH 8-9 with NaHCO$_3$ solution. The resulting mixture was extracted with CH$_2$Cl$_2$, and the organic layers were combined. The solvent was removed to afford 850 mg (89%) of the title compound as a yellow oil. LC-MS: (ES, m/z): 212.0

Step 3. Synthesis of N-[5-[(tert-butyldimethylsilyl)oxy]pyridin-2-yl]-4-(5-chloropyridin-2-yl)-1,4-diazepane-1-carboxamide

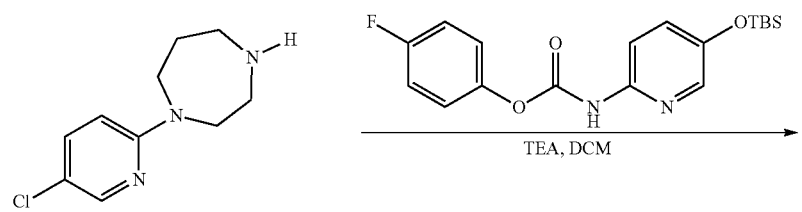

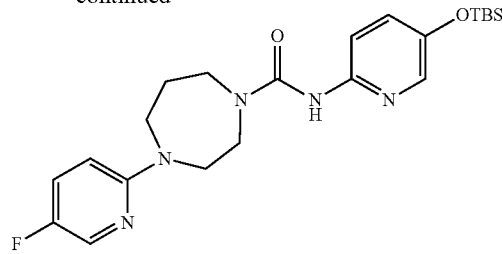

A solution of the product from the previous step (70 mg, 0.33 mmol, 1.20 eq.), 4-fluorophenyl N-5-[(tert-butyldimethylsilyl)oxy]pyridin-2-ylcarbamate (100 mg, 0.28 mmol, 1.00 eq.), and Et₃N (200 mg, 1.98 mmol, 7.18 eq.) in CH₂Cl₂ (10 mL) was stirred overnight in a 50-mL round-bottom flask at room temperature. The reaction was then quenched by the addition of water. The resulting solution was extracted with CH₂Cl₂, and the organic layers were combined and concentrated in vacuo, affording 100 mg (78%) of the title compound as a white solid. LC-MS (ES, m/z): 462.2

Step 4. Synthesis of 4-(5-chloropyridin-2-yl)-N-(5-hydroxypyridin-2-yl)-1,4-diazepane-1-carboxamide

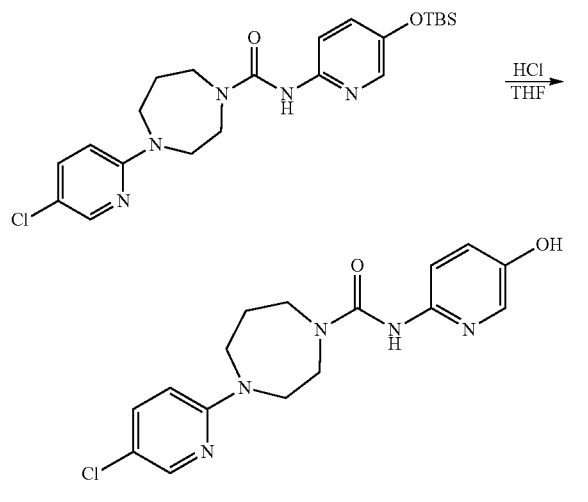

A solution of the product from the previous step (100 mg, 0.22 mmol, 1.00 eq.) in 2 N HCl (2 mL) and THF (5 mL) was stirred in a 50-mL round-bottom flask for 2 h at room temperature. The resulting mixture was concentrated in vacuo. The crude product was purified by Prep-HPLC with the following conditions: Instrument "A"; Column "D"; mobile phase, water (0.1% FA) and ACN (2.0% ACN up to 35.0% in 7 min); Detector, UV 254/220 nm, to afford 26.1 mg (35%) of the title compound as a white solid.

LC-MS: (ES, m/z): 348.3

¹H NMR (300 MHz, DMSO-d₆) δ 9.38 (s, 1H), 8.49 (s, 1H), 8.01 (d, J=2.7 Hz, 1H), 7.75 (d, J=2.9 Hz, 1H), 7.55-7.42 (m, 2H), 7.08 (dd, J=8.9, 3.0 Hz, 1H), 6.70 (d, J=9.2 Hz, 1H), 3.72 (m, 2H), 3.60 (m, 4H), 3.39 (m, 2H), 1.82 (m, 2H).

Example 86

N-(5-hydroxypyridin-2-yl)-4-[5-(trifluoromethyl)pyridin-2-yl]-1,4-diazepane-1-carboxamide

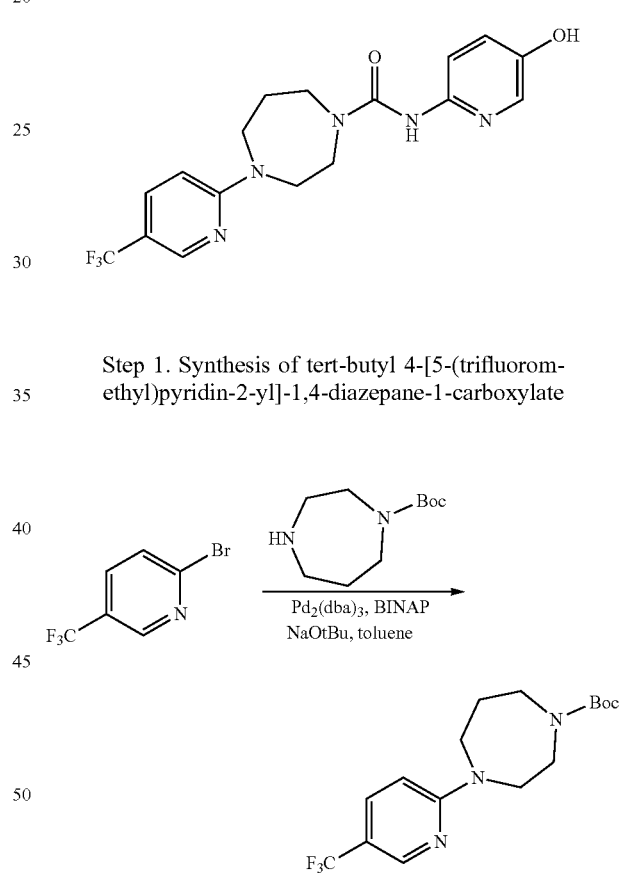

Step 1. Synthesis of tert-butyl 4-[5-(trifluoromethyl)pyridin-2-yl]-1,4-diazepane-1-carboxylate A solution of 2-bromo-5-(trifluoromethyl)pyridine (1 g, 4.42 mmol, 1.00 eq.), tert-butyl 1,4-diazepane-1-carboxylate (1.1 g, 5.49 mmol, 1.20 eq.) NaOtBu (1.28 g, 3.00 eq.), BINAP (140 mg, 0.22 mmol, 0.05 eq.), and Pd₂(dba)₃ (200 mg, 0.22 mmol, 0.05 eq.) in toluene (20 mL) was stirred in a 30-mL sealed tube under N₂ for 16 h at 90° C. in an oil bath. The reaction mixture was then diluted with water and extracted with 2×50 mL EtOAc. The combined organic layers were dried over Na₂SO₄ and concentrated in vacuo. The residue was purified by silica gel chromatography using EtOAc/hexane (1/1) to afford 1.2 g (79%) of the title compound as an off-white solid. LC-MS: (ES, m/z): 346.15.

Step 2. Synthesis of 1-[5-(trifluoromethyl)pyridin-2-yl]-1,4-diazepane

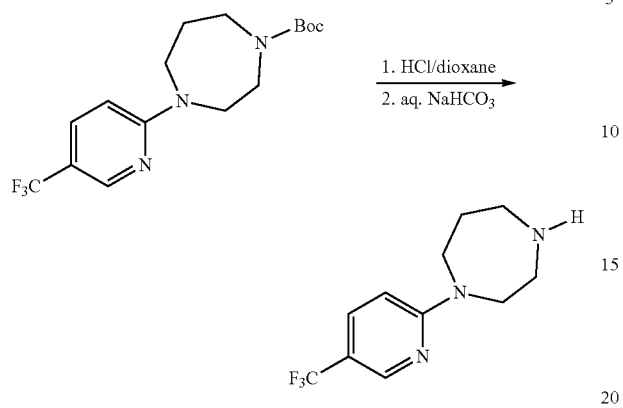

To a solution of the product from the previous step (1.2 g, 3.47 mmol, 1.00 eq.) in dioxane (10 mL) in a 250-mL round-bottom flask was added 4 N HCl/dioxane (5 mL) dropwise with stirring. The resulting solution was stirred for 4 h at room temperature. The pH value of the solution was adjusted to 7 with NaHCO$_3$ (2 mol/L). The resulting mixture was extracted with 2×50 mL EtOAc. The combined organic layers were dried over Na$_2$SO$_4$ and concentrated in vacuo. The residue was purified with silica gel chromatography using EtOAc/hexane (1/1) to afford 0.8 g (94%) of the title compound as an off-white solid. LC-MS: (ES, m/z): 246.20.

Step 3. Synthesis of N-[5-[(tert-butyldimethylsilyl)oxy]pyridin-2-yl]-4-[5-(trifluoromethyl)pyridin-2-yl]-1,4-diazepane-1-carboxamide

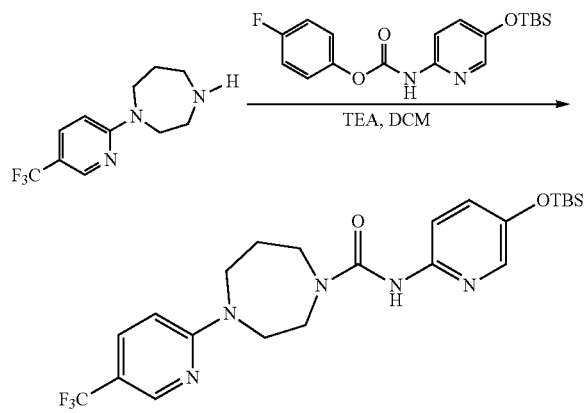

A solution of the product from the previous step (81 mg, 0.33 mmol, 1.20 eq.), 4-fluorophenyl N-5-[(tert-butyldimethylsilyl)oxy]pyridin-2-ylcarbamate (100 mg, 0.28 mmol, 1.00 eq.), and TEA (84 mg, 0.83 mmol, 3.00 eq.) in CH$_2$Cl$_2$ (5 mL) was stirred in a 40-mL vial for 16 h at room temperature. The resulting solution was diluted with water and extracted with 2×20 mL of CH$_2$Cl$_2$. The combined organic layers were dried over Na$_2$SO$_4$ and concentrated in vacuo. The residue was purified by silica gel column chromatography using EtOAc/hexane (1/1) to afford 100 mg (73%) of the title compound as an off-white solid. LC-MS: (ES, m/z): 496.05.

Step 4. Synthesis of N-(5-hydroxypyridin-2-yl)-4-[5-(trifluoromethyl)pyridin-2-yl]-1,4-diazepane-1-carboxamide

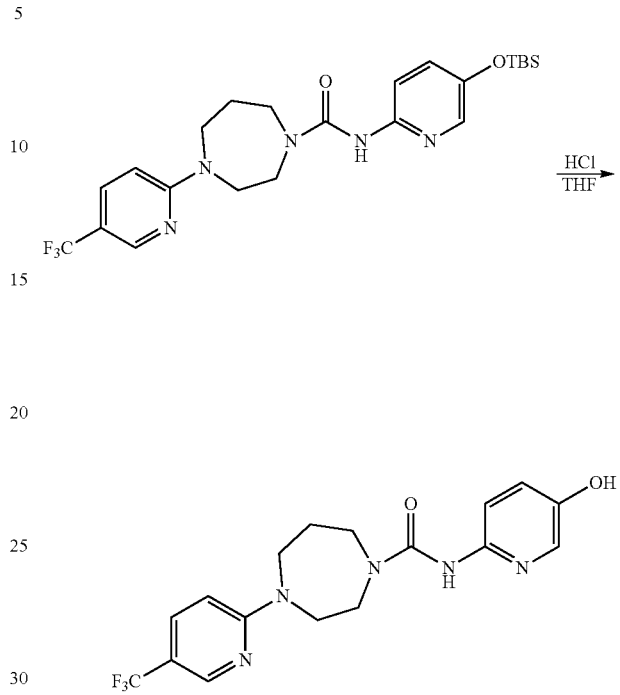

To a solution of the product from the previous step (100 mg, 0.20 mmol, 1.00 eq.) in THF (4 mL) in a 100-mL round-bottom flask was added 2 M HCl (2 mL) dropwise with stirring. The resulting solution was stirred for 2 h at room temperature. This was concentrated in vacuo. The crude product (100 mg) was purified by Prep-HPLC with the following conditions: Instrument "A" Column "A"; mobile phase, water (10 mM NH$_4$HCO$_3$) and ACN (30.0% ACN up to 50.0% in 8 min); Detector, UV 254/220 nm, to afford 50 mg (65%) of the title compound as an off-white solid.

LC-MS: (ES, m/z): 382.0

$^1$H NMR (300 MHz, DMSO-d$_6$) δ 9.41 (s, 1H), 8.52 (s, 1H), 8.37-8.30 (m, 1H), 7.78-7.66 (m, 2H), 7.42 (d, J=9.0 Hz, 1H), 7.05 (dd, J=8.9, 3.0 Hz, 1H), 6.81 (d, J=9.0 Hz, 1H), 3.80 (m, 2H), 3.66 (m, 4H), 3.42 (m, 2H), 1.84 (m, 2H).

Example 87

4-(3,4-difluorophenyl)-N-(5-hydroxypyridin-2-yl)-1,4-diazepane-1-carboxamide

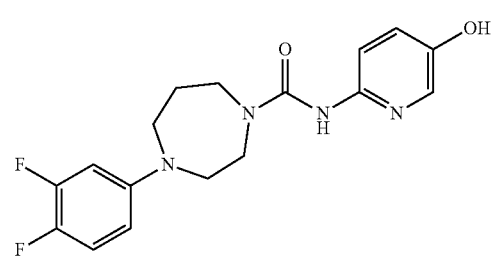 [SMILES: O=C(Nc1ccc(O)cn1)N1CCCN(c2ccc(F)c(F)c2)CC1]

213

Step 1. Synthesis of tert-butyl-4-(3,4-difluorophenyl)-1,4-diazepane-1-carboxylate

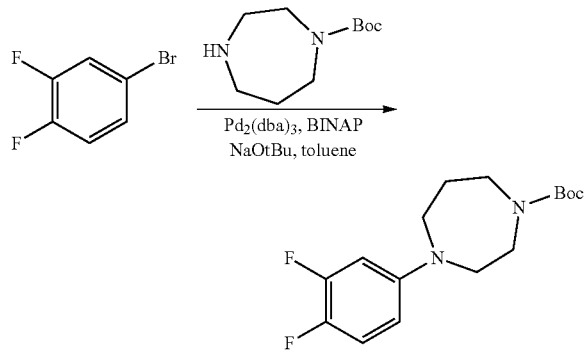

A solution of 4-bromo-1,2-difluorobenzene (1 g, 5.18 mmol, 1.00 eq.), tert-butyl 1,4-diazepane-1-carboxylate (1.25 g, 6.24 mmol, 1.20 eq.), NaOtBu (1.5 g, 3.00 eq.), BINAP (160 mg, 0.26 mmol, 0.05 eq.), and $Pd_2(dba)_3$ (240 mg, 0.26 mmol, 0.05 eq.) in toluene (20 mL) was stirred in a 30-mL sealed tube under $N_2$ for 16 h at 90° C. in an oil bath. The mixture was then diluted with water and extracted with 2×60 mL EtOAc. The combined organic layers were dried over $Na_2SO_4$ and concentrated in vacuo. The residue was purified by silica gel column chromatography using EtOAc/hexane (1/1) to afford 1.1 g (68%) of the title compound as an off-white solid. LC-MS: (ES, m/z): 313.

Step 2. Synthesis of 1-(3,4-difluorophenyl)-1,4-diazepane

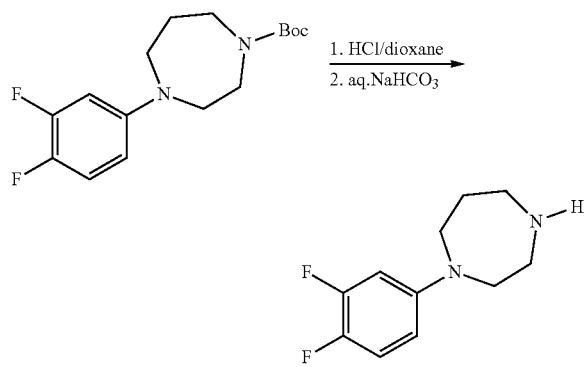

To a solution of the product from the previous step (1.1 g, 3.52 mmol, 1.00 eq.) in dioxane (10 mL). in a 250-mL round-bottom flask was added dropwise a solution of 4 N HCl/dioxane (5 mL) with stirring. The resulting solution was stirred for 4 h at room temperature. The pH value of the solution was adjusted to pH 7 with $NaHCO_3$ (2 mol/L). The resulting solution was extracted with 2×50 mL EtOAc, and the combined organic layers were dried over $Na_2SO_4$, and concentrated in vacuo. The residue was purified by silica gel column chromatography using EtOAc/hexane (1/1) to afford 0.5 g (67%) of the title compound as an off-white solid. LC-MS: (ES, m/z): 213.

214

Step 3. Synthesis of N-[5-[(tert-butyldimethylsilyl)oxy]pyridin-2-yl]-4-(3,4-difluorophenyl)-1,4-diazepane-1-carboxamide

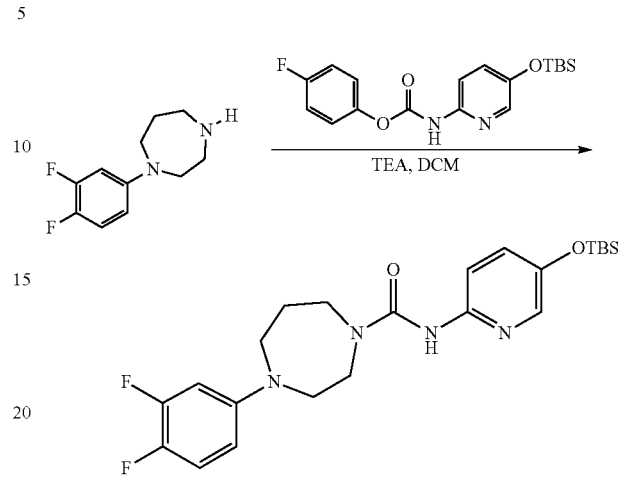

A solution of the product from the previous step (70 mg, 0.33 mmol, 1.20 eq.), 4-fluorophenyl N-(5-[(tert-butyldimethylsilyl)oxy]pyridin-2-yl)carbamate (100 mg, 0.28 mmol, 1.00 eq.), and TEA (84 mg, 0.83 mmol, 3.00 eq.) in $CH_2Cl_2$ (5 mL) was stirred in a 40 mL flask for 16 h at room temperature. The mixture was then diluted with water, and the resulting solution was extracted with 2×30 mL of $CH_2Cl_2$. The combined organic layers were dried over $Na_2SO_4$ and concentrated in vacuo. The residue was purified by silica gel column chromatography using EtOAc/hexane (1/1) to afford 105 mg (82%) of the title compound as an off-white solid. LC-MS: (ES, m/z): 463.

Step 4. Synthesis of 4-(3,4-difluorophenyl)-N-(5-hydroxypyridin-2-yl)-1,4-diazepane-1-carboxamide

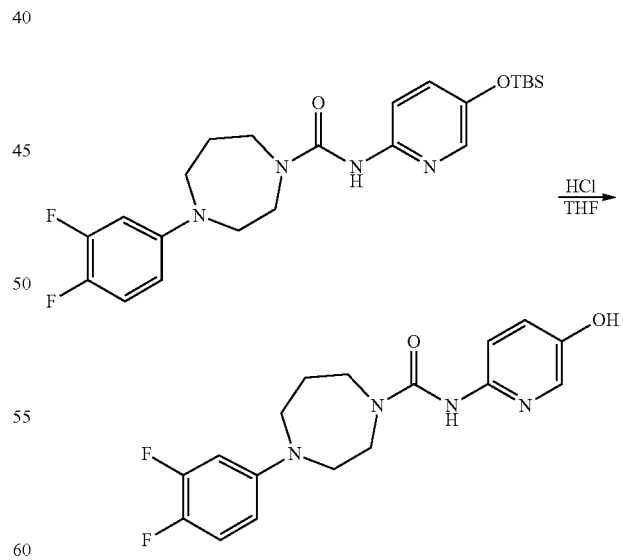

To a solution of the product from the previous step (105 mg, 0.23 mmol, 1.00 eq.) in THF (4 mL), in a 100-mL round-bottom flask was added 2 M aqueous HCl (2 mL) dropwise with stirring. The resulting solution was stirred for 2 h at room temperature, then concentrated in vacuo. The crude product (105 mg) was purified by Prep-HPLC under the following conditions: Instrument "A"; Column "A"; mobile phase, water (10 mM NH₄HCO₃) and ACN (30.0% ACN up to 50.0% in 8 min); Detector, UV 254/220 nm, to afford 54.5 mg (69%) of the title compound as an off-white solid.

LC-MS: (ES, m/z): 349.0

¹H NMR (300 MHz, DMSO-$d_6$) δ 9.40 (s, 1H), 8.50 (s, 1H), 7.76 (d, J=2.9 Hz, 1H), 7.48 (d, J=8.9 Hz, 1H), 7.21-7.02 (m, 2H), 6.72 (ddd, J=14.8, 6.9, 3.0 Hz, 1H), 6.47 (dq, J=8.0, 2.3 Hz, 1H), 3.70-3.44 (m, 6H), 3.36 (m, 2H), 1.84 (m, 2H).

Example 88

5-hydroxypyridin-2-yl 4-[5-(trifluoromethyl)pyridin-2-yl]piperazine-1-carboxylate

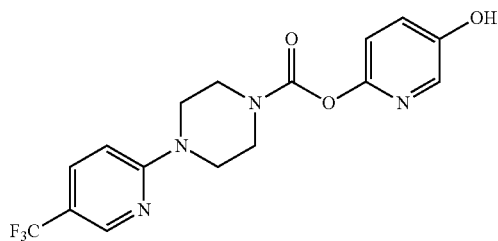 [SMILES: O=C(Oc1ccc(O)cn1)N1CCN(c2ccc(C(F)(F)F)cn2)CC1]

Step 1. Synthesis of 6-(benzyloxy)pyridin-3-ol

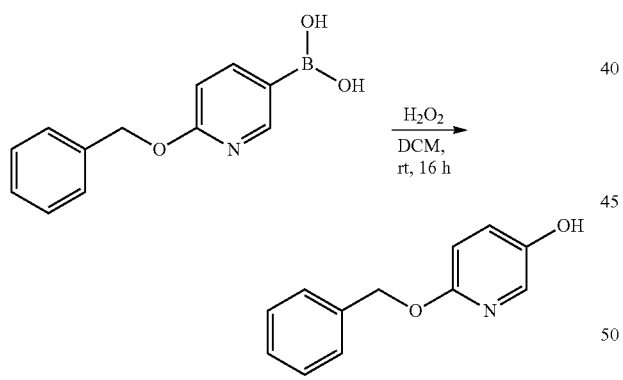

A solution of [6-(benzyloxy)pyridin-3-yl]boronic acid (2 g, 8.73 mmol, 1.00 eq.) and 30% H₂O₂ (2 mL) in CH₂Cl₂ (50 mL) was stirred overnight in a 100-mL round-bottom flask at room temperature. The resulting mixture was partitioned between water and CH₂Cl₂. The combined organic layers were concentrated in vacuo. The residue was purified by silica gel column chromatography using EtOAc/petroleum ether (1:3), to afford 1.4 g (80%) of the title compound as a white solid.

LC-MS: (ES, m/z): 202.0

¹H NMR (300 MHz, DMSO-$d_6$) δ 9.32 (s, 1H), 7.69 (dd, J=3.0, 0.6 Hz, 1H), 7.47-7.27 (m, 5H), 7.20 (dd, J=8.8, 3.0 Hz, 1H), 6.73 (d, J=8.8 Hz, 1H), 5.24 (s, 2H).

Step 2. Synthesis of 2-(benzyloxy)-5-[(tert-butyldimethylsilyl)oxy]pyridine

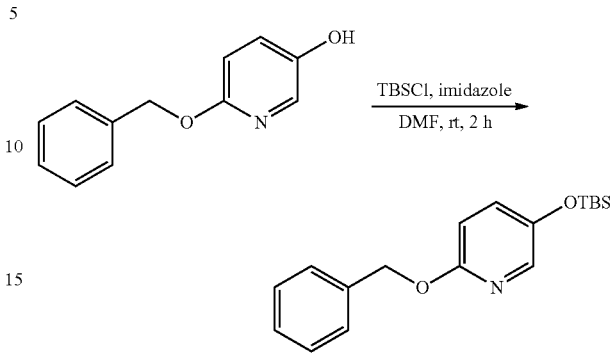

A solution of the product from the previous step (1.4 g, 6.96 mmol, 1.00 eq.), TBSCl (1.4 g, 9.27 mmol, 1.33 eq.) and imidazole (1 g, 14.71 mmol, 2.11 eq.) in DMF (30 mL) was stirred for 2 h in a 100-mL round-bottom flask at room temperature. The reaction was then quenched by the addition of water. The resulting solution was extracted with ether, and the organic layers were combined. The resulting mixture was washed with brine. The organic layer was concentrated in vacuo. The residue was purified by silica gel column chromatography using EtOAc/petroleum ether (1:10), to afford 2.0 g (91%) of the title compound as colorless oil. LC-MS (ES, m/z): 316.3

Step 3. Synthesis of 5-[(tert-butyldimethylsilyl)oxy]pyridin-2-ol

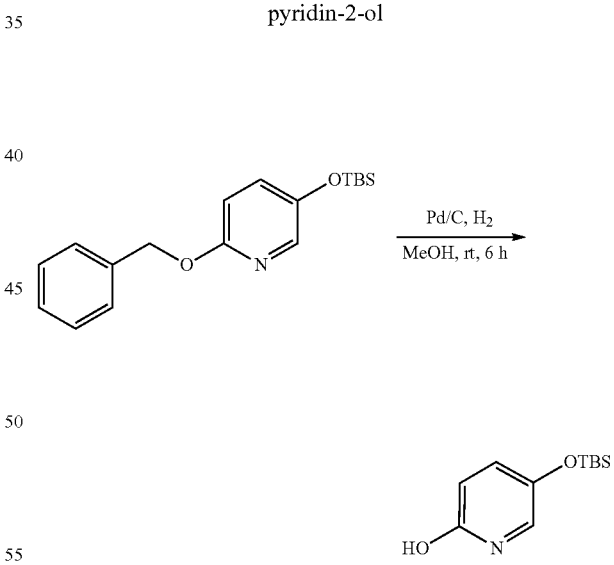

A solution of the product from the previous step (2 g, 6.34 mmol, 1.00 eq.) in MeOH (50 mL) was stirred overnight at room temperature over Pd/C (200 mg) in a 100-mL round-bottom flask under H₂. The solids were removed by filtration, and the filtrate was concentrated in vacuo, to afford 1.3 g (91%) of the title compound as a yellow solid. LC-MS (ES, m/z): 226.0

Step 4. Synthesis of 5-[(tert-butyldimethylsilyl)oxy]pyridin-2-yl 4-[5-(trifluoromethyl)pyridin-2-yl]piperazine-1-carboxylate

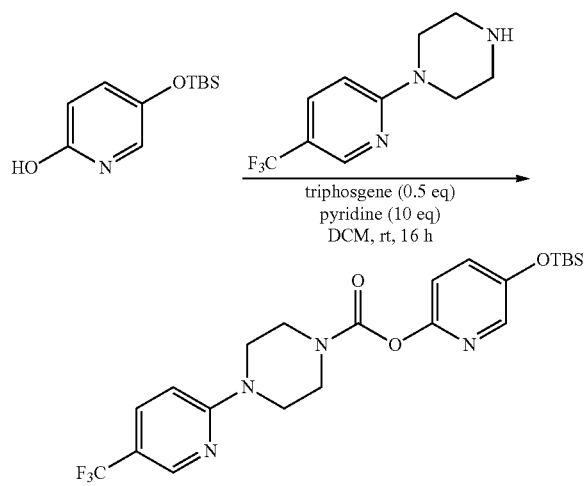

To a solution of the product from the previous step (225 mg, 1.00 mmol, 1.00 eq.) and triphosgene (300 mg, 1.01 mmol, 1.01 eq.) in CH$_2$Cl$_2$ (10 mL) was added pyridine (1 mL) dropwise with stirring at 0° C. After stirring at 0° C. for 30 mins, a solution of 1-[5-(trifluoromethyl)pyridin-2-yl]piperazine (231 mg, 1.00 mmol, 1.00 eq.) in CH$_2$Cl$_2$ (2 mL) was then added. The resulting mixture was stirred for 6 h at room temperature. The reaction was then quenched by the addition of water. The resulting solution was extracted with CH$_2$Cl$_2$, and the organic layers were combined and concentrated in vacuo. The residue was purified by silica gel column chromatography using EtOAc/petroleum ether (1:2), to afford 150 mg (31%) of the title compound as a white solid. LC-MS (ES, m/z): 483.4

Step 5. Synthesis of 5-hydroxypyridin-2-yl 4-[5-(trifluoromethyl)pyridin-2-yl]piperazine-1-carboxylate

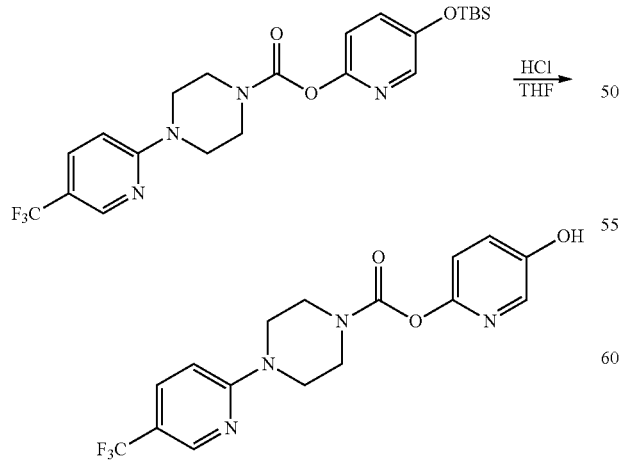

A solution of the product from the previous step (150 mg, 0.31 mmol, 1.00 eq.) and 2 N aq. HCl (2 mL) in THF (5 mL) was stirred for 2 h in a 50-mL round-bottom flask at room temperature. The resulting mixture was concentrated in vacuo. The crude product was purified by Prep-HPLC with the following conditions: Instrument "A"; Column "A"; mobile phase, water (10 mM NH$_4$HCO$_3$) and ACN (30.0% ACN up to 57.0% in 8 min); Detector, UV 254/220 nm, to afford 50.1 mg (44%) of the title compound as a white solid.
LC-MS (ES, m/z): 368.9
$^1$H NMR (300 MHz, DMSO-d$_6$) δ 9.87 (s, 1H), 8.45 (d, J=2.7 Hz, 1H), 7.84 (m, 2H), 7.28 (dd, J=8.7, 3.1 Hz, 1H), 7.00 (m, 2H), 3.91-3.70 (m, 6H), 3.56-3.53 (m, 2H).

Example 89

N-(5-hydroxypyridin-2-yl)-[1,1-biphenyl]-3-carboxamide

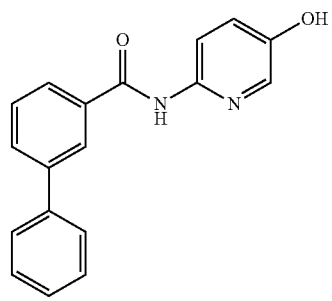 [SMILES: O=C(Nc1ccc(O)cn1)c1cccc(-c2ccccc2)c1]

Step 1. Synthesis of N-[5-[(tert-butyldimethylsilyl)oxy]pyridin-2-yl]-[1,1-biphenyl]-3-carboxamide

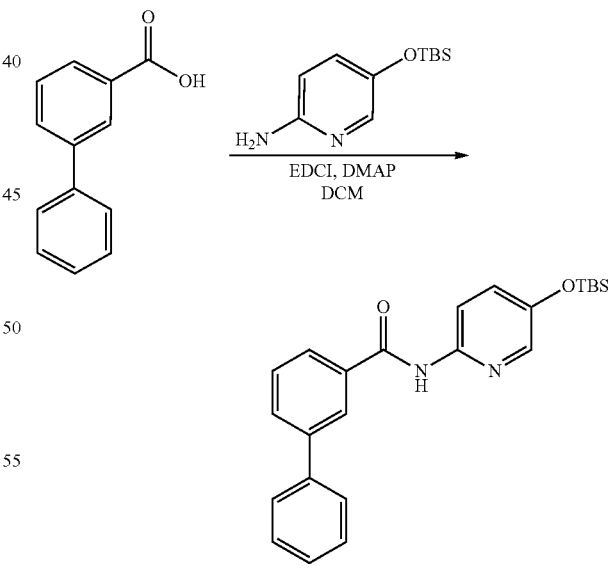

A solution of [1,1-biphenyl]-3-carboxylic acid (198 mg, 1.00 mmol, 1.00 eq.), EDCI (230 mg, 1.20 mmol, 1.20 eq.), 4-dimethylaminopyridine (122 mg, 1.00 mmol, 1.00 eq.), 5-[(tert-butyldimethylsilyl)oxy]pyridin-2-amine (224 mg, 1.00 mmol, 1.00 eq.) in CH$_2$Cl$_2$ (5 mL) was stirred a 40-mL vial for 16 h at room temperature. The mixture was then diluted with water and extracted with 2×20 mL EtOAc. The combined organic layers were dried over Na₂SO₄ and concentrated in vacuo. The residue was purified by prep-TLC using EtOAc/hexane (1/2) to afford 250 mg (61%) of the title compound as a light yellow solid. LC-MS: (ES, m/z): 405.35

Step 2. Synthesis of N-(5-hydroxypyridin-2-yl)-[1,1-biphenyl]-3-carboxamide

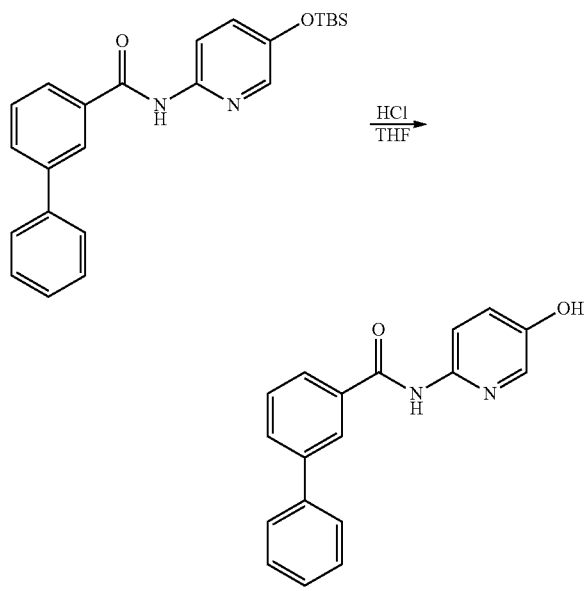

To a solution of the product from the previous step (250 mg, 0.62 mmol, 1.00 eq.) in THF (4 mL) in a 100-mL round-bottom flask was added 2 M HCl (2 mL) dropwise with stirring. The resulting solution was stirred for 2 h at room temperature, then concentrated in vacuo. The crude product (250 mg) was purified by Prep-HPLC with the following conditions: Instrument "A"; Column "A"; mobile phase, water (10 mM NH₄HCO₃) and ACN (10.0% ACN up to 74.0% in 8 min); Detector, UV 254/220 nm, to afford 149.4 mg (83%) of the title compound as an off-white solid. LC-MS: (ES, m/z): 291.0
¹H NMR (300 MHz, DMSO-d₆) δ 10.75 (s, 1H), 9.80 (s, 1H), 8.31 (s, 1H), 8.11-7.90 (m, 3H), 7.90-7.67 (m, 3H), 7.60 (m, 1H), 7.50 (m, 2H), 7.38 (m, 2H), 7.26 (dd, J=8.9, 3.0 Hz, 1H).

Example 90

N-(5-hydroxypyridin-2-yl)-4-(1-methyl-1H-pyrazol-4-yl)cyclohexane-1-carboxamide

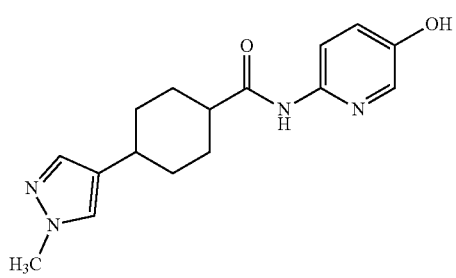 [SMILES: Cn1cc(C2CCC(C(=O)Nc3ccc(O)cn3)CC2)cn1]

Step 1. Synthesis of N-(5-((tert-butyldimethylsilyl)oxy)pyridin-2-yl)-4-(1-methyl-1H-pyrazol-4-yl)piperazine-1-carboxamide

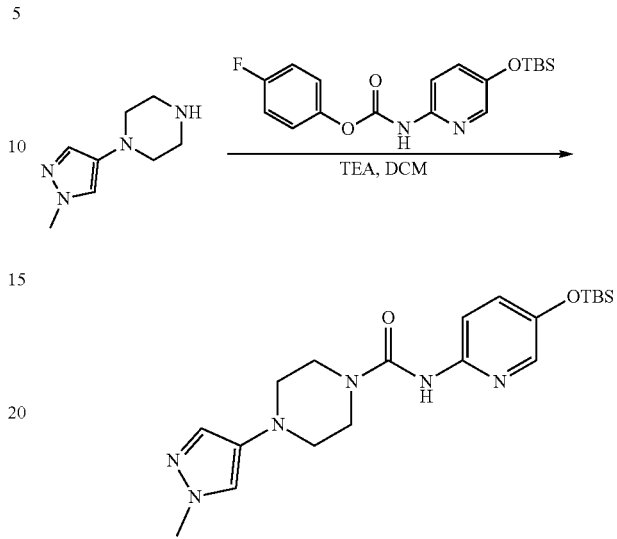

A solution of 1-(1-methyl-1H-pyrazol-4-yl)piperazine (70 mg, 0.42 mmol, 1.00 equiv), 4-fluorophenyl N-5-[(tert-butyldimethylsilyl)oxy]pyridin-2-ylcarbamate (120 mg, 0.33 mmol, 1.00 equiv) and Et₃N (100 mg, 0.99 mmol, 3.00 equiv) in CH₂Cl₂ (5 mL) was stirred for 16 h at room temperature, then diluted with water and extracted with 2×30 mL of EtOAc. The combined organic layers were dried over Na₂SO₄ and concentrated under vacuum, to afford the title compound as an off-white solid. LC-MS: (ES, m/z): 417.25.

Step 2. Synthesis of N-(5-hydroxypyridin-2-yl)-4-(1-methyl-1H-pyrazol-4-yl)piperazine-1-carboxamide

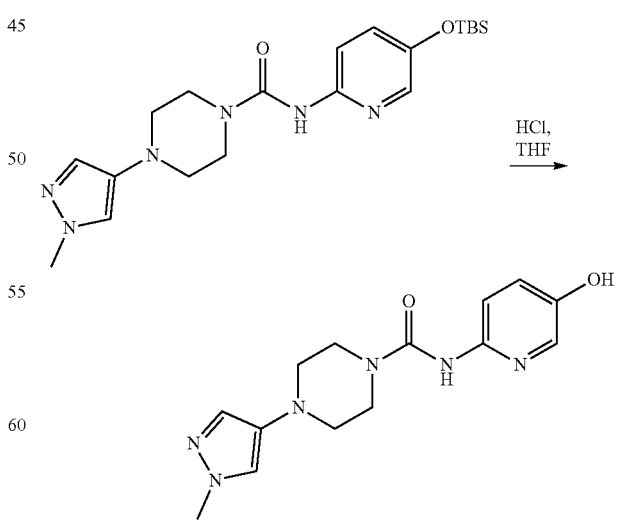

To a solution of the product from the previous step in THF (4 mL) was added 2 mL of 2 M HCl dropwise with stirring.

The resulting solution was stirred for 2 h at room temperature, then concentrated under vacuum. The crude product (110 mg) was purified by Prep-HPLC with the following conditions: Instrument "A"; Column "A"; mobile phase, water (10 mM NH$_4$HCO$_3$) and ACN (2.0% ACN up to 27.0% in 7 min); Detector, UV 254/220 nm; affording 54.3 mg (68%) of the title compound as an off-white solid.

LC-MS: (ES, m/z): 303.0

$^1$H NMR (300 MHz, DMSO-d$_6$) δ 8.86 (s, 1H), 7.77 (d, J=3.0 Hz, 1H), 7.56 (d, J=8.9 Hz, 1H), 7.26 (s, 1H), 7.22-7.06 (m, 2H), 3.70 (s, 3H), 3.52 (t, J=5.0 Hz, 4H), 2.80 (t, J=5.0 Hz, 4H)

The following compounds can generally be made using the methods described above. It is expected that these compounds when made will have activity similar to those that have been made in the examples above.

| IUPAC Name | Structure | Exact Mass |
|---|---|---|
| 4-(4-chlorophenyl)-N-(5-hydroxypyrimidin-2-yl)-piperazine-1-carboxamide | 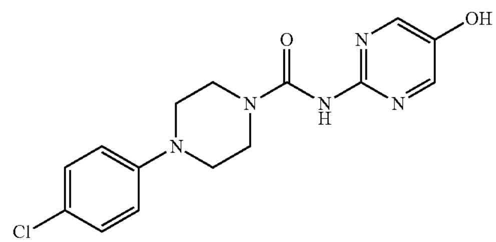 [SMILES: O=C(Nc1ncc(O)cn1)N1CCN(c2ccc(Cl)cc2)CC1] | 333.10 |
| 4-(5-chloropyridin-2-yl)-N-(5-hydroxypyrimidin-2-yl)-piperazine-1-carboxamide | 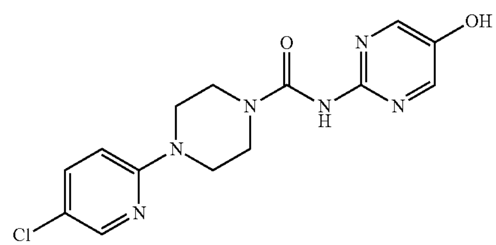 [SMILES: O=C(Nc1ncc(O)cn1)N1CCN(c2ccc(Cl)cn2)CC1] | 334.09 |
| 4-(4-chlorophenyl)-N-(6-hydroxypridazin-3-yl)-piperazine-1-carboxamide | 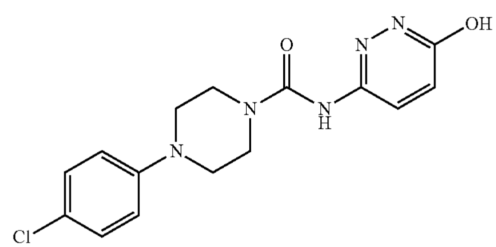 [SMILES: O=C(Nc1ccc(O)nn1)N1CCN(c2ccc(Cl)cc2)CC1] | 333.10 |
| 4-(5-chloropyridin-2-yl)-N-(6-hydroxypyridazin-3-yl)-piperazine-1-carboxamide | 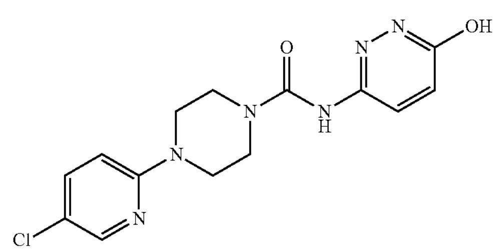 [SMILES: O=C(Nc1ccc(O)nn1)N1CCN(c2ccc(Cl)cn2)CC1] | 334.09 |
| 4-(4-chlorophenyl)-N-(5-hydroxypyridin-2-yl)-1,4-diazepane-1-carboxamide | 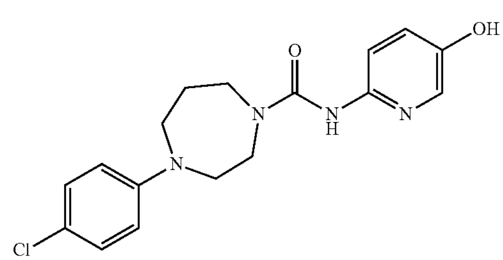 [SMILES: O=C(Nc1ccc(O)cn1)N1CCCN(c2ccc(Cl)cc2)CC1] | 346.12 |

-continued

| IUPAC Name | Structure | Exact Mass |
|---|---|---|
| 4-(5-chloropyridin-2-yl)-N-(5-hydroxypyridin-2-yl)-1,4-diazepane-1-carboxamide | 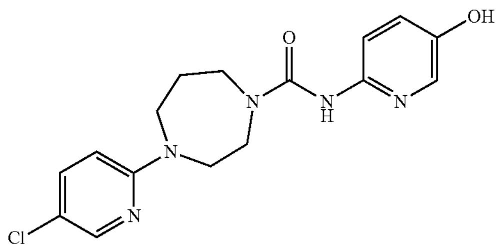 | 347.11 |
| 4-(4-fluorophenyl)-N-(5-hydroxypyrimidin-2-yl)-piperazine-1-carboxamide | 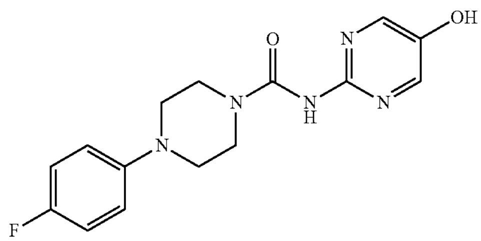 [SMILES: O=C(Nc1ncc(O)cn1)N1CCN(c2ccc(F)cc2)CC1] | 317.13 |
| 4-(5-fluoropyridin-2-yl)-N-(5-hydroxypyrimidin-2-yl)-piperazine-1-carboxamide | 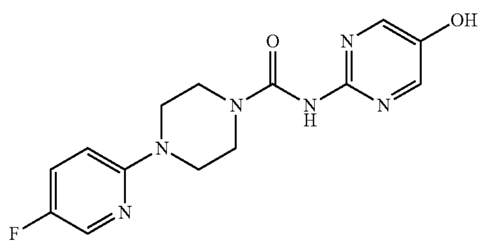 [SMILES: O=C(Nc1ncc(O)cn1)N1CCN(c2ccc(F)cn2)CC1] | 318.12 |
| 4-(4-fluorophenyl)-N-(6-hydroxypyridazin-3-yl)-piperazine-1-carboxamide | 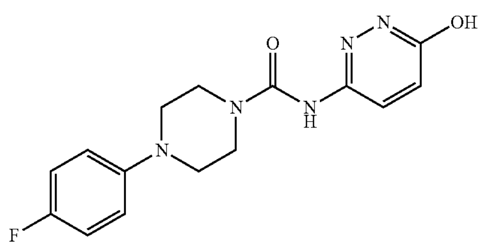 [SMILES: O=C(Nc1ccc(O)nn1)N1CCN(c2ccc(F)cc2)CC1] | 317.13 |
| 4-(5-fluoropyridin-2-yl)-N-(6-hydroxypyridazin-3-yl)-piperazine-1-carboxamide | 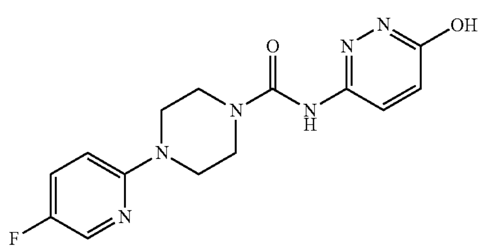 [SMILES: O=C(Nc1ccc(O)nn1)N1CCN(c2ccc(F)cn2)CC1] | 318.12 |
| 4-(4-fluorophenyl)-N-(5-hydroxypyridin-2-yl)-1,4-diazepane-1-carboxamide | 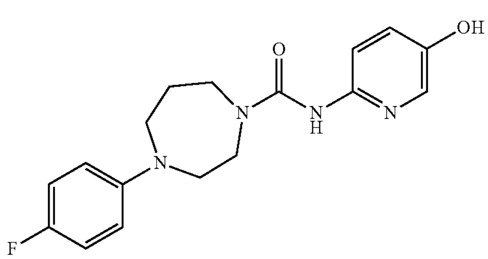 [SMILES: O=C(Nc1ccc(O)cn1)N1CCCN(c2ccc(F)cc2)CC1] | 330.15 |

| IUPAC Name | Structure | Exact Mass |
|---|---|---|
| 4-(5-fluoropyridin-2-yl)-N-(5-hydroxypyridin-2-yl)-1,4-diazepane-1-carboxamide | | 331.14 |
| N-(5-hydroxypyrimidin-2-yl)-4-(4-(trifluoromethyl)phenyl)piperazine-1-carboxamide | | 367.13 |
| N-(5-hydroxypyrimidin-2-yl)-4-(5-(trifluoromethyl)pyridin-2-yl)piperazine-1-carboxamide | | 368.12 |
| N-(6-hydroxypyridazin-3-yl)-4-(4-(trifluoromethyl)phenyl)piperazine-1-carboxamide | | 367.13 |
| N-(6-hydroxypyridazin-3-yl)-4-(5-(trifluoromethyl)pyridin-2-yl)piperazine-1-carboxamide | | 368.12 |
| N-(5-hydroxypyridin-2-yl)-4-(4-(trifluoromethyl)phenyl)-1,4-diazepane-1-carboxamide | | 380.15 |

-continued

| IUPAC Name | Structure | Exact Mass |
|---|---|---|
| N-(5-hydroxypyridin-2-yl)-4-(5-(trifluoromethyl)-pyridin-2-yl)-1,4-diazepane-1-carboxamide | 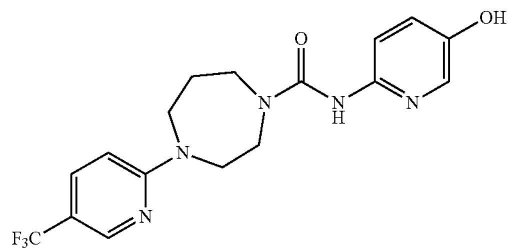 [SMILES: O=C(Nc1ccc(O)cn1)N1CCCN(c2ccc(C(F)(F)F)cn2)CC1] | 381.14 |
| 4-(2,4-difluorophenyl)-N-(5-hydroxypyrimidin-2-yl)-piperazine-1-carboxamide | 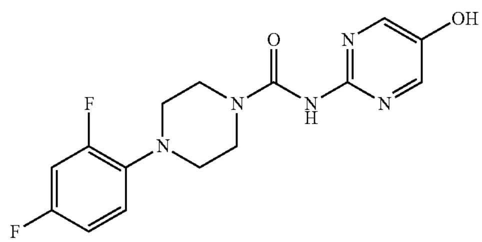 [SMILES: O=C(Nc1ncc(O)cn1)N1CCN(c2ccc(F)cc2F)CC1] | 335.12 |
| 4-(3,5-difluorophenyl-2-yl)-N-(5-hydroxypyrimidin-2-yl)piperazine-1-carboxamide | 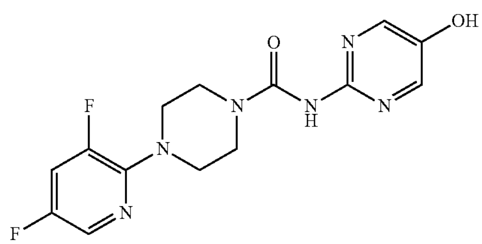 [SMILES: O=C(Nc1ncc(O)cn1)N1CCN(c2ncc(F)cc2F)CC1] | 336.11 |
| 4-(2,4-difluorophenyl)-N-(6-hydroxypyridazin-3-yl)-piperazine-1-carboxamide | 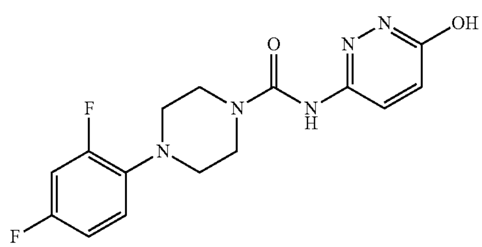 [SMILES: O=C(Nc1ccc(O)nn1)N1CCN(c2ccc(F)cc2F)CC1] | 335.12 |
| 4-(3,5-difluoropyridin-2-yl)-N-(6-hydroxypyridazin-3-yl)piperazine-1-carboxamide | 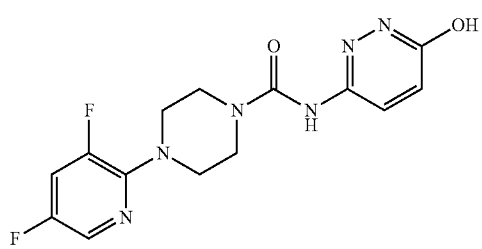 [SMILES: O=C(Nc1ccc(O)nn1)N1CCN(c2ncc(F)cc2F)CC1] | 336.11 |
| 4-(2,4-difluorophenyl)-N-(5-hydroxypyridin-2-yl)-1,4-diazepane-1-carboxamide | 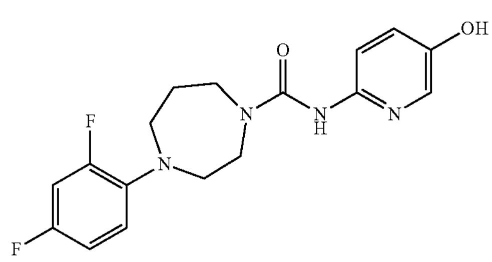 [SMILES: O=C(Nc1ccc(O)cn1)N1CCCN(c2ccc(F)cc2F)CC1] | 348.14 |

| IUPAC Name | Structure | Exact Mass |
|---|---|---|
| 4-(3,5-difluoropyridin-2-yl)-N-(5-hydroxypyridin-2-yl)-1,4-diazepane-1-carboxamide | 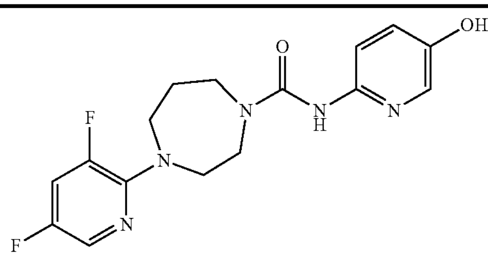 | 349.14 |
| 4-(3,4-difluorophenyl)-N-(5-hydroxypyrimidin-2-yl)-piperazine-1-carboxamide | 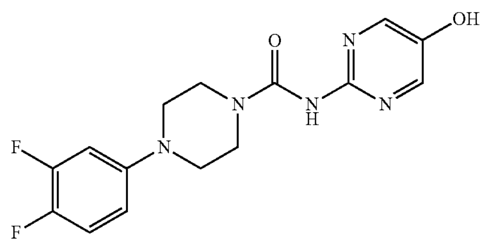 [SMILES: O=C(Nc1ncc(O)cn1)N1CCN(c2ccc(F)c(F)c2)CC1] | 335.12 |
| 4-(3,4-difluorophenyl)-N-(6-hydroxypyridazin-3-yl)-piperazine-1-carboxamide | 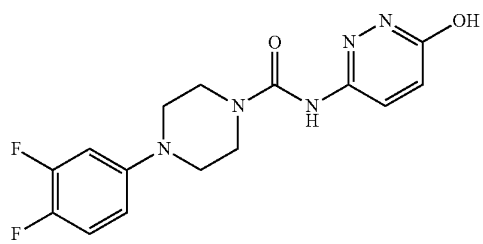 [SMILES: O=C(Nc1ccc(O)nn1)N1CCN(c2ccc(F)c(F)c2)CC1] | 335.12 |
| 4-(3,4-difluorophenyl)-N-(5-hydroxypyridin-2-yl)-1,4-diazepane-1-carboxamide | 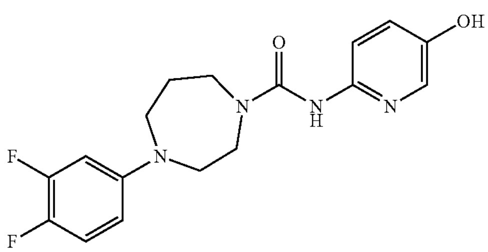 [SMILES: O=C(Nc1ccc(O)cn1)N1CCCN(c2ccc(F)c(F)c2)CC1] | 348.14 |
| N-(5-hydroxypyrimidin-2-yl)-4-(6-(trifluoromethyl)-pyridin-2-yl)piperazine-1-carboxamide | 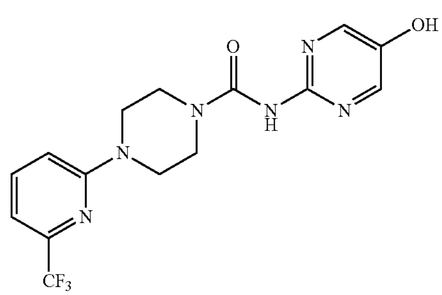 | 368.12 |
| N-(6-hydroxypyridazin-3-yl)-4-(6-(trifluoromethyl)-pyridin-2-yl)piperazine-1-carboxamide | 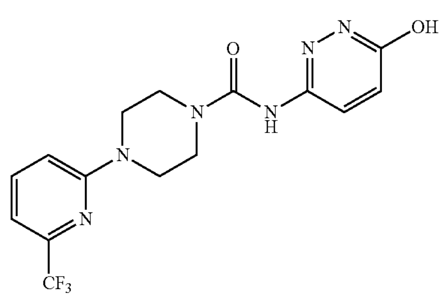 [SMILES: O=C(Nc1ccc(O)nn1)N1CCN(c2cccc(C(F)(F)F)n2)CC1] | 368.12 |

-continued

| IUPAC Name | Structure | Exact Mass |
|---|---|---|
| N-(5-hydroxypyridin-2-yl)-4-(6-(trifluoromethyl)-pyridin-2-yl)-1,4-diazepane-1-carboxamide | (structure) | 381.14 |
| 4-(5-fluoropyridin-2-yl)-N-(5-hydroxypyrimidin-2-yl)-piperidine-1-carboxamide | (structure) | 317.13 |
| 4-(5-fluoropyridin-2-yl)-N-(6-hydroxypyridazin-3-yl)-piperidine-1-carboxamide | (structure) | 317.13 |

The activity of the compounds in the compounds disclosed herein as Des1 inhibitors and as useful for the treatment of disease is illustrated in the following assays.

Biological Activity Assays

Des1 Activity Assays

The following are examples of in vitro cellular assays that may be used to evaluate the potential inhibitory activity of compounds disclosed herein against Des1 as well as disease-specific physiological consequences of Des1 inhibition.

Jurkat T Cell Measurement of Conversion of Dihydroceramide to Ceramide

Jurkat clone E6-1 cells were grown and then seeded at $10^6$ cells/mL in a 96-well plate (400 µL in each well. The cells were administered 100 µL of cell culture media containing 50-µM NBD-$C_6$-dihydroceramide (Des1 substrate), affording a final concentration of substrate of 10 µM. The cells were incubated with substrate at 4° C. for 30 minutes. Following the incubation at 4° C., the cell suspension was centrifuged at 1200 rpm for 3 minutes, and the cell pellet is resuspended in 400 µL of fresh media containing various concentrations of either fenretinide (known Des1 inhibitor control compound) or test article. The final concentrations of control compound and test compounds were tested in a range from 0-10 µM. The cells and compounds were incubated at 37° C. for 3 hours. Following the 3-hour incubation, the plate was centrifuged at 2500 g for 3 minutes at 4° C., followed by collection and transfer of 200 µL of the supernatant to a new 96-well plate with 300 µL of methanol an containing appropriate internal standards for liquid chromatography/tandem mass spectroscopy (LC/MS/MS) analysis (internal standard: 500 nM labetalol and 100 nM alprazolam). The samples were vortexed for 2 minutes followed by centrifugation at 3,220 g for 20 minutes. Following centrifugation, 200 µL of the supernatant was transferred to a new 96-well plate for LC-MS/MS analysis to determine the amount of NBD-C6-ceramide (Des1 product) produced. The assay was typically performed in duplicate. A reduction of at least 30% compared to vehicle control (0 µM test article) is indicative of an active compound, and a reduction of 75% compared to vehicle control is preferred. By way of example, fenretinide exhibits a half-maximal inhibitory concentration (IC50) of 100-250 nM, and a number of the compounds described herein exhibit $IC_{50}$ values<50 nM.

TABLE 1

Biological Activity.

| Ex | Des1 % Inhib (0.5 uM) | Des1 $IC_{50}$, µM |
|---|---|---|
| 1 | 89.62 | 0.042 |
| 2 | 91.74 | 0.025 |
| 3 | 87.89 | 0.053 |
| 4 | 94.31 | 0.023 |
| 5 | 91.52 | 0.032-0.051 |
| 6 | 81.83 | 0.069 |
| 7 | 93.95 | 0.026 |
| 8 | 94.93 | 0.013 |
| 9 | 93.76 | 0.017 |

TABLE 1-continued

Biological Activity.

| Ex | Des1 % Inhib (0.5 uM) | Des1 IC$_{50}$, µM |
|---|---|---|
| 10 | 15.03 | N.D. |
| 11 | 38.5 | N.D. |
| 12 | 90.52 | 0.054 |
| 13 | 93.04 | 0.009-0.033 |
| 14 | 95.91 | 0.003 |
| 15 | 81.83 | 0.110 |
| 16 | 31.4 | N.D. |
| 17 | 76.9 | N.D. |
| 18 | 96.64 | 0.004 |
| 19 | 76.7 | N.D. |
| 20 | 19.59 | N.D. |
| 21 | 69.35 | N.D. |
| 22 | N.D. | 0.014 |
| 23 | N.D. | 0.01 |
| 24 | N.D. | 0.064-0.094 |
| 25 | N.D. | 0.009 |
| 26 | N.D. | 0.012 |
| 27 | N.D. | 0.011 |
| 28 | 57.78 | N.D. |
| 29 | 58.57 | N.D. |
| 30 | 89.70 | 0.150 |
| 31 | N.D. | 0.34 |
| 32 | N.D. | 0.18 |
| 33 | 93.09 | 0.007 |
| 34 | 85.37 | N.D. |
| 35 | 91.28 | 0.003 |
| 36 | 94.89 | 0.023 |
| 37 | 80.7 | N.D. |
| 38 | 91.55 | 0.06 |
| 39 | 9.11 | N.D. |
| 40 | 89.14 | 0.013 |
| 41 | 95.07 | 0.013 |
| 42 | 81.43 | 0.035 |
| 43 | 96.99 | 0.006 |
| 44 | 95.01 | 0.008 |
| 45 | N.D. | 0.47 |
| 46 | 94.55 | 0.007 |
| 47 | 51.82 | N.D. |
| 48 | 39.75 | N.D. |
| 49 | N.D. | 0.13 |
| 50 | 83.02 | N.D. |
| 51 | 91.55 | 0.092 |
| 52 | N.D. | 0.029 |
| 53 | 94.84 | 0.004 |
| 54 | N.D. | 0.005 |
| 55 | 96.48 | 0.002 |
| 56 | 94.73 | 0.028 |
| 57 | 95.46 | 0.001 |
| 58 | 96.84 | 0.004 |
| 59 | 93.2 | 0.043 |
| 60 | 96 | 0.003 |
| 61 | 37.52 | N.D. |
| 62 | 69.38 | 0.31 |
| 63 | N.D. | >1.00 |
| 64 | 19.25 | N.D. |
| 65 | N.D. | >1.0 |
| 66 | 72.13 | N.D. |
| 67 | 85.33 | N.D. |
| 68 | 92.37 | 0.085 |
| 69 | 94.97 | 0.04 |
| 70 | 83.79 | 0.110 |
| 71 | 88.04 | 0.031 |
| 72 | 50.25 | N.D. |
| 73 | 41.94 | N.D. |
| 74 | 72.75 | N.D. |
| 75 | 91.17 | 0.062-0.086 |
| 76 | 75.11 | N.D. |
| 77 | 91.88 | 0.035 |
| 78 | 93.44 | 0.019-0.064 |
| 79 | 93.75 | 0.0076-0.07 |
| 80 | 56.86 | N.D. |
| 81 | 77.94 | N.D. |
| 82 | 78.37 | N.D. |
| 83 | 94.87 | 0.065 |
| 84 | N.D. | 0.1 |
| 85 | N.D. | 0.055 |
| 86 | 84.61 | 0.078 |
| 87 | 92.71 | 0.021 |
| 88 | 92.7 | 0.025 |
| 89 | 93.04 | 0.0029 |
| 90 | 39.2 | N.D. |

N.D. = not determined.

C2C12 Myotube Assay of Insulin-Stimulated Phosphorylation of Akt:

C2C12 myotubes are treated with 0.75 mM BSA-conjugated palmitate for 16 hours in the presence or absence of 7 non-zero concentrations of fenretinide (Des1 inhibitor control compound) or various test articles, followed by a 10-minute stimulation with insulin (100 nM). Cells are subsequently harvested and boiled in reducing SDS sample buffer and subjected to SDS-PAGE followed by detection of phosphorylated Akt, total Akt, and a suitable loading control (e.g. actin or GAPDH) by western blot using fluorescently-conjugated secondary antibodies. Band intensities are quantitated by an Odyssey imaging system (Li—COR), but could also be performed using HRP-conjugated secondary antibodies/enhanced chemiluminescence or by colorimetric readout.

Moreover, while currently contemplated for SDS-PAGE/immunoblot format, this assay could be adapted to ELISA or in-cell western (immunocytochemistry) formats for higher throughput testing of compounds. An increase of 30% compared to vehicle control (0 µM test article) is indicative of an active compound, and an increase of 50% compared to control is preferred. By way of example, fenretinide exhibits a half-maximal effective concentration (EC50) for increasing insulin-stimulated Akt phosphorylation in the presence of palmitate of 600 nM. Des1 inhibitors disclosed herein are expected to be effective in this assay.

Rodent High Fat Dietary Model of Insulin Resistance, Dyslipidemia, and NAFLD/NASH:

A standard model of human hyperlipidemia and insulin resistance is the mouse fed a high fat diet for several weeks. Test compounds are evaluated in this model as agents to restore insulin sensitivity and lower blood lipids. The chronic high fat diet is fed to mice to simulate a standard Western diet which is elevated in calories from high fat and carbohydrate intake. This and similar models of dietary induced obesity, insulin insensitivity and elevated serum lipids and cholesterol are used as mouse and rat models of human pathology including hyperlipidemia, type II diabetes, atherosclerosis, obesity, cardiovascular and liver disease. It is appreciated that the diet can be varied to a "fast food diet" to include more atherogenic factors (eg 2% cholesterol and 12% saturated fatty acids) to enhance the NASH phenotype. These models have been used as excellent predictors of efficacy in human clinical trials (PPAR and FXR agonists). Key endpoints used to assess therapeutic activity of candidate Des1 inhibitors including fasting blood glucose, insulin, triglycerides, cholesterol, hepatosteatosis, markers of hepatic inflammation, and fibrosis (including collagen detection). Glucose and insulin tolerance studies can also be performed. Glycosylated hemoglobin can also be measured as a more chronic marker of hyperglycemia. Hepatosteatosis (fatty liver) can be assessed by Oil Red O staining of liver sections as well as by quantitative determination of liver triglycerides. Des1 inhibitors are expected to demonstrate efficacy in this assay, improving insulin sensitivity, lowering blood lipids, reducing or preventing the development of hepatosteatosis, and/or generally demonstrating efficacy in measures of pathology relevant to dyslipidemia, type II diabetes, atherosclerosis, obesity, cardiovascular diseases, and/or liver diseases such as NASH or NAFLD. In the case of NAFLD/NASH, it is also appreciated that the efficacy of a Des1 inhibitor could potentially be enhanced by co-administration with an FXR agonist, an ASK1 inhibitor, an ACC inhibitor, a PPAR agonist, an ileal bile acid transport inhibitor, a DGAT2 inhibitor, an FGF19 analog, an FGF21 analog, an NLRP3 inflammasome inhibitor, a ketohexokinase inhibitor, and a caspase inhibitor. In the case of type 2 diabetes, it is appreciated that the efficacy of a Des1 inhibitor could potentially be enhanced by co-administration with metformin, a GLP-1 analog, a GLP-1 receptor agonist, a DPP-4 inhibitor, a sulfonylurea, a meglitidine, a PPAR agonist, an SGLT2 inhibitor, and insulin. In the case of dyslipidemia, it is also appreciated that the efficacy of a Des1 inhibitor could potentially be enhanced by co-administration with fibrates, niacin, omega 3 fatty acids, a statin, a bile resin, and a PCSK9 inhibitor.

Measurement of In Vivo Activity in a Models of Atherosclerosis:

A key workhorse rodent model of atherosclerosis is the high fat diet-fed ApoE−/− (ApoE knockout) mouse, which develops atherosclerotic lesions which can be measured in various aspects of the aorta. By way of example, male ApoE−/− mice of 8 weeks of age are fed a high fat diet for 30 days to establish atherosclerotic lesions. A control group of animals are terminated to assess aortic lesion status following the 30 days of high fat dieting. Subsequently, two groups of mice are switched to a standard chow diet for another 60 days, during which the animals are dosed with either vehicle, a candidates Des1 inhibitor, or a reference control compound (e.g. myriocin). Following the 60 days of dosing, mice are fasted overnight, and perfusion-fixed aortas are dissected to enable lesion analysis of the aortic sinus, aortic arch, and celiac branchpoint of the abdominal aorta. Morphometric analysis of these three aortic sites is conducted after the tissues are subjected to Verhoeff staining (Glaros et al. (2008) Myriocin slows the progression of established atherosclerotic lesions in apolipoprotein E gene knockout mice. *J. Lipid Res.* 49, 324-331).

Des1 inhibitors disclosed herein would be anticipated to prevent the development of or effect the regression of established atherosclerotic lesions.

Measurement of In Vitro Cellular Anti-Cancer Activity:

PC3 prostate cancer, MCF7 ER+ breast cancer cells, or various other cancer cell lines are cultured in DMEM (containing 10% fetal calf serum and penicillin-streptomycin). A frozen aliquot of cells is resuspended in 5 mL of warm media and centrifuged for 5 mins at 200 g. The supernatant is aspirated and the cell pellet resuspended in 5 mL media. Cells are then grown in tissue culture flasks at 37° C. with 5% $CO_2$ and passaged when 80-90% confluent 4 times before use. Cells are then incubated for 5 mins with Trypsin to separate from cell culture flanks. Before treatment with drug compounds, cells are plated at 2,500 cells/well in 96-well plates and incubated at 37° C. with 5% $CO_2$ in a humidified incubator for 24 hours prior. Fenretinide (Des1 control inhibitor) or various test articles are diluted in media to final concentrations ranging from 10 µM down to 0 µM, with DMSO as a vehicle control (final DMSO concentration of 0.1%). Cell culture supernatants are aspirated and replaced with media containing either fenretinide or various test articles. Drug treatments are performed in duplicate wells. Cells are incubated with drug compounds at 37° C. with 5% $CO_2$ in a humidified incubator for 72 hours prior to determination of cell viability. Following the 72-hour incubation with compounds, cell culture supernatants are then aspirated from wells and replaced with 100 µL of CellTiter Glo solution. Triplicate cell-free control wells containing only CellTiter solution are also included in each assay. Cells are then incubated at 37° C. with 5% $CO_2$ in a humidified incubator for 1 hour at which time absorbance is read at 490 nm by microplate reader instrument. Background absorbance (taken from cell-free control wells) is subtracted from each reading. To determine percentage inhibition of cell viability, absorbance readings for each drug treatment are expressed as a fraction of the vehicle control (0.1% DMSO) readings. For each drug concentration the mean (+/−SEM) is calculated and graphed using GraphPad Prism or other suitable scientific graphing package. A sigmoidal curved is fitted to the data and used to calculate the IC50 of each compound. A reduction of cancer cell viability by at least 30% compared to vehicle control (0 µM test article) is indicative of an active compound, and a reduction of 50% compared to control is preferred. Des1 inhibitors disclosed herein are expected to be effective in reducing cancer cell viability and thus to be effective in the treatment of cancer.

Measurement of In Vivo Anti-Cancer Activity:

Human tumor xenografts in immunocompromised mice (e.g. athymic nude mice), implanted either orthotopically or ectopically, represent the workhorse models for predicting the clinical efficacy of candidate anti-cancer agents. By way of example, in the case of ER+ breast cancer, ovariectomized estrogenized (0.72 mg/60 days 17β-estradiol (E2) time-released sc pellet) NU/NU mice (~6 weeks of age) are injected with $5 \times 10^6$ MCF7 cells (a human cell line derived from an ER+ breast cancer) into the axial mammary fat pad. Tumors are measured by caliper three times per week until tumor volume (($L^2 \cdot W$)/2) reaches 0.2 $cm^3$, followed by randomization of mice into treatment groups with test compounds in the presence or absence of standard-of-care agents (e.g. tamoxifen). Active Des1 inhibitors would be anticipated to show tumor growth inhibition or regression over a 28-day treatment period, indicative of potential anti-cancer activity of test compounds.

In addition, test compounds can also be assessed for potential anti-cancer activity in syngeneic and/or genetically-engineered mouse models of various tumors in order to have the benefit of having a fully intact immune system (e.g. MC38 model of colorectal cancer or KPC model of pancreatic ductal adenocarcinoma). Candidate Des1 inhibitors may inhibit the activity and/or recruitment of various cell types (e.g. myeloid-derived suppressor cells, regulatory T cells) which lead to immunosuppression in the tumor microenvironment, and thus have synergistic activity with various immune check-point inhibitors, including monoclonal antibody therapeutics targeting PD1, PD-L1, CTLA-4, CD47, and OX40, as well as small molecules targeting indoleamine-2,3-dioxygenase 1 or arginase-1, which are used to reawaken the immune system to enable immunological attack of the tumor. Such therapy would be anticipated to generate anti-tumor immunity and potentially a durable anti-tumor memory response.

Des1 inhibitors disclosed herein are expected to be effective as single agents as well as in combination with standard-of-care therapy in the treatment of cancer.

Measurement of Activity in In Vivo Model of Cystic Fibrosis:

Genetic ablation of the cystic fibrosis transmembrane conductance regulator (CFTR) in mice recapitulates a number of the clinical manifestations of cystic fibrosis observed in patients, and has become a workhorse pharmacology model of this disease. As ceramide has been demonstrated to accumulate in the lungs of mouse knockouts of CFTR (CFTR-KO) and to create a pro-inflammatory environment, measuring the ratio of lung arachidonic acid (AA—a lipid precursor to pro-inflammatory mediators) to docosahexaenoic acid (DHA). A high AA/DHA ratio is indicative a pro-inflammatory environment. Fenretinide, a known Des1 inhibitor, has previously been demonstrated to normalize this ratio (and hence reduce inflammation) in the lungs of CFTR-KO mice, as well as reduce susceptibility to infection with *Pseudomonas aeruginosa* (Guilbault et al. 2009 Cystic fibrosis fatty acid imbalance is linked to ceramide deficiency and corrected by fenretinide. Am. J. Respir. Cell Mol. Biol. 41, 100-106; Guilbault et al. 2008 Fenretinide corrects newly found ceramide deficiency in cystic fibrosis. Am. J. Respir. Cell Mol. Biol. 38, 47-56). Consequently, candidate Des1 inhibitors could be tested in this CFTR-KO mouse model of cystic fibrosis with key endpoints being the AA/DHA ratio as well as the inflammatory response to, and ability to clear, *Pseudomonas aeruginosa* challenge. Longer term, mice lacking CFTR develop substantial pulmonary fibrosis which can be assessed histologically (e.g. Sirius Red or trichrome staining of lung tissue) of by quantitative assessment of hydroxyproline in lung tissue. Des1 inhibitors disclosed herein would be anticipated to normalize the ratio of lung AA to DHA, normalize the ratio of circulating AA to DHA, reduce lung inflammation, and reduce lung fibrosis.

Measurement of In Vitro Cellular Anti-Fibrotic Activity:

Normal and SSc (diffuse systemic sclerosis) skin fibroblasts are cultured in DMEM supplemented with 10% FBS and 1% antibiotic antimycotic solution. Cells are incubated with serum-free media for 24 hours before specific treatments, including fenretinide (Des1 inhibitor control compound) and various test articles at concentrations ranging from 10 μM down to 0 μM (DMSO vehicle control, 0.1%) for 12-24 hours at 37° C. Smad3 (a downstream signaling intermediate of the TGFβ pathway) as well as collagen (COL1A1) are measured as in vitro surrogates of a pro-fibrotic state. A reduction of at least 30% compared to vehicle control (0 μM test article) is indicative of an active compound, and a reduction of 50% compared to control is preferred. Des1 inhibitors disclosed herein are expected to be effective in reducing measures and markers of fibrosis.

Measurement of In Vivo Anti-Fibrotic Activity:

Various rodent models exist for assessing potential in vivo anti-fibrotic activity of test compounds, including those representing fibrosis of the lungs, kidney, liver, and skin/connective tissues. By way of example, and in the case of liver fibrosis, rodents (mice or rats) are injected with a $CCl_4$, a hepatotoxin, followed by randomization of animals into treatment groups (using pirfenidone as a reference control compound) and assessment at 6-8 weeks post-$CCl_4$ injection. Key measures of liver fibrosis to assess potential therapeutic efficacy of test compounds include liver function tests (e.g. AST, ALT, bilirubin), hydroxyproline content in the liver, and Sirius Red staining of liver histological sections. An active Des1 inhibitor would be anticipated to substantially reduce the level of Sirius Red staining in the liver, as well as hydroxyproline level. Des1 inhibitors disclosed herein would be expected to reduce fibrosis of various organs, including liver, lung, kidney, heart, and skin.

Measurement of Disease-Modifying Activity in Multiple Sclerosis:

There are numerous mouse models of multiple sclerosis (MS), including those in which animals are immunized with myelin oligodendrocyte glycoprotein (MOG) (chronic progressive model) and proteolipoprotein (PLP) (relapsing/remitting model), as well as others which rely on adoptive cellular transfer technologies. By way of example, and in the case of the MOG chronic progressive model, chronic progressive EAE develops in C57BL/6 mice after immunization with an emulsion of $MOG_{35-55}$/CFA or $MOG_{1-125}$/CFA followed by injection of pertussis toxin. This model is used to test the potential of compounds to prevent or mitigate EAE disease. It can be run with the compound dosed from the time of immunization (prophylactic treatment), or with the aim of reversing the course of disease and facilitating recovery by dosing the compound from the time of EAE onset (therapeutic treatment). The model uses female C57BL/6 mice of age 10 to 14 weeks at the start of the study. Typically, EAE develops 8-18 days after immunization. EAE development is usually followed for 4 weeks (28 days) after immunization. Compounds can be assessed for their ability to reduce the severity or incidence of disease (both by scoring of limb weakness/paralysis and behavior, as well as by histopathology of the spinal card including extent of demyelination) in comparison to reference control compounds (e.g. fingolimod). An active Des1 inhibitor would be anticipated to reduce the severity of disease (clinical score), the extent of spinal cord demyelination, inflammatory cell infiltrates into the spinal cord, and number of apoptotic cells in the spinal cord. Active Des1 inhibitors could be combined with other therapeutics for multiple sclerosis, including fingolimod (and other sphingosine-1-phosphate receptor modulators), teriflunomide, dimethyl fumarate, PAD4 inhibitors, anti-CD20 and anti-CD52 mAbs, natalizumab, glatiramer acetate, and interferon-$. Des1 inhibitors disclosed herein would be expected to have disease-modifying activity or provide symptomatic relief in multiple sclerosis.

Measurement of Disease Modifying Anti-Rheumatic Drug (DMARD) Activity:

The collagen-induced arthritis (CIA) model is considered a suitable model for studying potential drugs active in human rheumatoid arthritis because of the many immunological and pathological similarities to human rheumatoid arthritis (RA), the involvement of localized major histocompatibility, complete class-II-restricted T helper lymphocyte activation, and the similarity of histological lesions. Features of this CIA model that are similar to that found in RA patients include: erosion of cartilage and bone at joint margins (as can be seen in radiographs), proliferative synovitis, symmetrical involvement of small and medium-sized peripheral joints in the appendicular, but not the axial, skeleton. The compounds disclosed herein can be tested for activity against autoimmune arthritis (e.g. reduction in severity or incidence of disease) using the protocols described in Rosloniec E F et al., "Collagen-Induced Arthritis," *Current Protocols in Immunology*, Unit 15.5 (1993). Compounds can be assessed for their ability to reduce the severity or incidence of disease (both by examination of the external appearance of the joints as well as their architecture by histopathology) in comparison to reference control compounds (e.g. dexamethasone). An active Des1 inhibitor would be anticipated to reduce severity and or incidence of disease in collagen-induced arthritis models. Active Des1 inhibitors could be administered in combination with various analgesics (including traditional NSAIDs and COX2-selective inhibitors), steroids, methotrexate, gold salts, hydroxychloroquine, PAD4 inhibitors, sulfasalazine, leflunomide, anti-TNFα, inhibitors of janus kinases, abatacept, rituximab, and anakinra. Des1 inhibitors disclosed herein would be expected to have disease-modifying activity or provide symptomatic relief in rheumatoid arthritis.

Measurement of Activity in Alzheimer's Disease

There are various animal models of neurodegenerative diseases, including Alzheimer's disease, Parkinson's disease, Huntington's disease, and amyotrophic lateral sclerosis. A standard mouse model known in the art is TgCRND8, an early-onset disease model that is transgenic for encoding the double mutant form of the amyloid precursor protein 695 (KM670/671NL1V717F) under the control of the PrP gene promoter. These mice develop the cortical $A\beta_{42}$ and hyperphosphorylated Tau protein which resemble some of the clinical features of Alzheimer's disease. Animals are dosed with Des1 inhibitors at 4 weeks of age for 4 months, followed by post-mortem assessment of brain ceramides, $A\beta_{42}$ and hyperphosphorylated Tau protein. An active Des1 inhibitor would be anticipated to lower brain ceramides, as well as the levels of the potentially disease-causing $A\beta_{42}$ and hyperphosphorylated Tau proteins. Des1 inhibitors could potentially be administered in combination with other therapeutics for Alzheimer's disease, including cholinesterase inhibitors and memantine. Des1 inhibitors disclosed herein would be expected to have disease-modifying activity or provide symptomatic relief in Alzheimer's disease.

Measurement of Activity in Amyotrophic Lateral Sclerosis:

The most commonly-used animal model of amyotrophic lateral sclerosis (ALS) is the SOD1-G93A transgenic mouse, with a phenotype which partially recapitulates what is observed clinically in patients. Mice develop paralysis in one or more limbs within a few months (accompanied by decreased longitudinal grip strength), and key disease endpoints include grip strength, as well as assay of lipid peroxidase activity (MDA) in spinal cord, and astrocytosis (GFAP) in ventral thalamus. Animals are dosed with Des1 inhibitors either early in disease (~12 weeks of age) or late in disease (18-20 weeks of age), followed by in-life assessments (grip strength) and post-mortem measurements (lipid peroxidase and astrocytosis). Active compounds would be anticipated to increase grip strength, decrease lipid peroxidase activity in the spinal cord, and decrease astrocytosis in the brain. Des1 inhibitors could also be dosed in combination with other therapeutics for ALS, including riluzole and/or edavarone. Des1 inhibitors disclosed herein would be expected to have disease-modifying activity or provide symptomatic relief in ALS.

Measurement of Activity in Models of Lipid Storage Disorders:

A representative lipid storage disorder in which a Des1 inhibitor would be anticipated to be efficacious is Farber disease, caused by the lack of activity of the lysosomal ceramide-degrading enzyme known as acid ceramidase (ASAH1). Mouse models in which ASAH1 mutated (e.g. P362R is an inactivating point mutation in the ASAH1 gene) recapitulate a number of key features of Farber disease, and serve as a readily-available system for assessing potential efficacy of drug candidates. There is a characteristic massive accumulation of ceramide into tissues, with corresponding infiltration of macrophages and elevated levels of various cytokines (e.g. MCP1) detectable in the circulation. Key assessments of potential Des1 inhibitor activity in this model include: levels of ceramide in liver, spleen, kidney, and heart; mass of spleen; plasma MCP1 level; and histopathology of liver and spleen to assess macrophage infiltration. Des1 inhibitors could also be dosed in combination with enzyme replacement therapy (e.g. recombinant human acid ceramidase).

Measurement of In Vivo Activity in a Model of Congestive Heart Failure:

A Des1 inhibitor would be anticipated to be efficacious in various types of congestive heart failure, including those secondary to ischemia, and associated with cardiomyopathy of diabetes, obesity, and lipotoxicity. A representative and standard model in the industry is conducted in mice examining the effects on the myocardium following occlusion of a coronary artery and or ascending aorta. Briefly, in the case of ischemia-induced heart failure, following chest opening of C47BL/6 mice, a 9-0 prolene is placed around the left anterior descending coronary artery 2 mm below the left atrium and ligated in order to model a myocardial infarction. Mice are subsequently randomized into vehicle and treatment groups (with a candidate Des1 inhibitor) and dosing is initiated either before, contemporaneous with, or following the coronary artery occlusion, for a total of 8 weeks (once or twice daily depending upon the Des1 inhibitor used). Treatment is anticipated to show improvements in cardiac function (as assessed by echocardiography and including such measures as fractional shortening and left ventricular end-diastolic diameter) as well as in endpoints assessed at take-down, including cardiac ceramide levels, inflammatory infiltrates (including macrophage infiltration), measures of cardiac apoptosis (including TUNEL staining), and/or cardiac remodeling including by fibrosis (including collagen levels). It is anticipated that treatment with a Des1 inhibitor could be improved by co-administration with a standard-of-care agent, including an angiotensin-converting enzyme (ACE) inhibitor, an angiotensin II receptor blocker (ARB), β-adrenergic receptor blocker (including carvedilol), diuretics (including furosemide), aldosterone antagonists (including eplerenone), inotropes (including milrinone), guanylate cyclase inhibitors, and/or digoxin.

Measurement of In Vivo Activity in a Model of Diabetic Kidney Disease:

A Des1 inhibitor would be anticipated to be efficacious in prevention or treatment of diabetic kidney disease (DKD or nephropathy), and as such would have efficacy in various animal models of DKD. A standard model relies on chemical damage (with streptozotocin, STZ) to pancreatic B-cells which induces hyperglycemia with resulting kidney damage. C57BL/6 mice are randomized into vehicle and treatment groups, and STZ is administered (IP at 200 mg/kg) to induce hyperglycemia and subsequent glomerular injury. Treatment could be initiated prior to, contemporaneous with, or subsequent to STZ-induced kidney injury for a duration of up to 4 weeks post STZ administration, and would be anticipated to improve kidney function (including assessments of glomerular filtration rate, BUN, and creatinine), glomerular integrity (albuminuria/proteinuria), and evidence of fibrosis (including collagen levels). Moreover, it is anticipated that treatment with a Des1 inhibitor could be improved by co-administration with a standard-of-care agent, including an ACE inhibitor, ARB, cholesterol-lowering agents (including statins and/or PCSK9 inhibitors), and medications that manage calcium phosphate levels for bone health (including sevelamer).

Measurement of In Vivo Activity in a Model of Acute Kidney Injury:

A Des1 inhibitor would be anticipated to be efficacious in the prevention or treatment of acute kidney injury, from various etiologies, including from ischemia/reperfusion and drug-induced (including from chemotherapy and imaging contrast agents). A standard model of acute kidney injury models the nephrotoxicity associated with cisplatin. C57BL/6 mice are randomized into vehicle or treatment groups and dosed starting 48 hours prior to or contemporaneously with an intraperitoneal injection of cisplatin (25 mg/kg), with continued once- or twice-daily dosing of vehicle or treatment for up to 72 hours post cisplatin injection. It is anticipated that treatment with a Des1 inhibitor would reduce cisplatin-induced increases in renal ceramide levels and improve kidney function (assessed by blood BUN and/or creatinine levels and/or glomerular filtration rate). It is also anticipated that treatment with a Des1 inhibitor could be improved by combination with a standard-of-care agent, including N-acetylcysteine.

Measurement of In Vivo Activity in a Model of Sarcopenia:

A Des1 inhibitor would be anticipated to be efficacious in the preservation of muscle mass in the context of sarcopenia, from a variety of etiologies including aging, chronic kidney disease, malignancy, or chemotherapy. A standard model of cancer cachexia-induced sarcopenia is as follows: On Day 0, BALB/c mice are randomized into vehicle and treatment groups, and castrated and implanted with $5 \times 10^5$ C26 mouse carcinoma cells into a flank. The mice are dosed with either vehicle or treatment once or twice-daily for two weeks starting on Day 11, and monitored every 3 days for tumor volume and body weight, and levator ani muscle weight at take-down. It is anticipated that treatment with a Des1 inhibitor would preserve skeletal muscle mass (eg levator ani muscle mass) and/or body weight. It is also anticipated that treatment with a Des1 inhibitor could be improved by combination with an another agent, including testosterone, a selective androgen receptor modulator, a ghrelin agonist, a myostatin antibody, an activin IIR antagonist, an ACE inhibitor, a beta antagonist, and a fast skeletal muscle troponin activator.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references, patents or applications, U.S. or foreign, cited in the application are hereby incorporated by reference as if written herein in their entireties. Where any inconsistencies arise, material literally disclosed herein controls.

What is claimed is:

1. A method of treating a Des1-mediated disorder in a subject in need thereof, comprising the step of administering to the subject a compound of structural Formula II

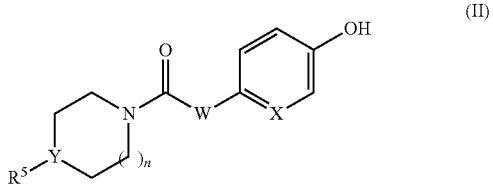

or a salt thereof, wherein:
W is —NH—;
X is N;
Y is chosen from CH and N;
$R^5$ is chosen from alkyl, cycloalkyl, heterocycloalkyl, aryl, heteroaryl, (aryl) alkyl, (heteroaryl) alkyl, (aryl) aryl, (heteroaryl) aryl, (aryl) heteroaryl, and (heteroaryl) heteroaryl, and is optionally substituted with 1, 2, or 3 $R^6$ groups; and
each $R^6$ is independently chosen from alkoxy, alkyl, amino, carboxy, cyano, halo, haloalkoxy, and hydroxy; and
n is chosen from 1 and 2.

2. The method according to claim 1, wherein the subject is a human.

3. The method according to claim 1, wherein the Des1-mediated disorder is a metabolic disorder.

4. The method according to claim 1, wherein the Des1-mediated disorder is a lipid storage disorder.

5. The method according to claim 1, wherein the Des1-mediated disorder is an autoimmune or chronic inflammatory disease.

6. The method according to claim 1, wherein the Des1-mediated disorder is a cardiovascular disease.

7. The method according to claim 1, wherein the Des1-mediated disorder ischemia/reperfusion injury.

8. The method according to claim 1, wherein the Des1-mediated disorder is fibrosis.

9. The method according to claim 1, wherein the Des1-mediated disorder is cancer.

10. The method according to claim 9, wherein the method further comprises administering non-chemical methods of cancer treatment.

11. The method according to claim 9, wherein the method further comprises administering radiation therapy.

12. The method according to claim 10, wherein the method further comprises administering surgery, thermoablation, focused ultrasound therapy, cryotherapy, or any combination thereof.

13. The method of claim 9, further comprising the sequential or co-administration of a second therapeutic agent.

14. The method of claim 13, wherein the second therapeutic agent is selected from a PD-1 inhibitor, a PD-L1 inhibitor, a CTLA-4 inhibitor, a CD47 inhibitor, an indoleamine-2,3-dioxygenase inhibitor, and an arginase inhibitor.

15. The method of claim 14, wherein the PD-1 inhibitor is selected from pembrolizumab, pidilizumab, AMP-224, AMP-514, PDR001, and nivolumab.

16. The method of claim 14, wherein the PD-L1 inhibitor is selected from atezolizumab, avelumab, and durvalumab.

17. The method of claim 14, wherein the CTLA-4 inhibitor is ipilimumab.

18. The method of claim 14, wherein the CD47 inhibitor is selected from CV1, Hu5F9-G4, CC-90002, and TTI-621.

19. The method of claim 14, wherein the indoleamine-2,3-dioxygenase inhibitor is selected from 1-methyltryptophan, INCB024360, indoximod, NLG919, norharmane, rosmarinic acid, epacadostat, and navoximod.

20. The method of claim 14, wherein the arginase inhibitor is selected from CB-1158 and norvaline.

21. The method as recited in claim 13, wherein the second therapeutic agent is a DNA-damaging agent.

22. The method as recited in claim 21, wherein the DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonate, or an antibiotic.

23. The method as recited in claim 22, wherein the platinating agent is selected from cisplatin, oxaliplatin, carboplatin, nedaplatin, lobaplatin, triplatin tetranitrate, picoplatin, satraplatin, and aroplatin.

24. The method as recited in claim 22, wherein the Topo I inhibitor is selected from camptothecin, topotecan, rubitecan and belotecan.

25. The method as recited in claim 22, wherein the Topo II inhibitor is selected from etoposide, daunorubicin, doxorubicin, aclarubicin, epirubicin, idarubicin, amrubicin, pirarubicin, valrubicin, zorubicin and teniposide.

26. The method as recited in claim 22, wherein the antimetabolite is selected from aminopterin, methotrexate, pemetrexed, raltitrexed, pentostatin, cladribine, clofarabine, fludarabine, thioguanine, mercaptopurine, fluorouracil, capecitabine, tegafur, carmofur, floxuridine, cytarabine, gemcitabine, azacitidine and hydroxyurea.

27. The method as recited in claim 22, wherein the alkylating agent is selected from mechlorethamine, cyclophosphamide, ifosfamide, trofosfamide, chlorambucil, melphalan, prednimustine, bendamustine, uramustine, estramustine, carmustine, lomustine, semustine, fotemustine, nimustine, ranimustine, streptozocin, busulfan, mannosulfan, treosulfan, carboquone, thioTEPA, triaziquone, triethylenemelamine, procarbazine, dacarbazine, temozolomide, altretamine, mitobronitol, actinomycin, bleomycin, mitomycin and plicamycin.

28. The method as recited in claim 13, wherein the second therapeutic agent is a CHK1 inhibitor.

29. The method as recited in claim 28, wherein the CHK1 inhibitor is selected from MK-8776, LY2603618, V158411, PF-477736, UCN-01, and AZD7762.

30. The method of claim 13, wherein the second therapeutic agent is an antagonistic monoclonal antibody (mAb).

31. The method of claim 30, wherein the antagonistic mAb is selected from a CTLA-4 mAb, a PD-1 mAb, and a PD-L1 mAb, a CD47 mAb, and an OX40 mAb.

* * * * *

UNITED STATES PATENT AND TRADEMARK OFFICE
CERTIFICATE OF CORRECTION

| | | |
|---|---|---|
| PATENT NO. | : 12,247,019 B2 | Page 1 of 1 |
| APPLICATION NO. | : 18/106305 | |
| DATED | : March 11, 2025 | |
| INVENTOR(S) | : Donna L. Romero et al. | |

It is certified that error appears in the above-identified patent and that said Letters Patent is hereby corrected as shown below:

In the Specification

In Column 1, Line 15, STATEMENT REGARDING FEDERALLY SPONSORED RESEARCH OR DEVELOPMENT, "2 R44 DK116450-02" should read --DK116450--.

Signed and Sealed this
Twenty-ninth Day of April, 2025

Coke Morgan Stewart
*Acting Director of the United States Patent and Trademark Office*